United States Patent

Hatley et al.

(10) Patent No.: US 8,143,264 B2
(45) Date of Patent: Mar. 27, 2012

(54) XANTHINE DERIVATIVES AS SELECTIVE HM74A AGONISTS

(75) Inventors: Richard Jonathan Daniel Hatley, Stevenage (GB); Andrew McMurtrie Mason, Stevenage (GB); Ivan Leo Pinto, Harlow (GB)

(73) Assignee: GlaxoSmithKline LLC, Philadelphia, PA (US)

( * ) Notice: Subject to any disclaimer, the term of this patent is extended or adjusted under 35 U.S.C. 154(b) by 595 days.

(21) Appl. No.: 12/063,434

(22) PCT Filed: Aug. 8, 2006

(86) PCT No.: PCT/EP2006/007865
§ 371 (c)(1),
(2), (4) Date: Feb. 9, 2008

(87) PCT Pub. No.: WO2007/017261
PCT Pub. Date: Feb. 15, 2007

(65) Prior Publication Data
US 2010/0168122 A1    Jul. 1, 2010

(30) Foreign Application Priority Data

Aug. 10, 2005 (GB) .................. 0516464.5
Apr. 19, 2006 (GB) .................. 0607736.6
Jul. 21, 2006 (GB) .................. 0614569.2

(51) Int. Cl.
*C07D 473/04* (2006.01)
*C07D 473/06* (2006.01)
*A61K 31/522* (2006.01)
*A61P 9/10* (2006.01)
*A61P 9/00* (2006.01)
*A61P 13/12* (2006.01)
*A61P 3/10* (2006.01)

(52) U.S. Cl. .............. 514/263.2; 544/268; 544/269; 544/270

(58) Field of Classification Search ............. 544/268, 544/269, 270; 514/263.2, 263.21, 263.22, 514/263.23, 263.24
See application file for complete search history.

(56) References Cited

U.S. PATENT DOCUMENTS

| | | | |
|---|---|---|---|
| 2,797,220 A | 6/1957 | Blicke et al. | |
| 5,473,070 A | 12/1995 | Underiner et al. | |
| 5,780,476 A | 7/1998 | Underiner et al. | |
| 5,807,861 A | 9/1998 | Klein et al. | |
| 5,981,535 A | 11/1999 | Spicer et al. | |
| 6,043,250 A | 3/2000 | Klein et al. | |
| 6,100,271 A | 8/2000 | Klein et al. | |
| 6,103,730 A | 8/2000 | Klein et al. | |
| 6,133,274 A | 10/2000 | Underiner et al. | |
| 6,323,201 B1 * | 11/2001 | Carson et al. | 514/234.2 |
| 6,469,017 B1 | 10/2002 | Klaus et al. | |
| 6,586,429 B2 * | 7/2003 | Gong et al. | 514/233.2 |
| 6,693,105 B1 | 2/2004 | Underiner et al. | |
| 6,774,130 B2 | 8/2004 | Klein et al. | |
| 6,780,865 B1 | 8/2004 | Porubek et al. | |
| 6,821,978 B2 | 11/2004 | Chackalamannil et al. | |
| 6,878,715 B1 * | 4/2005 | Klein et al. | 514/263.34 |
| 7,268,141 B2 | 9/2007 | Chackalamannil et al. | |
| 7,482,337 B2 | 1/2009 | Himmelsbach et al. | |
| 7,531,544 B2 | 5/2009 | Chackalamannil et al. | |
| 7,696,212 B2 | 4/2010 | Himmelsbach et al. | |
| 7,713,982 B2 | 5/2010 | Pinto | |
| 2002/0169174 A1 | 11/2002 | Chackalamannil et al. | |
| 2002/0198205 A1 | 12/2002 | Himmelsbach et al. | |
| 2003/0207901 A1 | 11/2003 | Underiner et al. | |
| 2004/0077645 A1 | 4/2004 | Himmelsbach et al. | |
| 2004/0087587 A1 | 5/2004 | Himmelsbach et al. | |
| 2004/0167137 A1 | 8/2004 | Chackalamannil et al. | |
| 2004/0229885 A1 | 11/2004 | Chackalamannil et al. | |
| 2005/0032748 A1 | 2/2005 | Klein et al. | |
| 2005/0049262 A1 | 3/2005 | Klein et al. | |

(Continued)

FOREIGN PATENT DOCUMENTS

EP    0389282    9/1990

(Continued)

OTHER PUBLICATIONS

Arch, et al. "Inhibition of Type 4 Cyclic Nucleotide Phosphodiesterase by 8-Chloroxanthines". *Archiv der Pharmazie*, 329(4): 205-208 (1996).

(Continued)

*Primary Examiner* — Mark Berch
(74) *Attorney, Agent, or Firm* — Grace C. Hsu; John Lemanowicz

(57) ABSTRACT

The present invention relates to a xanthine compound derivative which is 3-butyl-8-chloro-1-(3-{5-[(4-fluorophenyl)methyl]-2H-tetrazol-2-yl}propyl)-3,7-dihydro-1H-purine-2,6-dione:

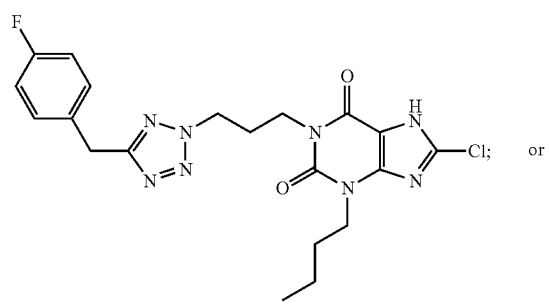

a pharmaceutically acceptable salt thereof, corresponding pharmaceutical formulations, combinations, preparation methods and methods or uses in treatment of diseases where under-activation of the HM74A receptor contributes to the disease or where activation of the receptor will be beneficial.

16 Claims, 3 Drawing Sheets

U.S. PATENT DOCUMENTS

| | | | |
|---|---|---|---|
| 2005/0075349 A1 | 4/2005 | Chackalamannil et al. | |
| 2005/0182077 A1 | 8/2005 | Chackalamannil et al. | |
| 2006/0205711 A1 | 9/2006 | Himmelsbach et al. | |
| 2006/0247226 A1 | 11/2006 | Himmelsbach et al. | |
| 2007/0135456 A1 | 6/2007 | Pinto et al. | |
| 2008/0058354 A1 | 3/2008 | Chackalamannil et al. | |
| 2008/0221108 A1 | 9/2008 | Hatley et al. | |
| 2009/0209561 A1* | 8/2009 | Hatley et al. | 514/263.22 |
| 2010/0010021 A1 | 1/2010 | Pinto et al. | |
| 2010/0099690 A1* | 4/2010 | Heer et al. | 514/263.34 |
| 2010/0144703 A1 | 6/2010 | Himmelsbach et al. | |
| 2010/0160354 A1 | 6/2010 | Pinto et al. | |
| 2010/0173916 A1 | 7/2010 | Himmelsbach et al. | |
| 2010/0179128 A1* | 7/2010 | Hatley et al. | 514/214.02 |
| 2010/0204250 A1 | 8/2010 | Himmelsbach et al. | |
| 2011/0144083 A1 | 6/2011 | Himmelsbach et al. | |
| 2011/0144095 A1 | 6/2011 | Himmelsbach et al. | |

FOREIGN PATENT DOCUMENTS

| | | |
|---|---|---|
| EP | 1 338 595 | 8/2003 |
| EP | 1171442 B1 | 7/2005 |
| WO | WO 92/09203 | 6/1992 |
| WO | WO 93/16699 | 9/1993 |
| WO | WO 93/17684 | 9/1993 |
| WO | WO 94/11001 | 5/1994 |
| WO | WO 94/22449 | 10/1994 |
| WO | WO 94/22863 | 10/1994 |
| WO | WO 94/24133 | 10/1994 |
| WO | WO 95/20589 | 8/1995 |
| WO | WO 95/22546 | 8/1995 |
| WO | WO 99/20280 | 4/1999 |
| WO | WO 99/36073 | 7/1999 |
| WO | WO 02/24698 | 3/2002 |
| WO | WO 02/68420 | 9/2002 |
| WO | WO 02/084298 | 10/2002 |
| WO | WO 03/004496 | 1/2003 |
| WO | WO 00/61583 | 10/2003 |
| WO | WO 2005/016870 | 2/2005 |
| WO | WO 2006/045564 | 5/2006 |
| WO | WO 2010/068581 | 6/2010 |

OTHER PUBLICATIONS

"Fibrate", Wikipedia, the free encyclopedia, pp. 1 to 3, Dec. 18, 2010).

U.S. Appl. No. 12/552,649, filed Sep. 2, 2009, Hatley et al.

U.S. Appl. No. 12/717,349, filed Mar. 4, 2010, Hatley et al.

Katsushima et al., "Structure-Activity Relationships of 8-Cycloalkyl_1, 3-Dipropylxanthines as Antagonists of Adenosine Receptors", J. of Med. Chem., American Chemical Society, Washington, DC, US, vol. 33, Jul. 1, 1990, pp. 1906-1910.

Arch, Jonathan et al., "Inhibition of Type 4 Cyclic Nucleotide Phosphodiesterase by 8-Chloraxanthines" Arch. Pharm. Pharm. Med. Chem., VCH Verlagsgesellschaft mbH, Weinheim, 1996, Germany) 329(4), pp. 205-208.

Jacobson, Kenneth et al., "Effect of Trifluoromethyl and Other Substituents on Activity of Xanthines at Adenosine Receptors", J. of Med. Chem., vol. 36, No. (18), ACS: 1993, pp. 2639-2644.

Kattus, Albert A., et al., "Diuretic Activity of Compounds Related to Xanthines, Uracils, and Triazines as Determined in Dogs", Bulletin of the Johns Hopkins Hospital, Baltimore, MD, 1951, 89, pp. 1-8.

Smellie, F. W., et al., "Alkylxanthines: Inhibition of Adenosine-Elicited Accumulation of Cyclic AMP in Brain Slices and of Brain Phosphodiesterase Activity", Permagon Press (USA): 1979, Life Sciences, vol. 24, No. 24, pp. 2475-2481.

* cited by examiner

Figure 1: XRPD data of substantially crystalline 3-Butyl-8-chloro-1-{4-[5-(2-pyridinyl)-1,2,4-oxadiazol-3-yl]butyl}-3,7-dihydro-1H-purine-2,6-dione form 1.

Figure 2: XRPD data of substantially crystalline 3-Butyl-8-chloro-1-{4-[5-(2-pyridinyl)-1,2,4-oxadiazol-3-yl]butyl}-3,7-dihydro-1H-purine-2,6-dione form 2.

Figure 3 Overlay of XRPD data for Form 1 (bottom), Form 2 (top) (data has been offset for clarity).

XANTHINE DERIVATIVES AS SELECTIVE HM74A AGONISTS

The present invention relates to compounds which are xanthine derivatives, processes for the manufacture of said derivatives, pharmaceutical formulations containing these compounds and the use of the compounds in therapy, for example, in the treatment of diseases where under-activation of the HM74A receptor contributes to the disease or where activation of the receptor will be beneficial.

Dyslipidaemia is a general term used to describe individuals with aberrant lipoprotein profiles. Clinically, the main classes of compounds used for the treatment of patients with dyslipidaemia, and therefore at risk of cardiovascular disease are the statins, fibrates, bile-acid binding resins and nicotinic acid. Nicotinic acid (Niacin, a B vitamin) has been used clinically for over 40 years in patients with various forms of dyslipidaemia. The primary mode of action of nicotinic acid is via inhibition of hormone-sensitive triglyceride lipase (HSL), which results in a lowering of plasma non-esterified fatty acids (NEFA) which in turn alters hepatic fat metabolism to reduce the output of LDL and VLDL (low and very low density lipoprotein). Reduced VLDL levels are thought to lower cholesterol ester transfer protein (CETP) activity to result in increased HDL (high density lipoprotein) levels which may be the cause of the observed cardiovascular benefits. Thus, nicotinic acid produces a very desirable alteration in lipoprotein profiles; reducing levels of VLDL and LDL whilst increasing HDL. Nicotinic acid has also been demonstrated to have disease modifying benefits, reducing the progression and increasing the regression of atherosclerotic lesions and reducing the number of cardiovascular events in several trials.

The observed inhibition of HSL by nicotinic acid treatment is mediated by a decrease in cellular cyclic adenosine monophosphate (cAMP) caused by the G-protein-mediated inhibition of adenylyl cyclase. Recently, the G-protein coupled receptors HM74 and HM74A have been identified as receptors for nicotinic acid (PCT patent application WO02/84298; Wise et. al. J Biol Chem., 2003, 278 (11), 9869-9874). The DNA sequence of human HM74A may be found in Genbank; accession number AY148884. Two further papers support this discovery, (Tunaru et. al. Nature Medicine, 2003, 9(3), 352-255 and Soga et. al. Biochem Biophys Res Commun., 2003, 303 (1) 364-369), however the nomenclature differs slightly. In the Tunaru paper what they term human HM74 we term HM74A and in the Soga paper HM74b is identical to HM74A. Cells transfected to express HM74A and/or HM74 gain the ability to elicit $G_i$ G-protein mediated responses following exposure to nicotinic acid. In mice lacking the homologue of HM74A (m-PUMA-G) nicotinic acid fails to reduce plasma NEFA levels.

Certain xanthine derivatives have been synthesised and disclosed in the prior art. For example, EP0389282 discloses xanthine derivatives as potential mediators of cerebrovascular disorders. A range of xanthine derivatives were identified as adenosine receptor antagonists by Jacobson et. al. in J. Med. Chem., 1993, 36, 2639-2644.

We now present a group of xanthine derivatives which are selective agonists of the nicotinic acid receptor HM74A and are thus of potential benefit in the treatment, prophylaxis and suppression of diseases where under-activation of this receptor either contributes to the disease or where activation of the receptor will be beneficial.

SUMMARY OF THE INVENTION

The present invention provides xanthine derivatives and the use of these derivatives in therapy, for example, in the treatment of diseases where under-activation of the HM74A receptor contributes to the disease or where activation of the receptor will be beneficial. For example, in treatment of diseases of lipid metabolism including dyslipidaemia or hyperlipoproteinaemia such as diabetic dyslipidaemia and mixed dyslipidaemia, heart failure, hypercholesteraemia, cardiovascular disease including atherosclerosis, arteriosclerosis, and hypertriglyceridaemia. As such, the compounds may also find favour as therapeutics for coronary artery disease, thrombosis, angina, chronic renal failure, peripheral vascular disease and stroke, as well as the cardiovascular indications associated with type II diabetes mellitus, type I diabetes, insulin resistance, hyperlipidaemia, anorexia nervosa, obesity. The compounds may also be of use in the treatment of inflammatory diseases or conditions, as set out further below.

Intermediates, formulations, methods and processes described herein form further embodiments of the invention.

DETAILED DESCRIPTION OF THE INVENTION

According to one aspect of this invention we provide at least one chemical entity selected from compounds of formula (I)

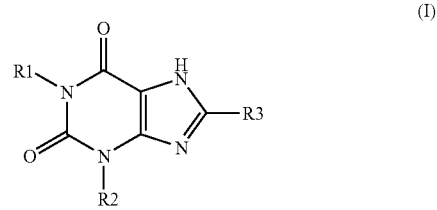

(I)

and pharmaceutically acceptable derivatives thereof, wherein
$R^1$ represents (alkylene)$_m$-X-(alkylene)$_n$-Y;
Wherein m and n represent the number of carbon atoms in the alkylene chain;
Wherein X represents a group selected from heteroaryl and heterocyclyl;
Wherein Y represents a group selected from aryl, heteroaryl and O-aryl;
which may be optionally substituted by one or more groups independently selected from $C_{1-6}$ alkyl, $C_{2-6}$alkenyl, $C_{2-6}$alkynyl, halogen, —(CH$_2$)$_q$NR$^5$R$^7$, —(CH$_2$)$_q$—(O)$_p$— (CH$_2$)$_q$—N(R$^5$)C(O)OR$^8$, —(CH$_2$)$_q$—N(R$^5$)C(O)R$^8$, —(CH$_2$)$_q$—(O)$_p$—(CH$_2$)$_q$—C(O)NR$^5$R$^6$, —(CH$_2$)$_q$—N (R$^5$)C(O)NR$^5$R$^6$, —(CH$_2$)$_q$—C(O)N((CH$_2$)$_m$OH)R$^5$, —(CH$_2$)$_q$—N(R$^5$)—S(O)$_2$R$^8$, —CH$_2$—S(O)$_2$NR$^5$R$^6$, —C$_{1-6}$ haloalkyl, —OCF$_3$, —OCH(F)$_2$, —OCH$_2$F, —C(O) OR$^5$, —OR$^5$, —R$^8$CN, CN, —SO$_2$R$^9$, —(CH$_2$)$_n$heteroaryl, —(CH$_2$)$_n$heterocyclyl, —(CH$_2$)$_n$cycloalkyl, —(CH$_2$)$_n$cycloalkenyl, and —(CH$_2$)$_n$aryl;
$R^2$ represents $C_{1-6}$ alkyl which may be optionally substituted by one or more groups independently selected from cycloalkyl, $C_{1-6}$ haloalkyl, halogen, —CN and —OR$^4$;
$R^3$ represents halogen;
$R^4$ represents a group selected from hydrogen, $C_{1-6}$ alkyl, $C_{2-6}$ alkenyl, $C_{2-6}$ alkynyl, —(CH$_2$)$_n$ cycloalkyl, —(CH$_2$)$_n$ cycloalkenyl, —(CH$_2$)$_n$ heterocyclyl, —(CH$_2$)$_n$ aryl, and —(CH$_2$)$_n$ heteroaryl;
$R^5$ and $R^6$ are independently selected from hydrogen and $C_{1-4}$ alkyl;
$R^7$ represents a group selected from $C_{1-6}$ alkyl, $C_{2-6}$ alkenyl, $C_{2-6}$ alkynyl, —(CH$_2$)$_t$ cycloalkyl, —(CH$_2$)$_t$ cycloalkenyl, —(CH$_2$)$_t$ heterocyclyl, —(CH$_2$)$_t$ aryl, and —(CH$_2$)$_t$ heteroaryl;

$R^8$ represents $C_{1-4}$ alkyl;

$R^9$ represents a group selected from $C_{1-6}$ alkyl $C_{2-6}$ alkenyl, $C_{2-6}$ alkynyl, —$(CH_2)_n$ cycloalkyl, —$(CH_2)_n$cycloalkenyl, —$(CH_2)_n$heterocyclyl, —$(CH_2)_n$ aryl, —$(CH_2)_n$heteroaryl, and CN;

m represents an integer selected from 3 and 4;

n represents an integer selected from 0 and 1;

p represents an integer selected from 0 and 1;

q represents an integer selected from 0, 1 and 2; and t represents an integer selected from 1 and 2.

The compound(s) are believed to be of use in the treatment of diseases where under-activation of the HM74A receptor contributes to the disease or where activation of the receptor will be beneficial. For example in treatment of diseases of lipid metabolism including dyslipidaemia and hyperlipoproteinaemia such as diabetic dyslipidaemia and mixed dyslipidaemia, heart failure, hypercholesteraemia, cardiovascular disease including atherosclerosis, arteriosclerosis, and hypertriglyceridaemia. As such, the compounds may also find favour as therapeutics for coronary artery disease, thrombosis, angina, chronic renal failure, peripheral vascular disease and stroke, as well as the cardiovascular indications associated with type II diabetes mellitus, type I diabetes, insulin resistance, hyperlipidaemia, anorexia nervosa, obesity. As such the compounds of the present invention may find use as agonists or partial agonists of HM74A. The compounds may also be of use in the treatment of inflammatory diseases or conditions, as set out further below.

In one embodiment of the present invention, X represents a heteroaryl. In another embodiment X represents a heteroaryl comprising a nitrogen heteroatom, for example, triazolyl, furazanyl, oxadiazolyl, tetrazolyl, imidazolyl or pyrazolyl. In a further embodiment X represents a group selected from oxadiazolyl and tetrazolyl.

In another embodiment, Y represents an optionally substituted group selected from aryl, for example phenyl or napthyl, heteroaryl, for example pyridinyl, thiazolyl, thienyl, benzofuranyl or indolyl, and O-aryl, for example O-phenyl. In a further embodiment, Y represents an optionally substituted group selected from aryl and heteroaryl. In one embodiment Y is selected from aryl.

In one embodiment of the present invention, Y may be optionally substituted by one or more of: $C_{1-6}$ alkyl, $C_{2-6}$ alkenyl, $C_{2-6}$ alkynyl, halogen, —$NH_2$, —$(CH_2)_q$—$(O)_p$—$(CH_2)_q$—$N(R^5)C(O)OR^8$, —$(CH_2)_q$—$N(R^5)C(O)R^8$, —$(CH_2)_q$—$(O)_p$—$(CH_2)_q$—$C(O)NR^5R^6$, —$(CH_2)_q$—$N(R^5)C(O)N(R^5)R^6$, —$(CH_2)_q$—$C(O)N((CH_2)_mOH)R^5$, —$(CH_2)_q$—$N(R^5)$—$S(O)_2R^8$, —$CH_2$—$S(O)_2N(R^5)R^6$, —$C_{1-6}$ haloalkyl, —$OCF_3$, —$OCH(F)_2$, —$OCH_2F$, —$C(O)OR^5$, —$OR^5$, —$R^8CN$, CN—$SO_2R^9$, —$(CH_2)_n$heteroaryl, —$(CH_2)_n$heterocycyl, —$(CH_2)_n$cycloalkyl, —$(CH_2)_n$cycloalkenyl, —$(CH_2)_n$aryl;

In a further embodiment, Y is substituted by one or more groups selected from $OR^5$ for example OH or $OCH_3$, halogen, for example F or Cl, aryl, for example phenyl, $C_{1-6}$ haloalkyl for example $CF_3$ or $CH_2CF_3$, $OCF_3$, $R^8CN$, CN, $(CH_2)_q$—N$(R^5)$—$S(O)_2R^8$, for example $NHSO_2CH_3$ and $SO_2R^9$, for example $SO_2CH_3$.

In yet a further embodiment Y is substituted by one or more groups selected from $OR^5$, halogen, $C_{1-6}$ haloalkyl, and —$(CH_2)_q$—$N(R^5)C(O)R^8$.

In another embodiment, Y is substituted by one or more groups selected from halogen, and $C_{1-6}$ haloalkyl.

In yet another embodiment, Y is not further substituted.

In one embodiment of the present invention, X and Y each independently represent a heteroaryl comprising a nitrogen heteroatom. In a further embodiment X represents oxadiazolyl and Y represents pyridinyl. In another embodiment X represents tetrazolyl and Y represents phenyl. In yet another embodiment of the present invention X represents oxadiazolyl and Y represents phenyl In one embodiment of the invention, m is 4 and n is 0. In a further embodiment, m is 3 and n is 1.

In one embodiment of the present invention, $R^2$ is selected from $C_{3-6}$ alkyl, for example butyl or pentyl, for example n-butyl or n-pentyl.

In a further embodiment of the present invention, $R^3$ is selected from chlorine and bromine. In another embodiment, $R^3$ represents chlorine.

In one embodiment of the present invention $R^7$ represents a group selected from $C_{1-6}$ alkyl, $C_{2-6}$ alkenyl, $C_{2-6}$ alkynyl, —$(CH_2)_t$ cycloalkyl, —$(CH_2)_n$cycloalkenyl, —$(CH_2)_t$ heterocyclyl, —$(CH_2)_t$ aryl, and —$(CH_2)_t$ heteroaryl;

In one embodiment of the present invention X represents oxadiazolyl, Y represents phenyl, $R^2$ is butyl, $R^3$ represents chlorine and m is 4 and n is 0.

With regard to stereoisomers, the compounds of formula (I) may have one or more asymmetric carbon atom and may occur as racemates, racemic mixtures and as individual enantiomers or diastereomers. All such isomeric forms are included within the present invention, including mixtures thereof.

Where a compound of formula (I) contains an alkenyl or alkenylene group, cis (E) and trans (Z) isomerism may also occur. The present invention includes the individual stereoisomers of the compound of the invention and, where appropriate, the individual tautomeric forms thereof, together with mixtures thereof.

Separation of diastereoisomers or cis and trans isomers may be achieved by conventional techniques, e.g. by fractional crystallisation, chromatography or HPLC of a stereoisomeric mixture of the agent may also be prepared from a corresponding optically pure intermediate or by resolution, such as HPLC of the corresponding racemate using a suitable chiral support or by fractional crystallisation of the diastereoisomeric salts formed by reaction of the corresponding racemate with a suitable optically active acid or base, as appropriate.

Furthermore, some of the crystalline forms of the compounds of formula (I) may exist as polymorphs, which are included in the present invention. One form may have an advantage over another form, for example one form may have improved stability over another form.

It is to be understood that the present invention includes any combination of particular embodiments and covers all combinations of particular substituents described hereinabove.

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

As used herein, the term "alkyl" (when used as a group or as part of a group) refers to a straight or branched hydrocarbon chain unless specified otherwise, containing the specified number of carbon atoms. For example, $C_3$-$C_6$alkyl means a straight or branched hydrocarbon chain containing at least 3 and at most 6 carbon atoms. Examples of alkyl as used herein include, but are not limited to methyl (Me), ethyl (Et), n-propyl and i-propyl.

The term "alkylene" as used herein means both straight and branched saturated or unsaturated chain, or cyclic saturated hydrocarbon linker groups. Examples of alkylene groups include methylene (—CH₂—), ethylene (—CH₂CH₂—), ethene (—CH=CH—), or cyclopropylene and the like. For example, as used herein, -(alkylene)$_m$-, where m is 3 represents —(CH₂)₃—, —C(CH₃)₂—, —CH₂CH=CH—, or -cyclopropylene- and the like. For example as used herein, -(alk)$_m$- where m is 4 represents —(CH₂)₄—, —CH₂C(CH₃)₂—, —CH₂CH=CHCH₂—, or —CH₂cyclopropylene- and the like. For example, as used herein -(alkylene)$_n$ where n=1 means —CH₂—. As used herein -(alkylene)$_n$ where n=0 means there is no alkylene linker at this position.

The term "alkenyl" as used herein refers to a straight or branched hydrocarbon chain containing the specified number of carbon atoms which contains one or more double bonds.

The term "alkynyl" as used herein refers to a straight or branched hydrocarbon chain containing the specified number of carbon atoms which contains one or more triple bonds.

The term "cycloalkyl" as used herein refers to a saturated monocyclic hydrocarbon ring of 3 to 8 carbon atoms. Examples of such groups include cyclopropyl, cyclobutyl, cyclopentyl, cyclohexyl, cycloheptyl and cyclooctyl.

The term "cycloalkenyl" as used herein refers to an unsaturated non-aromatic monocyclic hydrocarbon ring of 3 to 8 carbon atoms containing one or more carbon-carbon double bonds. Examples of such groups include cyclopropenyl, cyclobutenyl, cyclopentenyl, cyclohexenyl, cycloheptenyl, cyclooctenyl and the like.

The term "aryl" as used herein refers to a $C_{6-12}$ monocyclic, bicyclic or tricyclic hydrocarbon ring wherein at least one ring is aromatic. Examples of such groups include phenyl, naphthyl or tetrahydronaphthatenyl and the like.

The term "heteroaryl" as used herein refers to a 5-6 membered monocyclic aromatic ring or a fused 8-10 membered bicyclic aromatic ring, containing 1 to 4 heteroatoms, each independently selected from oxygen, nitrogen and sulphur. There may be one or more optional oxo substituents on the ring carbon atoms. Examples of such monocyclic aromatic rings include thienyl, furyl, furazanyl, pyrrolyl, triazolyl, tetrazolyl, imidazolyl, oxazolyl, thiazolyl, oxadiazolyl, isothiazolyl, isoxazolyl, thiadiazolyl, pyranyl, pyrazolyl, pyrimidyl, pyridazinyl, pyrazinyl, pyridyl, triazinyl, tetrazinyl and the like. Examples of such fused aromatic rings include quinolinyl, isoquinolinyl, quinazolinyl, quinoxalinyl, pteridinyl, cinnolinyl, phthalazinyl, naphthyridinyl, indolyl, isoindolyl, azaindolyl, indolizinyl, indazolyl, purinyl, pyrrolopyridinyl, furopyridinyl, benzofuranyl, isobenzofuranyl, benzothienyl, benzoimidazolyl, benzoxazolyl, benzoisoxazolyl, benzothiazolyl, benzoisothiazolyl, benzoxadiazolyl, benzothiadiazolyl and the like.

The term "heterocyclyl" as used herein refers to a 4-7 membered monocyclic ring or a fused 8-12 membered bicyclic ring which may be saturated or partially unsaturated containing 1 to 4 heteroatoms each independently selected from oxygen, nitrogen or sulphur. There may be one or more optional oxo substituents on the ring carbon atoms. Examples of such monocyclic rings include pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridinyl, tetrahydropyrimidinyl, tetrahydrothiophenyl, tetrahydrothiopyranyl, diazepanyl, azepanyl and the like. Examples of such bicyclic rings include indolinyl, isoindolinyl, benzopyranyl, quinuclidinyl, 2,3,4,5-tetrahydro-1H-3-benzazepine, tetrahydroisoquinolinyl and the like.

The terms "halogen" or "halo" as used herein refer to for example, a fluorine, chlorine, bromine or iodine atom.

The term "$C_{1-6}$ haloalkyl" as used herein refers to a $C_{1-6}$ alkyl group as defined herein wherein at least one hydrogen atom is replaced with halogen. Examples of such groups include fluoroethyl, trifluoromethyl, trifluoroethyl and the like.

As used herein, where a group is referred to as being "substituted" by another group or having "one or more substituents" unless a particular position for such a substitution is specified it is to be understood that a substitution may be present at any position in the group.

The term "pharmaceutically acceptable derivative" as used herein refers to any pharmaceutically acceptable derivative of a compound of the present invention, for example, salts, solvates or esters, which upon administration to a mammal, such as a human, is capable of providing (directly or indirectly) such a compound or an active metabolite thereof. Such derivatives are clear to those skilled in the art, without undue experimentation, and with reference to the teaching of Burger's Medicinal Chemistry And Drug Discovery, 5th Edition, Vol 1: Principles And Practice, which is incorporated herein by reference.

As used herein, the term "pharmaceutically acceptable" used in relation to an ingredient (active ingredient, diluent, excipient or carrier) which may be included in a pharmaceutical formulation for administration to a patient, refers to that ingredient being acceptable in the sense of being compatible with any other ingredients present in the pharmaceutical formulation and not being deleterious to the recipient thereof.

As used herein, the term "solvate" refers to a complex of variable stoichiometry formed by a solute (in this invention, a compound of formula (I) or a pharmaceutically acceptable derivative thereof) and a solvent. Such solvents for the purposes of the present invention may not interfere with the biological activity of the solute. The solvent used may be a pharmaceutically acceptable solvent. Examples of suitable pharmaceutically acceptable solvents include water, ethanol and acetic acid. An example of a solvent that may be used is water, in which case the solvate may be referred to as a hydrate of the solute in question.

It will be appreciated that, for pharmaceutical use, the "salt or solvate" referred to above will be a pharmaceutically acceptable salt or solvate. However, other salts or solvates may find use, for example, in the preparation of a compound of formula (I) or in the preparation of a pharmaceutically acceptable salt or solvate thereof.

Pharmaceutically acceptable salts include those described by Berge, Bighley and Monkhouse, *J. Pharm. Sci.*, 1977, 66, 1-19. Suitable pharmaceutically acceptable salts include alkali metal salts formed from the addition of alkali metal bases such as alkali metal hydroxides. Examples of suitable alkali metal salts include sodium salts and potassium salts. Other suitable pharmaceutically acceptable salts include alkaline earth metal salts such as calcium salts and magnesium salts, ammonium salts; or salts with organic bases such as ethanolamine, triethanolamine, ethylene diamine, triethylmine, choline and meglumine; or salts with amino acids such as arginine, lysine and histidine.

Esters may be active in their own right and/or be hydrolysable under in vivo conditions in the human body. Suitable pharmaceutically acceptable in vivo hydrolysable ester groups include those which break down readily in the human body to leave the parent acid or its salt. An ester may be formed at a carboxylic acid (—C(O)OH) group, by methods well known in the art involving reaction with the corresponding alcohol. For example, esters may be $C_{1-6}$alkyl esters, e.g. methyl esters, ethyl esters, and the like.

As used herein, the term "compounds of the invention" means the compounds according to Formula I and the pharmaceutically acceptable derivatives thereof. The term "a compound of the invention" means any one of the compounds of the invention as defined above.

As used herein the term "at least one chemical entity" means at least one chemical substance chosen from the group of compounds consisting of compounds of formula I and pharmaceutically acceptable derivatives thereof.

In one aspect of the invention there is provided substantially crystalline 3-Butyl-8-chloro-1-{4-[5-(2-pyridinyl)-1,2,4-oxadiazol-3-yl]butyl}-3,7-dihydro-1H-purine-2,6-dione form 1. In another aspect of the invention there is provided substantially crystalline 3-Butyl-8-chloro-1-{4-[5-(2-pyridinyl)-1,2,4-oxadiazol-3-yl]butyl}-3,7-dihydro-1H-purine-2,6-dione form 2.

Thermal analysis on samples of substantially crystalline 3-Butyl-8-chloro-1-{4-[5-(2-pyridinyl)-1,2,4-oxadiazol-3-yl]butyl}-3,7-dihydro-1H-purine-2,6-dione forms 1 and 2 was carried out. Thus, there is provided substantially crystalline 3-Butyl-8-chloro-1-{4-[5-(2-pyridinyl)-1,2,4-oxadiazol-3-yl]butyl}-3,7-dihydro-1H-purine-2,6-dione (form 1 or form 2) having a melting point onset measured by DSC (±0.5° C.) of: 160° C. or greater and 147° C. or greater, respectively.

Samples of substantially crystalline 3-Butyl-8-chloro-1-{4-[5-(2-pyridinyl)-1,2,4-oxadiazol-3-yl]butyl}-3,7-dihydro-1H-purine-2,6-dione form 1, and 3-Butyl-8-chloro-1-{4-[5-(2-pyridinyl)-1,2,4-oxadiazol-3-yl]butyl}-3,7-dihydro-1H-purine-2,6-dione form 2, prepared as described hereinafter, gave the X-ray powder diffraction patterns of FIGS. 1-2. The X-ray diffraction pattern is unique to the crystalline form. The substantially crystalline forms exhibit diffraction patterns with a unique set of diffraction peaks which can be expressed in 2 theta angles) (°).

2 Theta diffraction angles account for positions of various peaks in the X-ray diffraction pattern. Slight variations in observed 2 theta angles are expected based on the specific diffractometer employed and the analyst's sample preparation technique.

The substantially crystalline forms of 3-Butyl-8-chloro-1-{4-[5-(2-pyridinyl)-1,2,4-oxadiazol-3-yl]butyl}-3,7-dihydro-1H-purine-2,6-dione can be identified by the presence of a characteristic 2 theta angle peak, or by multiple 2 theta angles which are reasonably characteristic of the particular crystalline forms. To identify substantially crystalline 3-Butyl-8-chloro-1-{4-[5-(2-pyridinyl)-1,2,4-oxadiazol-3-yl]butyl}-3,7-dihydro-1H-purine-2,6-dione (form 1), these peaks occur at the following positions, expressed in 2 theta angles (±0.1 degrees): 5.4, 6.7, 9.7, 11.1, 12.9, 14.0, 15.6, 16.3, 16.7, 23.1 degrees. To identify substantially crystalline 3-Butyl-8-chloro-1-{4-[5-(2-pyridinyl)-1,2,4-oxadiazol-3-yl]butyl}-3,7-dihydro-1H-purine-2,6-dione (form 2), these peaks occur at the following positions, expressed in 2 theta angles (±0.1 degrees): 5.2, 6.6, 10.4, 11.2, 13.4, 15.6, 18.1, 19.5, 20.9 degrees. In one embodiment at least one of the foregoing 2 theta angles are employed to identify substantially crystalline 3-Butyl-8-chloro-1-{4-[5-(2-pyridinyl)-1,2,4-oxadiazol-3-yl]butyl}-3,7-dihydro-1H-purine-2,6-dione form 1 and substantially crystalline 3-Butyl-8-chloro-1-{4-[5-(2-pyridinyl)-1,2,4-oxadiazol-3-yl]butyl}-3,7-dihydro-1H-purine-2,6-dione form 2. In other embodiments at least 2, 3, 4 or 5 (where applicable) of the foregoing 2 theta angles are employed to identify substantially crystalline 3-Butyl-8-chloro-1-{4-[5-(2-pyridinyl)-1,2,4-oxadiazol-3-yl]butyl}-3,7-dihydro-1H-purine-2,6-dione form 1, substantially crystalline 3-Butyl-8-chloro-1-{4-[5-(2-pyridinyl)-1,2,4-oxadiazol-3-yl]butyl}-3,7-dihydro-1H-purine-2,6-dione form 2.

Some margin of error is present in each of the 2 theta angle assignments. The margin of error in the foregoing 2 theta angles is approximately ±0.1 degrees for each of the foregoing peak assignments.

Since some margin of error is possible in the assignment of 2 theta angles, the preferred method of comparing X-ray powder diffraction patterns in order to identify a particular crystalline form is to overlay the X-ray powder diffraction pattern of the unknown form over the X-ray powder diffraction pattern of a known form. For example, one skilled in the art can overlay an X-ray powder diffraction pattern of an unidentified form of 3-Butyl-8-chloro-1-{4-[5-(2-pyridinyl)-1,2,4-oxadiazol-3-yl]butyl}-3,7-dihydro-1H-purine-2,6-dione, obtained using the methods described herein, see FIG. 3 for example, and readily determine whether the X-ray diffraction pattern of the unidentified form is substantially the same as the X-ray powder diffraction pattern of substantially crystalline 3-Butyl-8-chloro-1-{4-[5-(2-pyridinyl)-1,2,4-oxadiazol-3-yl]butyl}-3,7-dihydro-1H-purine-2,6-dione Form 1 or 2. If the X-ray powder diffraction pattern is substantially the same as that shown in any of FIGS. 1-2, the previously form can be readily and accurately identified.

As used herein, the term "substantially crystalline form" means that it is substantially free of amorphous form 3-Butyl-8-chloro-1-{4-[5-(2-pyridinyl)-1,2,4-oxadiazol-3-yl]butyl}-3,7-dihydro-1H-purine-2,6-dione. By "substantially free" is meant containing less than 50% of the amorphous form, in one aspect less than 20% of the amorphous form, in another aspect less than 10% of the amorphous form, in another aspect less than 5% of the amorphous form, in another aspect less than 2% of the amorphous form, in another aspect less than 1% of the amorphous form.

The present invention provides a method for the preparation of substantially crystalline 3-Butyl-8-chloro-1-{4-[5-(2-pyridinyl)-1,2,4-oxadiazol-3-yl]butyl}-3,7-dihydro-1H-purine-2,6-dione form as described herein.

Compounds of formula (I) are of potential therapeutic benefit in the treatment and amelioration of the symptoms of many diseases of lipid metabolism including dyslipidaemia and hyperlipoproteinaemia such as diabetic dyslipidaemia and mixed dyslipidaemia, heart failure, hypercholesteraemia, cardiovascular disease including atherosclerosis, arteriosclerosis, and hypertriglyceridaemia, type II diabetes mellitus, type I diabetes, insulin resistance, hyperlipidaemia, anorexia nervosa, obesity. As such, the compounds may also find favour as therapeutics for coronary artery disease, thrombosis, angina, chronic renal failure, peripheral vascular disease and stroke.

It has been reported that the HM74 and HM74A receptors are involved in inflammation (WO02084298). Inflammation represents a group of vascular, cellular and neurological responses to trauma. Inflammation can be characterised as the movement of inflammatory cells such as monocytes, neutrophils and granulocytes into the tissues. This is usually associated with reduced endothelial barrier function and oedema into the tissues. Inflammation with regards to disease typically is referred to as chronic inflammation. Such chronic inflammation may manifest itself through disease symptoms. The aim of anti-inflammatory therapy is therefore to reduce this chronic inflammation and allow for the physiological process of healing and tissue repair to progress.

Examples of inflammatory diseases or conditions for which the compounds of the present invention may demonstrate utility include those of the joint, for example arthritis (e.g. rheumatoid arthritis, osteoarthritis, prosthetic joint failure), or the gastrointestinal tract (e.g. ulcerative colitis, Crohn's disease, and other inflammatory bowel and gastrointestinal diseases, gastritis and mucosal inflammation resulting from infection, the enteropathy provoked by non-steroidal anti-inflammatory drugs), of the lung (e.g. adult respiratory distress syndrome, asthma, cystic fibrosis, or chronic obstructive pulmonary disease), of the heart (e.g. myocarditis), of nervous tissue (e.g. multiple sclerosis), of the pancreas, (e.g. inflammation associated with diabetes melitus and complications thereof, of the kidney (e.g. glomerulonephritis), of the skin (e.g. dermatitis, psoriasis, eczema, urticaria, burn injury), of the eye (e.g. glaucoma) as well as of transplanted organs (e.g. rejection) and multi-organ diseases (e.g. systemic lupus erythematosis, sepsis) and inflammatory sequelae of viral or bacterial infections and inflammatory conditions associated with atherosclerosis and following hypoxic or ischaemic insults (with or without reperfusion), for example in the brain or in ischaemic heart disease.

In one embodiment, the compounds of this invention are useful in the treatment and prevention of inflammation, diabetes and cardiovascular diseases or conditions including atherosclerosis, arteriosclerosis, hypertriglyceridemia, and mixed dyslipidaemia.

Nicotinic acid has a significant side effect profile, possibly because it is dosed at high level (gram quantities daily). The most common side effect is an intense cutaneous flushing. In certain embodiments of the present invention the compounds may exhibit reduced side effects compared to nicotinic acid. HM74A has been identified as a high affinity receptor for nicotinic acid whilst HM74 is a lower affinity receptor. The compounds of the present invention show greater affinity for HM74A than for HM74 therefore may find use as selective HM74A agonists or partial agonists.

The potential for compounds of formula (I) to activate HM74A may be demonstrated, for example, using the following in vitro whole cell assays:

In-Vitro Testing

For transient transfections, HEK293T cells (HEK293 cells stably expressing the SV40 large T-antigen) were maintained in DMEM containing 10% foetal calf serum and 2 mM glutamine. Cells were seeded in 90 mm culture dishes and grown to 60-80% confluence (18-24 h) prior to transfection. Human HM74A (GenBank™ accession number AY148884) was subcloned in to a mammalian expression vector (pcDNA3; Invitrogen) and transfected using Lipofectamine™ reagent. For transfection, 9 µg of DNA was mixed with 30 µl Lipofectamine in 0.6 ml of Opti-MEM (Life Technologies Inc.) and was incubated at room temperature for 30 min prior to the addition of 1.6 ml of Opti-MEM. Cells were exposed to the Lipofectamine/DNA mixture for 5 h and 6 ml of 20% (v/v) foetal calf serum in DMEM was then added. Cells were harvested 48 h after transfection. Pertussis toxin treatment was carried out by supplementation into media at 50 ngml$^{-1}$ for 16 h. All transient transfection studies involved co-transfection of receptor together with the $G_{i/o}$ G protein, $G_{o1}\alpha$.

For generation of stable cell lines the above method was used to transfect CHO-K1 cells seeded in six well dishes grown to 30% confluence. These cells were maintained in DMEM-Ham's F-12 media (available from Invitrogen) containing 10% foetal calf serum and 2 mM glutamine. 48 h post-transfection the media was supplemented with 400 µg/ml Geneticin (G418, Gibco) for selection of antibiotic resistant cells. Clonal CHO-K1 cell lines stably expressing HM74A were confirmed by [$^{35}$S]-GTPγS binding measurements, following the addition of nicotinic acid.

P2 membrane preparation—Plasma membrane-containing P2 particulate fractions were prepared from cell pastes frozen at −80° C. after harvest. All procedures were carried out at 4° C. Cell pellets were resuspended in 1 ml of 10 mM Tris-HCl and 0.1 mM EDTA, pH 7.5 (buffer A) and by homogenisation for 20 s with a Ultra Turrax followed by passage (5 times) through a 25-gauge needle. Cell lysates were centrifuged at 1,000 g for 10 min in a microcentrifuge to pellet the nuclei and unbroken cells and P2 particulate fractions were recovered by microcentrifugation at 16,000 g for 30 min. P2 particulate fractions were resuspended in buffer A and stored at −80° C. until required.

[$^{35}$S]-GTPγS binding—assays were performed at room temperature in 384-well format based on methods described previously, (Wieland, T. and Jakobs, K. H. (1994) *Methods Enzymol.* 237, 3-13). Briefly, the dilution of standard or test compounds were prepared and added to a 384-well plate in a volume of 10 µl Membranes (HM74A or HM74) were diluted in assay buffer (20 mM HEPES, 100 mM NaCl, 10 mM $MgCl_2$, pH7.4) supplemented with saponin (60 µg/ml), Leadseeker WGA beads (Amersham; 250 µg/well) and 10 µM GDP, so that the 20 µl volume added to each well contains 5 µg of membranes. [$^{35}$S]-GTPγS (1170 Ci/mmol, Amersham) was diluted (1:1500) in assay buffer and 20 µl added to each well. Following the addition of the radioligand, the plates were sealed, pulse spun and incubated for 4 hours at room temperature. At the end of the incubation period the plates were read on a Leadseeker machine (VIEWLUX PLUS; Perkin-Elmer) to determine the levels of specific binding.

These assays were refined by reducing the final assay volume to 10 µl. For this 10 µl assay a revised protocol was used. This involved the use of only 100 nl of standard or test compound per well of a 384-well plate and 1.5 µg membrane and 100 µg Leadseeker WGA beads. For the low volume protocol, membrane, beads and [$^{35}$S]-GTPγS were mixed together and then 10 µl of this mix were dispensed to each well. Incubation and plate read were identical for the 10 µl and 50 µl assays.

All exemplified compounds were tested in one or both of the [$^{35}$S]-GTPγS binding assays described above (i.e. the 10 µl and 50 µl assays).

Data was analysed by curve fitting as carried out using a Four Parameter Logistical equation using the XC50 software package (max 2 points deleted from any one curve). Specific binding is expressed as $pEC_{50}$ and as % efficacy compared to the maximal response of nicotinic acid binding.

In-Vivo Testing

Compounds of the invention can be tested in male Spague-Dawley rats (200-250 g) which have been fasted for at least 12 hours prior to the study. The compounds are dosed intravenously at either 1 or 3 mg/kg (5 ml/kg) or by oral gavage at doses ranging from 1-30 mg/kg (10 ml/kg). Blood samples (0.3 ml tail vein bleed) can be taken pre-dose and at three times post-dose (times ranging from 15 minutes to 6 hours post-dose). Each blood sample is transferred to a heparin tube (Becton Dickinson Microtainer, PST LH) and centrifuged (10,000 g for 5 minutes) to produce a plasma sample. The plasma samples are assayed for levels of non-esterified fatty acids (NEFA) using a commercially available kit (Randox). Inhibition of plasma NEFA levels, relative to pre-dose levels, are used as a surrogate for HM74A agonist activity.

In order to determine whether compounds of the invention exhibit the flushing response associated with nicotinic acid they can be dosed to conscious guinea-pigs. Male Dunkin Hartley guinea pigs (300-600 g; n=10-20 per group) are fasted for at least 12 hours, but not in excess of 24 hours prior to experimentation. Pre-study blood samples (0.5 ml) are taken from each animal by cardiac puncture under recovery anaesthesia (Isoflurane 3.5% with additional O2 (1 L/min)). Ear temperature measurements are taken by placing the left ear of each animal over an infra-red temperature probe. Measurements are taken at one minute intervals from 5 minutes pre-dose to 30 minutes post-dose. Temperature measurements are then taken at 15 minute intervals up to 2 hours post-dose. Animals receive test compounds by oral gavage (5 ml/kg). Blood samples (0.5 ml) are taken by cardiac puncture under terminal anaesthesia. Blood samples are taken from individual animals to provide data at 0.5, 1, 2, 3, and 4 hours post-dose. All blood samples are placed on a blood roller for 5 minutes then stored on ice until the end of the study. Following centrifugation (12000 g for 5 min) the plasma is transferred into fresh tubes and stored at $-20°$ C. until assayed for NEFA concentrations.

Some compounds according to Formula (I) have been synthesised (see synthetic examples below) and tested in the $[^{35}S]$-GTPγS binding assays discussed above.

Some compounds according to formula (I) including: 8-chloro-3-(3,3-dimethylbutyl)-1-[2-(ethyloxy)ethyl]-3,7-dihydro-1H-purine-2,6-dione; have utility as intermediates in the production of other compounds according to formula (I).

The exemplified compounds (Examples 1-512) have a $pEC_{50}$ of 4.3 (+/−0.3 log unit) or greater and an efficacy of 30% or greater (in relation to nicotinic acid) in the $[^{35}S]$-GTPγS binding assays described above, in which they were tested.

General Purification and Analytical Methods:

LC/MS: Method

Analytical HPLC was conducted on a Supelcosil™ ABZ+ PLUS column (Supelco) (3 µm, 3.3 cm×4.6 mm ID) eluting with 0.1% $HCO_2H$ and 0.01 M ammonium acetate in water (solvent A), and 95% MeCN and 5% water (containing 0.5% $HCO_2H$) (solvent B), using the following elution gradient 0-0.7 min 0% B, 0.7-4.2 min 0→100% B, 4.2-4.6 minutes 100% B, 4.6-4.8 min 100→0% B at a flow rate of 3 ml/min. The diode array UV detection was carried out in the range 215 to 330 nm. The mass spectra (MS) were recorded on a Waters ZQ mass spectrometer using electrospray positive ionisation [(ES+ve to give $MH^+$ and $M(NH_4)^+$ molecular ions] or electrospray negative ionisation [(ES-ve to give $(M-H)^-$ molecular ion] modes. Only the parent ion of major isotopes quoted.

$^1H$ NMR spectra were recorded using a Bruker DPX 400 MHz spectrometer using tetramethylsilane as the standard.

Biotage™ chromatography refers to purification carried out using either the Flash 40i or Flash 150i purification systems, sold by Biotage AB, using cartridges pre-packed with KPSil (silica).

Companion™ system refers to the Teledyne Isco Combiflash Companion™ purification system. This is a gradient controlled purification system with integral, variable wavelength UV detection with the capability to trigger automated fraction collection by UV threshold.

Mass directed autoprep (MDAP) refers to methods where the material was purified by high performance liquid chromatography using either a Supelcosil™ ABZ+5 µm column (10 cm×20 mm i.d.) or a Supelcosil™ ABZ+10 µm column (15 cm×30 mm i.d.) with a suitable gradient of solvent A: 0.1% $HCO_2H$ in water and solvent B: 95% MeCN, 5% water (containing 0.5% $HCO_2H$). The Waters 2767 inject/collector was triggered by a MicroMass ZQ Mass Spectrometer on detecting the mass of interest (using Micromass MassLynx software).

Preparative HPLC (Autoprep HPLC or Autoprep) refers to methods where the material was purified by high performance liquid chromatography on a Supelcosil™ ABZ+5 µm column (10 cm×21.2 mm i.d.) with a suitable gradient of 0.1% $HCO_2H$ in water and MeCN (with 0.5% $HCO_2H$). The Gilson 233 fraction collector was triggered by UV detection.

SPE (solid phase extraction) refers to the use of polyethylene cartridges which are pre-packed with sorbent used for purification. The sorbent contained in these cartridges will be specified. Examples used are detailed below:

C18 SPE refers to the use of cartridges pre-packed with 40 µM C18 functionalised silica sorbent (sold by Varian Inc.). The compound was loaded, typically in 50:50 DMSO/MeOH, onto a cartridge previously conditioned with MeCN and equilibrated with 5% MeCN in water. The product was eluted with a suitable gradient of 0.1% $HCO_2H$ in water and MeCN (0.5% $HCO_2H$).

Aminopropyl SPE or column refers to the use of cartridges pre-packed with 40 µm-120 µm aminopropyl functionalized silica (sold by Varian Inc.). The crude product is typically loaded in DCM/MeOH mixtures onto a cartridge previously conditioned with MeOH. The neutral components were eluted with MeOH and/or DCM (3 or 4 column volumes) and the acidic components usually eluted with an eluent containing a proportion of AcOH (2-20%).

Oasis™ Cartridges/Oasis™ SPE's refer to SPE cartridges packed with a polymeric sorbent manufactured by the Waters Corporation. These are typically conditioned with 3 column volumes of MeOH and equilibrated with water before the sample is loaded. Salts and inorganics are eluted with water and the product typically eluted with MeOH or MeCN.

GreenHouse™ refers to a 24 reaction parallel synthesiser platform available from RDT Ltd, UK As indicated above, compounds of Formula (I) may find use in human or veterinary medicine, for example as activators of HM74A, in the management of dyslipidaemia and hyperlipoproteinaemia.

Thus, there is provided as another embodiment of the present invention at least one compound of formula (I) or a pharmaceutically acceptable derivative thereof, for use in human or veterinary medicine, for example in the treatment of disorders of lipid metabolism including dyslipidaemia and hyperlipoproteinaemia such as diabetic dyslipidaemia and mixed dyslipidaemia, heart failure, hypercholesteraemia, cardiovascular disease including atherosclerosis, arteriosclerosis, and hypertriglyceridaemia, type II diabetes mellitus, type I diabetes, insulin resistance, hyperlipidaemia, anorexia nervosa and obesity. As such, the compounds are also provided for use in the treatment of coronary artery disease, thrombosis, angina, chronic renal failure, peripheral vascular disease and stroke.

There is provided as a further embodiment of the present invention at least one compound of formula (I) or a pharmaceutically acceptable derivative thereof, for use in the manufacture of a medicament for the treatment of disorders of lipid metabolism including dyslipidaemia and hyperlipoproteinaemia such as diabetic dyslipidaemia and mixed dyslipidaemia, heart failure, hypercholesteraemia, cardiovascular disease including atherosclerosis, arteriosclerosis, and hypertriglyceridaemia, type II diabetes mellitus, type I diabetes, insulin resistance, hyperlipidaemia, anorexia nervosa, obesity. As such, the compounds are also provided for use in the treatment of coronary artery disease, thrombosis, angina, chronic renal failure, peripheral vascular disease and stroke.

It will be appreciated that references herein to treatment extend to prophylaxis, prevention of recurrence and suppression of symptoms as well as the treatment of established conditions.

In one embodiment of the invention, there is provided at least one compound of formula (I) or a pharmaceutically acceptable derivative thereof for use in the treatment of disorders of lipid metabolism including dyslipidaemia and hyperlipoproteinaemia. For example, the use is provided of at least one compound of Formula (I) or a pharmaceutically acceptable derivative thereof in the treatment of diabetic dyslipidaemia, mixed dyslipidaemia, heart failure, hypercholesteraemia, type II diabetes mellitus, type I diabetes, insulin resistance, hyperlipidaemia, anorexia nervosa, obesity, coronary artery disease, thrombosis, angina, chronic renal failure, stroke and cardiovascular disease including atherosclerosis, arteriosclerosis, and hypertriglyceridaemia.

It is to be understood that this embodiment of the present invention includes any combination of particular embodiments and covers all combinations of particular substituents described herein above for compounds of Formula (I).

Additionally, the present invention provides the use of at least one compound of formula (I) or a pharmaceutically acceptable derivative thereof, in the manufacture of a medicament for the treatment of inflammatory diseases or conditions of the joint, for example, arthritis (e.g. rheumatoid arthritis, osteoarthritis, prosthetic joint failure), or of the gastrointestinal tract (e.g. ulcerative colitis, Crohn's disease, and other inflammatory bowel and gastrointestinal diseases, gastritis and mucosal inflammation resulting from infection, the enteropathy provoked by non-steroidal anti-inflammatory drugs), of the lung (e.g. adult respiratory distress syndrome, asthma, cystic fibrosis, or chronic obstructive pulmonary disease), of the heart (e.g. myocarditis), of nervous tissue (e.g. multiple sclerosis), of the pancreas, (e.g. inflammation associated with diabetes melitus and complications thereof, of the kidney (e.g. glomerulonephritis), of the skin (e.g. dermatitis, psoriasis, eczema, urticaria, burn injury), of the eye (e.g. glaucoma) as well as of transplanted organs (e.g. rejection) and multi-organ diseases (e.g. systemic lupus erythematosis, sepsis) and inflammatory sequelae of viral or bacterial infections and inflammatory conditions associated with atherosclerosis and following hypoxic or ischaemic insults (with or without reperfusion), for example in the brain or in ischaemic heart disease.

In a further or alternative embodiments there is provided a method for the treatment of a human or animal subject with a condition where under-activation of the HM74A receptor contributes to the condition or where activation of the receptor will be beneficial, which method comprises administering to said human or animal subject an effective amount of at least one compound of formula (I) or a pharmaceutically acceptable derivative thereof.

Again, it is to be understood that this embodiment of the present invention includes any combination of particular embodiments and covers all combinations of particular substituents described herein above for compounds of Formula (I).

In one embodiment, the present invention provides a method for the treatment of disorders of lipid metabolism including dyslipidaemia and hyperlipoproteinaemia such as diabetic dyslipidaemia and mixed dyslipidaemia, heart failure, hypercholesteraemia, cardiovascular disease including atherosclerosis, arteriosclerosis, and hypertriglyceridaemia, type II diabetes mellitus, type I diabetes, insulin resistance, hyperlipidaemia, anorexia nervosa and obesity, which method comprises administering to said human or animal subject an effective amount of at least one compound of formula (I) or a pharmaceutically acceptable derivative thereof. As such, these compounds may also find favour in methods for the treatment of coronary artery disease, thrombosis, angina, chronic renal failure, peripheral vascular disease and stroke, which methods comprise administering to said human or animal subject an effective amount of at least one compound of formula (I) or a pharmaceutically acceptable derivative thereof.

The amount of a compound of formula (I) or a pharmaceutically acceptable derivative thereof which is required to achieve the desired biological effect will, of course, depend on a number of factors, for example, the mode of administration and the precise clinical condition of the recipient. In general, the daily dose will be in the range of 0.1 mg-1 g/kg, typically 0.1-100 mg/kg. An intravenous dose may, for example, be in the range of 0.01 mg to 0.1 g/kg, typically 0.01 mg to 10 mg/kg, which may conveniently be administered as an infusion of from 0.1 μg to 1 mg, per minute. Infusion fluids suitable for this purpose may contain, for example, from 0.01 μg to 0.1 mg, per millilitre. Unit doses may contain, for example, from 0.01 μg to 1 g of a compound of the invention. Thus ampoules for injection may contain, for example, from 0.01 μg to 0.1 g and orally administrable unit dose formulations, such as tablets or capsules, may contain, for example, from 0.1 mg to 1 g, for example from 5 mg to 50 mg.

A compound of formula (I) or a pharmaceutically acceptable derivative thereof may be employed as the compound per se in the treatment of a disease where under-activation of the HM74A receptor contributes to the disease or where activation of the receptor will be beneficial, an example of this is where a compound of the present invention is presented with an acceptable carrier in the form of a pharmaceutical formulation. The carrier must, of course, be acceptable in the sense of being compatible with the other ingredients of the formulation and must not be deleterious to the recipient. The carrier may be a solid or a liquid, or both, and may be formulated with the compound of the invention as a unit-dose formulation, for example, a tablet, which may contain from 0.05% to 95% by weight of the compound of the invention.

The formulations include those suitable for oral, rectal, topical, buccal (e.g. sub-lingual) and parenteral (e.g. subcutaneous, intramuscular, intradermal or intravenous) administration.

There is also provided according to the invention a process for preparation of such a pharmaceutical composition which comprises mixing the ingredients.

Formulations suitable for oral administration may be presented in discrete units, such as capsules, cachets, lozenges or tablets, each containing a predetermined amount of a a compound of formula (I) or a pharmaceutically acceptable derivative thereof; as a powder or granules; as a solution or a suspension in an aqueous or non-aqueous liquid; or as an oil-in-water or water-in-oil emulsion. In general, the formulations are prepared by uniformly and intimately admixing the compound of formula (I) or a pharmaceutically acceptable derivative thereof, with a liquid or finely divided solid carrier, or both, and then, if necessary, shaping the product. For example, a tablet may be prepared by compressing or moulding a powder or granules of the compound of formula (I) or a pharmaceutically acceptable derivative thereof optionally with one or more accessory ingredients. Compressed tablets may be prepared by compressing, in a suitable machine, the compound in a free-flowing form, such as a powder or granules optionally mixed with a binder, lubricant, inert diluent and/or surface active/dispersing agent(s). Moulded tablets may be made by moulding, in a suitable machine, the powdered compound moistened with an inert liquid diluent.

Tablets and capsules for oral administration may contain conventional excipients such as binding agents, for example syrup, acacia, gelatin, sorbitol, tragacanth, mucilage of starch or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, hydroxypropylmethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

Formulations suitable for buccal (sub-lingual) administration include lozenges comprising a compound of the invention in a flavoured base, usually sucrose and acacia or tragacanth, and pastilles comprising the compound of the invention in an inert base such as gelatin and glycerin or sucrose and acacia.

Formulations of the present invention suitable for parenteral administration conveniently comprise sterile aqueous preparations of a compound of formula (I) or a pharmaceutically acceptable derivative thereof, the formulation may be isotonic with the blood of the intended recipient. These preparations could be administered intravenously, although administration may also be effected by means of subcutaneous, intramuscular, or intradermal injection. Such preparations may conveniently be prepared by admixing the compound of formula (I) or a pharmaceutically acceptable derivative thereof with water and rendering the resulting solution sterile and isotonic with the blood. Injectable compositions according to the invention will generally contain from 0.1 to 5% w/w of the compound of formula (I) or a pharmaceutically acceptable derivative thereof.

Thus, formulations of the present invention suitable for parenteral administration comprising a compound of formula (I) or a pharmaceutically acceptable derivative thereof may be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as antioxidants, buffers, antimicrobial agents and/or toxicity adjusting agents. Examples of formulations suitable for oral administration include formulations comprising a compound of formula (I) or a pharmaceutically acceptable derivative thereof, in 10% DMSO and 90% sodium hydrogen carbonate in sterile saline. Examples of formulations suitable for intravenous administration include formulations comprising a compound of formula (I) or a pharmaceutically acceptable derivative thereof, in 5% or 10% DMSO and 95% or 90% sodium hydrogen carbonate in sterile water. Alternatively, the therapeutically active agent may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

Formulations suitable for rectal administration may be presented as unit-dose suppositories. These may be prepared by admixing a a compound of formula (I) or a pharmaceutically acceptable derivative thereof with one or more conventional solid carriers, for example, cocoa butter or glycerides and then shaping the resulting mixture.

Formulations suitable for topical application to the skin may take the form of an ointment, cream, lotion, paste, gel, spray, aerosol, or oil. Carriers which may be used include vaseline, lanolin, polyethylene glycols, alcohols, and combinations of two or more thereof. The compound of formula (I) or a pharmaceutically acceptable derivative thereof is generally present at a concentration of from 0.1 to 15% w/w of the composition, for example, from 0.5 to 2%.

By topical administration as used herein, we include administration by insufflation and inhalation. Examples of various types of preparation for topical administration include ointments, creams, lotions, powders, pessaries, sprays, aerosols, capsules or cartridges for use in an inhaler or insufflator or drops (e.g. eye or nose drops).

Ointments and creams may, for example, be formulated with an aqueous or oily base with the addition of suitable thickening and/or gelling agents and/or solvents. Such bases may thus, for example, include water and/or an oil such as liquid paraffin or a vegetable oil such as arachis oil or castor oil or a solvent such as a polyethylene glycol. Thickening agents which may be used include soft paraffin, aluminium stearate, cetostearyl alcohol, polyethylene glycols, microcrystalline wax and beeswax.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents or suspending agents.

Spray compositions may be formulated, for example, as aqueous solutions or suspensions or as aerosols delivered from pressurised packs, with the use of a suitable propellant, e.g. dichlorodifluoromethane, trichlorofluoromethane, dichlorotetrafluoroethane, 1,1,1,2,3,3,3-heptafluoropropane, 1,1,1,2-tetrafluorethane, carbon dioxide or other suitable gas.

Capsules and cartridges for use in an inhaler or insufflator, of for example gelatin, may be formulated containing a powder mix of a compound of the invention and a suitable powder base such as lactose or starch.

The pharmaceutical compositions according to the invention may also be used in combination with other therapeutic agents, for example in combination with other classes of dyslipidaemic drugs (e.g. statins, fibrates, bile-acid binding resins or nicotinic acid).

The compounds of the instant invention may be used in combination with one or more other therapeutically active agents for example in combination with other classes of dyslipidaemic drugs e.g. 3-hydroxy-3-methylglutaryl-coenzyme A reductase inhibitors (statins) or fibrates or bile acid binding resins or nicotinic acid. The invention thus provides, in a further embodiment, the use of such a combination in the treatment of diseases where under-activation of the HM74A receptor contributes to the disease or where activation of the receptor will be beneficial and the use of at least one compound of formula (I) or a pharmaceutically acceptable derivative thereof in the manufacture of a medicament for the combination therapy of disorders of lipid metabolism including dyslipidaemia and hyperlipoproteinaemia such as diabetic dyslipidaemia and mixed dyslipidaemia, heart failure, hypercholesteraemia, cardiovascular disease including atherosclerosis, arteriosclerosis, and hypertriglyceridaemia, type II diabetes mellitus, type I diabetes, insulin resistance, hyperlipidaemia, anorexia nervosa and obesity.

When the compounds of the present invention are used in combination with other therapeutically active agents, the compounds may be administered either together or separately, sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further embodiment of the invention. The individual components of such combinations may be administered either together or separately, sequentially or simultaneously in separate or combined pharmaceutical formulations.

When combined in the same formulation it will be appreciated that the two components must be stable and compatible with each other and the other components of the formulation and may be formulated for administration. When formulated separately they may be provided in any convenient formulation, conveniently in such a manner as are known for such compounds in the art.

When in combination with a second therapeutic agent active against the same disease, the dose of each component may differ from that when the compound is used alone. Appropriate doses will be readily appreciated by those skilled in the art.

The invention thus provides, in a further embodiment, a combination comprising at least one compound of formula (I) or a pharmaceutically acceptable derivative thereof together with another therapeutically active agent.

The combination referred to above may conveniently be presented for use in the form of a pharmaceutical formulation and thus pharmaceutical formulations comprising a combination as defined above together with a pharmaceutically acceptable carrier thereof represent a further embodiment of the invention.

The compounds of the present invention and pharmaceutically acceptable derivatives thereof may be prepared by the methodology described hereinafter, constituting a further embodiment of this invention.

In one embodiment the present invention provides a method for the preparation of compound(s) of formula (I) from an appropriate starting material, for example compound(s) of formula (II):

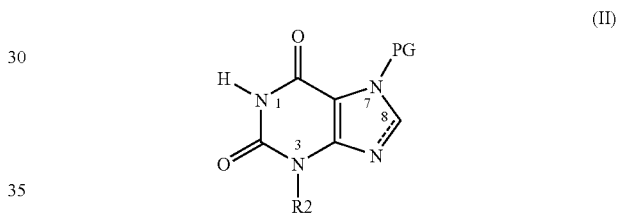

wherein PG=protecting group, the method comprising:
(i) alkylation at N1 of an N7 protected xanthine;
(ii) alkylation at N3 of an N7 protected xanthine;
(iii) halogenation at C8; and
(iv) de-protection of N7;
in any order providing de-protection is carried out after alkylation.

Process 1:

A process according to the invention for preparing compound(s) of formula (I) in which R1 incorporates a heterocyclyl, heteroaryl or aryl and R1 represents Cl.

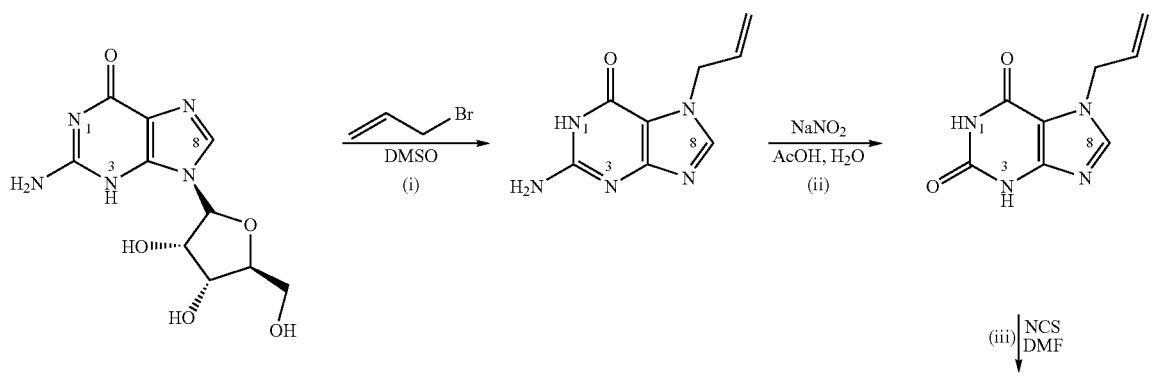

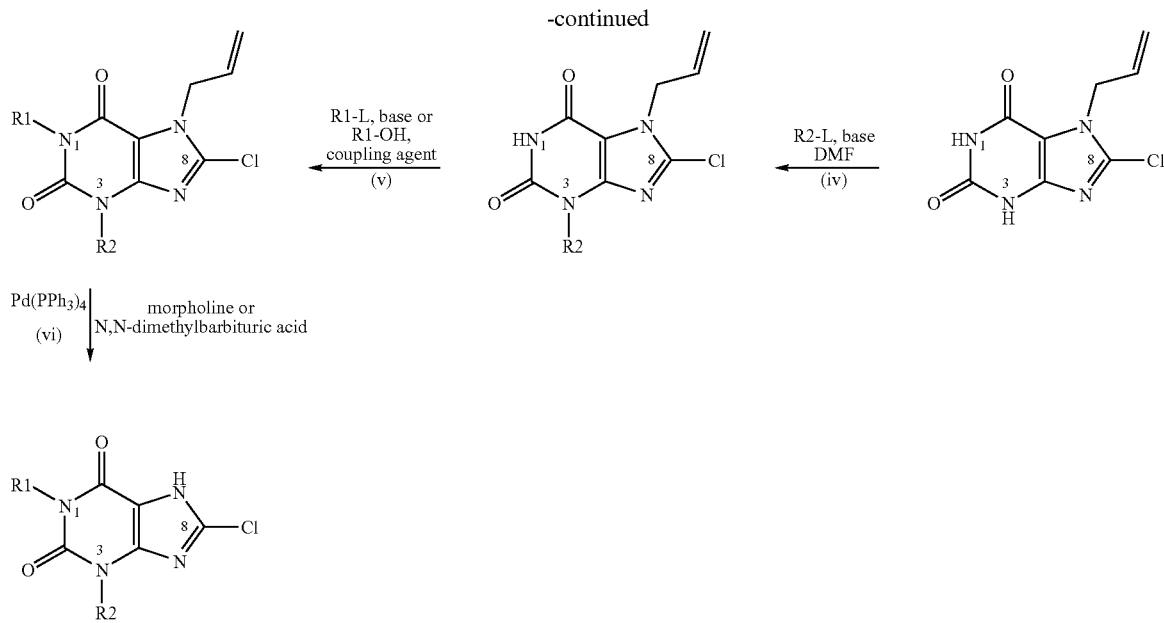

i) Alkylation of guanine with allyl bromide
ii) Diazotisation with sodium nitrite followed by hydrolysis to form the xanthine
iii) Chlorination
iv) Alkylation at N3 (Examples of suitable bases include $Na_2CO_3$, $Cs_2CO_3$, $K_2CO_3$)
v) Alkylation at N1 (Examples of suitable bases include $Na_2CO_3$, $Cs_2CO_3$, $K_2CO_3$)
vi) Palladium catalysed removal of the allyl group wherein L represents a leaving group, for example halogen.

Process 2:

A process according to the invention for preparing intermediates in which R1 incorporates an amide, carbamate or urea, which may be useful for production of compound(s) of formula (I).

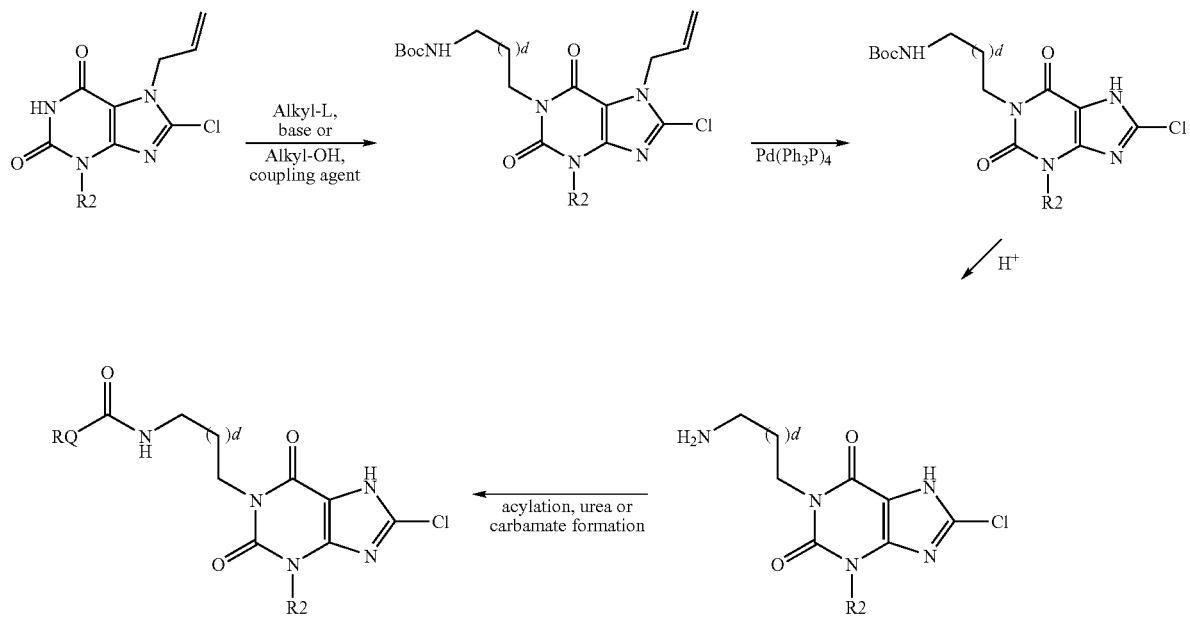

wherein L represents a leaving group, for example halogen, d represents (m−1) (i.e. d together with the preceding methylene=m), R represents -(alkylene)$_n$-Y and Q may or may not be present, and if present represents either O or NR5.

Process 3:

A process for preparing intermediates in which R1 incorporates a 'reverse' carbamate or ester, which may be useful for production of compound(s) of formula (I).

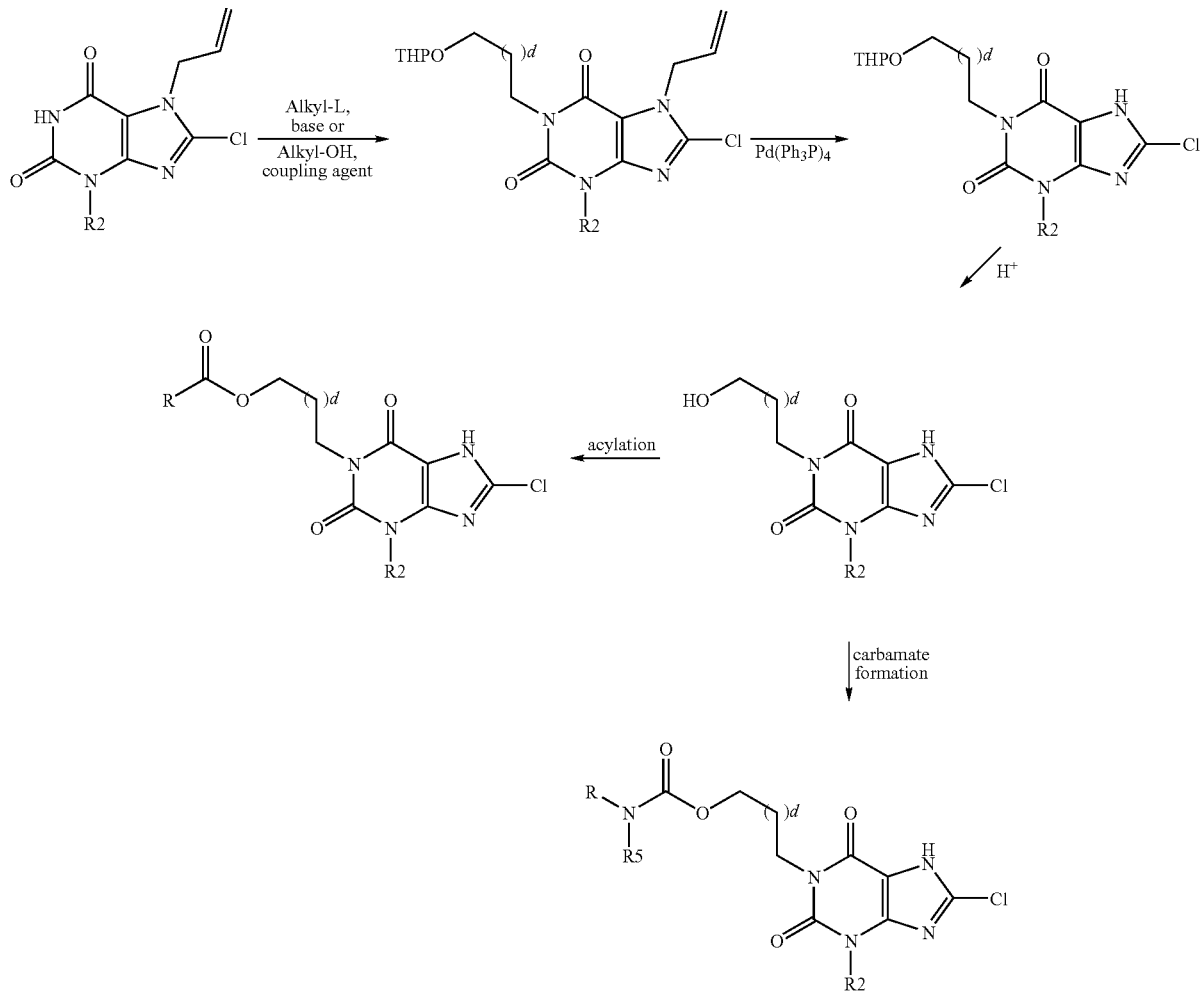

wherein L represents a leaving group, for example halogen, d represents (m−1), and R represents -(alk)$_n$-Y.

Process 4:

A process according to the invention for preparing intermediates in which R1 incorporates an ester or amide, which may be useful for production of compound(s) of formula (I).

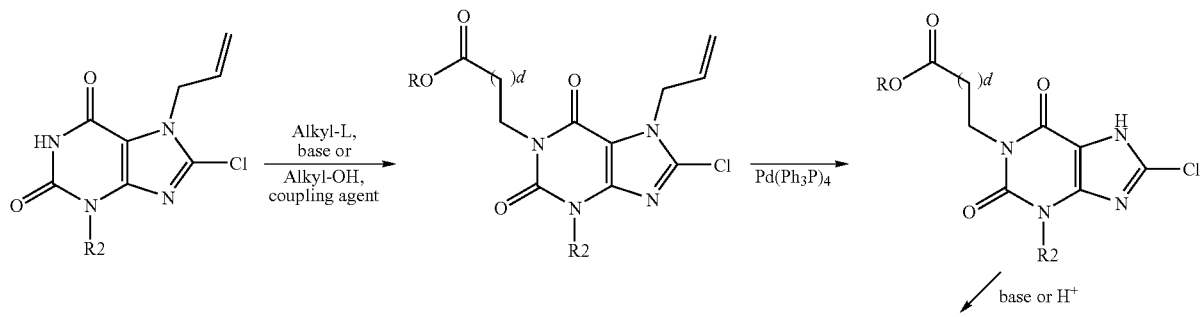

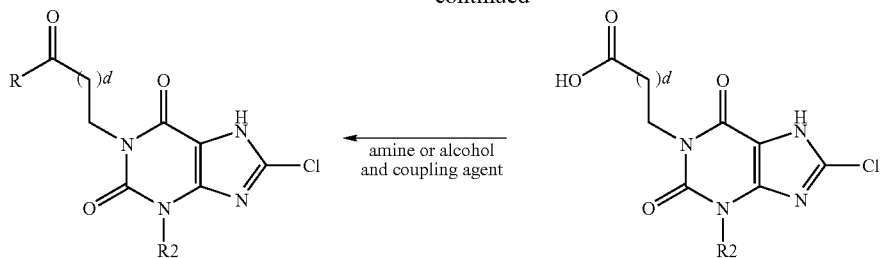
wherein L represents a leaving group, for example halogen, d represents (m−1), and R represents —NR⁵R⁷ or —OR⁵.
Process 5:
A process according to the invention for preparing compound(s) of formula (I) in which X incorporates a pyrazole, imidazole or tetrazole.
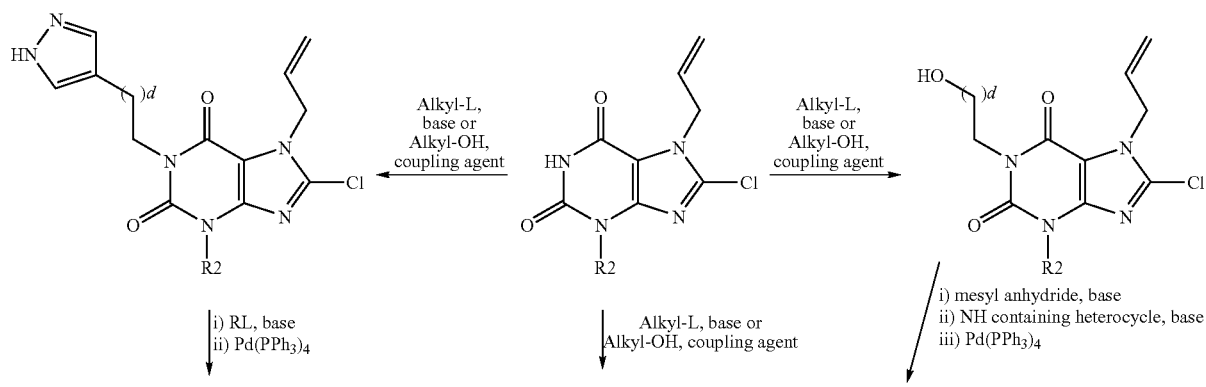
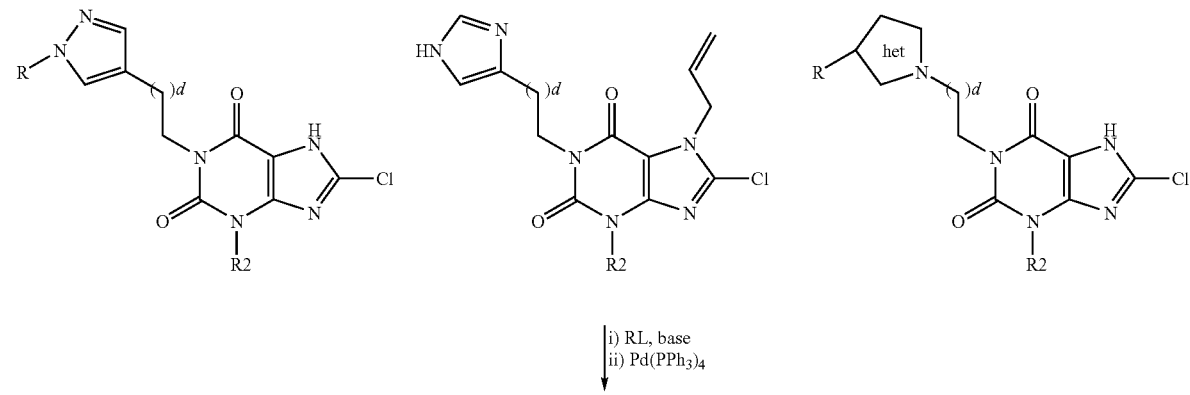
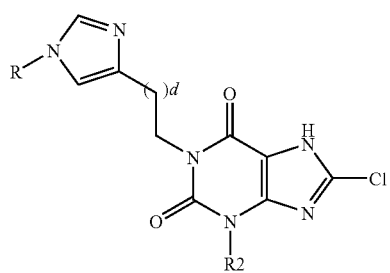

wherein L represents a leaving group, for example halogen, d represents (m–1), and R represents -(alk)$_n$-Y.

Process 6:

A process according to the invention for preparing compound(s) of formula (I) in which X incorporates an oxadiazole.

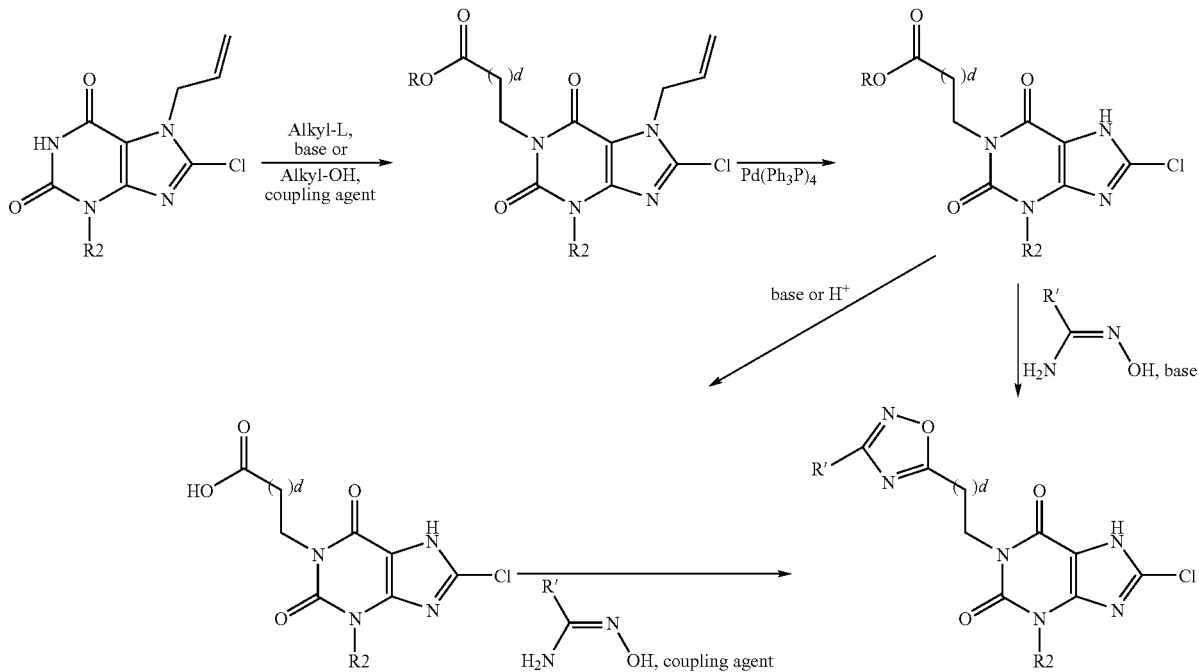

wherein L represents a leaving group, for example halogen, d represents (m–1), R represents an alkyl group and R' represents -(alk)$_n$-Y.

Process 7:

A process according to the invention for preparing compound(s) of formula (I) in which X incorporates an oxadiazole

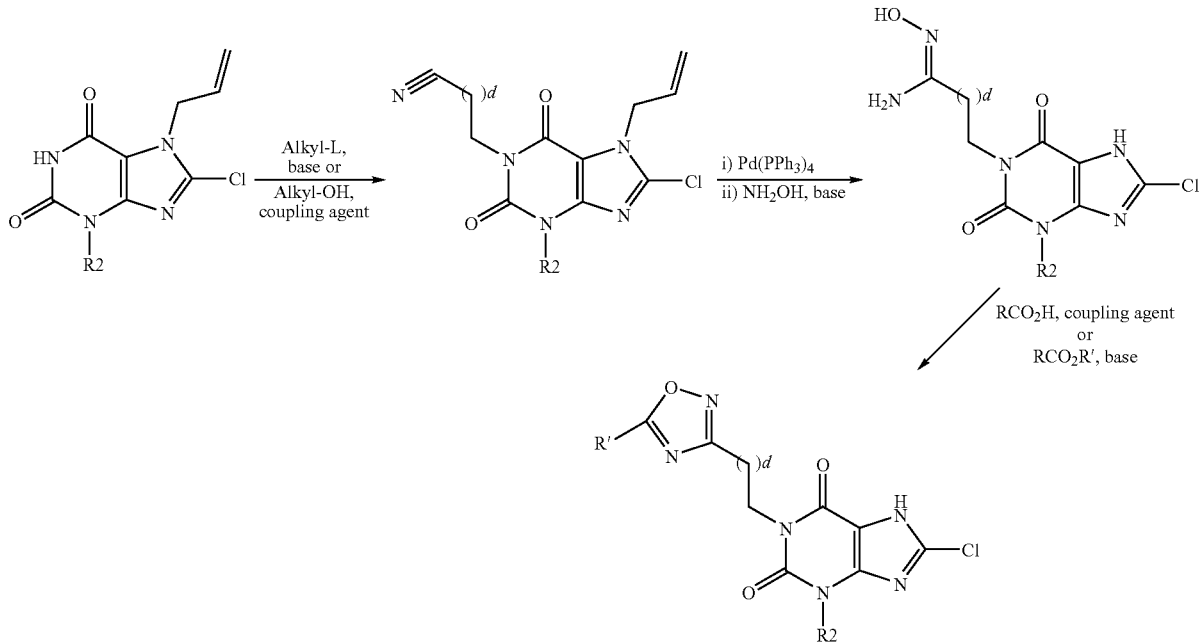

wherein L represents a leaving group, for example halogen, d represents (m−1), R represents an alkyl group and R' represents -(alk)$_n$-Y.

Process 8:

A process according to the invention for preparing intermediates in which $R^3$ is CN, which may be useful for preparation of compound(s) of formula (I). This comprises steps (i) and (ii) of Process 1 followed by:

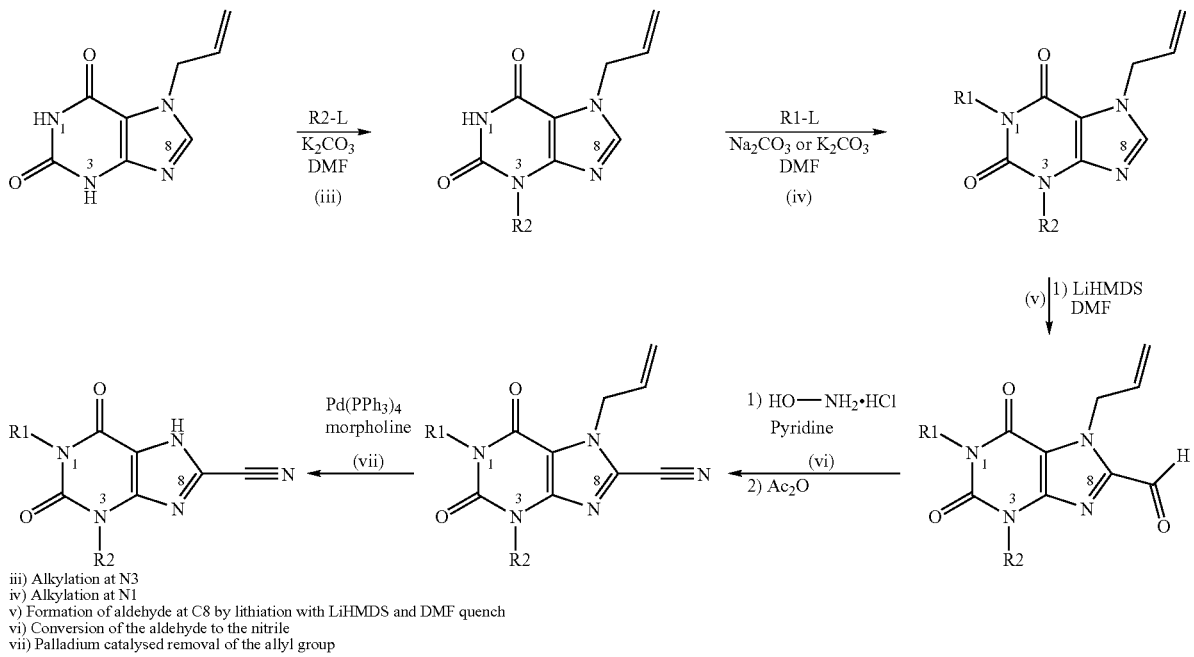

iii) Alkylation at N3
iv) Alkylation at N1
v) Formation of aldehyde at C8 by lithiation with LiHMDS and DMF quench
vi) Conversion of the aldehyde to the nitrile
vii) Palladium catalysed removal of the allyl group wherein L represents a leaving group.

Process 9:

A process according to the invention for preparing compound(s) of formula (I) in which $R^3$ is Cl or Br comprises steps (i) to (iv) of Process 8 followed by:

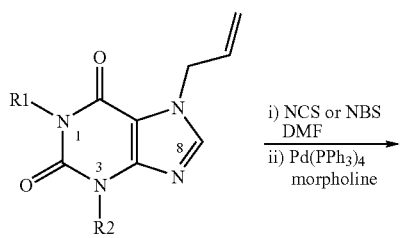

-continued

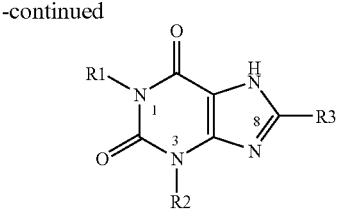

R3 = Cl or Br i) Halogenation at C8 using NCS or NBS
ii) Palladium catalysed removal of the allyl group Process 10:

A process according to the invention for preparing compound(s) of formula (I) in which $R^3$ is Cl comprises:

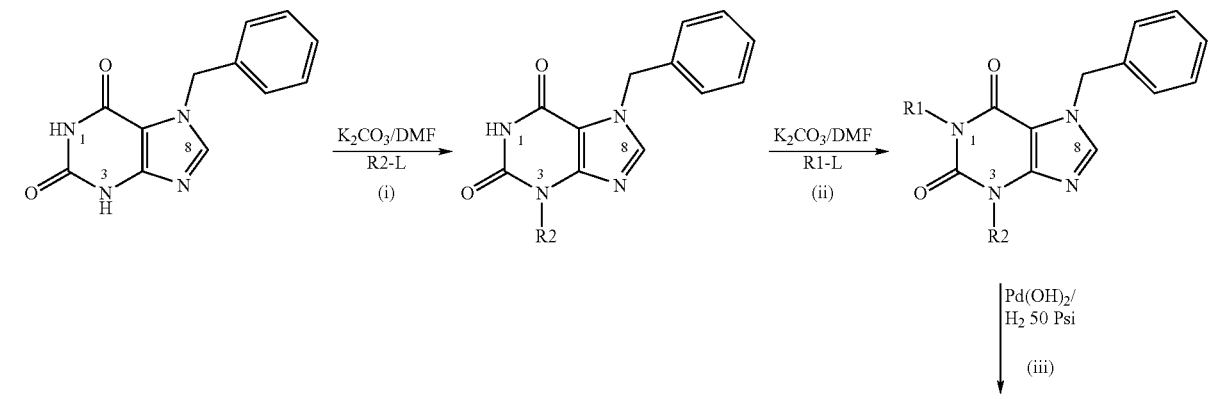

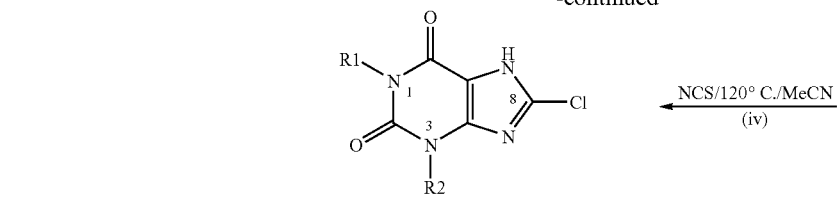
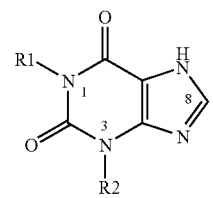

i) Alkylation at N3
ii) Alkylation at N1
iii) Debenzylation
iii) Chlorination at C8 wherein L represents a leaving group

Process 11:

A process according to the invention for preparing compound(s) of formula (I) in which $R^1$ differs from $R^2$ and $R^3$ is Cl comprises steps (i) to (v) of Process 1 (where $R^2$ from process 1 is specifically SEM or MEM) followed by:

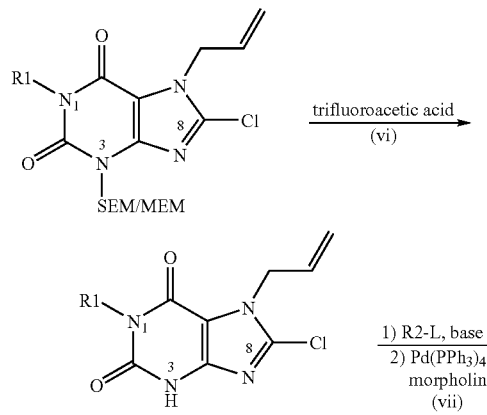

vi) Cleavage of MEM or SEM protecting group group
vii) Alkylation of N3 followed by palladium catalysed removal of the allyl group wherein L represents a leaving group Process 12:

A process according to the invention for preparing compound(s) of formula (I) in which $R^3$ is Cl, Br or I comprises steps (i) to (iv) of Process 8 followed by:

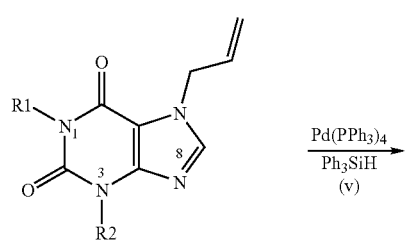

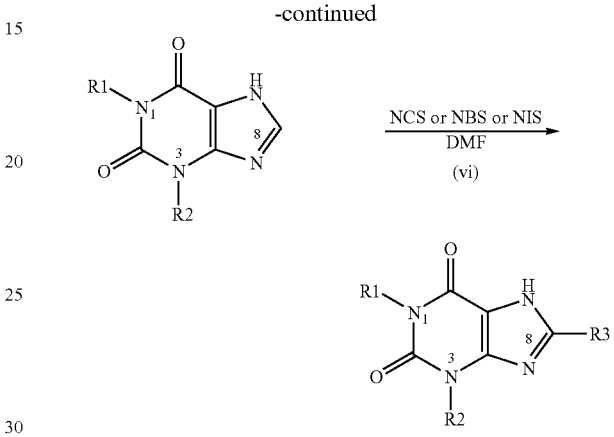

v) Palladium catalysed removal of allyl group
vi) Halogenation at C8 using NCS, NBS, or NIS Process 13:

A process according to the invention for preparing compound(s) of formula (I) comprises:

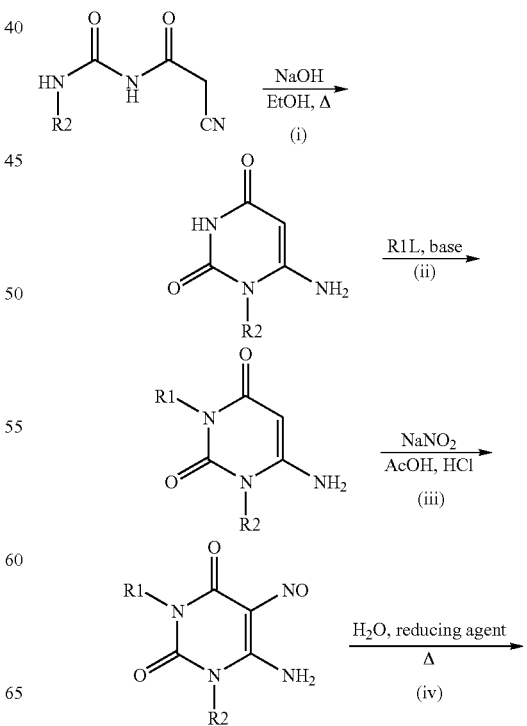

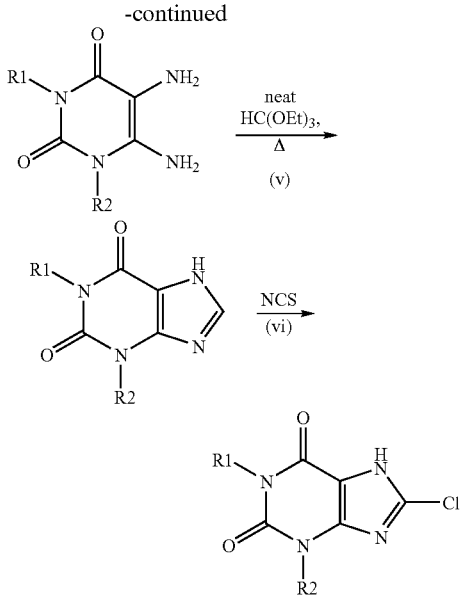

i) Pyrimidinedione formation
ii) Alkylation at N1
iii) Nitrosation
iv) Reduction using Na₂S₂O₄ or a similar reducing agent
v) Xanthine formation
vi) Halogenation at C8 using NCS wherein L represents a leaving group Process 14:

A process according to the invention for preparing compound(s) of formula (I):

fication column such as Silica Redisep™ cartridges and subsequent eluting with a suitable solvent such as dichloromethane containing ethyl acetate.

Where desired or necessary, as a final stage in any of the above synthetic processes, a resultant compound of formula (I) can be converted into a pharmaceutically acceptable derivative, for example a resultant compound of formula (I) can be converted into a salt form or vice versa or converting one salt form into another pharmaceutically acceptable salt form. These processes will be known to a person skilled in the art.

ABBREVIATIONS

AcOH Acetic acid
atm Atmosphere
br Broad (NMR)
CDI Carbonyldiimidazole
d Doublet (NMR)
DBAD Di-t-butylazodicarboxylate
DCM Dichloromethane
DIPEA Diisopropylethylamine
DMSO Dimethylsulfoxide
DMF N,N-Dimethylformamide
EtOAc Ethyl acetate
EtOH Ethanol
h Hour(s)
IPA Isopropyl alcohol
m Multiplet (NMR)
MDAP Mass directed autoprep
MeCN Acetonitrile
MeOH Methanol

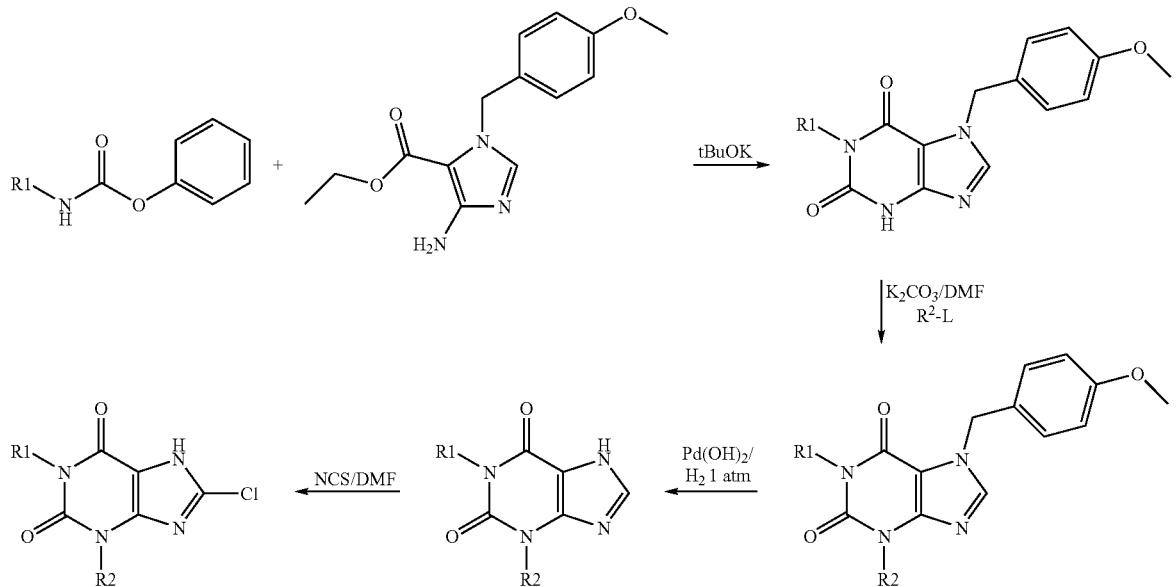

wherein L represents a leaving group.

As an additional step to the general processes described above, and in particular for use in the preparation of the examples below, there are several ways of purifying resulting compounds, one or more of which may be of use in the present invention, for example the use of MDAP, by recrystallisation from one or more suitable solvents such as ethyl acetate, absolute ethanol, acetonitrile or methanol, or by use of purimin Minute(s)
NCS N-Chlorosuccinimide
NBS N-bromosuccinimide
NIS N-iodosuccinimide
q Quartet (NMR)
rt Room temperature
RT Retention time
Singlet (NMR)

SPE Solid phase extraction cartridge
t Triplet (NMR)
TFA Trifluoroacetic acid
THF Tetrahydrofuran
DMEM Dulbecco's Modified Eagle's Medium
HEPES 4-(2-Hydroxyethyl)piperazine-1-ethanesulphonic acid
LiHMDS Lithium hexamethyldisilylamide
Δ Heat
SEM 2-(trimethylsilyl)ethoxymethyl
MEM 2-methoxyethoxymethyl
Boc t-butoxycarbonyl
THP tetrahydropyran

Figure 1:
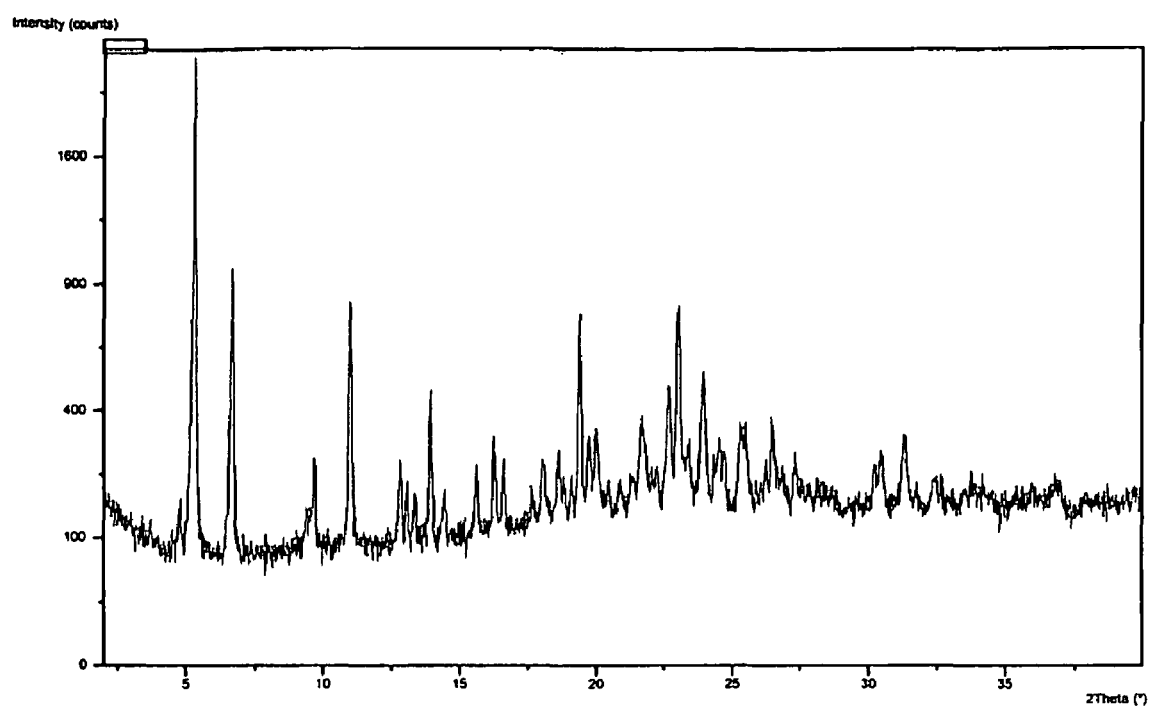
FIG. 1: XRPD data of substantially crystalline 3-Butyl-8-chloro-1-{4-[5-(2-pyridinyl)-1,2,4-oxadiazol-3-yl]butyl}-3,7-dihydro-1H-purine-2,6-dione form 1.

The following non-limiting examples illustrate the present invention:

SYNTHETIC EXAMPLES

It should be noted that the assignment of (Z)-stereochemistry set out in the compounds exemplified below has not been confirmed by experimental data. The person skilled in the art will also recognise that there can be interconversion between E & Z isomers. (Dondoni, Alessandro; Lunazzi, Lodovico; Giorgianni, Patrizia; Macciantelli, Dante. Carbon-nitrogen rotational barrier as a stereochemical probe of benzamidoximes. Journal of Organic Chemistry (1975), 40(20), 2979-80)

Example 1

8-Chloro-1-(3-{1-[(2-chloro-6-fluorophenyl)methyl]-1H-pyrazol-4-yl}propyl)-3-pentyl-3,7-dihydro-1H-purine-2,6-dione a) 8-Chloro-1-(3-{1-[(2-chloro-6-fluorophenyl)methyl]-1H-pyrazol-4-yl}propyl)-3-pentyl-3,7-dihydro-1H-purine-2,6-dione

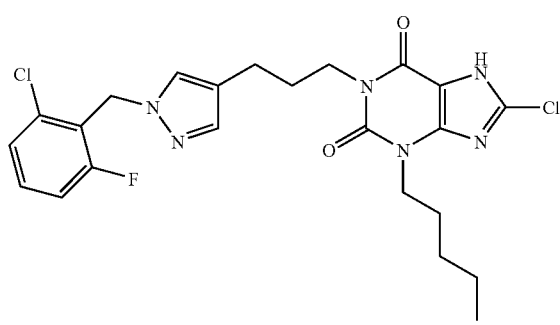

8-Chloro-3-pentyl-7-(2-propen-1-yl)-1-[3-(1H-pyrazol-4-yl)propyl]-3,7-dihydro-1H-purine-2,6-dione (61 mg, 0.15 mmol) in dry DMF (2 ml) was stirred with sodium carbonate (64 mg, 0.6 mmol) and 2-chloro-6-fluorobenzyl bromide (134 mg, 0.6 mmol) and heated at 45° C. for 18 h under nitrogen. After cooling to rt the mixture was degassed by evacuating and readmitting nitrogen, and stirred with tetrakis (triphenylphosphine)palladium(0) (35 mg, 0.303 mmol) and morpholine (0.13 ml) for 5.5 h. The mixture was partitioned between EtOAc and 2M HCl, the organic phase separated and evaporated and the residue purified by aminopropyl SPE (5 g, washing with THF-MeOH (1:1) then neat MeOH and finally eluting with DCM-MeOH (1:1) containing 5% AcOH) to give the title compound (57 mg) as a solid.

LC/MS: m/z 507 [MH]$^+$, RT 3.64 min.

b) 8-Chloro-3-pentyl-7-(2-propen-1-yl)-1-[3-(1H-pyrazol-4-yl)propyl]-3,7-dihydro-1H-purine-2,6-dione

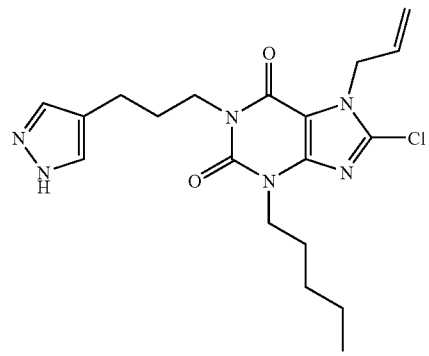

3-Pentyl-8-chloro-7-(2-propen-1-yl)-3,7-dihydro-1H-purine-2,6-dione (5 g, 16.86 mmol) and 3-(1H-pyrazol-4-yl)propan-1-ol (2.12 g, 16.8 mmol) were stirred in dry THF (150 ml) at 3° C. Dibenzyl azodicarboxylate (10.05 g, 33.7 mmol) was added followed by the dropwise addition of triphenylphosphine (8.83 g, 33.7 mmol) in dry THF (70 ml). The mixture was allowed to warm to it and stirred for 18 h. Water (1 ml) was added and the solvents evaporated. The residue was taken up in Et$_2$O (200 ml) from which a white solid, mostly triphenylphosphine oxide, crystallised and was filtered off. The filtrate was concentrated and further by-products crystallised from ether-cyclohexane. The remaining filtrate was concentrated (19.2 g) and purified on a Biotage™ system (400 g) eluting with EtOAc-cyclohexane (2:1) to afford the title compound as a white solid (2.89 g).

LC/MS: m/z 405 [MH]$^+$, RT 3.19 min.

The following compounds (Table 1) were prepared using a method analogous to that for Example 1, from the corresponding benzyl halides.

TABLE 1

| Example | structure | Yield (mg) | LC/MS: |
|---|---|---|---|
| 2 | 8-chloro-3-pentyl-1-(3-{1-[(2,4,6-trifluorophenyl)methyl]-1H-pyrazol-4-yl}propyl)-3,7-dihydro-1H-purine-2,6-dione | 68 | m/z 509 [MH]$^+$ RT 3.58 min |
| 3 | 8-chloro-1-(3-{1-[(2-chloro-4-fluorophenyl)methyl]-1H-pyrazol-4-yl}propyl)-3-pentyl-3,7-dihydro-1H-purine-2,6-dione | 56 | m/z 507 [MH]$^+$ RT 3.73 min |
| 4 | 8-chloro-1-(3-{1-[(2,6-difluorophenyl)methyl]-1H-pyrazol-4-yl}propyl)-3-pentyl-3,7-dihydro-1H-purine-2,6-dione | 29 | m/z 491 [MH]$^+$ RT 3.53 min |
| 5 | 8-chloro-1-(3-{1-[(2-fluorophenyl)methyl]-1H-pyrazol-4-yl}propyl)-3-pentyl-3,7-dihydro-1H-purine-2,6-dione | 32* | m/z 473 [MH]$^+$ RT 3.55 min |

$^a$after additional purification by MDAP.

NMR Details for Selected Examples from Table 1

Example 2

8-chloro-3-pentyl-1-(3-{1-[(2,4,6-trifluorophenyl)methyl]-1H-pyrazol-4-yl}propyl)-3,7-dihydro-1H-purine-2,6-dione $^1$H NMR (DMSO-d$_6$) δ: 0.85 (t, 3H, J=7 Hz), 1.20-1.40 (m, 4H), 1.60-1.70 (m, 2H), 1.70-1.82 (m, 2H), 2.39 (t, 2H, J=8 Hz), 3.83-3.94 (m, 4H), 5.24 (s, 2H), 7.18-7.30 (m, 3H), 7.57 (s, 1H).

Example 6

8-Chloro-1-(3-{1-[(2,4-difluorophenyl)methyl]-1H-pyrazol-4-yl}propyl)-3-pentyl-3,7-dihydro-1H-purine-2,6-dione

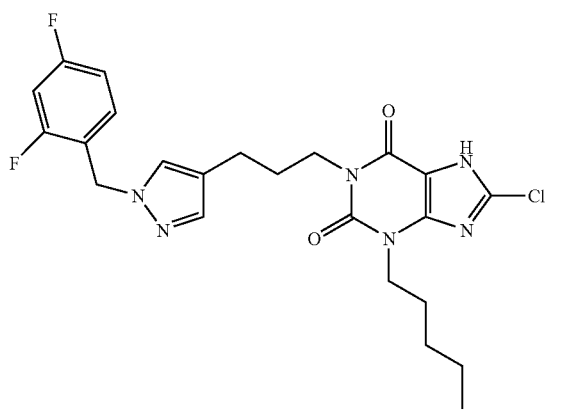

8-Chloro-3-pentyl-7-(2-propen-1-yl)-1-[3-(1H-pyrazol-4-yl)propyl]-3,7-dihydro-1H-purine-2,6-dione (81 mg, 0.2 mmol) and sodium carbonate (85 mg, 0.8 mmol) were stirred in dry DMF (2 ml) with 2,4-difluorobenzyl bromide (166 mg, 0.8 mmol) at 45° C. for 18 h. The mixture was degassed and stirred with tetrakis(triphenylphosphine)palladium(0) (46 mg, 0.04 mmol) and morpholine (176 mg, 2 mmol) at rt for 6 h. The reaction was worked up and purified by aminopropyl SPE (5 g, washing with THF-MeOH (1:1) then neat MeOH, eluting with DCM-MeOH (1:1) with 5% added AcOH) to yield the title compound (37.7 mg) as a solid.

LC/MS: m/z 491 [MH]$^+$, RT 3.42 min.

The following compounds (Table 1) were prepared using a method analogous to that for Example 6, from the corresponding benzyl halides.

TABLE 2

| Example | Structure | Yield (mg) | LC/MS: |
|---|---|---|---|
| 7 | 8-chloro-3-pentyl-1-{3-[1-(phenylmethyl)-1H-pyrazol-4-yl]propyl}-3,7-dihydro-1H-purine-2,6-dione | 17* | m/z 455 [MH]$^+$ RT 3.52 min |

TABLE 2-continued

| Example | Structure | Yield (mg) | LC/MS: |
|---|---|---|---|
| 8 | 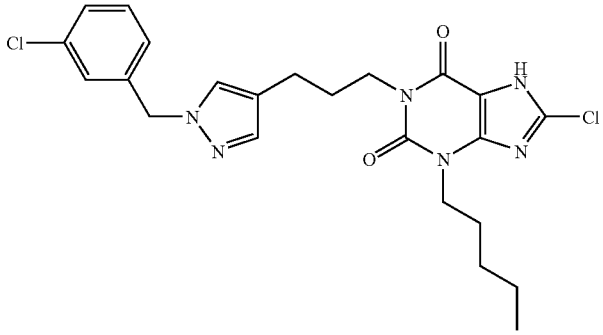<br>8-chloro-1-(3-{1-[(3-chlorophenyl)methyl]-1H-pyrazol-4-yl}propyl)-3-pentyl-3,7-dihydro-1H-purine-2,6-dione | 11.6* | m/z 489 [MH]$^+$<br>RT 3.52 min |
| 9 | 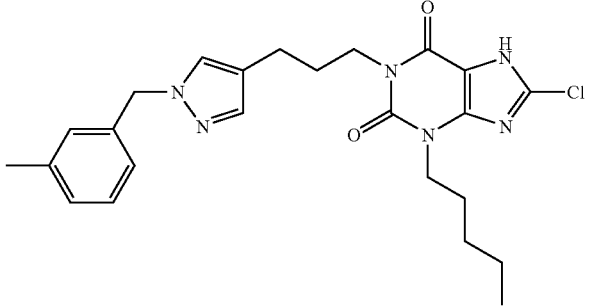<br>8-chloro-1-(3-{1-((3-methylphenyl)methyl]-1H-pyrazol-4-yl}propyl)-3-pentyl-3,7-dihydro-1H-purine-2,6-dione | 33 | m/z 469 [MH]$^+$<br>RT 3.54 min |
| 10 | 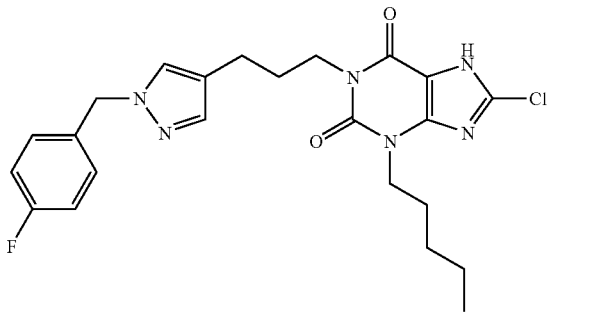<br>8-chloro-1-(3-{1-[(4-fluorophenyl)methyl]-1H-pyrazol-4-yl}propyl)-3-pentyl-3,7-dihydro-1H-purine-2,6-dione | 42 | m/z 473 [MH]$^+$<br>RT 3.44 min |

$^a$after additional purification by MDAP.

NMR Details for Selected Examples from Table 2

Example 6

$^1$H NMR (d$^6$ DMSO) 0.85 (3H, t, J=7 Hz), 1.21-1.34 (4H, m), 1.58-1.68 (2H, m), 1.71-1.80 (2H, m), 2.41 (2H, t, J=8 Hz), 3.84-3.93 (4H, m), 5.26 (2H, s), 7.02-7.09 (1H, m), 7.15-7.29 (2H, m), 7.31 (1H, s), 7.61 (1H, s).

Example 7

8-chloro-3-pentyl-1-{3-[1-(phenylmethyl)-1H-pyrazol-4-yl]propyl}-3,7-dihydro-1H-purine-2,6-dione $^1$H NMR (DMSO-d$_6$) δ: 0.87 (t, 3H, J=7 Hz), 1.20-1.36 (m, 4H), 1.60-1.70 (m, 2H), 1.72-1.85 (m, 2H), 2.42 (t, 2H, J=8 Hz), 3.83-3.95 (m, 4H), 5.24 (s, 2H), 7.13-7.38 (m, 6H), 7.61 (s, 1H).

Example 11

8-Chloro-1-(3-{1-[(2-chlorophenyl)methyl]-1H-pyrazol-4-yl}propyl)-3-pentyl-3,7-dihydro-1H-purine-2,6-dione

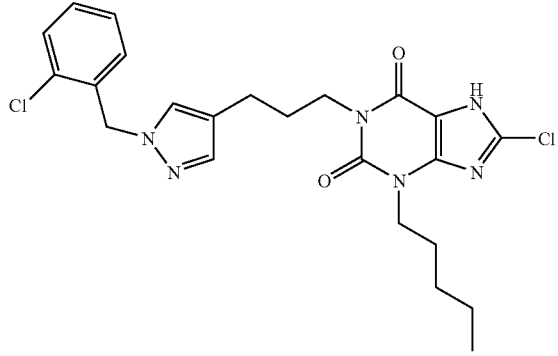

Prepared by the method for 8-chloro-1-(3-{1-[(2,4-difluorophenyl)methyl]-1H-pyrazol-4-yl}propyl)-3-pentyl-3,7-dihydro-1H-purine-2,6-dione, Example 6 but from 2-chlorobenzyl bromide (164 mg, 0.8 mmol). However, in order to complete the deprotection step further tetrakis(triphenylphosphine)palladium(0) (40 mg) and morpholine (0.15 ml) were added and stirring continued for a further 5.5 h. Purification by aminopropyl SPE as above afforded the title compound as a solid (42 mg).
LC/MS: m/z 489 [MH]$^+$, RT 3.67 min.

Example 12

3-Butyl-8-chloro-1-{3-[1-(phenylmethyl)-1H-imidazol-4-yl]propyl}-3,7-dihydro-1H-purine-2,6-dione a) 3-Butyl-8-chloro-1-{3-[1-(phenylmethyl)-1H-imidazol-4-yl]propyl}-3,7-dihydro-1H-purine-2,6-dione

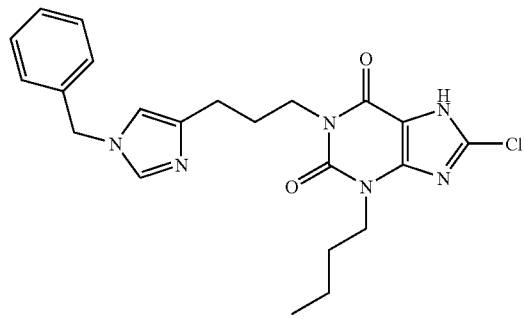

A solution of 3-butyl-8-chloro-1-[4-(1H-imidazol-4-yl)butyl]-7-(2-propen-1-yl)-3,7-dihydro-1H-purine-2,6-dione (300 mg, 0.77 mmol) in anhydrous THF (5 ml) was treated with benzyl bromide (144 mg, 0.84 mmol) and DIPEA (147 μl, 0.84 mmol). The mixture was left to stir at rt under nitrogen for 4 days. The mixture was partitioned between EtOAc and 2M HCl (aq). The organic layer was separated, washed with brine, dried (MgSO$_4$) and concentrated. The crude was purified by a silica SPE column using a 0.5-5% MeOH/DCM gradient. The product fractions were combined and concentrated under high vacuum. The product was dissolved in THF (5 ml) then Pd(PPh$_3$)$_4$ (88 mg, 0.077 mmol) and morpholine (670 μl, 7.67 mmol) were added and the mixture left to stir at rt under nitrogen for 3 h. 88 mg of Pd(PPh$_3$)$_4$ (0.077 mmol) was added and the mixture was left to stir at rt under nitrogen for 16 h. The mixture was partitioned between EtOAc and H$_2$O. The organic layer was separated and the aqueous layer was extracted with EtOAc (×2). The organic layers were combined, washed with brine, dried (MgSO$_4$) and concentrated. The crude product was purified by MDAP to give the title compound as a white solid (9 mg, 2%).

LC/MS: m/z 441 [MH]$^+$, RT 2.50 min.

$^1$H NMR (DMSO-d$_6$) δ: 0.89 (t, 3H, J=7.5 Hz), 1.28 (m, 2H), 1.60 (m, 2H), 1.79 (m, 2H), 2.48 (t overlapping with DMSO, 2H, J=7.5 Hz), 3.89 (m, 4H), 5.17 (s, 2H), 7.08 (s, 1H), 7.31, (m, 6H), 8.03 (s, 1H).

b) 3-Butyl-8-chloro-1-[3-(1H-imidazol-4-yl)propyl]-7-(2-propen-1-yl)-3,7-dihydro-1H-purine-2,6-dione

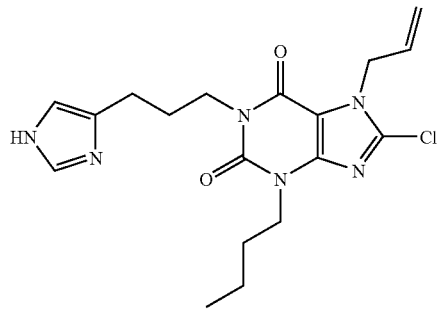

A solution of 3-butyl-8-chloro-7-(2-propen-1-yl)-3,7-dihydro-1H-purine-2,6-dione (2.8 g, 9.9 mmol) in anhydrous THF (60 ml) was treated with 3-(1H-imidazol-4-yl)-1-propanol (1.5 g, 12 mmol) in anhydrous THF (10 ml) and PPh$_3$ (3.4 g, 13 mmol). DBAD (2.9 g, 13 mmol) was added in one portion and the mixture was left to stir at rt, under nitrogen for 18 h. The mixture was partitioned between EtOAc and H$_2$O. The aqueous layer was extracted and washed with EtOAc. The organic layers were combined, washed with brine, dried (MgSO$_4$) and concentrated. The crude product was purified by a silica SPE cartridge using a MeOH/EtOAc gradient (0.5%-7% MeOH). The product fractions were combined and concentrated by to give the title compound as a white solid (2.16 g, 55%).

LC/MS: m/z 391 [MH]$^+$, RT 2.40 min.

c) 3-Butyl-8-chloro-7-(2-propen-1-yl)-3,7-dihydro-1H-purine-2,6-dione

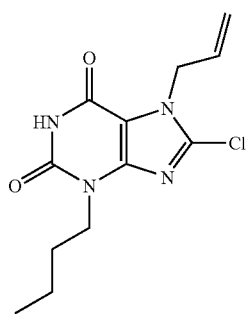

To a solution of 3-butyl-7-(2-propen-1-yl)-3,7-dihydro-1H-purine-2,6-dione (3.34 g, 13.4 mmol) in anhydrous DMF (19 ml) was added NCS (1.97 g, 14.8 mmol) and left to stir at rt under nitrogen for 22 h. The mixture was concentrated in vacuo to give a yellow solid which was filtered and washed with MeOH to provide a first crop. The filtrate was concentrated to a solid and washed with MeOH to provide a second crop and repeated a further two occasions to provide the title compound. On the final wash the filtrate was further purified by SPE (Si, 20 g) cartridge eluting with EtOAc:cyclohexane (1:1). The combined solids were dried under vacuum to afford the title compound (2.42 g, 64%).

LC/MS: m/z 283 [MH]$^+$.

Example 13

3-Butyl-8-chloro-1-(3-{1-[(2,3-difluorophenyl)methyl]-1H-imidazol-4-yl}propyl)-3,7-dihydro-1H-purine-2,6-dione

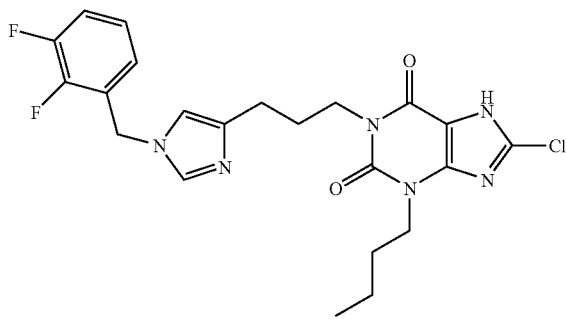

A solution of 3-butyl-8-chloro-1-[4-(1H-imidazol-4-yl)butyl]-7-(2-propen-1-yl)-3,7-dihydro-1H-purine-2,6-dione (150 mg, 0.38 mmol) in anhydrous DMF (3 ml) was treated with 1-(bromomethyl)-2,4-difluorobenzene (54 µl, 0.42 mmol) and DIPEA (73 µl, 0.42 mmol). The mixture was left to stir at rt under nitrogen for 3 days. The mixture was partitioned between EtOAc and 2M HCl (aq). The organic layer was separated, washed with brine, dried (MgSO$_4$) and concentrated. The crude product was purified on a silica SPE column using a DCM to load the material onto the column and wash through the impurities then a 0-5% MeOH/DCM gradient to elute the compound. The product fractions were combined and concentrated and the residues dissolved in anhydrous DMF (3 ml). The solution was degassed then Pd(PPh$_3$)$_4$ (39 mg, 0.034 mmol) and morpholine (200 µl, 2.3 mmol) were added and the mixture left to stir at rt under nitrogen for 3 h. The crude product was purified by an aminopropyl SPE using MeOH to load the compound onto the column and wash through the impurities then a 0-5% AcOH/MeOH gradient to elute the product. The product fractions were combined and concentrated by high vacuum to leave the title compound as a white solid (14 mg, 7%).

LC/MS: m/z 477 [MH]$^+$, RT 2.54 min.

Example 14

3-Butyl-8-chloro-1-[3-(1-{[2-(trifluoromethyl)phenyl]methyl}-1H-imidazol-4-yl)propyl]-3,7-dihydro-1H-purine-2,6-dione

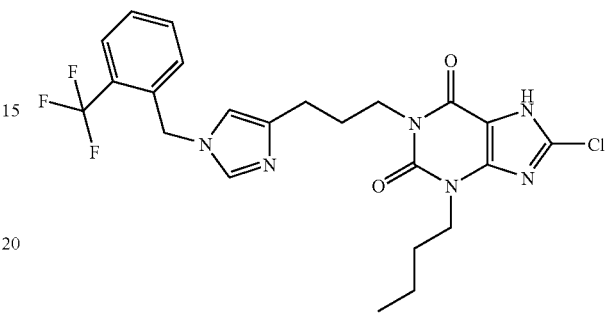

A solution of 3-butyl-8-chloro-1-[4-(1H-imidazol-4-yl)butyl]-7-(2-propen-1-yl)-3,7-dihydro-1H-purine-2,6-dione (150 mg, 0.38 mmol) in anhydrous DMF (3 ml) was treated with 1-(chloromethyl)-2-(trifluoromethyl)benzene (61 µl, 0.42 mmol) and DIPEA (73 µl, 0.42 mmol). The mixture was left to stir at rt under nitrogen for 3 days. The mixture was partitioned between EtOAc and 2M HCl (aq). The organic layer was separated, washed with brine, dried (MgSO$_4$) and concentrated. The crude product was purified on a silica SPE column using DCM to load the material onto the column and wash through the impurities then a 0-5% MeOH/DCM gradient to elute the compound. The product fractions were combined and concentrated and the residues dissolved in anhydrous DMF (3 ml). The solution was degassed then Pd(PPh$_3$)$_4$ (35 mg, 0.030 mmol) and morpholine (174 µl, 2.0 mmol) were added and the mixture left to stir at rt under nitrogen for 3 h. The crude product was purified by an aminopropyl SPE using MeOH to load the compound onto the column and wash through the impurities then a 0-5% AcOH/MeOH gradient to elute the product. The product fractions were combined and concentrated by high vacuum to leave the title compound as a white solid (50 mg, 26%).

LC/MS: m/z 509 [MH]$^+$, RT 2.64 min.

Example 15

3-Butyl-8-chloro-1-[3-(1-{[3-(trifluoromethyl)phenyl]methyl}-1H-imidazol-4-yl)propyl]-3,7-dihydro-1H-purine-2,6-dione

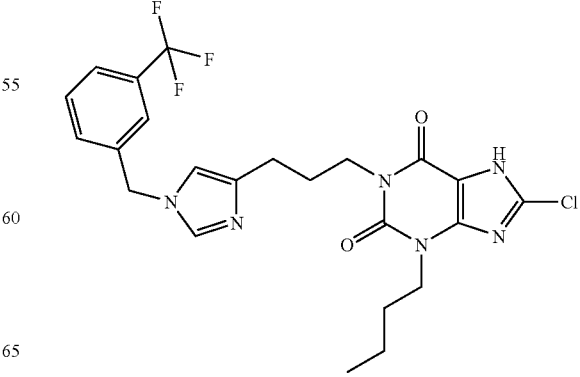

A solution of 3-butyl-8-chloro-1-[4-(1H-imidazol-4-yl)butyl]-7-(2-propen-1-yl)-3,7-dihydro-1H-purine-2,6-dione (150 mg, 0.38 mmol) in anhydrous DMF (3 ml) was treated with 1-(chloromethyl)-3-(trifluoromethyl)benzene (65 μl, 0.42 mmol) and DIPEA (73 μl, 0.42 mmol). The mixture was left to stir at rt under nitrogen for 3 days. The mixture was partitioned between EtOAc and 2M HCl (aq). The organic layer was separated, washed with brine, dried (MgSO₄) and concentrated. The crude product was purified on a silica SPE column using a DCM to load the material onto the column and wash through the impurities then a 0-5% MeOH/DCM gradient to elute the compound. The product fractions were combined and concentrated and the residues dissolved in anhydrous DMF (3 ml). The solution was degassed then Pd(PPh₃)₄ (30 mg, 0.027 mmol) and morpholine (156 μl, 1.8 mmol) were added and the mixture left to stir at rt under nitrogen for 3 h. The crude product was purified by an aminopropyl SPE using MeOH to load the compound onto the column and wash through the impurities then a 0-5% AcOH/MeOH gradient to elute the product. The product fractions were combined and concentrated by high vacuum to leave the title compound as a white solid (18 mg, 9%).

LC/MS: m/z 509 [MH]⁺, RT 2.78 min.

Example 16

3-Butyl-8-chloro-1-{3-[3-(phenylmethyl)-1-yl]propyl}-3,7-dihydro-1H-purine-2,6-dione a) 3-Butyl-8-chloro-1-{3-[3-(phenylmethyl)-1H-1,2,4-triazol-1-yl]propyl}-3,7-dihydro-1H-purine-2,6-dione

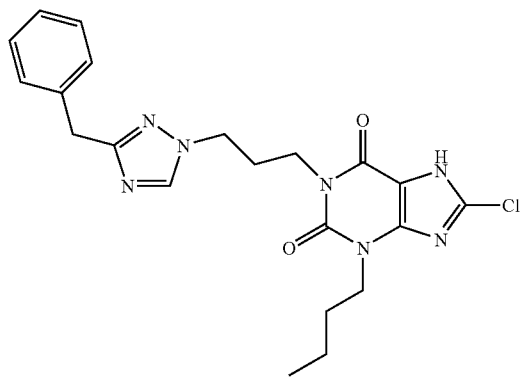

A solution of 3-butyl-8-chloro-1-{3-[3-(phenylmethyl)-1H-1,2,4-triazol-1-yl]propyl}-7-(2-propen-1-yl)-3,7-dihydro-1H-purine-2,6-dione (669 mg, 1.39 mmol) in THF (7 ml) was degassed by applying a vacuum and then nitrogen was introduced. Pd(PPh₃)₄ (160 mg, 0.14 mmol) was added and the mixture degassed once more. Morpholine (1.2 ml, 13.9 mmol) was added and the mixture was stirred under nitrogen for 18 h, then partitioned between 2M HCl (aq) and EtOAc. The organic layer was separated and the aqueous layer extracted again with EtOAc. The combined extracts were washed with brine, dried (MgSO₄) and concentrated, giving a yellow residue. MeOH was added and then passed down an aminopropyl SPE with the product eluting with 2-3% AcOH/MeOH. The product fractions were combined and concentrated giving a pale yellow solid (380 mg). Approximately a quarter of the material was purified by autoprep HPLC and rest was crystallised from MeOH:DMSO (1:1) giving the title compound as a white solid (125 mg, 31%).

LC/MS: m/z 442 [MH]⁺, RT 3.0 min.

$^1$H NMR (DMSO-d₆) δ: 0.89 (t, 3H, J=7 Hz), 1.30 (m, 2H), 1.62 (m, 2H), 2.07 (m, 2H), 3.90 (m, 6H), 4.13 (t, 2H, J=7 Hz), 7.24 (m, 5H), 8.36 (1H, s), 14.5 (br s, 1H).

b) 3-Butyl-8-chloro-1-{3-[3-(phenylmethyl)-1H-1,2,4-triazol-1-yl]propyl}-7-(2-propen-1-yl)-3,7-dihydro-1H-purine-2,6-dione

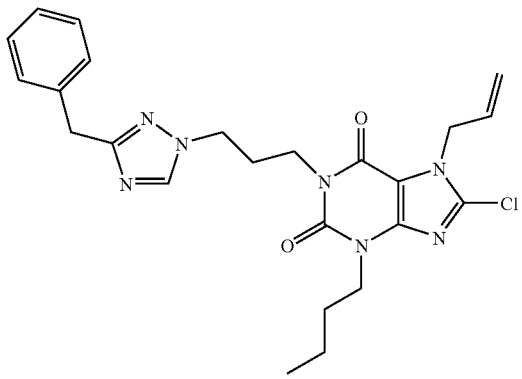

A solution of 3-(phenylmethyl)-1H-1,2,4-triazole (2.1 g, 13.2 mmol) in MeOH (40 ml) was treated with 0.5M NaOMe in MeOH (29 ml) followed by 1,3-dibromopropane (1.7 ml). After stirring for 5 h at 50° C. the mixture was partitioned between 2M HCl (aq) and EtOAc. The organic layer was separated, washed with brine, dried (MgSO₄) and concentrated, giving an oily residue (1.0 g). To this was added butyl-8-chloro-7-(2-propen-1-yl)-3,7-dihydro-1H-purine-2,6-dione (917 mg, 3.2 mmol) and Cs₂CO₃ (1.2 g, 3.6 mmol). DMF (15 ml) was added and the mixture was stirred at 50° C. for 20 h then partitioned between 2M HCl (aq) and EtOAc. The organic layer was separated, washed with brine, dried (MgSO₄) and concentrated. The resulting oil (1.52 g) was passed down a silica SPE (50 g) column eluting with EtOAc/cyclohexane mixtures. Two isomeric products of the triazole were obtained as a 2:1 mixture, in favour of the title compound, as a yellow paste (697 mg, 67% based on ratio of isomers present).

LC/MS: m/z 482 [MH]⁺, RT 3.3 min.

Example 17

8-Chloro-3-pentyl-1-{3-[5-(phenylmethyl)-2H-tetrazol-2-yl]propyl}-3,7-dihydro-1H-purine-2,6-dione

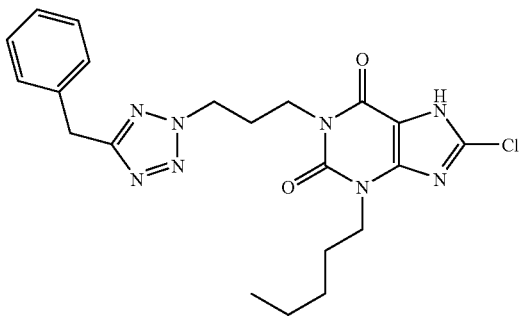

A solution of 5-benzyl-1H-tetrazole (1.0 g, 6.24 mmol) in MeOH (5 ml) was treated with 1-chloro-3-iodopropane (1.0 ml, 9.36 mmol) and a solution of 0.5M NaOMe in MeOH (4.7 ml, 9.36 mmol). The reaction was heated at reflux for 18 h then partitioned between 2M HCl (aq) and EtOAc. The organic layer was separated and the aqueous layer extracted once more with EtOAc. The combined extracts were washed with brine, dried (MgSO$_4$) and concentrated, giving a yellow solid. (796 mg). 700 mg of this material was reacted with 8-chloro-3-pentyl-7-(2-propen-1-yl)-3,7-dihydro-1H-purine-2,6-dione (732 mg, 2.47 mmol) and Cs$_2$CO$_3$ (967 mg, 3.0 mmol) in DMF (20 ml) at 75° C. for 24 h. The reaction was allowed to cool to rt and the mixture was degassed by applying a vacuum and then nitrogen was introduced. Pd(PPh$_3$)$_4$ (428 mg, 0.37 mmol) was added and the mixture degassed once more. Morpholine (2.1 ml, 24.7 mmol) was added and the mixture was stirred under nitrogen for 3 h, then partitioned between 2M HCl (aq) and EtOAc. The organic layer was separated and the aqueous layer extracted once more. The combined extracts were concentrated, giving a yellow residue. MeOH was added and then passed down an aminopropyl SPE, the product eluting with 2-3% AcOH/MeOH. The product fractions were combined and concentrated then purified by the MDAP to give the title compound as a white solid (35 mg, 3%).

LC/MS: m/z 457 [MH]$^+$, RT 3.5 min.

$^1$H NMR; (DMSO-d$_6$) δ: 0.85 (t, 3H, J=7 Hz), 1.21-1.34 (m, 4H), 1.62 (m, 2H), 2.22 (m, 2H), 3.88 (t, 2H, J=7 Hz), 3.97 (t, 2H, J=7 Hz), 4.17 (s, 2H), 4.67 (t, 2H, J=7 Hz), 7.20-7.32 (m, 5H), 14.5 (br s, 1H).

Example 18

3-Butyl-8-chloro-1-{3-[5-(phenylmethyl)-2H-tetrazol-2-yl]propyl}-3,7-dihydro-1H-purine-2,6-dione

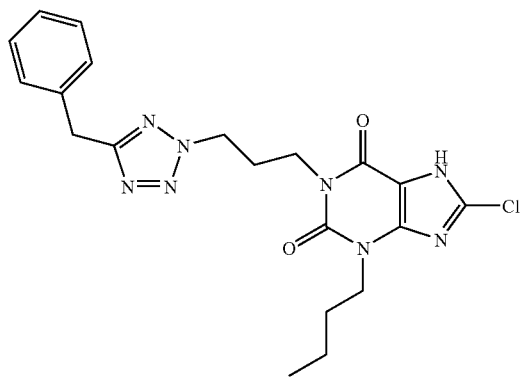

A solution of 5-benzyl-1H-tetrazole (1.8 g, 11.2 mmol) in MeOH (30 ml) was treated with 1,3-dibromopropane (5.7 ml, 56.2 mmol) and 0.5M NaOMe in MeOH (31.5 ml) then stirred at 40° C. under nitrogen for 60 h. The mixture was partitioned between 2M HCl (aq) and EtOAc. The organic layer was separated, washed with brine, dried (MgSO$_4$) and concentrated. Partial purification by SPE (20 g silica, cyclohexane/EtOAc mixtures) and by the Companion™ system (silica SPE, cyclohexane/EtOAc mixtures) gave an oil (1.98 g, 62% of a mixture of isomers, 2:1 in favour of 2-(3-bromopropyl)-5-(phenylmethyl)-2H-tetrazole) which was taken on crude in the next step.

A mixture of 3-butyl-8-chloro-7-(2-propen-1-yl)-3,7-dihydro-1H-purine-2,6-dione (1.74 g, 6.1 mmol), crude 2-(3-bromopropyl)-5-(phenylmethyl)-2H-tetrazole) (1.9 g, 6.8 mmol), Cs$_2$CO$_3$ (2.2 g, 6.8 mmol) and DMF (60 ml) was stirred at 45° C. under nitrogen for 24 h. The mixture was degassed by applying a vacuum and then nitrogen was introduced. Pd(PPh$_3$)$_4$ (705 mg, 0.61 mmol) was added and the mixture degassed once more. Morpholine (5.4 ml, 61.4 mmol) was added and the mixture was stirred under nitrogen for 4 h, and then partitioned between 2M HCl (aq) and EtOAc. The organic layer was separated, washed with brine, dried (MgSO$_4$) and concentrated, giving a yellow residue. MeOH was added and then passed down an aminopropyl column with the product eluting with 2% AcOH/MeOH. The product was further purified by the Companion™ system using EtOAc/cyclohexane mixtures. The resulting solid was stirred with boiling Et$_2$O and filtered after cooling to rt. The title compound was collected as a white solid (1.01 g, 37%) and dried at 50° C. under vacuum.

LC/MS: m/z 443 [MH]$^+$, RT 3.3 min.

$^1$H NMR (DMSO-d$_6$) δ: 0.89 (t, 3H, J=7 Hz), 1.29 (m, 2H), 1.61 (m, 2H), 2.22 (m, 2H), 3.89 (t, 2H, J=7 Hz), 3.97 (t, 2H, J=7 Hz), 4.17 (s, 2H), 4.67 (t, 2H, J=7 Hz), 7.20-7.32 (m, 5H), 14.5 (br s, 1H).

Example 19

8-Chloro-1-(3-{5-[(4-fluorophenyl)methyl]-2H-tetrazol-2-yl}propyl)-3-(4,4,4-trifluorobutyl)-3,7-dihydro-1H-purine-2,6-dione a) 8-Chloro-1-(3-{5-[(4-fluorophenyl)methyl]-2H-tetrazol-2-yl}propyl)-3-(4,4,4-trifluorobutyl)-3,7-dihydro-1H-purine-2,6-dione

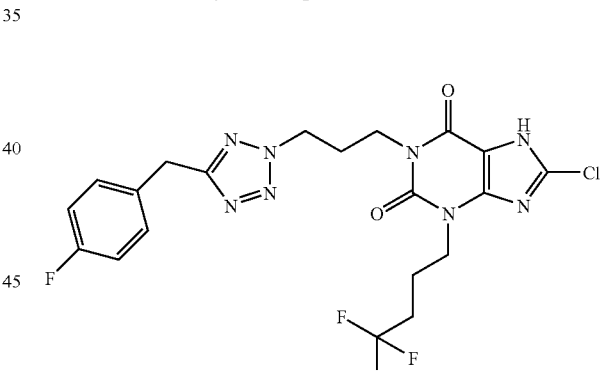

5-[(4-Fluorophenyl)methyl]-1H-tetrazole (75 mg, 0.4 mmol) was treated with potassium carbonate (100 mg, 0.7 mmol) and DMF (3 ml). The mixture was treated with a solution of 3-[8-chloro-2,6-dioxo-7-(2-propen-1-yl)-3-(4,4,4-trifluorobutyl)-2,3,6,7-tetrahydro-1H-purin-1-yl]propyl methanesulfonate (100 mg, 0.2 mmol) in DMF (0.5 ml). The mixture was stirred and heated at 60° C. 3 hours then cooled and evaporated. The residue was partitioned between chloroform (4 ml) and water (2 cm$^3$). 1 cm$^3$ of saturated aqueous sodium bicarbonate (3 ml) was added to each. The mixture was separated and the organic phase evaporated. The residue was dissolved in anhydrous THF (3 ml) and the mixture degassed by the cautious successive application of vacuum and nitrogen pressure to the mixture. The mixture was treated with tetrakis(triphenylphosphine)palladium(0) (10 mg, 0.008 mmol) and morpholine (0.2 ml, 2.3 mmol) and then stirred in a nitrogen atmosphere for 2 h. The mixture was evaporated and partitioned between chloroform (4 ml) and saturated aqueous ammonium chloride (3 ml). The mixture was separated, and the aqueous phase re-extracted with chloroform. The organic phase was evaporated and the residue dissolved in MeOH (3 ml). The solution was added to the top of a 2 g aminopropyl SPE and washed with MeOH (15 ml). The desired product was eluted from the cartridge with a 3% v/v solution of AcOH in MeOH (20 ml). Product containing fractions were combined and evaporated and the residue subjected to purification by flash column chromatography (gradient elution from 10:1 cyclohexane/EtOAc to EtOAc). Product-containing fractions were combined and evaporated to yield the product as a colourless oil. Trituration in minimal diethyl ether caused the product to solidify and this was thoroughly dried to yield the title compound as a white solid (18.7 mg, 18%).

LC/MS: m/z 515 [MH]$^+$, RT 3.31 min.

$^1$H NMR (CDCl$_3$) δ: 2.06 (m, 2H), 2.21 (m, 2H), 2.45 (m, 2H), 4.17 (m, 4H), 4.24 (t, 2H, J=7.0 Hz), 4.70 (t, 2H, J=7.2 Hz), 6.96 (m, 2H), 7.25 (m, 2H).

b) 3-[8-Chloro-2,6-dioxo-7-(2-propen-1-yl)-3-(4,4,4-trifluorobutyl)-2,3,6,7-tetrahydro-1H-purin-1-yl] propyl methanesulfonate

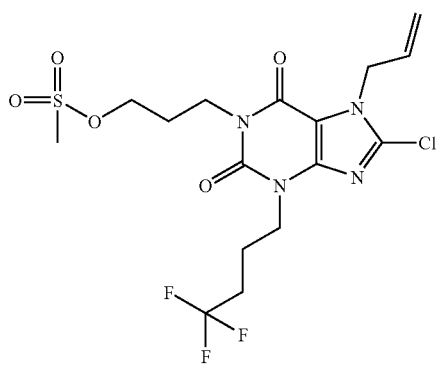

A solution of 8-chloro-1-(3-hydroxypropyl)-7-(2-propen-1-yl)-3-(4,4,4-trifluorobutyl)-3,7-dihydro-1H-purine-2,6-dione (0.82 g, 2.1 mmol) in DCM (20 ml) was treated with triethylamine (0.42 ml, 3.1 mmol) and methanesulfonic anhydride (0.40 g, 2.3 mmol). After 1 h the mixture was treated with saturated aqueous sodium bicarbonate (20 ml). The mixture was separated and the organic phase dried (MgSO$_4$), filtered and evaporated to give the title compound (0.91 g), which was used without further purification.

LC/MS: m/z 473 [MH]$^+$, RT 3.17 min.

c) 8-Chloro-1-(3-hydroxypropyl)-7-(2-propen-1-yl)-3-(4,4,4-trifluorobutyl)-3,7-dihydro-1H-purine-2,6-dione

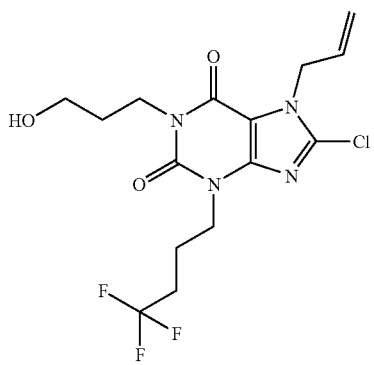

A solution of 8-chloro-7-(2-propen-1-yl)-3-(4,4,4-trifluorobutyl)-3,7-dihydro-1H-purine-2,6-dione (1.0 g, 3.0 mmol) in DMF (15 ml) was treated with caesium carbonate (1.16 g, 3.6 mmol) and 3-bromo-1-propanol (0.3 ml, 3.3 mmol). The mixture was heated at 60° C. for 4 h and then cooled and evaporated. The residue was partitioned between EtOAc (50 ml) and water (50 ml). The organic phase was dried (MgSO$_4$), filtered and evaporated. The product was purified by flash chromatography using a gradient elution from cyclohexane to EtOAc. Product-containing fractions were combined and evaporated to give the title compound as a colourless oil (0.82 g, 75%).

LC/MS: m/z 395 [MH]$^+$, RT 2.90 min.

d) 8-Chloro-7-(2-propen-1-yl)-3-(4,4,4-trifluorobutyl)-3,7-dihydro-1H-purine-2,6-dione

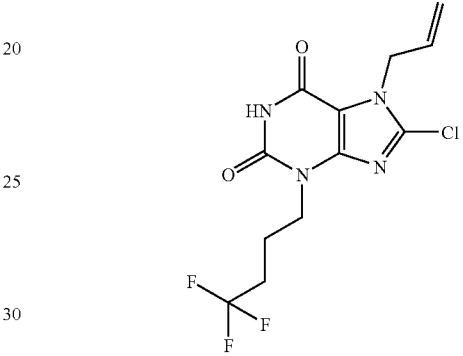

A solution of 8-chloro-7-(2-propen-1-yl)-3,7-dihydro-1H-purine-2,6-dione (2.0 g, 8.8 mmol) in DMF (20 ml) was treated with sodium carbonate (1.15 g, 10.8 mmol) and 4-bromo-1,1,1-trifluorobutane (1.86 g, 9.7 mmol). The mixture was stirred at 50° C. for 18 h then cooled and evaporated. The residue was partitioned between EtOAc (100 ml) and saturated aqueous sodium bicarbonate (50 ml). The organic phase was dried (MgSO$_4$), filtered and evaporated. The residue was triturated in a mixture of diethyl ether and cyclohexane then the product filtered off and dried to yield the title compound as a white solid (1.18 g, 40%).

LC/MS: m/z 337 [MH]$^+$, RT 2.83 min.

e) 5-[(4-Fluorophenyl)methyl]-1H-tetrazole

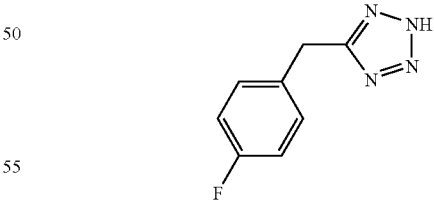

A mixture of triethylammonium chloride (4.14 g, 30 mmol) and sodium azide (1.95 g, 30 mmol) was treated with a solution of (4-fluorophenyl)acetonitrile (1.35 g, 10 mmol) in toluene (14 ml) and the mixture was stirred and heated at 100° C. for 5 h. The cooled mixture was treated with water (10 ml) and the mixture separated. The aqueous phase was stirred and treated dropwise with concentrated hydrochloric acid until the product had precipitated from solution. The precipitated product was filtered off, washed with water and dried to yield the title compound as a white solid (1.27 g, 72%).

LC/MS: m/z 179 [MH]$^+$, RT 2.24 min.

The compounds in Table 3 were prepared using a method analogous to that for Example 19: 8-chloro-1-(3-{5-[(4-fluorophenyl)methyl]-2H-tetrazol-2-yl}propyl)-3-(4,4,4-trifluorobutyl)-3,7-dihydro-1H-purine-2,6-dione, with the appropriate methanesulfonate and tetrazole. MDAP was employed to further purify those compounds insufficiently pure following normal phase chromatography.

Methanesulfonates intermediates and their precursor alcohols were prepared according to the following procedures:

3-[8-Chloro-2,6-dioxo-7-(2-propen-1-yl)-3-propyl-2,3,6,7-tetrahydro-1H-purin-1-yl]propyl methanesulfonate

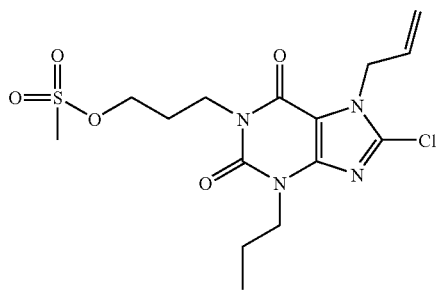

A solution of 8-chloro-1-(3-hydroxypropyl)-7-(2-propen-1-yl)-3-propyl-3,7-dihydro-1H-purine-2,6-dione (1.99 g, 6.1 mmol) in DCM (50 ml) was treated with triethylamine (1.2 ml, 8.6 mmol) and methanesulfonic anhydride (1.2 g, 6.9 mmol). After 1.5 h the mixture was treated with water (50 ml). The mixture was separated and the aqueous phase extracted with DCM (25 ml), the combined organic phases dried (MgSO$_4$), filtered and evaporated to give the title compound as a pale yellow oil (2.38 g), which was used without further purification.

LC/MS: m/z 405 [MH]$^+$, RT 2.93 min.

3-[3-Butyl-8-chloro-2,6-dioxo-7-(2-propen-1-yl)-2,3,6,7-tetrahydro-1H-purin-1-yl]propyl methanesulfonate

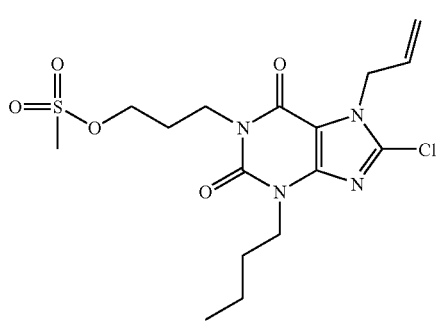

Prepared according to the method used for 3-[8-chloro-2,6-dioxo-7-(2-propen-1-yl)-3-propyl-2,3,6,7-tetrahydro-1H-purin-1-yl]propyl methanesulfonate to give the title compound as a pale yellow oil (2.44 g).

LC/MS: m/z 419 [MH]$^+$, RT 3.14 min.

8-Chloro-1-(3-hydroxypropyl)-7-(2-propen-1-yl)-3-propyl-3,7-dihydro-1H-purine-2,6-dione

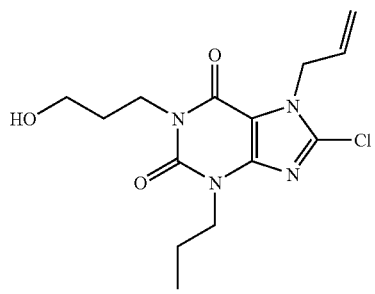

A solution of 8-chloro-7-(2-propen-1-yl)-3-propyl-3,7-dihydro-1H-purine-2,6-dione (3.0 g, 11.1 mmol) in DMF (20 ml) was treated with caesium carbonate (3.7 g, 11.4 mmol) and 3-bromo-1-propanol (1.6 g, 11.5 mmol). The mixture was heated at 60° C. for 4 h and then cooled and evaporated. The residue was partitioned between EtOAc (60 ml) and saturated aqueous sodium bicarbonate (50 ml). The aqueous phase was extracted with EtOAc (60 ml), the combined organic phases were dried (MgSO$_4$), filtered and evaporated. The product was purified using the Companion™ system and a gradient elution from cyclohexane to EtOAc. Product containing fractions were combined and evaporated to give the title compound as a colourless oil (2.6 g).

LC/MS: m/z 327 [MH]$^+$, RT 2.62 min.

3-Butyl-8-chloro-1-(3-hydroxypropyl)-7-(2-propen-1-yl)-3,7-dihydro-1H-purine-2,6-dione

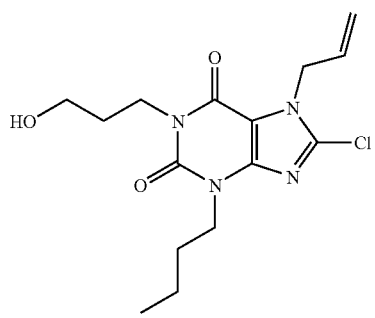

Prepared according to the method used for 8-chloro-1-(3-hydroxypropyl)-7-(2-propen-1-yl)-3-propyl-3,7-dihydro-1H-purine-2,6-dione to give the title compound as a colourless oil (2.3 g).

LC/MS: m/z 341 [MH]$^+$, RT 2.85 min.

TABLE 3

| # | Structure | Name | Yield | LC/MS: |
|---|---|---|---|---|
| 20 | 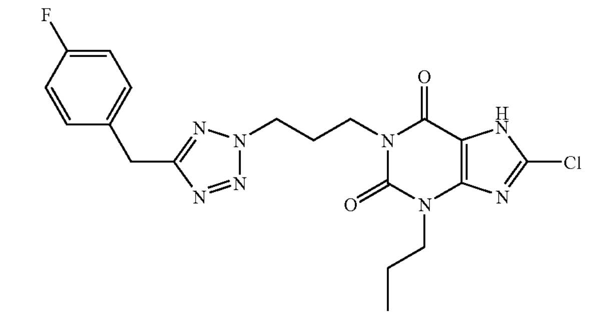 | 8-chloro-1-(3-{5-[(4-fluorophenyl)methyl]-2H-tetrazol-2-yl}propyl)-3-propyl-3,7-dihydro-1H-purine-2,6-dione | 12.4 mg (14%) | m/z 447 [MH]+ RT 3.14 min |
| 21 | 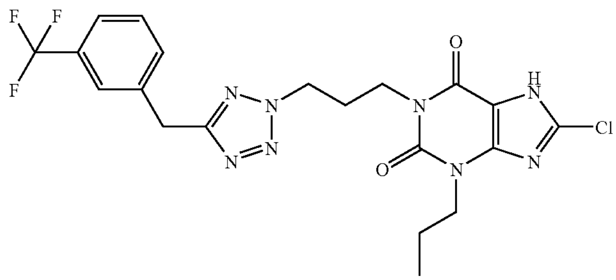 | 8-chloro-3-propyl-1-[3-(5-{[3-(trifluoromethyl)phenyl]methyl}-2H-tetrazol-2-yl)propyl]-3,7-dihydro-1H-purine-2,6-dione | 8.0 mg (8%) | m/z 497 [MH]+ RT 3.36 min |
| 22 | 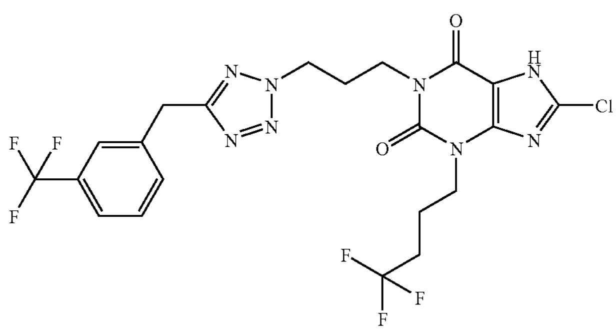 | 8-chloro-3-(4,4,4-trifluorobutyl)-1-[3-(5-{[3-(trifluoromethyl)phenyl]methyl}-2H-tetrazol-2-yl)propyl]-3,7-dihydro-1H-purine-2,6-dione | 21.0 mg (19%) | m/z 565 [MH]+ RT 3.34 min |
| 23 | 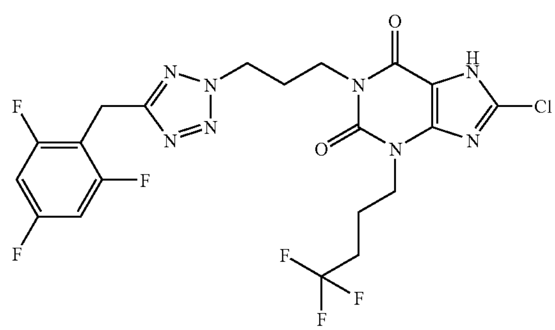 | 8-chloro-3-(4,4,4-trifluorobutyl)-1-(3-{5-[(2,4,6-trifluorophenyl)methyl]-2H-tetrazol-2-yl}propyl)-3,7-dihydro-1H-purine-2,6-dione | 17.0 mg (15%) | m/z 551 [MH]+ RT 3.27 min |
| 24 | 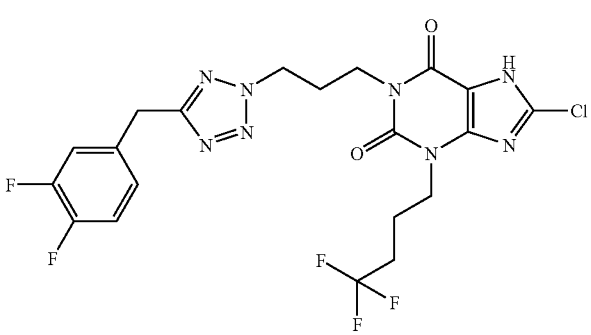 | 8-chloro-1-(3-{5-[(3,4-difluorophenyl)methyl]-2H-tetrazol-2-yl}propyl)-3-(4,4,4-trifluorobutyl)-3,7-dihydro-1H-purine-2,6-dione | 19.1 mg (18%) | m/z 533 [MH]+ RT 3.36 min |

TABLE 3-continued

| # | Structure | Name | Yield | LC/MS: |
|---|---|---|---|---|
| 25 | 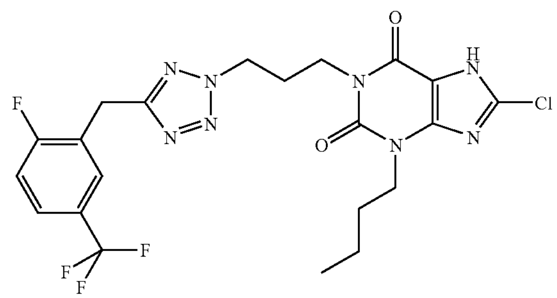 | 3-butyl-8-chloro-1-[3-(5-{[2-fluoro-5-(trifluoromethyl)phenyl]methyl}-2H-tetrazol-2-yl)propyl)-3,7-dihydro-1H-purine-2,6-dione | 23.9 mg (23%) | m/z 529 [MH]+ RT 3.50 min |
| 26 | 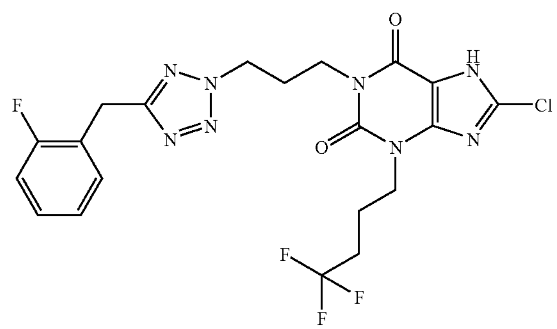 | 8-chloro-1-(3-{5-[(2-fluorophenyl)methyl]-2H-tetrazol-2-yl}propyl)-3-(4,4,4-trifluorobutyl)-3,7-dihydro-1H-purine-2,6-dione | 19.8 mg (19%) | m/z 515 [MH]+ RT 3.31 min |
| 27 | 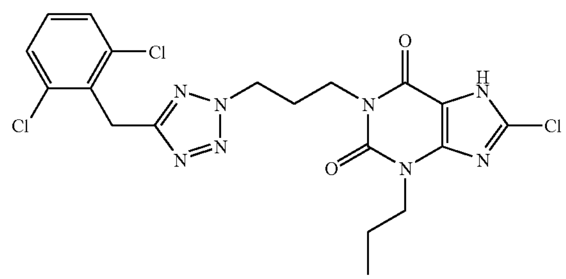 | 8-chloro-1-(3-{5-[(2,6-dichlorophenyl)methyl]-2H-tetrazol-2-yl}propyl)-3-propyl-3,7-dihydro-1H-purine-2,6-dione | 50.7 mg (51%) | m/z 497 [MH]+ RT 3.33 min |
| 28 | 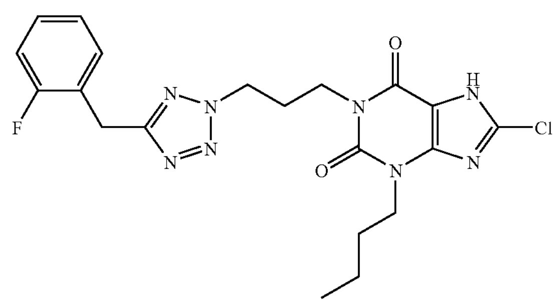 | 3-butyl-8-chloro-1-(3-{5-[(2-fluorophenyl)methyl]-2H-tetrazol-2-yl}propyl)-3,7-dihydro-1H-purine-2,6-dione | 46.4 mg (48%) | m/z 461 [MH]+ RT 3.27 min |
| 29 | 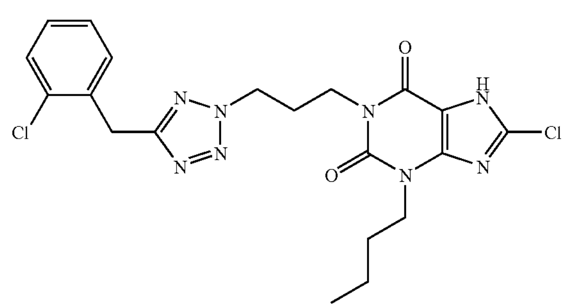 | 3-butyl-8-chloro-1-(3-{5-[(2-chlorophenyl)methyl]-2H-tetrazol-2-yl}propyl)-3,7-dihydro-1H-purine-2,6-dione | 25.4 mg (27%) | m/z 477 [MH]+ RT 3.40 min |

TABLE 3-continued

| # | Structure | Name | Yield | LC/MS: |
|---|---|---|---|---|
| 30 | 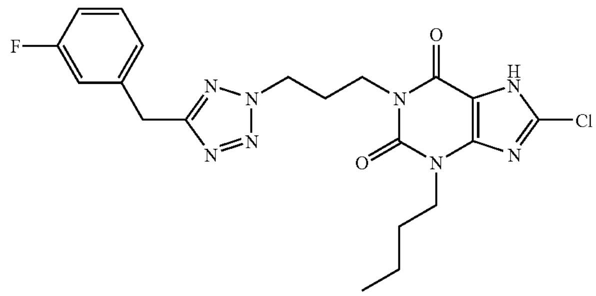 | 3-butyl-8-chloro-1-(3-{5-[(3-fluorophenyl)methyl]-2H-tetrazol-2-yl}propyl)-3,7-dihydro-1H-purine-2,6-dione | 36.8 mg (40%) | m/z 461 [MH]+ RT 3.31 min |
| 31 | 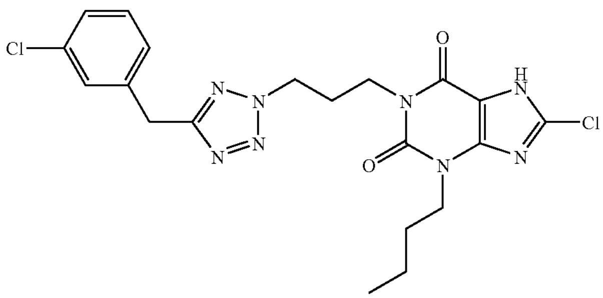 | 3-butyl-8-chloro-1-(3-{5-[(3-chlorophenyl)methyl]-2H-tetrazol-2-yl}propyl)-3,7-dihydro-1H-purine-2,6-dione | 38.5 mg (40%) | m/z 477 [MH]+ RT 3.45 min |
| 32 | 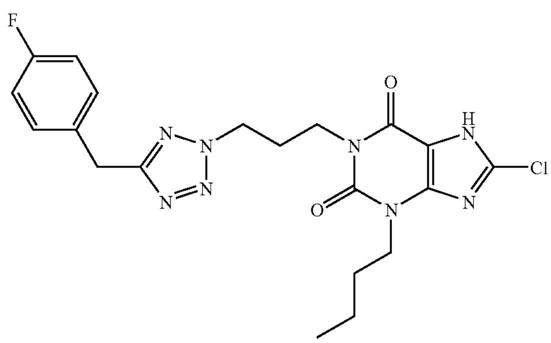 | 3-butyl-8-chloro-1-(3-{5-[(4-fluorophenyl)methyl]-2H-tetrazol-2-yl}propyl)-3,7-dihydro-1H-purine-2,6-dione | 31.6 mg (34%) | m/z 461 [MH]+ RT 3.31 min |
| 33 | 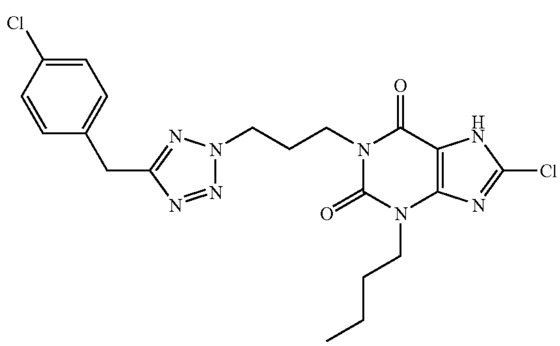 | 3-butyl-8-chloro-1-(3-{5-[(4-chlorophenyl)methyl]-2H-tetrazol-2-yl}propyl)-3,7-dihydro-1H-purine-2,6-dione | 33.1 mg (35%) | m/z 477 [MH]+ RT 3.46 min |
| 34 | 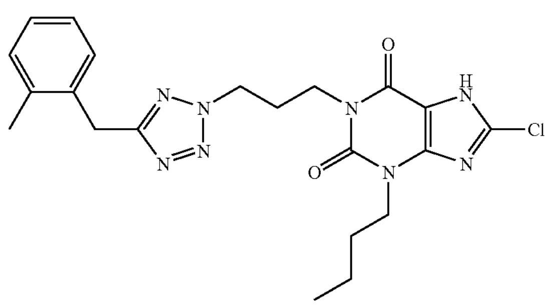 | 3-butyl-8-chloro-1-(3-{5-[(2-methylphenyl)methyl]-2H-tetrazol-2-yl}propyl)-3,7-dihydro-1H-purine-2,6-dione | 39.5 mg (43%) | m/z 457 [MH]+ RT 3.37 min |

TABLE 3-continued

| # | Structure | Name | Yield | LC/MS: |
|---|---|---|---|---|
| 35 | 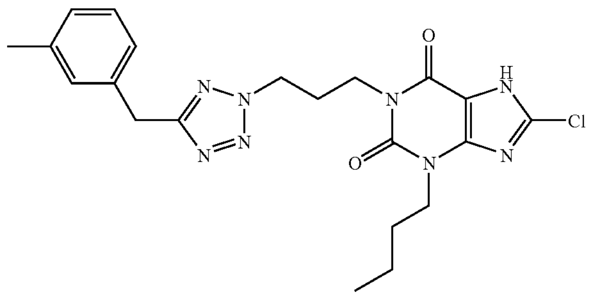 | 3-butyl-8-chloro-1-(3-{5-[(3-methylphenyl)methyl]-2H-tetrazol-2-yl}propyl)-3,7-dihydro-1H-purine-2,6-dione | 36.5 mg (40%) | m/z 457 [MH]+ RT 3.40 min |
| 36 | 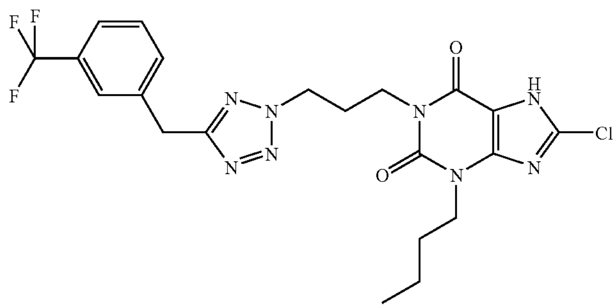 | 3-butyl-8-chloro-1-[3-(5-{[3-(trifluoromethyl)phenyl]methyl}-2H-tetrazol-2-yl)propyl]-3,7-dihydro-1H-purine-2,6-dione | 43.7 mg (43%) | m/z 511 [MH]+ RT 3.50 min |
| 37 | 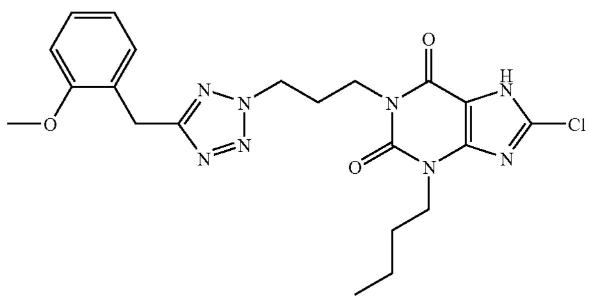 | 3-butyl-8-chloro-1-[3-(5-{[2-(methyloxy)phenyl]methyl}-2H-tetrazol-2-yl)propyl]-3,7-dihydro-1H-purine-2,6-dione | 28.6 mg (30%) | m/z 473 [MH]+ RT 3.29 min |
| 38 | 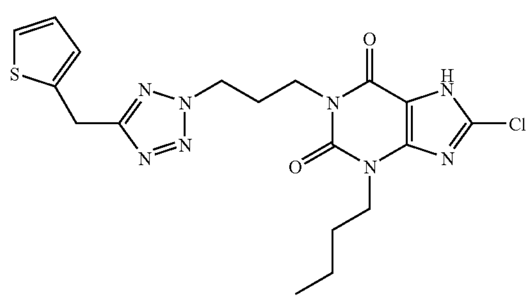 | 3-butyl-8-chloro-1-{3-[5-(2-thienylmethyl)-2H-tetrazol-2-yl]propyl}-3,7-dihydro-1H-purine-2,6-dione | 33.4 mg (37%) | m/z 449 [MH]+ RT 3.20 min |
| 39 | 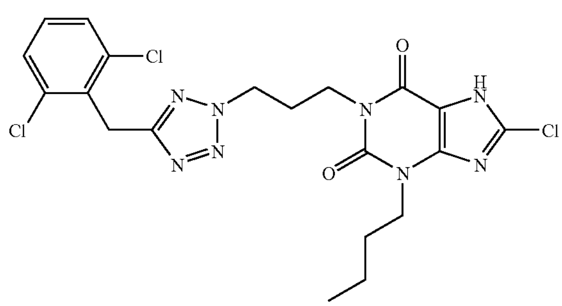 | 3-butyl-8-chloro-1-(3-{5-[(2,6-dichlorophenyl)methyl]-2H-tetrazol-2-yl}propyl)-3,7-dihydro-1H-purine-2,6-dione | 36.4 mg (36%) | m/z 511 [MH]+ RT 3.49 min |

| # | Structure | Name | Yield | LC/MS: |
|---|---|---|---|---|
| 40 | 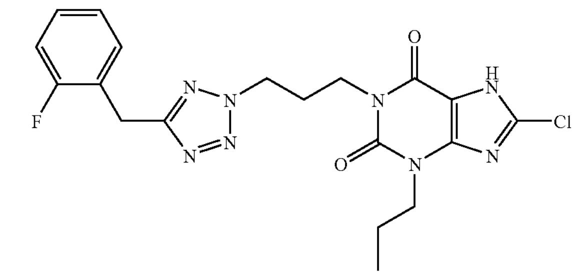 | 8-chloro-1-(3-{5-[(2-fluorophenyl)methyl]-2H-tetrazol-2-yl}propyl)-3-propyl-3,7-dihydro-1H-purine-2,6-dione | 5.6 mg (6%) | m/z 447 [MH]+ RT 3.10 min |
| 41 | 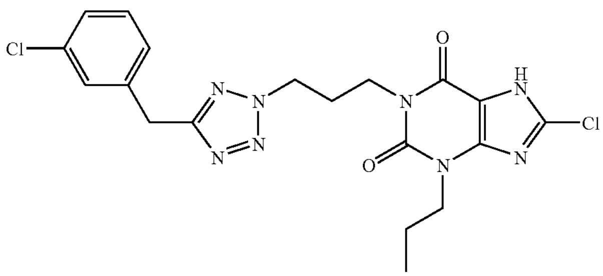 | 8-chloro-1-(3-{5-[(3-chlorophenyl)methyl]-2H-tetrazol-2-yl}propyl)-3-propyl-3,7-dihydro-1H-purine-2,6-dione | 5.9 mg (6%) | m/z 463 [MH]+ RT 3.29 min |
| 42 | 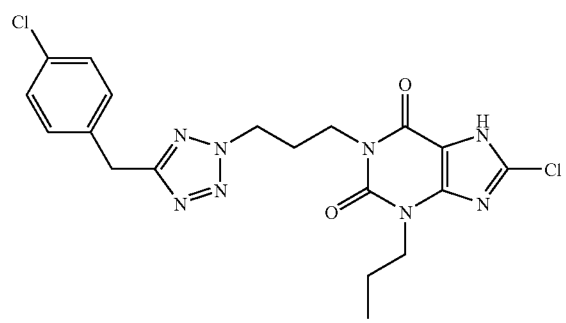 | 8-chloro-1-(3-{5-[(4-chlorophenyl)methyl]-2H-tetrazol-2-yl}propyl)-3-propyl-3,7-dihydro-1H-purine-2,6-dione | 14.9 mg (16%) | m/z 463 [MH]+ RT 3.30 min |
| 43 | 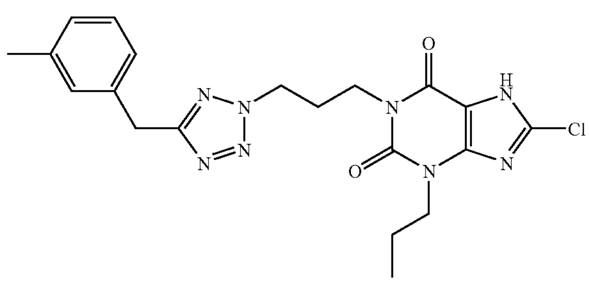 | 8-chloro-1-(3-{5-[(3-methylphenyl)methyl]-2H-tetrazol-2-yl})propyl)-3-propyl-3,7-dihydro-1H-purine-2,6-dione | 17.5 mg (20%) | m/z 443 [MH]+ RT 3.23 min |
| 44 | 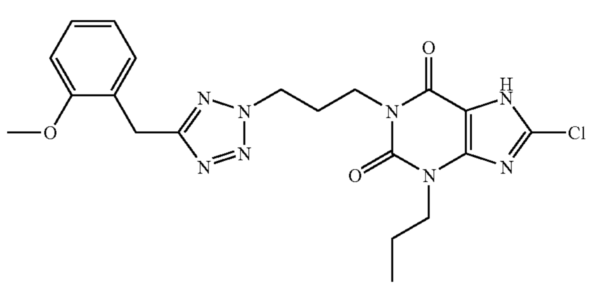 | 8-chloro-1-[3-(5-{[2-(methyloxy)phenyl]methyl}-2H-tetrazol-2-yl)propyl]-3-propyl-3,7-dihydro-1H-purine-2,6-dione | 14.5 mg (16%) | m/z 459 [MH]+ RT 3.12 min |

TABLE 3-continued

| # | Structure | Name | Yield | LC/MS: |
|---|---|---|---|---|
| 45 | 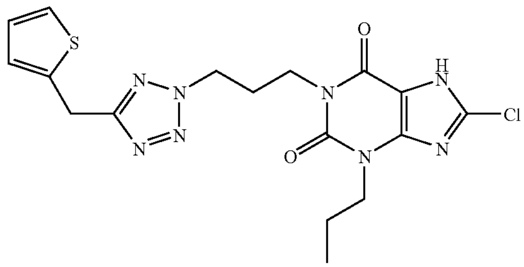 | 8-chloro-3-propyl-1-{3-[5-(2-thienylmethyl)-2H-tetrazol-2-yl]propyl}-3,7-dihydro-1H-purine-2,6-dione | 17.0 mg (20%) | m/z 435 [MH]+ RT 3.02 min |
| 46 | 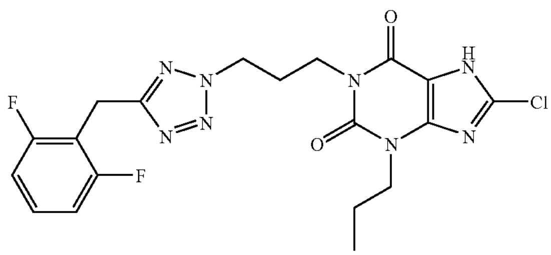 | 8-chloro-1-(3-{5-[(2,6-difluorophenyl)methyl]-2H-tetrazol-2-yl}propyl)-3-propyl-3,7-dihydro-1H-purine-2,6-dione | 18.4 mg (20%) | m/z 465 [MH]+ RT 3.11 min |
| 47 | 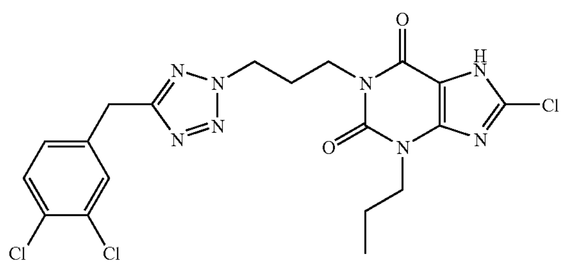 | 8-chloro-1-(3-{5-[(3,4-dichlorophenyl)methyl]-2H-tetrazol-2-yl}propyl)-3-propyl-3,7-dihydro-1H-purine-2,6-dione | 19.4 mg (20%) | m/z 497 [MH]+ RT 3.44 min |
| 48 | 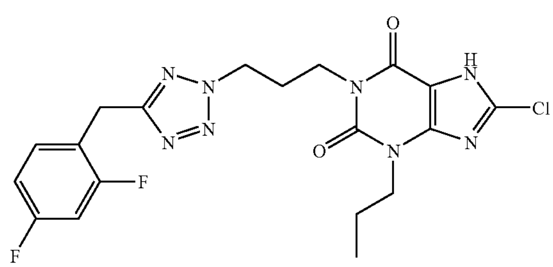 | 8-chloro-1-(3-{5-[(2,4-difluorophenyl)methyl]-2H-tetrazol-2-yl}propyl)-3-propyl-3,7-dihydro-1H-purine-2,6-dione | 19.1 mg (21%) | m/z 465 [MH]+ RT 3.16 min |
| 49 | 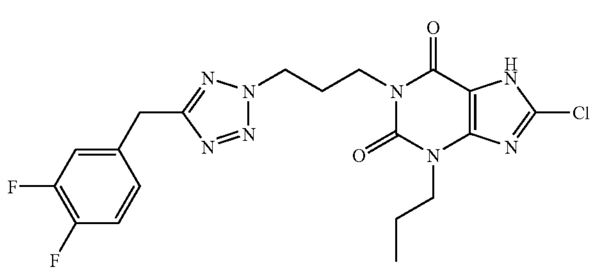 | 8-chloro-1-(3-{5-[(3,4-difluorophenyl)methyl]-2H-tetrazol-2-yl}propyl)-3-propyl-3,7-dihydro-1H-purine-2,6-dione | 21.5 mg (23%) | m/z 465 [MH]+ RT 3.19 min |
| 50 | 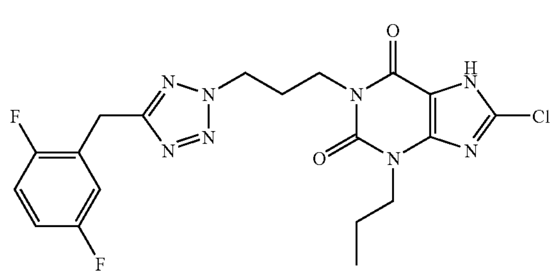 | 8-chloro-1-(3-{5-[(2,5-difluorophenyl)methyl]-2H-tetrazol-2-yl}propyl)-3-propyl-3,7-dihydro-1H-purine-2,6-dione | 8.5 mg (9%) | m/z 465 [MH]+ RT 3.14 min |

TABLE 3-continued

| # | Structure | Name | Yield | LC/MS: |
|---|-----------|------|-------|--------|
| 51 | 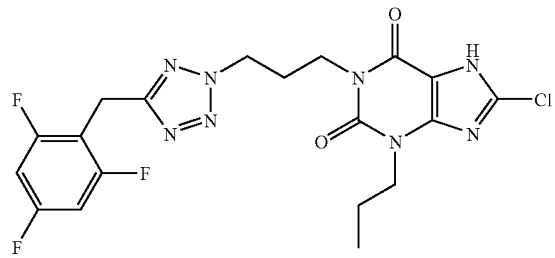 | 8-chloro-3-propyl-1-(3-{5-[(2,4,6-trifluorophenyl)methyl]-2H-tetrazol-2-yl}propyl)-3,7-dihydro-1H-purine-2,6-dione | 17.4 mg (18%) | m/z 483 [MH]+ RT 3.09 min |
| 52 | 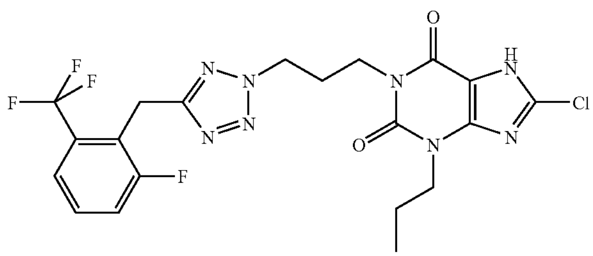 | 8-chloro-1-[3-(5-{[2-fluoro-6-(trifluoromethyl)phenyl]methyl}-2H-tetrazol-2-yl)propyl]-3-propyl-3,7-dihydro-1H-purine-2,6-dione | 22.3 mg (22%) | m/z 515 [MH]+ RT 3.28 min |
| 53 | 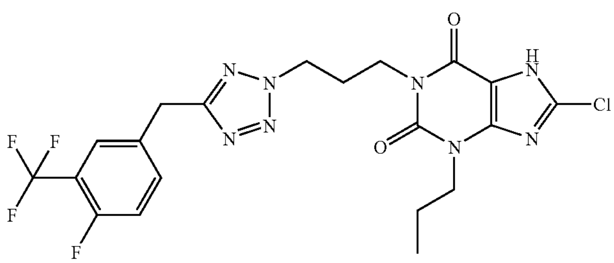 | 8-chloro-1-[3-(5-{[4-fluoro-3-(trifluoromethyl)phenyl]methyl}-2H-tetrazol-2-yl)propyl]-3-propyl-3,7-dihydro-1H-purine-2,6-dione | 17.2 mg (17%) | m/z 515 [MH]+ RT 3.30 min |
| 54 | 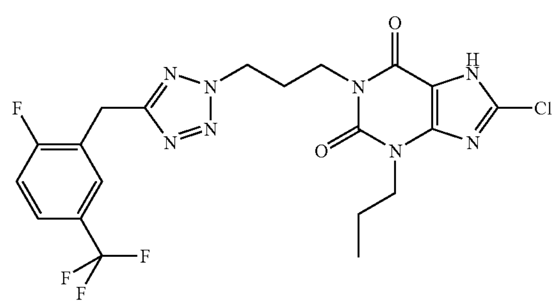 | 8-chloro-1-[3-(5-{[2-fluoro-5-(trifluoromethyl)phenyl]methyl}-2H-tetrazol-2-yl)propyl]-3-propyl-3,7-dihydro-1H-purine-2,6-dione | 18.2 mg (18%) | m/z 515 [MH]+ RT 3.34 min |
| 55 | 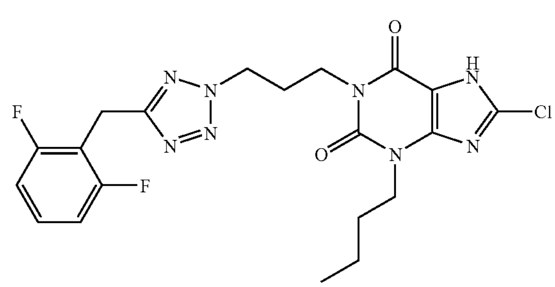 | 3-butyl-8-chloro-1-(3-{5-[(2,6-difluorophenyl)methyl]-2H-tetrazol-2-yl}propyl)-3,7-dihydro-1H-purine-2,6-dione | 18.2 mg (19%) | m/z 479 [MH]+ RT 3.29 min |

TABLE 3-continued

| # | Structure | Name | Yield | LC/MS: |
|---|---|---|---|---|
| 56 | 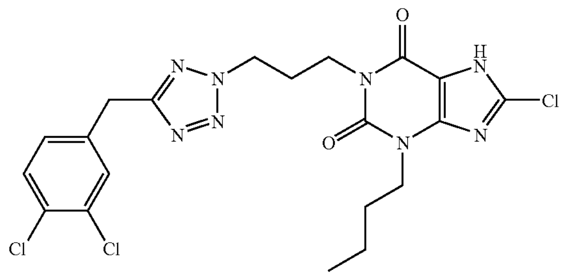 | 3-butyl-8-chloro-1-(3-{5-[(3,4-dichlorophenyl)methyl]-2H-tetrazol-2-yl}propyl)-3,7-dihydro-1H-purine-2,6-dione | 20.1 mg (20%) | m/z 511 [MH]+ RT 3.58 min |
| 57 | 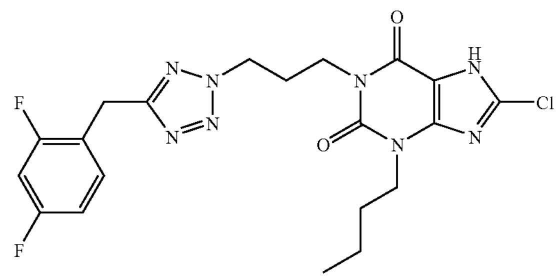 | 3-butyl-8-chloro-1-(3-{5-[(2,4-difluorophenyl)methyl]-2H-tetrazol-2-yl}propyl)-3,7-dihydro-1H-purine-2,6-dione | 19.3 mg (20%) | m/z 479 [MH]+ RT 3.33 min |
| 58 | 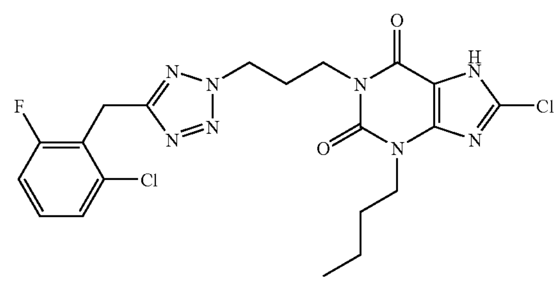 | 3-butyl-8-chloro-1-(3-{5-[(2-chloro-6-fluorophenyl)methyl]-2H-tetrazol-2-yl}propyl)-3,7-dihydro-1H-purine-2,6-dione | 18.9 mg (19%) | m/z 495 [MH]+ RT 3.33 min |
| 59 | 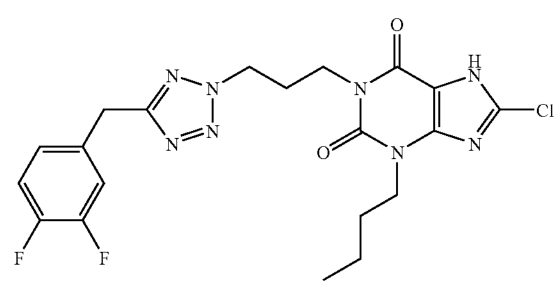 | 3-butyl-8-chloro-1-(3-{5-[(3,4-difluorophenyl)methyl]-2H-tetrazol-2-yl}propyl)-3,7-dihydro-1H-purine-2,6-dione | 21.7 mg (23%) | m/z 479 [MH]+ RT 3.33 min |
| 60 | 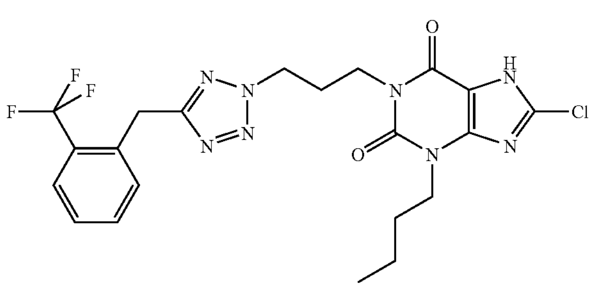 | 3-butyl-8-chloro-1-[3-(5-{[2-(trifluoromethyl)phenyl]methyl}-2H-tetrazol-2-yl)propyl]-3,7-dihydro-1H-purine-2,6-dione | 18.1 mg (18%) | m/z 511 [MH]+ RT 3.32 min |

TABLE 3-continued

| # | Structure | Name | Yield | LC/MS: |
|---|-----------|------|-------|--------|
| 61 | 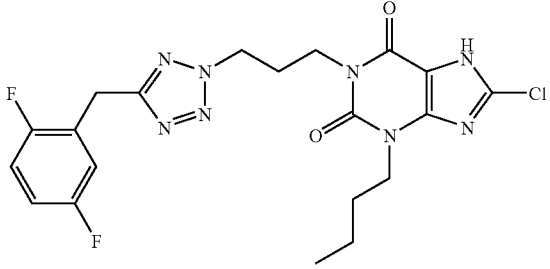 | 3-butyl-8-chloro-1-(3-{5-[(2,5-difluorophenyl)methyl]-2H-tetrazol-2-yl}propyl)-3,7-dihydro-1H-purine-2,6-dione | 24.0 mg (25%) | m/z 479 [MH]+ RT 3.31 min |
| 62 | 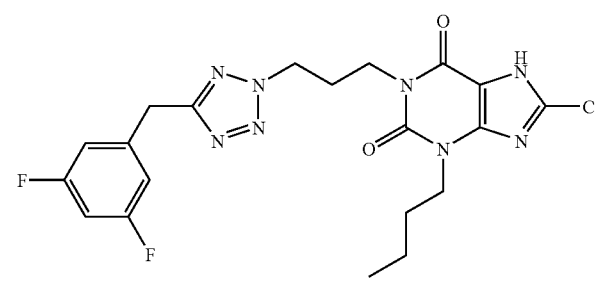 | 3-butyl-8-chloro-1-(3-{5-[(3,5-difluorophenyl)methyl]-2H-tetrazol-2-yl}propyl)-3,7-dihydro-1H-purine-2,6-dione | 15.9 mg (17%) | m/z 479 [MH]+ RT 3.38 min |
| 63 | 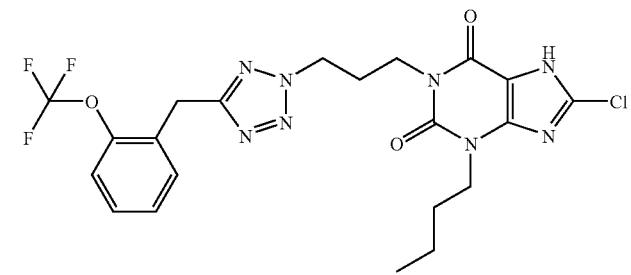 | 3-butyl-8-chloro-1-{3-[5-({2-[(trifluoromethyl)oxy]phenyl}methyl)-2H-tetrazol-2-yl]propyl}-3,7-dihydro-1H-purine-2,6-dione | 32.8 mg (31%) | m/z 527 [MH]+ RT 3.51 min |
| 64 | 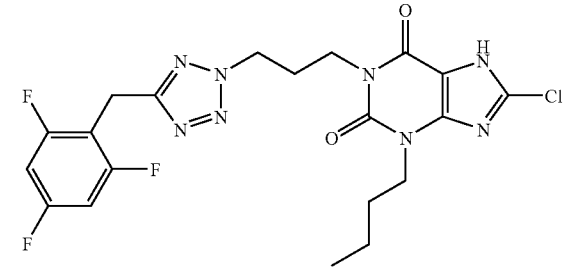 | 3-butyl-8-chloro-1-(3-{5-[(2,4,6-trifluorophenyl)methyl]-2H-tetrazol-2-yl}propyl)-3,7-dihydro-1H-purine-2,6-dione | 20.7 mg (21%) | m/z 497 [MH]+ RT 3.35 min |
| 65 | 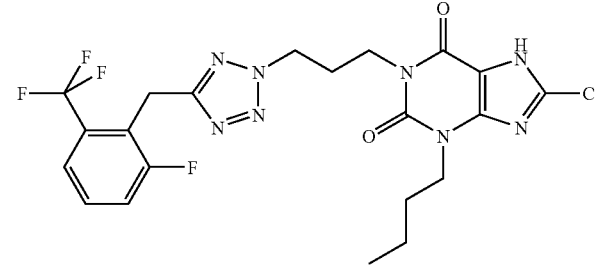 | 3-butyl-8-chloro-1-[3-(5-{[2-fluoro-6-(trifluoromethyl)phenyl]methyl}-2H-tetrazol-2-yl)propyl]-3,7-dihydro-1H-purine-2,6-dione | 23.9 mg (23%) | m/z 529 [MH]+ RT 3.44 min |

| # | Structure | Name | Yield | LC/MS: |
|---|---|---|---|---|
| 66 | 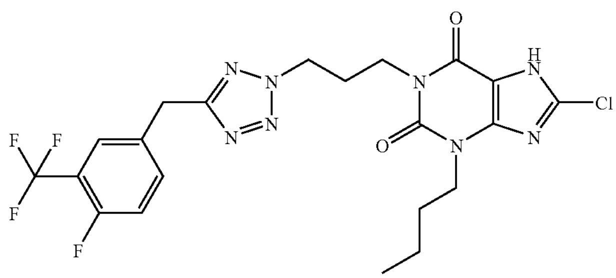 | 3-butyl-8-chloro-1-[3-(5-{[4-fluoro-3-(trifluoromethyl)phenyl]methyl}-2H-tetrazol-2-yl)propyl]-3,7-dihydro-1H-purine-2,6-dione | 13.9 mg (13%) | m/z 529 [MH]+ RT 3.53 min |
| 67 | 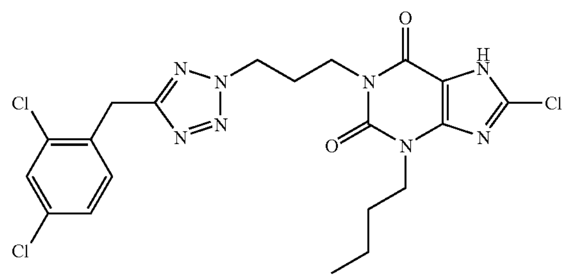 | 3-butyl-8-chloro-1-(3-{5-[(2,4-dichlorophenyl)methyl]-2H-tetrazol-2-yl}propyl)-3,7-dihydro-1H-purine-2,6-dione | 17.5 mg (17%) | m/z 511 [MH]+ RT 3.63 min |

NMR Details for Selected Examples from Table 3

Example 20

8-Chloro-1-(3-{5-[(4-fluorophenyl)methyl]-2H-tetrazol-2-yl}propyl)-3-propyl-3,7-dihydro-1H-purine-2,6-dione $^1$H NMR (CDCl$_3$) δ: 0.99 (t, 3H, J=7.5 Hz), 1.80 (m, 2H), 2.46 (m, 2H), 4.06 (m, 2H), 4.18 (s, 2H), 4.25 (t, 2H, J=7 Hz), 4.70 (t, 2H, J=7.5 Hz), 6.96 (m, 2H), 7.26 (m, 2H), 13.15 (br s, 1H).

Example 23

8-Chloro-3-(4,4,4-trifluorobutyl)-1-(3-{5-[(2,4,6-trifluorophenyl)methyl]-2H-tetrazol-2-yl}propyl)-3,7-dihydro-1H-purine-2,6-dione $^1$H NMR (CDCl$_3$) δ: 2.07 (m, 2H), 2.21 (m, 2H), 2.44 (m, 2H), 4.18 (t, 2H, J=7.1 Hz), 4.20 (s, 2H), 4.24, (t, 2H, J=6.8 Hz), 4.68 (t, 2H, J=7.3 Hz), 6.67 (t, 2H, J=8.1 Hz), 13.04 (br s, 1H).

Example 24

$^1$H NMR (CDCl$_3$): 2.03-2.10 (m, 2H), 2.16-2.28 (m, 2H), 2.43-2.50 (m, 2H), 4.16-4.19 (m, 2H), 4.17 (s, 2H), 4.24 (t, 2H, J=7.1 Hz), 4.71 (t, 2H, J=7.1 Hz), 7.00-7.13 (m, 3H), 13.06 (bs, 1H).

Example 27

$^1$H NMR (CDCl$_3$): 0.99 (t, 3H, J=7.5 Hz), 1.76-1.86 (m, 2H), 2.40-2.47 (m, 2H), 4.05-4.09 (m, 2H), 4.23-4.26 (m, 2H), 4.54 (s, 2H), 4.65-4.69 (m, 2H), 7.14-7.18 (m, 1H), 7.31-7.33, (m, 2H), 13.18 (bs, 1H).

Example 28

$^1$H NMR (CDCl$_3$): 0.97 (t, 3H, J=7.5 Hz), 1.36-1.46 (m, 2H), 1.71-1.79 (m, 2H), 2.42-2.49 (m, 2H), 4.08-4.11 (m, 2H), 4.25 (s, 2H), 4.24-4.27 (m, 2H), 4.68-4.71 (m, 2H), 7.02-7.09 (m, 2H), 7.20-7.26, (m, 2H), 13.14 (bs, 1H).

Example 29

$^1$H NMR (CDCl$_3$): 0.97 (t, 3H, J=7.5 Hz), 1.36-1.45 (m, 2H), 1.71-1.79 (m, 2H), 2.42-2.49 (m, 2H), 4.09 (t, 2H, J=7.5 Hz), 4.26 (t, 2H, J=7.5 Hz), 4.34 (s, 2H), 4.70 (t, 2H, J=7.3 Hz), 7.18-7.21 (m, 2H), 7.25-7.27, (m, 1H), 7.35-7.37, (m, 1H), 13.34 (bs, 1H).

Example 30

3-Butyl-8-chloro-1-(3-{5-[(3-fluorophenyl)methyl]-2H-tetrazol-2-yl}propyl)-3,7-dihydro-1H-purine-2,6-dione $^1$H NMR (CDCl$_3$) δ: 0.97 (t, 3H, J=7 Hz), 1.40 (m, 2H), 1.75 (m, 2H), 2.46 (m, 2H), 4.10 (t, 2H, J=7.5 Hz), 4.21 (s, 2H), 4.26 (t, 2H, J=6.5 Hz), 4.70 (t, 2H, J=7.5 Hz), 6.90 (m, 1H), 6.99 (m, 1H), 7.07 (m, 1H), 7.25 (m, 1H), 13.25 (br s, 1H).

Example 31

$^1$H NMR (CDCl$_3$): 0.99 (t, 3H, J=7.5 Hz), 1.38-1.48 (m, 2H), 1.73-1.81 (m, 2H), 2.44-2.51 (m, 2H), 4.12 (t, 2H, J=7.5 Hz), 4.20 (s, 2H), 4.27 (t, 2H, J=7.5 Hz), 4.70 (t, 2H, J=7.3 Hz), 6.95-7.00 (m, 2H), 7.26-7.30, (m, 2H), 13.35 (bs, 1H).

Example 32

3-Butyl-8-chloro-1-(3-{5-[(4-fluorophenyl)methyl]-2H-tetrazol-2-yl}propyl)-3,7-dihydro-1H-purine-2,6-dione $^1$H NMR (CDCl$_3$) δ: 0.99 (t, 3H, J=7 Hz), 1.43 (m, 2H), 1.77 (m, 2H), 2.48 (m, 2H), 4.12 (t, 2H, J=7.5 Hz), 4.20 (s, 2H), 4.27 (t, 2H, J=7 Hz), 4.72 (t, 2H, J=7.5 Hz), 6.98 (m, 2H), 7.27 (m, 2H), 13.35 (br s, 1H).

Example 33

3-Butyl-8-chloro-1-(3-{5-[(4-chlorophenyl)methyl]-2H-tetrazol-2-yl}propyl)-3,7-dihydro-1H-purine-2,6-dione ¹H NMR (CDCl₃) δ: 1.02 (t, 3H, J=7.5 Hz), 1.45 (m, 2H), 1.79 (m, 2H), 2.50 (m, 2H), 4.14 (t, 2H, J=7.5 Hz), 4.22 (s, 2H), 4.29 (t, 2H, J=7 Hz), 4.75 (t, 2H, J=7.5 Hz), 7.27 (s, 4H), 13.35 (br s, 1H).

Example 48

8-Chloro-1-(3-{5-[(2,4-difluorophenyl)methyl]-2H-tetrazol-2-yl}propyl)-3-propyl-3,7-dihydro-1H-purine-2,6-dione ¹H NMR (CDCl₃) δ: 0.99 (t, 3H, J=7.5 Hz), 1.80 (m, 2H), 2.45 (m, 2H), 4.06 (m, 2H), 4.20 (s, 2H), 4.25 (t, 2H, J=7 Hz), 4.70 (t, 2H, J=7.5 Hz), 6.80 (m, 2H), 7.23 (m, 1H).

Example 51

8-Chloro-3-propyl-1-(3-{5-[(2,4,6-trifluorophenyl)methyl]-2H-tetrazol-2-yl}propyl)-3,7-dihydro-1H-purine-2,6-dione ¹H NMR (CDCl₃) δ: 0.99 (t, 3H, J=7.3 Hz), 1.80 (m, 2H), 1.98 (m, 2H), 2.01 (m, 2H), 4.20 (s, 2H), 4.25 (t, 2H, J=6.5 Hz), 4.67 (t, 2H, J=7.3 Hz), 6.68 (t, 2H, J=8.1 Hz).

Example 52

¹H NMR (CDCl₃): 0.99 (t, 3H, J=7.3 Hz), 1.76-1.85 (m, 2H), 2.39-2.46 (m, 2H), 4.05-4.08 (m, 2H), 4.24 (t, 2H, J=7.1 Hz), 4.39 (s, 2H), 4.64 (t, 2H, J=7.1 Hz), 7.29-7.32 (m, 1H), 7.38-7.44, (m, 1H), 7.49-7.51, (m, 1H), 13.17 (bs, 1H).

Example 59

¹H NMR (CDCl₃): 0.99 (t, 3H, J=7.6 Hz), 1.36-1.45 (m, 2H), 1.71-1.79 (m, 2H), 2.42-2.49 (m, 2H), 4.09 (t, 2H, J=7.5 Hz), 4.17 (s, 2H), 4.24 (t, 2H, J=7.5 Hz), 4.71 (t, 2H, J=7.3 Hz), 7.00-7.14 (m, 3H), 13.07 (bs, 1H).

Example 61

¹H NMR (CDCl₃): 0.96 (t, 3H, J=7.2 Hz), 1.32-1.47 (m, 2H), 1.68-1.80 (m, 2H), 2.40-2.51 (m, 2H), 4.06-4.12 (m, 2H), 4.22 (s, 2H), 4.22-4.27 (m, 2H), 4.67-4.73 (m, 2H), 6.84-7.04 (m, 3H), 13.05 (bs, 1H).

Example 64

3-Butyl-8-chloro-1-(3-{5-[(2,4,6-trifluorophenyl)methyl]-2H-tetrazol-2-yl}propyl)-3,7-dihydro-1H-purine-2,6-dione ¹H NMR (CDCl₃) δ: 0.97 (t, 3H, J=7.3 Hz), 1.41 (m, 2H), 1.75 (m, 2H), 2.44 (m, 2H), 4.10 (t, 2H, J=7.5 Hz), 4.20 (s, 2H), 4.25 (t, 2H, J=6.5 Hz), 4.67 (t, 2H, J=7.4 Hz), 6.67 (t, 2H, J=8.0 Hz), 13.25 (br s, 1H).

Example 68

8-Chloro-3-pentyl-1-{3-[3-(phenylmethyl)-1,2,4-oxadiazol-5-yl]propyl}-3,7-dihydro-1H-purine-2,6-dione a) 8-Chloro-3-pentyl-1-{3-[3-(phenylmethyl)-1,2,4-oxadiazol-5-yl]propyl}-3,7-dihydro-1H-purine-2,6-dione

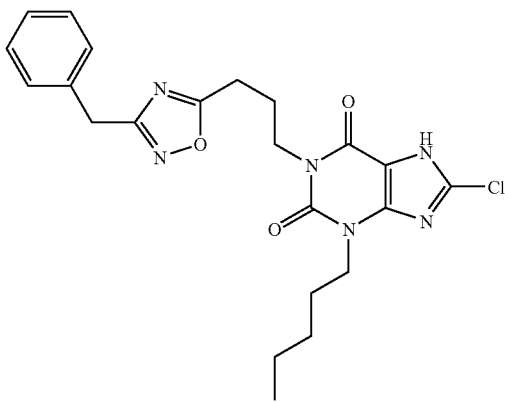

A solution of 3-[3-(phenylmethyl)-1,2,4-oxadiazol-5-yl]-1-propanol (88 mg, 0.4 mmol) in THF (4 ml) was treated with 8-chloro-3-pentyl-7-(2-propen-1-yl)-3,7-dihydro-1H-purine-2,6-dione (100 mg, 0.34 mmol) and PPh₃ (115 mg, 0.44 mmol) under nitrogen. DBAD (101 mg, 0.44 mmol) was added in one portion and the reaction left to react for 5 h. The mixture was degassed by applying a vacuum and then nitrogen was introduced. Pd(PPh₃)₄ (39 mg, 0.034 mmol) was added and the mixture degassed once more. Morpholine (294 μl, 3.4 mmol) was added and the mixture was stirred under nitrogen for 3 h. The mixture was partitioned between 2M HCl (aq) and EtOAc. The organic layer was separated, washed with brine, dried (MgSO₄) and concentrated. The title compound was obtained as a white solid after purification by MDAP (64 mg, 42%).

LC/MS: m/z 457 [MH]⁺, RT 3.4 min.

¹H NMR (DMSO-d₆) δ: 0.85 (t, 3H, J=7 Hz), 1.22-1.34 (m, 4H), 1.62 (m, 2H), 2.02 (m, 2H), 2.91 (t, 2H, J=7 Hz), 3.88 (t, 2H, J=7 Hz), 3.95-4.00 (m, 4H), 7.22-7.33 (m, 5H), 14.5 (br s, 1H).

b) 3-[3-(Phenylmethyl)-1,2,4-oxadiazol-5-yl]-1-propanol

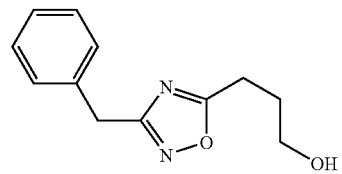

A mixture of γ-butyrolactone (223 µl, 2.9 mmol), benzamidine oxime (480 mg, 3.2 mmol), 21% solution of NaOEt in EtOH (1.3 ml) and EtOH (3 ml) was heated in the microwave at 140° C. for 10 min. The mixture was partitioned between 2M HCl (aq) and EtOAc. The organic layer was separated, washed with brine, dried (MgSO$_4$) and concentrated. The title product was purified over silica using the Companion™ system to give a pale yellow oil (143 mg, 23%).

LC/MS: m/z 219 [MH]$^+$, RT 2.4 min.

Example 69

8-Chloro-1-(3-{3-[(4-chlorophenyl)methyl]-1,2,4-oxadiazol-5-yl}propyl)-3-pentyl-3,7-dihydro-1H-purine-2,6-dione a) 8-Chloro-1-(3-{3-[(4-chlorophenyl)methyl]-1,2,4-oxadiazol-5-yl}propyl)-3-pentyl-3,7-dihydro-1H-purine-2,6-dione

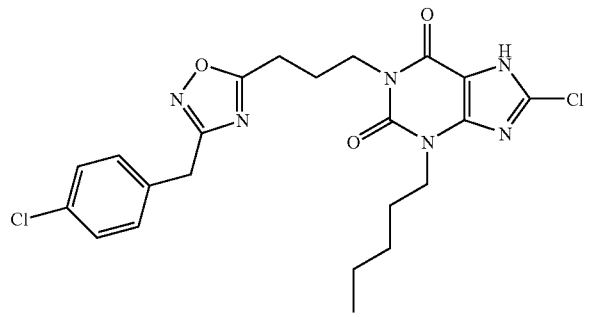

A solution of 8-chloro-1-(3-{3-[(4-chlorophenyl)methyl]-1,2,4-oxadiazol-5-yl}propyl)-3-pentyl-7-(2-propen-1-yl)-3,7-dihydro-1H-purine-2,6-dione (0.18 g, 0.34 mmol) in DMF (5 ml) was degassed by sequential evacuation of the flask and admission of nitrogen (×3) and morpholine (0.5 ml, 5.8 mmol), and Pd(PPh$_3$)$_4$ (80 mg, 0.068 mmol) added. The solution was stirred for 72 h then concentrated and the residues loaded onto an aminopropyl SPE (10 g) with MeOH. Elution with MeOH followed by 5% AcOH/MeOH provided the title compound as a pale yellow solid, which was washed with ether to yield a white solid (0.053 g, 32%).

LC/MS: m/z 491 [MH]$^+$, RT 3.69 min b) 8-Chloro-1-(3-{3-[(4-chlorophenyl)methyl]-1,2,4-oxadiazol-5-yl}propyl)-3-pentyl-7-(2-propen-1-yl)-3,7-dihydro-1H-purine-2,6-dione i)

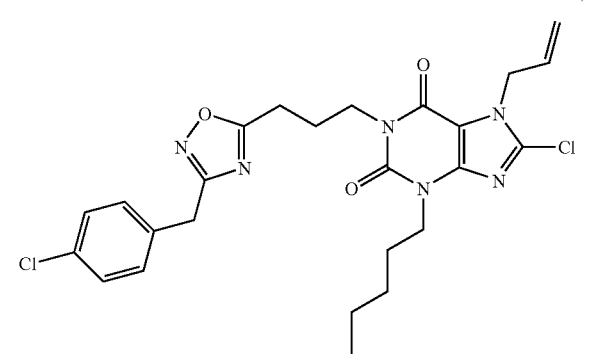

i) A mixture of γ-butyrolactone (8 ml, 104 mmol), 4-chlorobenzamidine oxime (3.0 g, 16.25 mmol), 30% solution of NaOMe in MeOH (5 ml) and MeOH (80 ml) was refluxed for 30 h, cooled and concentrated. The residues were purified by flash chromatography over silica eluting with DCM/EtOH/0.88 aq ammonia (200:8:1) to provide a yellow oil (13 g). This material was dissolved in DCM (150 ml) and washed with 2M sodium hydroxide (100 ml) and the organics separated, dried and concentrated to yield 3-{3-[(4-chlorophenyl)methyl]-1,2,4-oxadiazol-5-yl}-1-propanol as a viscous oil (3.95 g, 96%) which was used in the next step.

ii) To a solution of 8-chloro-3-pentyl-7-(2-propen-1-yl)-3,7-dihydro-1H-purine-2,6-dione (0.10 g, 0.34 mmol), 3-{3-[(4-chlorophenyl)methyl]-1,2,4-oxadiazol-5-yl}-1-propanol (0.086 g, 0.34 mmol) and triphenylphosphine (0.186 g, 0.69 mmol) in THF (5 ml) was added dibenzylazodicarboxylate (0.204 g, 0.68 mmol) and the solution stirred for 18 h. The solution was then concentrated and the residues chromatographed over silica (20 g, SPE) eluting with DCM initially then DCM/Et$_2$O mixtures to yield the title compound contaminated with dibenzylazodicarboxylate by-products (0.18 g). Material used crude in deprotection step.

LC/MS: m/z 531 [MH]$^+$, RT 3.83 min.

Example 70

8-Chloro-1-{3-[3-(phenylmethyl)-1,2,4-oxadiazol-5-yl]propyl}-3-propyl-3,7-dihydro-1H-purine-2,6-dione a) 8-Chloro-1-{3-[3-(phenylmethyl)-1,2,4-oxadiazol-5-yl]propyl}-3-propyl-3,7-dihydro-1H-purine-2,6-dione

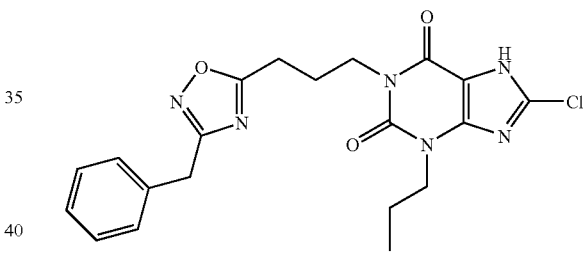

A solution of 8-chloro-7-(2-propen-1-yl)-3-propyl-3,7-dihydro-1H-purine-2,6-dione (200 mg, 0.74 mmol) in THF (4 ml) was treated with 3-[3-(phenylmethyl)-1,2,4-oxadiazol-5-yl]-1-propanol (195 mg, 0.89 mmol) and PPh$_3$ (254 mg, 0.96 mmol). DBAD (223 mg, 0.96 mmol) was added in one portion and the mixture was left to stir at rt under nitrogen for 18 h. The mixture was partitioned between EtOAc and 2M HCl (aq). The organic layer was separated, washed with brine, dried (MgSO$_4$) and concentrated. The crude product was purified by a silica SPE column using a 0-70% cyclohexane/EtOAc gradient. The product fractions were combined, concentrated and further purified by a silica SPE column using a 0-60% cyclohexane/EtOAc gradient. The product fractions were combined and concentrated then dissolved in anhydrous THF (4 ml). The solution was degassed by high vacuum then Pd(PPh$_3$)$_4$ (86 mg, 0.074 mmol) and morpholine (644 µl, 7.4 mmol) were added and the mixture left to stir at rt under nitrogen for 1 day. The mixture was partitioned between EtOAc and HCl (aq). The organic layer was separated, washed with brine, dried (MgSO$_4$) and concentrated by high vacuum. The crude product was purified by an aminopropyl SPE using MeOH to load the compound onto the column and wash through the impurities then a 2-4% AcOH/MeOH gradient to elute the product. The product fractions were combined and concentrated by high vacuum to leave the title compound as a white solid (74 mg, 23%).

LC/MS: m/z 429 [MH]$^+$, RT 3.14 min.

¹H NMR; (DMSO-d₆) δ: 0.87 (t, 3H, J=7.5 Hz), 1.65 (m, 2H), 2.02 (m, 2H), 2.91 (t, 2H, J=7.5 Hz), 3.86 (t, 2H, J=7 Hz), 3.97 (s, t overlapping, 4H), 7.27 (m, 5H) 14.46 (s, 1H).

b) 8-Chloro-7-(2-propen-1-yl)-3-propyl-3,7-dihydro-1H-purine-2,6-dione

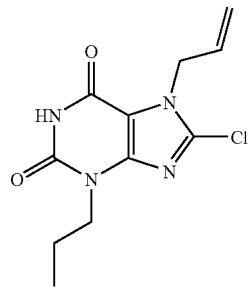

A mixture of 8-chloro-7-(2-propen-1-yl)-3,7-dihydro-1H-purine-2,6-dione (1.5 g, 6.6 mmol), 1-iodopropane (1.2 g, 6.9 mmol) and sodium carbonate (0.9 g, 8.5 mmol) in DMF (40 ml) was heated at 50° C. for 18 h. The reaction mixture was concentrated in vacuo and the residue treated with water (60 ml) and extracted with EtOAc (3×80 ml). The combined organic extracts were dried (MgSO₄) filtered and evaporated. The residue was triturated with ether/cyclohexane, the solid was filtered off and dried to afford the title compound (0.82 g, 46%).
LC/MS: m/z 269 [MH]⁺.

Example 71

8-Chloro-3-pentyl-1-{3-[3-(3-thienylmethyl)-1,2,4-oxadiazol-5-yl]propyl}-3,7-dihydro-1H-purine-2,6-dione a) 8-Chloro-3-pentyl-1-{3-[3-(3-thienylmethyl)-1,2,4-oxadiazol-5-yl]propyl}-3,7-dihydro-1H-purine-2,6-dione

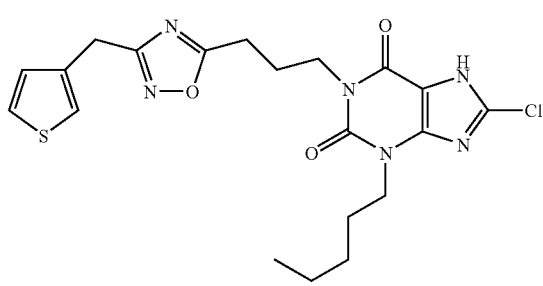

A mixture of ethyl 4-(8-chloro-2,6-dioxo-3-pentyl-2,3,6,7-tetrahydro-1H-purin-1-yl)butanoate (70 mg, 0.19 mmol), N-hydroxy-2-(3-thienyl)ethanimidamide (36 mg, 0.23 mmol), 21% solution of NaOEt in EtOH (78 μl, 0.21 mmol) and EtOH (1.5 ml) was heated in the microwave at 140° C. for 10 min. After cooling the reaction was partitioned between 2M HCl (aq) and EtOAc. The organic layer was separated and the aqueous layer extracted again with EtOAc. The combined extracts were concentrated and purified by MDAP. The title compound was freeze dried from 1,4-dioxane to give a white solid (27 mg, 31%).
LC/MS: m/z 463 [MH]⁺, RT 3.4 min.

b) Ethyl 4-(8-chloro-2,6-dioxo-3-pentyl-2,3,6,7-tetrahydro-1H-purin-1-yl)butanoate

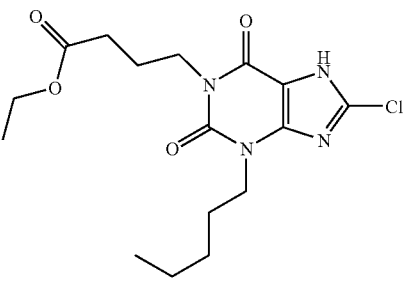

A solution of 8-chloro-3-pentyl-7-(2-propen-1-yl)-3,7-dihydro-1H-purine-2,6-dione (3.0 g, 10.1 mmol) in anhydrous DMF (35 ml) was treated with Cs₂CO₃ (3.6 g, 11.1 mmol) and ethyl 4-bromobutyrate (1.6 ml, 11.1 mmol). The mixture was stirred at rt for 18 h then degassed under a gentle vacuum, then nitrogen introduced. This was repeated twice. Pd(PPh₃)₄ (1.17 g, 1.0 mmol) was added and the mixture degassed once more. Morpholine (8.8 ml, 101 mmol) was added and left to stir for 3 h at rt. The mixture was partitioned between 2M HCl (aq) and EtOAc. The organic layer was separated, washed with brine, dried (MgSO₄) and concentrated, giving a yellow solid (5.16 g). The residue was taken up in MeOH and divided into two equal portions, and then each passed down an aminopropyl SPE (20 g), eluting with MeOH followed by 5% AcOH/MeOH. The product fractions were combined and concentrated giving the title compound as a near white solid (3.01 g, 80%).
LC/MS: m/z 371 [MH]⁺, RT 3.2 min.

Example 72

3-Butyl-8-chloro-1-{3-[3-(2,3-difluorobenzyl)-1,2,4-oxadiazol-5-yl]propyl}-3,7-dihydro-1H-purine-2,6-dione a) 3-Butyl-8-chloro-1-{3-[3-(2,3-difluorobenzyl)-1,2,4-oxadiazol-5-yl]propyl}-3,7-dihydro-1H-purine-2,6-dione

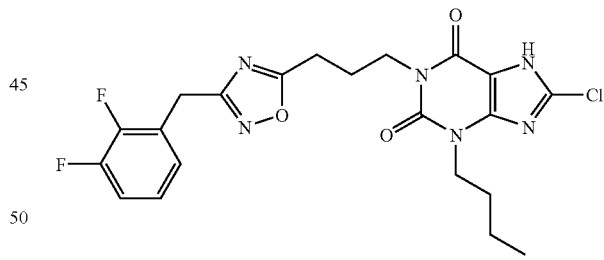

2,3-Difluorophenylacetonitrile (23 mg, 0.15 mmol) was dissolved in EtOH (1 ml). Hydroxylamine hydrochloride (14 mg, 0.20 mmol) was added, followed by water (0.5 ml) and potassium carbonate (41 mg, 0.3 mmol). The mixture was heated at reflux overnight and then cooled and partitioned between EtOAc and brine. The organic phase was evaporated and the crude amidoxime thus obtained was dissolved in EtOH (1 ml). Ethyl 4-(3-butyl-8-chloro-2,6-dioxo-2,3,6,7-tetrahydro-1H-purin-1-yl)butanoate (43 mg, 0.12 mmol) and 21% by wt. ethanolic sodium ethoxide ((0.067 ml, 0.18 mmol) was added and the mixture heated in the microwave reactor at 140° C. for 10 min. The mixture was partitioned between EtOAc and 2M HCl, the organic phase evaporated and the product purified by MDAP to provide the title compound as a solid (13 mg).
LC/MS: m/z 479 [MH]⁺, RT 3.52 min.

¹H NMR (MeOH-d₄) δ: 0.96 (t, 3H, J=7 Hz), 1.34-1.45 (m, 2H), 1.65-1.75 (m, 2H), 2.13-2.22 (m, 2H), 2.97 (t, 2H, J=7 Hz), 4.00 (t, 2H, J=7 Hz), 4.05 (s, 2H), 4.12 (t, 2H, J=7 Hz), 7.03-7.25 (m, 3H).

b) Ethyl 4-(3-butyl-8-chloro-2,6-dioxo-2,3,6,7-tetrahydro-1H-purin-1-yl)butanoate

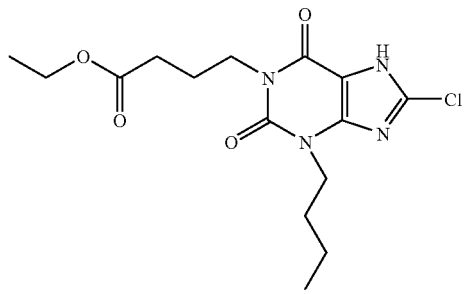

To 3-butyl-8-chloro-7-(2-propen-1-yl)-3,7-dihydro-1H-purine-2,6-dione (6.0 g, 21.24 mmol) in dry DMF (100 ml) was added Cs₂CO₃ (7.62 g, 23.36 mmol) followed by ethyl 4-bromobutyrate (4.556 g, 23.36 mmol). The mixture was heated at 55° C. for 18 h and allowed to cool then degassed by repeatedly evacuating and readmitting nitrogen. Morpholine (14.9 g, 171 mmol) was added followed by tetrakis(triphenylphosphine)palladium(0) (4.0 g, 3.46 mmol) and the mixture was stirred for 4 h. EtOAc (300 ml) and 2M HCl (150 ml) and water (100 ml) were added and the organic phase separated, washed with brine (3×100 ml) and filtered. The filtrate was dried (Na₂SO₄) and evaporated. The crude product (10 g) was purified by aminopropyl SPE (3×20 g), loading in THF/MeOH (1:1), washing with THF/MeOH (1:1) and neat MeOH and eluting the product with DCM/MeOH (1:1) containing 5% added AcOH to afford the title compound (5.08 g).

LC/MS: m/z 357 [MH]⁺, RT 3.06 min.

¹H NMR (d⁴ MeOH) 0.96 (3H, t, J=7 Hz), 1.33-1.42 (2H, m), 1.64-1.74 (2H, m), 2.12-2.21 (2H, m), 2.95 (2H, t, J=8 Hz), 3.99 (2H, t, J=7 Hz), 4.03 (2H, s), 4.11 (2H, t, J=7 Hz), 7.03-7.21 (3H, m).

Example 73

3-Butyl-8-chloro-1-{3-[3-(2-chlorobenzyl)-1,2,4-oxadiazol-5-yl]propyl}-3,7-dihydro-1H-purine-2,6-dione

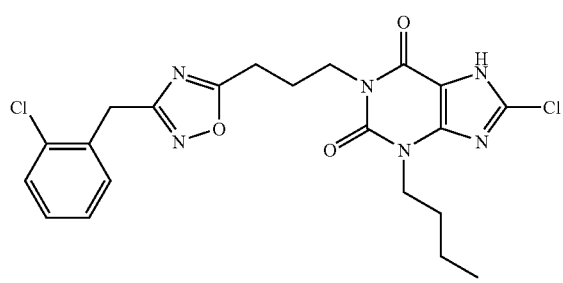

Ethyl 4-(3-butyl-8-chloro-2,6-dioxo-2,3,6,7-tetrahydro-1H-purin-1-yl)butanoate (53 mg, 0.15 mmol) and (1Z)-2-(2-chlorophenyl)-N-hydroxyethanimidamide (30 mg, 0.18 mmol; Entry 1, table 7) were heated in EtOH (0.75 ml) with 21% ethanolic sodium ethoxide (0.083 ml, 0.22 mmol) at 140° C. for 10 min. The mixture was then partitioned between EtOAc and 2M HCl and the organic phase evaporated. The product was purified by MDAP to yield the title compound as a solid (34.8 mg).

LC/MS: m/z 477 [MH]⁺, RT 3.59 min.

¹H NMR (d⁶ DMSO) 0.89 (3H, t, J=8 Hz), 1.24-1.34 (2H, m), 1.56-1.65 (2H, m), 1.98-2.07 (2H, m), 2.92 (2H, t, J=7 Hz), 3.89 (2H, t, J=7 Hz), 3.98 (2H, t, J=7 Hz), 4.09 (2H, s), 7.28-7.48 (4H, m).

Example 74

3-Butyl-8-chloro-1-{3-[3-(4-fluorobenzyl)-1,2,4-oxadiazol-5-yl]propyl}-3,7-dihydro-1H-purine-2,6-dione

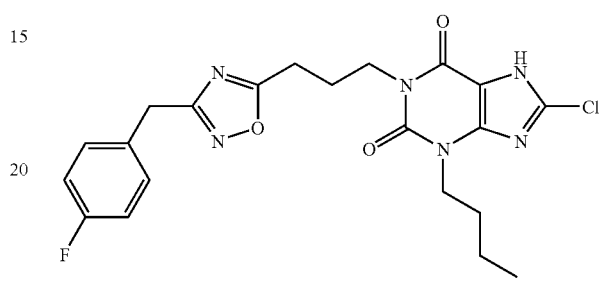

Starting from (1Z)-2-(4-fluorophenyl)-N-hydroxyethanimidamide (28 mg, 0.18 mmol; Entry 2, Table 7) was similarly obtained the title compound as a solid (10.0 mg).

LC/MS: m/z 461 [MH]⁺, RT 3.49 min.

Example 75

3-Butyl-8-chloro-1-{3-[3-(2,3-dichlorobenzyl)-1,2,4-oxadiazol-5-yl]propyl}-3,7-dihydro-1H-purine-2,6-dione

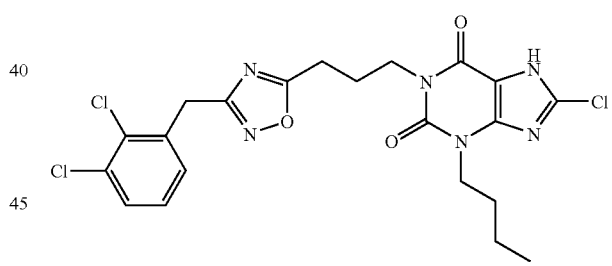

Ethyl 4-(3-butyl-8-chloro-2,6-dioxo-2,3,6,7-tetrahydro-1H-purin-1-yl)butanoate (53 mg, 0.15 mmol) and (1Z)-2-(2,3-dichlorophenyl)-N-hydroxyethanimidamide (36 mg, 0.165 mmol; Entry 3, Table 7) and 21% ethanolic sodium ethoxide (0.083 ml, 0.22 mmol) were heated together in EtOH (0.75 ml) in the microwave reactor at 140° C. for 10 min. The mixture was then partitioned between EtOAc and 2M HCl, the organic phase separated, evaporated and the product purified by MDAP to give the title compound as a solid (42.1 mg).

LC/MS: m/z 511, 513, 515 (isotopes) [MH]⁺, RT 3.66 min.

The following compounds (Table 4) were prepared using a method analogous to that for Example 75, using the appropriate amidoxime, (with the exceptions that for Example 87 (Table 4) during workup the pH was adjusted to 5 prior to extraction with EtOAc; and in the case of Example 88 (Table 4) the crude product was stirred for 18 h with EtOH (1 ml) and 2M NaOH (0.5 ml) and Example 89 (Table 4) was stirred for 18 h with EtOH (0.75 ml) and 2M NaOH (0.5 ml) prior to repeat workup and purification by MDAP).

TABLE 4

| Example | Structure | Amidoxime (see table 7) | Wt of amidoxime Mg | Yield mg | LC/MS: |
|---|---|---|---|---|---|
| 76 | 3-butyl-8-chloro-1-{3-[3-(3-fluorobenzyl)-1,2,4-oxadiazol-5-yl]propyl}-3,7-dihydro-1H-purine-2,6-dione | 4 | 28 | 32.4 | m/z 461 [MH]+ RT 3.41 min |
| 77 | 3-butyl-8-chloro-1-{3-[3-(3,4-difluorobenzyl)-1,2,4-oxadiazol-5-yl]propyl}-3,7-dihydro-1H-purine-2,6-dione | 5 | 31 | 28.3 | m/z 479 [MH]+ RT 3.46 min |
| 78 | 3-butyl-8-chloro-1-{3-[3-(3-chloro-2-fluorobenzyl)-1,2,4-oxadiazol-5-yl]propyl}-3,7-dihydro-1H-purine-2,6-dione | 6 | 33 | 32.3 | m/z 495 [MH]+ RT 3.55 min |
| 79 | 1-{3-[3-(1,3-benzodioxol-5-ylmethyl)-1,2,4-oxadiazol-5-yl]propyl}-3-butyl-8-chloro-3,7-dihydro-1H-purine-2,6-dione | 10 | 32 | 30.5 | m/z 487 [MH]+ RT 3.27 min |

TABLE 4-continued

| Example | Structure | Amidoxime (see table 7) | Wt of amidoxime Mg | Yield mg | LC/MS: |
|---|---|---|---|---|---|
| 80 | 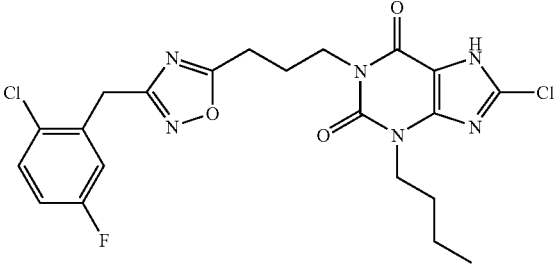<br>3-butyl-8-chloro-1-(3-{3-[(2-chloro-5-fluorophenyl)methyl]-1,2,4-oxadiazol-5-yl}propyl)-3,7-dihydro-1H-purine-2,6-dione | 19 | 33 | 26.2 | m/z 495 [MH]+ RT 3.47 min |
| 81 | 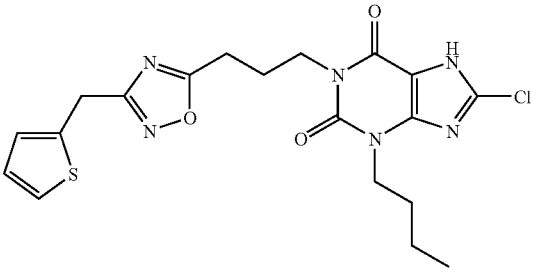<br>3-butyl-8-chloro-1-{3-[3-(2-thienylmethyl)-1,2,4-oxadiazol-5-yl]propyl}-3,7-dihydro-1H-purine-2,6-dione | 21 | 26 | 33.4 | m/z 449 [MH]+ RT 3.23 min |
| 82 | 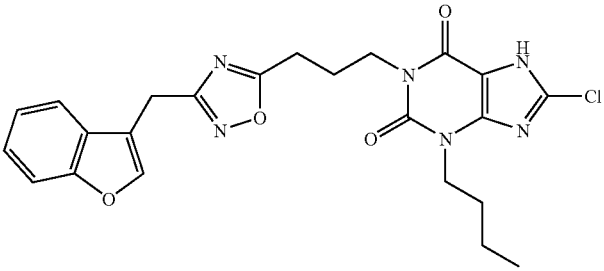<br>1-{3-[3-(1-benzofuran-3-ylmethyl)-1,2,4-oxadiazol-5-yl]propyl}-3-butyl-8-chloro-3,7-dihydro-1H-purine-2,6-dione | 22 | 31 | 27.3 | m/z 483 [MH]+ RT 3.47 min |
| 83 | 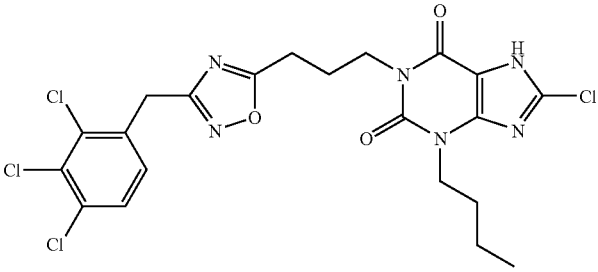<br>3-butyl-8-chloro-1-(3-{3-[(2,3,4-trichlorophenyl)methyl]-1,2,4-oxadiazol-5-yl}propyl)-3,7-dihydro-1H-purine-2,6-dione | 15 | 42 | 29.8 | m/z 545 [MH]+ RT 3.79 min |

TABLE 4-continued

| Example | Structure | Amidoxime (see table 7) | Wt of amidoxime Mg | Yield mg | LC/MS: |
|---|---|---|---|---|---|
| 84 | 3-butyl-8-chloro-1-(3-{3-[(2,5-difluorophenyl)methyl]-1,2,4-oxadiazol-5-yl}propyl)-3,7-dihydro-1H-purine-2,6-dione | 16 | 31 | 34.8 | m/z 479 [MH]$^+$ RT 3.35 min |
| 85 | 3-butyl-8-chloro-1-(3-{3-[(2,6-difluorophenyl)methyl]-1,2,4-oxadiazol-5-yl}propyl)-3,7-dihydro-1H-purine-2,6-dione | 17 | 31 | 38.2 | m/z 479 [MH]$^+$ RT 3.31 min |
| 86 | 3-butyl-8-chloro-1-(3-{3-[(3,5-difluorophenyl)methyl]-1,2,4-oxadiazol-5-yl)propyl)-3,7-dihydro-1H-purine-2,6-dione | 18 | 31 | 35.4 | m/z 479 [MH]$^+$ RT 3.39 min |

TABLE 4-continued

| Example | Structure | Amidoxime (see table 7) | Wt of amidoxime Mg | Yield mg | LC/MS: |
|---|---|---|---|---|---|
| 87 | 3-butyl-8-chloro-1-{3-[3-(1H-indol-3-ylmethyl)-1,2,4-oxadiazol-5-yl]propyl}-3,7-dihydro-1H-purine-2,6-dione | 20 | 31 | 16.1 | m/z 482 [MH]$^+$ RT 3.31 min |
| 88 | 3-butyl-8-chloro-1-(3-{3-[(3-hydroxyphenyl)methyl]-1,2,4-oxadiazol-5-yl}propyl)-3,7-dihydro-1H-purine-2,6-dione | 7 | 28 | 10 | m/z 459 [MH]$^+$ RT 3.07 min |
| 89 | N-[3-({5-[3-(3-butyl-8-chloro-2,6-dioxo-2,3,6,7-tetrahydro-1H-purin-1-yl)propyl]-1,2,4-oxadiazol-3-yl}methyl)phenyl]methanesulfonamide | 25 | 40 | 28.4 | m/z 536 [MH]$^+$ RT 3.03 min |

NMR Details for Selected Examples from Table 4

Example 76

3-butyl-8-chloro-1-{3-[3-(3-fluorobenzyl)-1,2,4-oxadiazol-5-yl]propyl}-3,7-dihydro-1H-purine-2,6-dione $^1$H NMR (DMSO-d$_6$) δ: 0.90 (t, 3H, J=7 Hz), 1.25-1.36 (m, 2H), 1.56-1.67 (m, 2H), 2.0-2.1 (m, 2H), 2.94 (t, 2H, J=7 Hz), 3.90 (t, 2H, J=7 Hz), 3.98 (t, 2H, J=7 Hz), 4.02 (s, 2H), 7.05-7.15 (m, 3H), 7.32-7.40 (m, 1H).

Example 77

3-Butyl-8-chloro-1-(3-[3-(3,4-difluorobenzyl)-1,2,4-oxadiazol-5-yl]propyl)-3,7-dihydro-1H-purine-2,6-dione $^1$H NMR (DMSO-d$_6$) δ: 0.89 (t, 3H, J=7.5 Hz), 1.25-1.34 (m, 2H), 1.56-1.65 (m, 2H), 1.99-2.07 (m, 2H), 2.92 (t, 2H, J=7 Hz), 3.89 (t, 2H, J=7 Hz), 3.98 (t, 2H, J=7 Hz), 4.02 (s, 2H), 7.10-7.15 (m, 1H), 7.32-7.39 (m, 2H), 14.45 (br s, 1H).

Example 79

1-{3-[3-(1,3-benzodioxol-5-ylmethyl)-1,2,4-oxadiazol-5-yl]propyl}-3-butyl-8-chloro-3,7-dihydro-1H-purine-2,6-dione $^1$H NMR (DMSO-d$_6$) δ: 0.90 (t, 3H, J=7 Hz), 1.25-1.36 (m, 2H), 1.58-1.68 (m, 2H), 1.98-2.09 (m, 2H), 2.92 (t, 2H, J=7 Hz), 3.88-3.95 (m, 4H), 3.99 (t, 2H, J=7 Hz), 5.98 (s, 2H), 6.70-6.86 (m, 3H).

Example 87

3-butyl-8-chloro-1-{3-[3-(1H-indol-3-ylmethyl)-1,2,4-oxadiazol-5-yl]propyl}-3,7-dihydro-1H-purine-2,6-dione $^1$H NMR (DMSO-d$_6$) δ: 0.89 (t, 3H, J=7 Hz), 1.23-1.36 (m, 2H), 1.56-1.67 (m, 2H), 1.96-2.08 (m, 2H), 2.90 (t, 2H, J=7 Hz), 3.90 (t, 2H, J=7 Hz), 3.99 (t, 2H, J=7 Hz), 4.04 (s, 2H), 6.92-7.50 (m, 5H), 10.95 (s, 1H).

Example 88

3-butyl-8-chloro-1-(3-{3-[(3-hydroxyphenyl)methyl]-1,2,4-oxadiazol-5-yl}propyl)-3,7-dihydro-1H-purine-2,6-dione $^1$H NMR (DMSO-d$_6$) δ: 0.90 (t, 3H, J=7 Hz), 1.25-1.38 (m, 2H), 1.57-1.68 (m, 2H), 1.96-2.07 (m, 2H), 2.92 (t, 2H, J=7 Hz), 3.86 (s, 2H), 3.89 (t, 2H, J=7 Hz), 3.99 (t, 2H, J=7 Hz), 6.58-6.68 (m, 3H), 7.08 (m, 1H), 9.40 (s, 1H).

Example 89

N-[3-({5-[3-(3-Butyl-8-chloro-2,6-dioxo-2,3,6,7-tetrahydro-1H-purin-1-yl)propyl]-1,2,4-oxadiazol-3-yl}methyl)phenyl]methanesulfonamide $^1$H NMR (DMSO-d$_6$) δ: 0.89 (t, 3H, J=7.5 Hz), 1.24-1.34 (m, 2H), 1.56-1.65 (m, 2H), 1.97-2.06 (m, 2H), 2.91 (t, 2H, J=7.5 Hz), 2.97 (s, 3H), 3.90 (t, 2H, J=7.5 Hz), 3.96 (s, 2H), 3.97 (t, 2H, J=7 Hz), 6.96-6.99 (m, 1H), 7.06-7.13 (m, 2H), 7.26 (t, 1H, J=8 Hz), 9.75 (s, 1H), 14.45 (br s, 1H).

Example 90

3-Butyl-8-chloro-1-(3-{3-[(3,4-dichlorophenyl)methyl]-1,2,4-oxadiazol-5-yl}propyl)-3,7-dihydro-1H-purine-2,6-dione

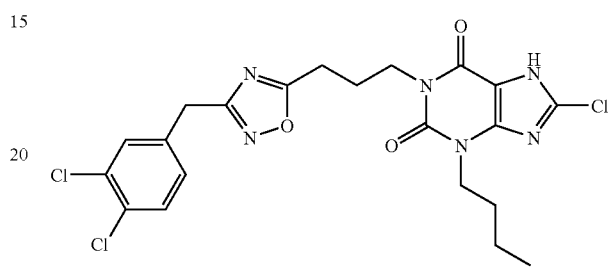

Ethyl 4-(3-butyl-8-chloro-2,6-dioxo-2,3,6,7-tetrahydro-1H-purin-1-yl)butanoate (71 mg, 0.2 mmol), (1Z)-2-(3,4-dichlorophenyl)-N-hydroxyethanimidamide (48 mg, 0.22 mmol) and 21% by wt. ethanolic sodium ethoxide (0.111 ml, 0.3 mmol) were heated together in EtOH (1 ml) in the microwave reactor at 140° C. for 10 min. The mixture was then partitioned between EtOAc and 2M HCl, the organic phase separated and evaporated, and the crude product was purified by MDAP to give the title compound as a solid (48.8 mg).

LC/MS: m/z 511, 513 [MH]$^+$, RT 3.65 min.

The following compounds (Table 5) were prepared using a method analogous to that for Example 90, using the appropriate amidoxime (with the exception that for Example 91, 0.185 ml, (0.5 mmol) of 21% sodium ethoxide was added in order to allow for the amidoximes being the hydrochloride salts).

TABLE 5

| Example | Structure | Amidoxime | Wt of amidoxime mg | Yield mg | LC/MS: |
|---|---|---|---|---|---|
| 91 | 3-butyl-8-chloro-1-[3-(3-{[3-(trifluoromethyl)phenyl]methyl}-1,2,4-oxadiazol-5-yl)propyl]-3,7-dihydro-1H-purine-2,6-dione | (1Z)-N-hydroxy-2-[3-(trifluoromethyl)phenyl]ethanimidamide hydrochloride | 56 | 46.5 | m/z 511 [MH]$^+$ RT 3.63 min |

TABLE 5-continued

| Example | Structure | Amidoxime | Wt of amidoxime mg | Yield mg | LC/MS: |
|---|---|---|---|---|---|
| 92 | 3-butyl-8-chloro-1-(3-{3-[(2,6-dichlorophenyl)methyl]-1,2,4-oxadiazol-5-yl}propyl)-3,7-dihydro-1H-purine-2,6-dione | (1Z)-N-2-(2,6-dichlorophenyl)-N-hydroxy-ethanimidamide | 48 | 53.8 | m/z 511 [MH]$^+$ RT 3.64 min |
| 93 | 3-butyl-8-chloro-1-{3-[3-(1-naphthalenylmethyl)-1,2,4-oxadiazol-5-yl]propyl}-3,7-dihydro-1H-purine-2,6-dione | (1Z)-N-hydroxy-2-(1-naphthalenyl)ethanimidamide | 44 | 48.6 | m/z 493 [MH]$^+$ RT 3.67 min |
| 94 | 3-butyl-8-chloro-1-(3-{3-[(4-chlorophenyl)methyl]-1,2,4-oxadiazol-5-yl}propyl)-3,7-dihydro-1H-purine-2,6-dione | (1Z)-2-(4-chlorophenyl)-N-hydroxy-ethanimidamide | 41 | 35.6 | m/z 477 [MH]$^+$ RT 3.60 min |

TABLE 5-continued

| Example | Structure | Amidoxime | Wt of amidoxime mg | Yield mg | LC/MS: |
|---|---|---|---|---|---|
| 95 | 3-butyl-8-chloro-1-(3-{3-[(3-chlorophenyl)methyl]-1,2,4-oxadiazol-5-yl}propyl)-3,7-dihydro-1H-purine-2,6-dione | (1Z)-2-(3-chlorophenyl)-N-hydroxy-ethanimidamide | 41 | 39.4 | m/z 477 [MH]+ RT 3.64 min |
| 96 | 3-butyl-8-chloro-1-(3-{3-[(4-hydroxyphenyl)methyl]-1,2,4-oxadiazol-5-yl}propyl)-3,7-dihydro-1H-purine-2,6-dione | (1Z)-N-hydroxy-2-(4-hydroxyphenyl)-ethanimidamide | 36 | 53.5 | m/z 459 [MH]+ RT 3.08 min |
| 97 | 3-butyl-8-chloro-1-[3-(3-{[3-(trifluoromethyl)-1H-pyrazol-1-yl]methyl}-1,2,4-oxadiazol-5-yl)propyl]-3,7-dihydro-1H-purine-2,6-dione | (1Z)-N-hydroxy-2-[3-(trifluoromethyl)-1H-pyrazol-1-yl]ethanimidamide | 46 | 58.1 | m/z 501 [MH]+ RT 3.33 min |
| 98 | 3-butyl-8-chloro-1-{3-[3-(3-thienylmethyl)-1,2,4-oxadiazol-5-yl]propyl}-3,7-dihydro-1H-purine-2,6-dione | (1Z)-N-hydroxy-2-(3-thienyl)-ethanimidamide | 34 | 32.6 | m/z 449 [MH]+ RT 3.31 min |

NMR Details for Selected Examples from Table 5

Example 91

$^1$H NMR (d$^6$ DMSO) 0.88 (3H, t, J=7 Hz), 1.24-1.33 (2H, m), 1.56-1.65 (2H, m), 1.98-2.06 (2H, m), 2.92 (2H, t, J=7 Hz), 3.89 (2H, t, J=7 Hz), 3.97 (2H, t, J=7 Hz), 4.14 (2H, s), 7.52-7.70 (4H, m).

Example 94

3-butyl-8-chloro-1-(3-{3-[(4-chlorophenyl)methyl]-1,2,4-oxadiazol-5-yl}propyl)-3,7-dihydro-1H-purine-2,6-dione $^1$H NMR (DMSO-d$_6$) δ: 0.89 (t, 3H, J=7 Hz), 1.23-1.37 (m, 2H), 1.55-1.67 (m, 2H), 1.97-2.09 (m, 2H), 2.90 (t, 2H, J=7 Hz), 3.88 (t, 2H, J=7 Hz), 3.97 (t, 2H, J=7 Hz), 4.00 (s, 2H), 7.27-7.40 (m, 4H).

Example 96

3-butyl-8-chloro-1-(3-{3-[(4-hydroxyphenyl)methyl]-1,2,4-oxadiazol-5-yl}propyl)-3,7-dihydro-1H-purine-2,6-dione $^1$H NMR (DMSO-d$_6$) δ: 0.90 (t, 3H, J=7 Hz), 1.23-1.37 (m, 2H), 1.57-1.68 (m, 2H), 1.96-2.08 (m, 2H), 2.90 (t, 2H, J=7 Hz), 3.82 (s, 2H), 3.90 (t, 2H, J=7 Hz), 3.98 (t, 2H, J=7 Hz), 6.68 (d, 2H, J=9 Hz), 7.04 (d, 2H, J=9 Hz), 9.32 (s, 1H).

Example 97

3-butyl-8-chloro-1-[3-(3-{[3-(trifluoromethyl)-1H-pyrazol-1-yl]methyl}-1,2,4-oxadiazol-5-yl)propyl]-3,7-dihydro-1H-purine-2,6-dione $^1$H NMR (DMSO-d$_6$) δ: 0.90 (t, 3H, J=7 Hz), 1.23-1.36 (m, 2H), 1.57-1.69 (m, 2H), 1.95-2.08 (m, 2H), 2.95 (t, 2H, J=7 Hz), 3.91 (t, 2H, J=7 Hz), 3.97 (t, 2H, J=7 Hz), 5.62 (s, 2H), 6.79 (s, 1H), 8.10 (s, 1H).

Example 99

3-Butyl-8-chloro-1-[3-(3-{[3-(ethyloxy)-4-hydroxyphenyl]methyl}-1,2,4-oxadiazol-5-yl)propyl]-3,7-dihydro-1H-purine-2,6-dione

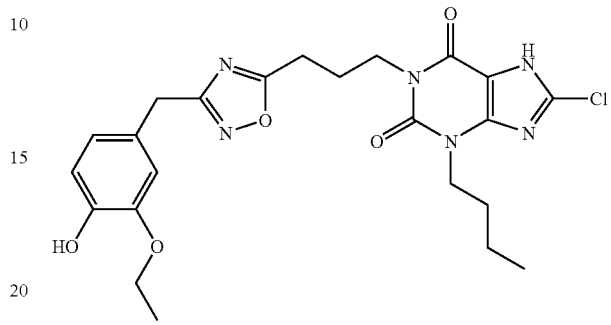

Ethyl 4-(3-butyl-8-chloro-2,6-dioxo-2,3,6,7-tetrahydro-1H-purin-1-yl)butanoate (53 mg, 0.15 mmol) and (1Z)-2-[3-(ethyloxy)-4-hydroxyphenyl]-N-hydroxyethanimidamide (35 mg, 0.165 mmol; entry 11, Table 7) were mixed in EtOH (0.75 ml). Ethanolic sodium ethoxide (21% by wt., 0.083 ml, 0.22 mmol) was added and the mixture was heated in the microwave at 140° C. for 10 min. A further 0.055 ml (0.15 mmol) of NaOEt solution was then added and the mixture heated for a further 10 min period at 140° C. The mixture was partitioned between EtOAc and 2M HCl and the organic phase evaporated and purified by MDAP to give the title compound as a solid (29.6 mg).

LC/MS: m/z 503 [MH]$^+$, RT 3.15 min.

The following compounds (Table 6) were prepared using a method analogous to that for Example 99, using the appropriate amidoxime (with the exception that for Example 100 (Table 6), the crude product after workup was stirred with EtOH (1 ml) and 2M NaOH (0.5 ml) overnight in order to hydrolyse residual starting ester, prior to repeat HCl workup and purification by MDAP).

TABLE 6

| Example | Structure | Amidoxime (see table 7) | Wt of aldoxime mg | Yield mg | LC/MS: |
|---|---|---|---|---|---|
| 100 | 3-butyl-8-chloro-1-[3-(3-{[4-hydroxy-3-(methyloxy)phenyl]methyl}-1,2,4-oxadiazol-5-yl)propyl]-3,7-dihydro-1H-purine-2,6-dione | 12 | 32 | 19.3 | m/z 489 [MH]$^+$ RT 2.98 min |

| Example | Structure | Amidoxime (see table 7) | Wt of aldoxime mg | Yield mg | LC/MS: |
|---|---|---|---|---|---|
| 101 | N-[3-({5-[3-(3-butyl-8-chloro-2,6-dioxo-2,3,6,7-tetrahydro-1H-purin-1-yl)propyl]-1,2,4-oxadiazol-3-yl}methyl)phenyl]acetamide | 14 | 34 | 23.6 | m/z 500 [MH]+ RT 2.94 min |

NMR Details for Selected Examples from Table 6

Example 101

N-[3-({5-[3-(3-butyl-8-chloro-2,6-dioxo-2,3,6,7-tetrahydro-1H-purin-1-yl)propyl]-1,2,4-oxadiazol-3-yl}methyl)phenyl]acetamide $^1$H NMR (DMSO-d$_6$) δ: 0.90 (t, 3H, J=7 Hz), 1.25-1.38 (m, 2H), 1.57-1.68 (m, 2H), 1.95-2.07 (m, 5H), 2.92 (t, 2H, J=7 Hz), 3.91 (t, 2H, J=7 Hz), 3.94 (s, 2H), 3.98 (m, 2H), 6.88-7.50 (m, 4H), 9.90 (s, 1H).

Example 102

3-Butyl-8-chloro-1-(3-{3-[(2-chloro-4-fluorophenyl)methyl]-1,2,4-oxadiazol-5-yl}propyl)-3,7-dihydro-1H-purine-2,6-dione Ethyl 4-(3-butyl-8-chloro-2,6-dioxo-2,3,6,7-tetrahydro-1H-purin-1-yl)butanoate (100 mg, 0.28 mmol) and (1Z)-2-(2-chloro-4-fluorophenyl)-N-hydroxyethanimidamide (62.4 mg, 0.308 mmol) and 21% by wt. ethanolic sodium ethoxide (0.157 ml, 0.42 mmol) were heated together in a microwave reactor in EtOH (1.5 ml) at 140° C. for 10 min. The mixture was worked up by partitioning between EtOAc and 2M HCl. The organic phase was evaporated and purified by MDAP to afford the title compound as a solid (73 mg).

LC/MS: m/z 495 [MH]+, RT 3.55 min.

Example 103

8-Chloro-3-ethyl-1-{3-[3-(phenylmethyl)-1,2,4-oxadiazol-5-yl]propyl}-3,7-dihydro-1H-purine-2,6-dione a) 8-Chloro-3-ethyl-1-{3-[3-(phenylmethyl)-1,2,4-oxadiazol-5-yl]propyl}-3,7-dihydro-1H-purine-2,6-dione A solution of 8-chloro-3-ethyl-7-(2-propen-1-yl)-3,7-dihydro-1H-purine-2,6-dione (150 mg, 0.59 mmol) in anhydrous THF (4 ml) was treated with 3-[3-(phenylmethyl)-1,2,4-oxadiazol-5-yl]-1-propanol (154 mg, 0.71 mmol) and triphenylphosphine (200 mg, 0.76 mmol). DBAD (162 mg, 0.71 mmol) was added in one portion and the mixture was left to stir at rt, under nitrogen for 18 h. The mixture was degassed by high vacuum then Pd(PPh$_3$)$_4$ (68 mg, 0.059 mmol) and morpholine (515 μl, 5.9 mmol) were added. The mixture was left to stir at rt, under nitrogen, for 3 h. The mixture was partitioned between EtOAc and 2M HCl (aq). The organic layer was separated, washed with brine, dried (MgSO$_4$) and concentrated by high vacuum. The crude material was purified by an aminopropyl SPE using MeOH to load the compound onto the column and wash through the impurities, then with 2% AcOH/MeOH to elute the compound. The UV active fractions were combined and concentrated by high vacuum. The product was further purified by MDAP. The product fractions were combined and concentrated to give the title compound as a white solid (61 mg, 25%).

LC/MS: m/z 415 [MH]+, RT 3.01 min $^1$H NMR; (DMSO-d$_6$) δ: 1.19 (t, 3H, J=7 Hz), 2.93 (m, 2H), 2.91 (t, 2H, J=7.5 Hz), 3.96 (m, 6H), 7.27 (m, 5H) 14.46 (s, 1H).

b) 8-Chloro-3-ethyl-7-(2-propen-1-yl)-3,7-dihydro-1H-purine-2,6-dione

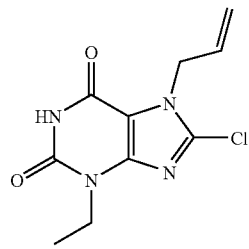

A solution of 8-chloro-7-(2-propen-1-yl)-3,7-dihydro-1H-purine-2,6-dione (10 g, 0.044 mol) in anhydrous DMF (100 ml) was treated with iodoethane (5.4 ml, 0.068 mol) and $Na_2CO_3$ (4.9 g, 0.046 mol). The reaction mixture was left to stir at rt under nitrogen for 2 days. Iodoethane (0.35 ml, 0.0044 mol) was added and the mixture was left to stir at rt for 1 day. The mixture was partitioned between EtOAc and 2M HCl. The organic layer was separated, washed sequentially with saturated sodium sulphite solution and brine, dried ($MgSO_4$) and concentrated. The crude solid was washed with $Et_2O$ to give the title compound as a white solid (8.37 g, 75%).

LC/MS: m/z 255 $[MH]^+$, RT 2.35 min.

Example 104

8-Chloro-1-(3-{3-[(3-chlorophenyl)methyl]-1,2,4-oxadiazol-5-yl}propyl)-3-pentyl-3,7-dihydro-1H-purine-2,6-dione

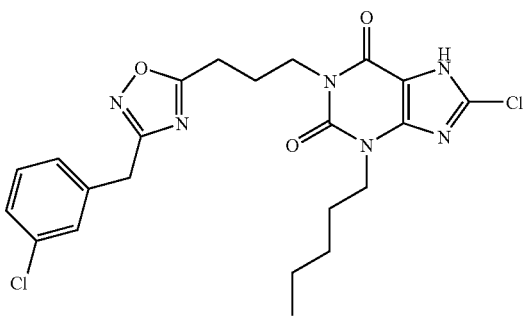

Ethyl 5-(8-chloro-2,6-dioxo-3-pentyl-2,3,6,7-tetrahydro-1H-purin-1-yl)pentanoate (70 mg, 0.19 mmol) was dissolved in EtOH. The solution was treated with a 21% solution of NaOEt in EtOH (78 µl, 0.21 mmol) and (1Z)-2-(3-chlorophenyl)-N-hydroxyethanimidamide (38 mg, 0.21 mmol). The reaction was heated in the microwave at 140° C. for 10 min. The mixture was partitioned between EtOH and 2M HCl (aq). The organic layer was decanted off and concentrated. The crude product was purified on the MDAP. The product fractions were combined and concentrated to give the title compound as a white solid (46 mg, 49%).

LC/MS: m/z 491 $[MH]^+$, RT 3.64 min.

$^1H$ NMR (DMSO-$d_6$) δ: 0.85 (t, 3H, J=7 Hz), 1.27 (m, 4H), 1.62 (m, 2H), 2.02 (m, 2H), 2.92 (t, 2H, J=7.5 Hz), 3.88 (t, 2H, J=7 Hz), 3.97 (t, 2H, J=6.5 Hz), 4.02 (s, 2H), 7.23 (d, 1H, J=7 Hz), 7.34 (m, 3H).

Example 105

8-Chloro-1-(3-{3-[(3,4-dichlorophenyl)methyl]-1,2,4-oxadiazol-5-yl}propyl)-3-pentyl-3,7-dihydro-1H-purine-2,6-dione

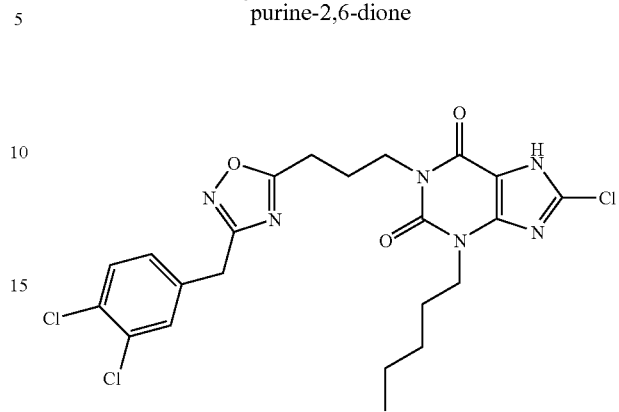

Ethyl 5-(8-chloro-2,6-dioxo-3-pentyl-2,3,6,7-tetrahydro-1H-purin-1-yl)pentanoate (70 mg, 0.19 mmol) was dissolved in EtOH. The solution was treated with a 21% solution of NaOEt in EtOH (78 µl, 0.21 mmol) and (1Z)-2-(3,4-dichlorophenyl)-N-hydroxyethanimidamide (46 mg, 0.21 mmol). The reaction was heated in the microwave at 140° C. for 10 min. The mixture was partitioned between EtOH and 2M HCl (aq). The organic layer was decanted off and concentrated. The crude product was purified on the MDAP. The product fractions were combined and concentrated to give the title compound as a white solid (66 mg, 66%).

LC/MS: m/z 527 $[MH]^+$, RT 3.80 min.

Example 106

8-Chloro-1-(3-{3-[(2,6-dichlorophenyl)methyl]-1,2,4-oxadiazol-5-yl}propyl)-3-pentyl-3,7-dihydro-1H-purine-2,6-dione

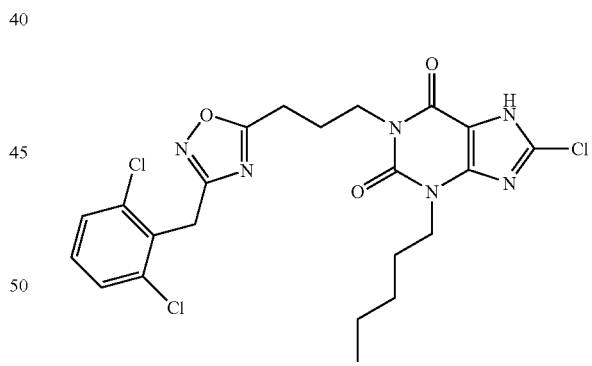

Ethyl 5-(8-chloro-2,6-dioxo-3-pentyl-2,3,6,7-tetrahydro-1H-purin-1-yl)pentanoate (70 mg, 0.19 mmol) was dissolved in EtOH. The solution was treated with a 21% solution of NaOEt in EtOH (78 µl, 0.21 mmol) and (1Z)-2-(2,6-dichlorophenyl)-N-hydroxyethanimidamide (46 mg, 0.21 mmol). The reaction was heated in the microwave at 140° C. for 10 min. The mixture was partitioned between EtOH and 2M HCl (aq). The organic layer was decanted off and concentrated by nitrogen blowdown. The crude product was purified on the MDAP. The product fractions were combined and concentrated to give the title compound as a white solid (80 mg, 80%).

LC/MS: m/z 526 $[MH]^+$, RT 3.6 min.

Example 107

8-Chloro-1-(3-{3-[(2-chloro-4-fluorophenyl)methyl]-1,2,4-oxadiazol-5-yl}propyl)-3-pentyl-3,7-dihydro-1H-purine-2,6-dione

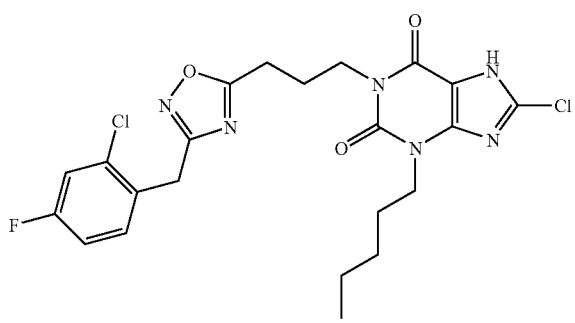

Ethyl 5-(8-chloro-2,6-dioxo-3-pentyl-2,3,6,7-tetrahydro-1H-purin-1-yl)pentanoate (70 mg, 0.19 mmol) was dissolved in EtOH. The solution was treated with a 21% solution of NaOEt in EtOH (78 μl, 0.21 mmol) and (1Z)-2-(2-chloro-4-fluorophenyl)-N-hydroxyethanimidamide (42 mg, 0.21 mmol). The reaction was heated in the microwave at 140° C. for 10 min. The mixture was partitioned between EtOH and 2M HCl (aq). The organic layer was decanted off and concentrated. The crude product was purified on the MDAP. The product fractions were combined and concentrated to give the title compound as a white solid (65 mg, 67%).

LC/MS: m/z 509 [MH]+, RT 3.63 min.

Example 108

3-Butyl-8-chloro-1-{3-[3-(phenylmethyl)-1,2,4-oxadiazol-5-yl]propyl}-3,7-dihydro-1H-purine-2,6-dione

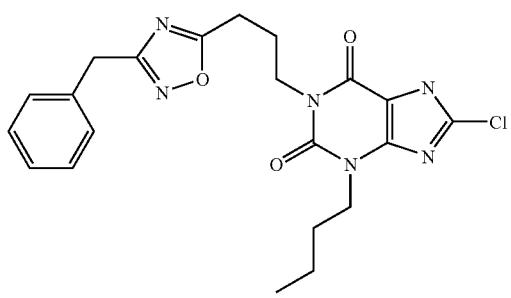

A solution of 3-butyl-8-chloro-7-(2-propen-1-yl)-3,7-dihydro-1H-purine-2,6-dione (205 mg, 0.73 mmol) in anhydrous THF (4 ml) was treated with 3-[3-(phenylmethyl)-1,2,4-oxadiazol-5-yl]-1-propanol (190 mg, 0.87 mmol) and PPh$_3$ (247 mg, 0.94 mmol). DBAD (217 mg, 0.94 mmol) was added in one portion and the mixture was stirred at rt under nitrogen for 18 h. The mixture was degassed by high vacuum then Pd(PPh$_3$)$_4$ (84 mg, 0.073 mmol) and morpholine (636 μl, 7.3 mmol) were added. The mixture was stirred at rt under nitrogen for 3 h. The mixture was partitioned between EtOAc and 2M HCl (aq) and the organic layer separated, washed with brine, dried (MgSO$_4$) and concentrated. The crude material was purified by an aminopropyl column using MeOH to load the compound onto the column and wash through the impurities, then with 2-4% AcOH/MeOH gradient to remove the compound from the column. Further purification was effected by MDAP to give the title compound as a white solid (75 mg, 23%).

LC/MS: m/z 443 [MH]+, RT 3.37 min.

$^1$H NMR; (DMSO-d$_6$) δ: 0.89 (t, 3H, J=7.5 Hz), 1.29 (m, 2H), 1.61 (m, 2H), 2.02 (m, 2H), 2.91 (t, 2H, J=7.5 Hz), 3.89 (t, 2H, J=7 Hz), 3.97 (m, 4H), 7.27 (m, 5H) 14.46 (s, 1H).

Example 109

8-Chloro-1-(3-{3-[(4-hydroxyphenyl)methyl]-1,2,4-oxadiazol-5-yl}propyl)-3-pentyl-3,7-dihydro-1H-purine-2,6-dione

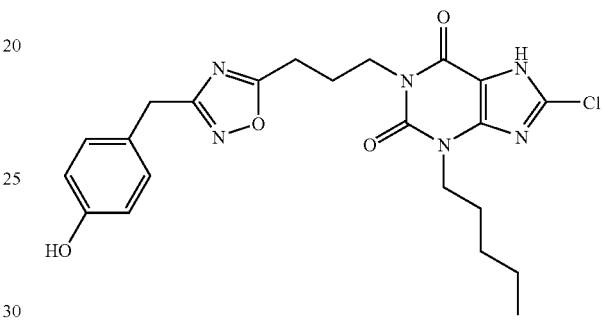

Ethyl 5-(8-chloro-2,6-dioxo-3-pentyl-2,3,6,7-tetrahydro-1H-purin-1-yl)pentanoate (29 mg, 0.078 mmol) and (1Z)—N-hydroxy-2-(4-hydroxyphenyl)ethanimidamide (14 mg, 0.084 mmol) were heated in EtOH (1 ml) with 21% ethanolic sodium ethoxide (0.043 ml, 0.117 mmol) under microwave irradiation at 140° C. for 10 min. The mixture was partitioned between EtOAc and 2M HCl and the organic phase evaporated. This material was stirred with EtOH (1 ml) and 2M NaOH (0.5 ml) for 18 h, before being worked up again by partition between EtOAc and 2M HCl. Purification by MDAP afforded the title compound (6.5 mg).

LC/MS: m/z 473 [MH]+, RT 3.34 min.

$^1$H NMR (MeOH-d$_4$) δ: 0.92 (t, 3H, J=7 Hz), 1.25-1.45 (m, 4H), 1.68-1.78 (m, 2H), 2.11-2.21 (m, 2H), 2.93 (t, 2H, J=7 Hz), 3.82 (s, 2H), 3.98 (t, 2H, J=7 Hz), 4.10 (t, 2H, J=7 Hz), 6.70 (d, 2H, J=10 Hz), 7.02 (d, 2H, J=10 Hz).

Example 110

3-Butyl-8-chloro-1-(3-{3-[(phenyloxy)methyl]-1,2,4-oxadiazol-5-yl}propyl)-3,7-dihydro-1H-purine-2,6-dione

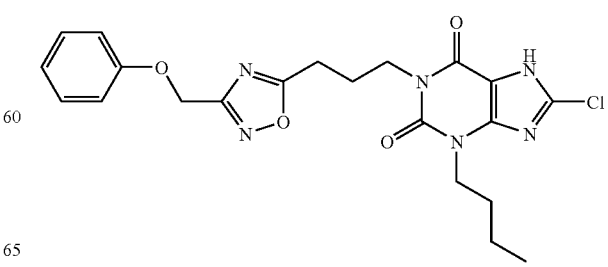

To ethyl 4-(3-butyl-8-chloro-2,6-dioxo-2,3,6,7-tetrahydro-1H-purin-1-yl)butanoate (26 mg, 0.073 mmol) and (1Z)—N-hydroxy-2-(phenyloxy)ethanimidamide hydrochloride (16 mg, 0.079 mmol) in EtOH (1 ml) was added 21% wt. ethanolic sodium ethoxide solution (0.068 ml, 0.183 mmol) and the mixture was heated under microwave irradiation at 140° C. for 10 min. The mixture was partitioned between EtOAc and 2M HCl, the organic phase dried (Na$_2$SO$_4$) evaporated and purified by MDAP to give title compound as a gum which solidified upon trituration with ether (5.9 mg).

LC/MS: m/z 459 [MH]$^+$, RT 3.39 min.

$^1$H NMR (DMSO-d$_6$) δ: 0.90 (t, 3H, J=8 Hz), 1.22-1.36 (m, 2H), 1.57-1.68 (m, 2H), 2.02-2.14 (m, 2H), 3.00 (t, 2H, J=8 Hz), 3.90 (t, 2H, J=7 Hz), 4.00 (t, 2H, J=7 Hz), 5.18 (s, 2H), 6.95-7.35 (m, 5H).

Example 111

3-Butyl-8-chloro-1-(3-{3-[(3,5-dichlorophenyl)methyl]-1,2,4-oxadiazol-5-yl}propyl)-3,7-dihydro-1H-purine-2,6-dione

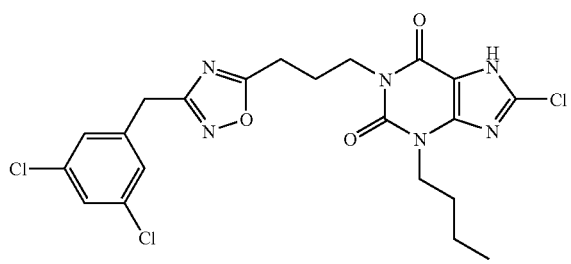

To ethyl 4-(3-butyl-8-chloro-2,6-dioxo-2,3,6,7-tetrahydro-1H-purin-1-yl)butanoate (185 mg, 0.52 mmol) and (1Z)-2-(3,5-dichlorophenyl)-N-hydroxyethanimidamide (126 mg, 0.58 mmol; Entry 23, Table 7) in dry EtOH (2 ml) was added 21% wt. ethanolic sodium ethoxide solution (0.29 ml, 0.78 mmol) and the mixture was heated by microwaves at 140° C. for 10 min. The reaction was worked up by partition between EtOAc and 2M HCl and evaporating the organic phase. Purification by MDAP afforded the title compound as a solid (135 mg).

LC/MS: m/z 511 [MH]$^+$, RT 3.71 min.

Example 112

3-Butyl-8-chloro-1-(3-{3-[(2,4,6-trifluorophenyl)methyl]-1,2,4-oxadiazol-5-yl}propyl)-3,7-dihydro-1H-purine-2,6-dione

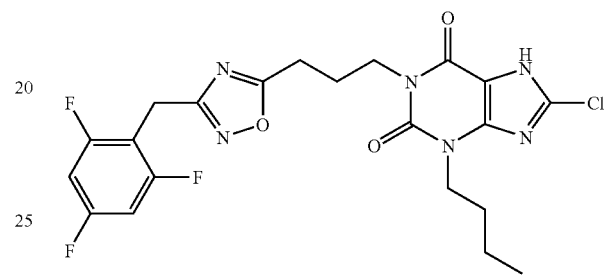

Similarly prepared starting from (1Z)—N-hydroxy-2-(2,4,6-trifluorophenyl)ethanimidamide (119 mg, 0.58 mmol; Entry 24, Table 7) in a yield of 135 mg.

LC/MS: m/z 497 [MH]$^+$, RT 3.39 min.

$^1$H NMR (DMSO-d$_6$) δ: 0.90 (t, 3H, J=7 Hz), 1.24-1.36 (m, 2H), 1.55-1.66 (m, 2H), 1.96-2.06 (m, 2H), 2.91 (t, 2H, J=8 Hz), 3.91 (t, 2H, J=8 Hz), 3.94-4.02 (m, 4H), 7.18-7.28 (m, 2H).

Amidoximes:

These are available by the methods detailed below and exemplified by analogues in Table 7.

TABLE 7

| | | (Intermediates) | | | |
|---|---|---|---|---|---|
| Entry | Structure | Name | Method | Yield mg | LC/MS: |
| 1 | | (1Z)-2-(2-chlorophenyl)-N-hydroxyethanimidamide | G | 38 | 185 [MH]$^+$ RT 1.04 min |
| 2 | | (1Z)-2-(4-fluorophenyl)-N-hydroxyethanimidamide | G | 42 | m/z 169 [MH]$^+$ RT 0.72 min |
| 3 | | (1Z)-2-(2,3-dichlorophenyl)-N-hydroxyethanimidamide | B | 64 | m/z 219 [MH]$^+$ RT 1.83 min |

TABLE 7-continued (Intermediates)

| Entry | Structure | Name | Method | Yield mg | LC/MS: |
|---|---|---|---|---|---|
| 4 | 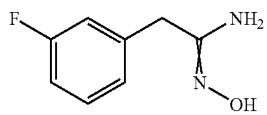 | (1Z)-2-(3-fluorophenyl)-N-hydroxyethanimidamide | A | 78 | m/z 169 [MH]+ RT 0.62 min |
| 5 | 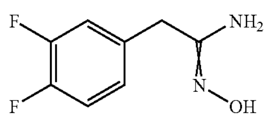 | (1Z)-2-(3,4-difluorophenyl)-N-hydroxyethanimidamide | A | 88 | m/z 187 [MH]+ RT 0.74 min |
| 6 | 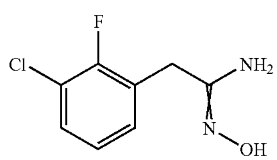 | (1Z)-2-(3-chloro-2-fluorophenyl)-N-hydroxyethanimidamide | A | 92 | m/z 203 [MH]+ RT 1.40 min |
| 7 | 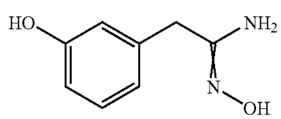 | (1Z)-N-hydroxy-2-(3-hydroxyphenyl)-hydroxyethanimidamide | A | 67 | m/z 167 [MH]+ RT 0.46 min |
| 8 | 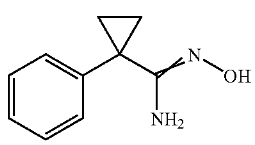 | N-hydroxy-1-phenylcyclopropanecarboximidamide | C | 75 | m/z 177 [MH]+ RT 1.06 min |
| 9 | 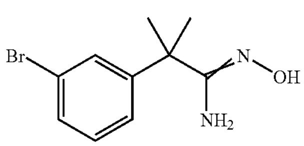 | (1Z)-2-(3-bromophenyl)-N-hydroxy-2-methylpropanimidamide | D | 74 | m/z 257 [MH]+ RT 2.04 min |
| 10 | 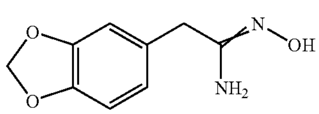 | (1Z)-2-(1,3-benzodioxal-5-yl)-N-hydroxyethanimidamide | C | 98 | m/z 195 [MH]+ RT 0.73 min |
| 11 | 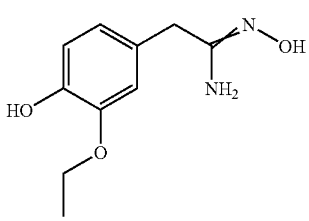 | (1Z)-2-[3-(ethyloxy)-4-hydroxyphenyl]-N-hydroxyethanimidamide | C | 109 | m/z 211 [MH]+ RT 0.76 min |
| 12 | 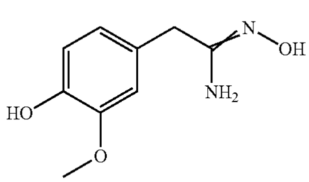 | (1Z)-N-hydroxy-2-[4-hydroxy-3-(methyloxy)phenyl]ethanimidamide | C | 98 | m/z 197 [MH]+ RT 0.50 min |

TABLE 7-continued (Intermediates)

| Entry | Structure | Name | Method | Yield mg | LC/MS: |
|---|---|---|---|---|---|
| 13 | 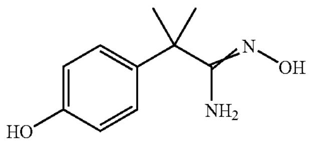 | (1Z)-N-hydroxy-2-(4-hydroxyphenyl)-2-methylpropanimidamide | D | 66 | m/z 195 [MH]+ RT 0.85 min |
| 14 | 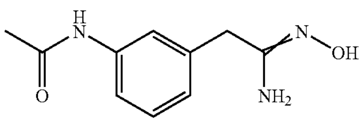 | N-{3-[(2Z)-2-(hydroxyamino)-2-iminoethyl]phenyl}acetamide | C | 91 | m/z 208 [MH]+ RT 0.73 min |
| 15 | 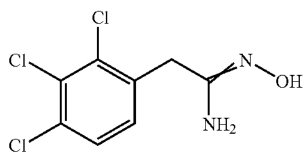 | (1Z)-N-hydroxy-2-(2,3,4-trichlorophenyl)ethanimidamide | C | 124 | m/z 253 [MH]+ RT 2.29 min |
| 16 | 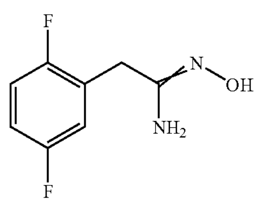 | (1Z)-2-(2,5-difluorophenyl)-N-hydroxyethanimidamide | C | 89 | m/z 187 [MH]+ RT 0.66 min |
| 17 | 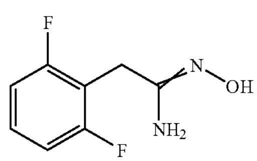 | (1Z)-2-(2,6-difluorophenyl)-N-hydroxyethanimidamide | C | 86 | m/z 187 [MH]+ RT 0.62 min |
| 18 | 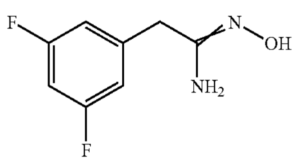 | (1Z)-2-(3,5-difluorophenyl)-N-hydroxyethanimidamide | C | 96 | m/z 187 [MH]+ RT 0.80 min |
| 19 | 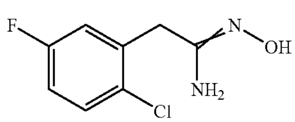 | (1Z)-2-(2-chloro-5-fluorophenyl)-N-hydroxyethanimidamide | C | 97 | m/z 203 [MH]+ RT 0.90 min |
| 20 | 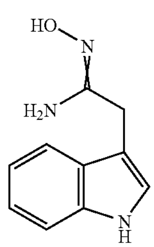 | (1Z)-N-hydroxy-2-(1H-indol-3-yl)ethanimidamide | C | 95 | m/z 190 [MH]+ RT 0.90 min |
| 21 | 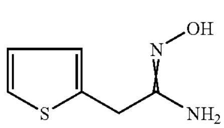 | (1Z)-N-hydroxy-2-(2-thienyl)ethanimidamide | C | 74 | m/z 157 [MH]+ RT 0.38 min |

TABLE 7-continued (Intermediates)

| Entry | Structure | Name | Method | Yield mg | LC/MS: |
|---|---|---|---|---|---|
| 22 | 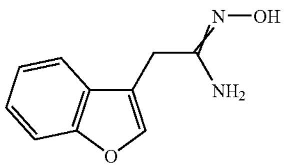 | (1Z)-2-(1-benzofuran-3-yl)-N-hydroxyethanimidamide | C | 87 | m/z 191 [MH]+ RT 1.46 min |
| 23 | 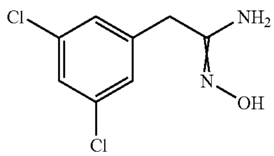 | (1Z)-2-(3,5-dichlorophenyl)-N-hydroxyethanimidamide | E | 165 | m/z 219 [MH]+ RT 2.03 min |
| 24 | 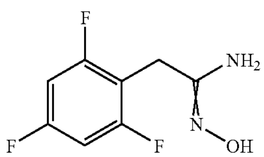 | (1Z)-N-hydroxy-2-(2,4,6-trifluorophenyl)ethanimidamide | F | 297 | m/z 205 [MH]+ RT 0.66 min |
| 25 | 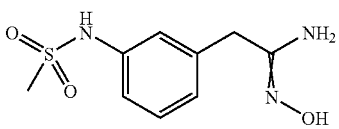 | (1Z)-N-hydroxy-2-{3-[(methylsulfonyl)amino]phenyl}ethanimidamide | C | 125 | m/z 244 [MH]+ RT 0.63 min |

It should be noted that ⫽ as used herein represents a double bond of undefined geometry.

Method A

The corresponding nitrile (0.5 mmol) was stirred in EtOH (1.5 ml) with 50% aqueous hydroxylamine solution (0.08 ml, 1.3 mmol) and heated at 65° C. for 4.5 h. After cooling the crude reaction mixture was loaded onto an SCX SPE cartridge (2 g) and washed with MeOH, then the amidoxime product was eluted with 2M ammonia in MeOH.

Method B

Similar to Method A except that the product crystallised out from the crude reaction mixture and was isolated by filtration instead of by SCX.

Method C

Similar to Method A except that the product was purified on a 5 g SCX cartridge.

Method D

Similar to Method C except that the heating period was 18 h.

Method E

Similar to Method C except that the scale was 0.753 mmol of nitrile.

Method F

Similar to Method A except that the scale was 1.5 mmol of nitrile and purification was on a 10 g SCX cartridge.

Method G

Similar to Method A except that the heating time was 2.75 h and the scale was 0.25 mmol of nitrile.

Example 113

3-Butyl-8-chloro-1-(3-{5-[(3-chlorophenyl)methyl]-1,2,4-oxadiazol-3-yl}propyl)-3,7-dihydro-1H-purine-2,6-dione a) 3-Butyl-8-chloro-1-(3-{5-[(3-chlorophenyl)methyl]-1,2,4-oxadiazol-3-yl}propyl)-3,7-dihydro-1H-purine-2,6-dione

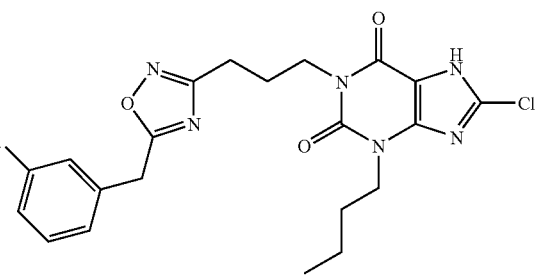

(3-Chlorophenyl)acetic acid (0.1 mmol), N-[3-(dimethylamino)propyl]-N'-ethylcarbodiimide hydrochloride (21 mg, 0.11 mmol) and 1H-1,2,3-benzotriazol-1-ol (15 mg, 0.11 mmol) were stirred in 1-methyl-2-pyrrolidinone (1 ml). To this was added (1Z)-4-(3-butyl-8-chloro-2,6-dioxo-2,3,6,7-tetrahydro-1H-purin-1-yl)-N-hydroxybutanimidamide (34 mg, 0.1 mmol) and the mixture stirred at rt for 17 h and then at 80° C. for 24 h. The reaction mixture was purified, without further modification, by preparative HPLC (auto prep) to give the title compound (13 mg, 27%).

LC/MS: m/z 477, 479 [MH]+, RT 3.5 min.

$^1$H NMR (CDCl$_3$) δ: 0.96 (t, 3H, J=7 Hz), 1.32-1.47 (m, 2H), 1.68-1.80 (m, 2H), 2.12-2.24 (m, 2H), 2.83 (t, 2H, J=7.5 Hz), 4.05-4.24 (m, 6H), 7.16-7.30 (m, 4H).

b) (1Z)-4-(3-butyl-8-chloro-2,6-dioxo-2,3,6,7-tetrahydro-1H-purin-1-yl)-N-hydroxybutanimidamide

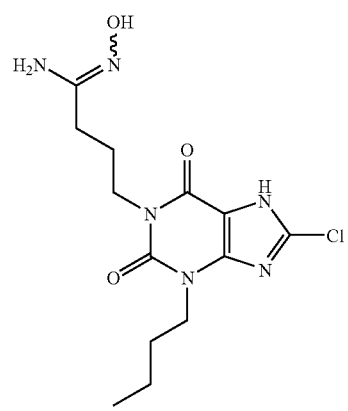

4-(3-Butyl-8-chloro-2,6-dioxo-2,3,6,7-tetrahydro-1H-purin-1-yl)butanenitrile (1 g, 0.0032 mol) was stirred in EtOH (3.5 ml) and water (1.8 ml). Hydroxylamine hydrochloride (344 mg, 0.0049 mol) and potassium carbonate (652 mg, 0.0049 mol) were added and the mixture heated at 80° C. for 3 days. After cooling the crude reaction mixture was evaporated. The crude product was dissolved in water, neutralised to pH7 with HCl, and loaded onto an Oasis™ cartridge (2 g). This was eluted with water to remove the salts and then with MeOH, to give the title compound (957 mg, 86%).

LC/MS: m/z 343, 345 [MH]$^+$, RT 2.04 min.

c) 4-(3-Butyl-8-chloro-2,6-dioxo-2,3,6,7-tetrahydro-1H-purin-1-yl)butanenitrile

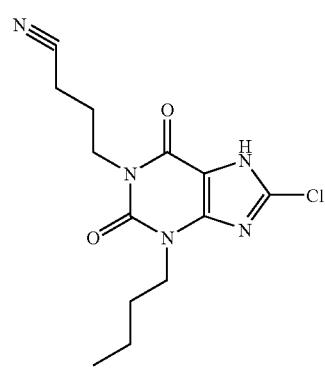

4-[3-Butyl-8-chloro-2,6-dioxo-7-(2-propen-1-yl)-2,3,6,7-tetrahydro-1H-purin-1-yl]butanenitrile (2.1 g, 6 mmol) was stirred in a mixture of nitrogen degassed DCM (20 ml) and AcOH (2 ml). Tetrakis(triphenylphosphine)palladium (675 mg, 0.6 mmol) and phenyl silane (7.4 ml, 60 mmol) were added and the mixture stirred at rt for 2 d. This was then evaporated and the residue triturated with a mixture of diethylether:cyclohexane (1:1) to afford the title compound (1.47 g, 60%) as a white solid.

LC/MS: m/z 310 [MH]$^+$, RT 2.66 min.

d) 4-[3-Butyl-8-chloro-2,6-dioxo-7-(2-propen-1-yl)-2,3,6,7-tetrahydro-1H-purin-1-yl]butanenitrile

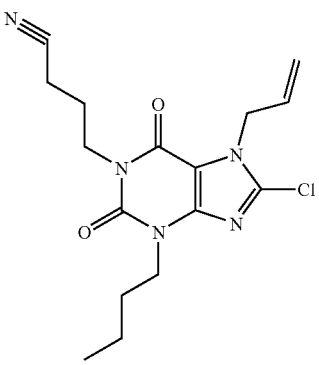

3-butyl-8-chloro-7-(2-propen-1-yl)-3,7-dihydro-1H-purine-2,6-dione (2.0 g, 0.0072 mol) in dry MeCN (20 ml) was added Cs$_2$CO$_3$ (4.68 g, 0.0144 mol) followed by bromobutyronitrile (1.38 g, 0.0094 mol). The mixture was heated at 80° C. for 18 h and then allowed to cool. The reaction mixture was evaporated and the crude product partitioned between EtOAc and HCl (2N). The organic phase was separated and washed with brine, dried (MgSO$_4$) and evaporated to give the crude product. This was purified by silica SPE (50 g), eluting with cyclohexane:ethylacetate (2:1 to 1:1) to afford the title compound as a clear oil (2.1 g, 85%).

LC/MS: m/z 350 [MH]$^+$, RT 3.10 min.

The following compounds (Table 8) were prepared using a method analogous to that for Example 113, from the corresponding acids and (1Z)-4-(3-butyl-8-chloro-2,6-dioxo-2,3,6,7-tetrahydro-1H-purin-1-yl)-N-hydroxybutanimidamide.

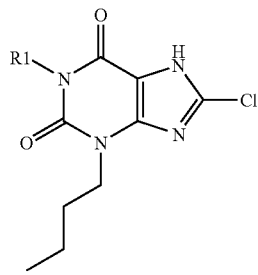

Where * is used in the examples herein it indicates the attachment point of the R group to the xanthine core.

TABLE 8

| Example | Compound: R1 = | | Yield % | LC/MS: |
|---|---|---|---|---|
| 114 | 3-butyl-8-chloro-1-[3-(5-{[3-(methyloxy)phenyl]methyl}-1,2,4-oxadiazol-3-yl)propyl]-3,7-dihydro-1H-purine-2,6-dione | 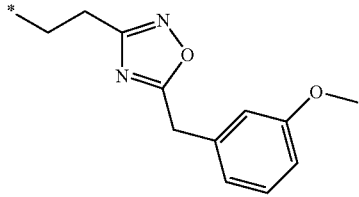 | 22 | m/z 473 [MH]+ RT 3.3 min |
| 115 | 3-butyl-8-chloro-1-[3-(5-{[3-(trifluoromethyl)phenyl]methyl}-1,2,4-oxadiazol-3-yl)propyl]-3,7-dihydro-1H-purine-2,6-dione | 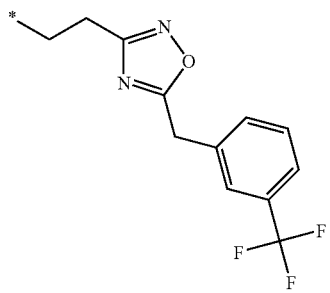 | 23 | m/z 511 [MH]+ RT 3.5 min |
| 116 | 3-butyl-8-chloro-1-(3-{5-[(2-chloro-4-fluorophenyl)methyl]-1,2,4-oxadiazol-3-yl}propyl)-3,7-dihydro-1H-purine-2,6-dione | 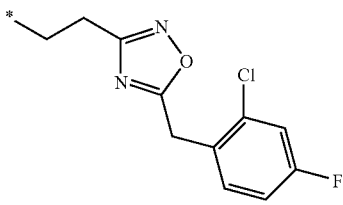 | 28 | m/z 495 [MH]+ RT 3.5 min |
| 117 | 1-{3-[5-(1,3-benzodioxol-5-ylmethyl)-1,2,4-oxadiazol-3-yl]propyl}-3-butyl-8-chloro-3,7-dihydro-1H-purine-2,6-dione | 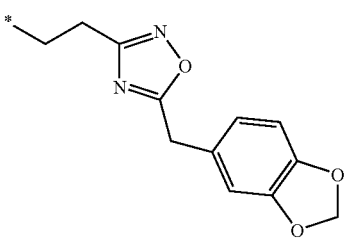 | 27 | m/z 487 [MH]+ RT 3.3 min |
| 118 | 3-butyl-8-chloro-1-(3-{5-[(4-fluorophenyl)methyl]-1,2,4-oxadiazol-3-yl}propyl)-3,7-dihydro-1H-purine-2,6-dione | 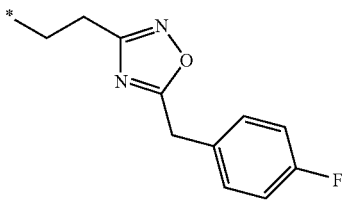 | 28 | m/z 461 [MH]+ RT 3.3 min |
| 119 | 3-butyl-8-chloro-1-[3-(5-{[2-(methyloxy)phenyl]methyl}-1,2,4-oxadiazol-3-yl)propyl]-3,7-dihydro-1H-purine-2,6-dione | 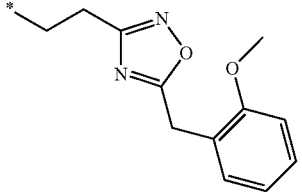 | 21 | m/z 473 [MH]+ RT 3.3 min |

TABLE 8-continued

| Example | | Compound: R1 = | Yield % | LC/MS: |
|---|---|---|---|---|
| 120 | 1-{3-[5-(1-benzofuran-4-ylmethyl)-1,2,4-oxadiazol-3-yl]propyl}-3-butyl-8-chloro-3,7-dihydro-1H-purine-2,6-dione | 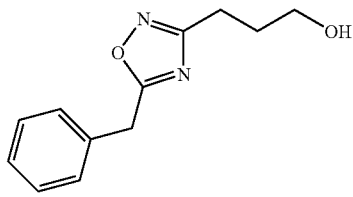 | 24 | m/z 483 [MH]+ RT 3.4 min |

NMR Details for Selected Examples from Table 8

Example 115

$^1$H NMR (CDCl$_3$) 0.96 (3H, t, J=7.5 Hz), 1.32-1.47 (2H, m), 1.65-1.81 (2H, m), 2.12-2.25 (2H, m), 2.84 (2H, t, J=7.5 Hz), 4.02 (2I-1, t, 7.5 Hz), 4.22 (2H, t, 7 Hz), 4.24 (2H, s), 7.40-7.62 (4H, m).

Example 121

8-Chloro-3-pentyl-1-{3-[5-(phenylmethyl)-1,2,4-oxadiazol-3-yl]propyl}-3,7-dihydro-1H-purine-2,6-dione a) 8-Chloro-3-pentyl-1-{3-[5-(phenylmethyl)-1,2,4-oxadiazol-3-yl]propyl}-3,7-dihydro-1H-purine-2,6-dione

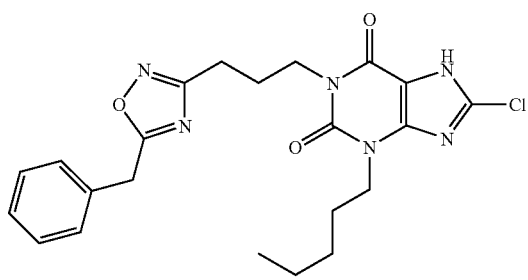

To a stirred solution of 8-chloro-3-pentyl-7-(2-propen-1-yl)-3,7-dihydro-1H-purine-2,6-dione (0.20, 0.67 mmol) in THF (5 ml) was added 3-[5-(phenylmethyl)-1,2,4-oxadiazol-3-yl]-1-propanol (0.162 g, 0.74 mmol), DBAD (0.186 g, 0.81 mmol) and triphenylphosphine (0.212 g, 0.81 mmol) and the solution stirred for 18 h. To the solution was added Pd(PPh$_3$)$_4$ (75 mg, 0.067 mmol) and morpholine (604 µl, 6.7 mmol) were added and stirred for at rt under nitrogen for a further 3 h. 75 mg of Pd(PPh$_3$)$_4$ was added and the mixture left to stir for another 3 h. The mixture was partitioned between EtOAc and 2M HCl (aq). The organic layer was separated, washed with brine, dried (MgSO$_4$) and concentrated. The crude material was purified by an aminopropyl SPE using MeOH to load the compound onto the column and wash through the impurities, then with 2-4% AcOH/MeOH to elute the compound. The product fractions were combined and concentrated then further purified by MDAP. The product fractions were combined and concentrated give the title compound as a white solid (51 mg, 20%).

LC/MS: m/z 457 [MH]+, RT 3.54 min.

b) 3-[5-(Phenylmethyl)-1,2,4-oxadiazol-3-yl]-1-propanol

A mixture of (1E)-4,4-bis(ethyloxy)-N-hydroxybutanimidamide (3.2 g, 16.8 mmol), ethyl phenylacetate (2.3 ml, 14.4 mmol) and sodium ethoxide (21% solution in EtOH, 6.4 ml) was heated in a microwave at 140° C. for 10 min. The material was combined with that from a second reaction (using 1.2 g of (1E)-4,4-bis(ethyloxy)-N-hydroxybutanimidamide and conducted as above) and partitioned between 1M HCl solution and EtOAc. The organic layer was separated, washed with brine, dried and concentrated to provide 5-[3,3-bis(ethyloxy)propyl]-5-(phenylmethyl)-1,2,4-oxadiazole which was used without purification in the next stage.

Crude 3-[3,3-bis(ethyloxy)propyl]-5-(phenylmethyl)-1,2,4-oxadiazole (5.63 g, 19.4 mmol) in EtOH (75 ml) was stirred with p-toluenesulphonic acid (0.738 g, 3.9 mmol) for 21 h and the mixture partitioned between EtOAc and water. The organics were isolated washed with water and brine, dried and concentrated to a red oil. This material contained significant amounts of acetal, therefore the oil was dissolved in THF (15 ml) and treated with 2M HCl solution for 2 h then partitioned between EtOAc and water. The organics were isolated washed with brine, dried and concentrated to yield 3-[5-(phenylmethyl)-1,2,4-oxadiazol-3-yl]propanal as a red/brown oil (3.77 g) which was used crude in the next stage.

A solution of crude 3-[5-(phenylmethyl)-1,2,4-oxadiazol-3-yl]propanal (3.76 g, 17.4 mmol) in MeOH (60 ml) was cooled to 0° C. and sodium borohydride (0.724 g, 19.1 mmol) added portionwise over 30 min. The cooling bath was removed and the solution stirred for a further 1 h then partitioned between 1M HCl and EtOAc. The organic layer was separated and the aqueous extracted with EtOAc. The combined extracts were washed with brine, dried and concentrated to an orange liquid. This was purified on a 50 g silica SPE eluting with cyclohexane/EtOAc (20% to 80% gradient elution) to provide the title compound as a yellow oil (2.24 g).

LC/MS: m/z 210 [MH]+.

c) (1E)-4,4-bis(ethyloxy)-N-hydroxybutanimidamide

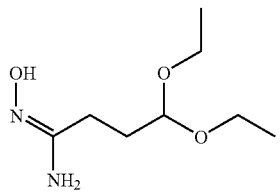

A mixture of 3-cynopropionaldehyde diethylacetal (6.12 g, 39 mmol), hydroxylamine hydrochloride (4.06 g, 58.4 mmol), potassium carbonate (10.76 g, 77.9 mmol) in water (20 ml) and EtOH (40 ml) was refluxed for 24 h. The mixture was allowed to cool and then partitioned between water and EtOAc. The organic layer was separated and the aqueous extracted with EtOAc. The combined organic fractions were washed with brine, dried and concentrated to provide the title compound as a colourless oil contaminated with ~20% starting nitrile (6.03 g, 81%).
LC/MS: m/z 191 [MH]$^+$.

Example 122

8-Chloro-1-{3-[5-(phenylmethyl)-1,2,4-oxadiazol-3-yl]propyl}-3-propyl-3,7-dihydro-1H-purine-2,6-dione

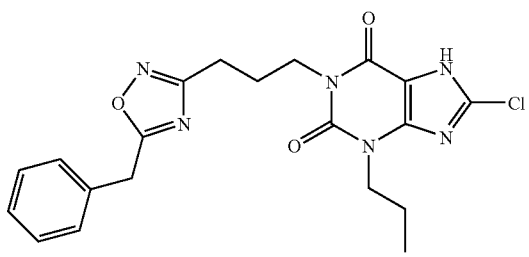

A solution of 8-chloro-7-(2-propen-1-yl)-3-propyl-3,7-dihydro-1H-purine-2,6-dione (200 mg, 0.74 mmol) in THF (4 ml) was treated with 3-[5-(phenylmethyl)-1,2,4-oxadiazol-3-yl]-1-propanol (195 mg, 0.89 mmol) and PPh$_3$ (254 mg, 0.96 mmol). DBAD (223 mg, 0.96 mmol) was added in one portion and the mixture was left to stir at rt under nitrogen for 18 h. The mixture was partitioned between EtOAc and 2M HCl (aq). The organic layer was separated, washed with brine, dried (MgSO$_4$) and concentrated by high vacuum. The crude product was purified on a silica SPE column using a 0-70% cyclohexane/EtOAc gradient. The product fractions were combined, concentrated by high vacuum and purified on a silica SPE column using a 0-60% cyclohexane/EtOAc gradient. The product fractions were combined and concentrated then dissolved in anhydrous THF (4 ml). The solution was degassed by high vacuum then Pd(PPh$_3$)$_4$ (61 mg, 0.053 mmol) and morpholine (460 μl, 5.3 mmol) were added and the mixture left to stir at rt under nitrogen for 1 day. The mixture was partitioned between EtOAc and 2M HCl (aq). The organic layer was separated, washed with brine, dried (MgSO$_4$) and concentrated by high vacuum. The crude product was purified by an aminopropyl SPE using MeOH to load the compound onto the column and wash through the impurities then a 2-4% AcOH/MeOH gradient to elute the product. The product fractions were combined and concentrated to leave the title compound as a white solid (36 mg, 11%).
LC/MS: m/z 429 [MH]$^+$, RT 3.14 min.

$^1$H NMR (DMSO-d$_6$) δ: 0.86 (t, 3H, J=7.5 Hz), 1.65 (m, 2H), 1.93 (m, 2H), 2.70 (t, 2H, J=7.5 Hz), 3.86 (t, 2H, J=7 Hz), 3.96 (t, 2H, J=7 Hz), 4.28 (s, 2H), 7.32 (m, 5H).

Example 123

3-Butyl-8-chloro-1-{3-[5-(phenylmethyl)-1,2,4-oxadiazol-3-yl]propyl}-3,7-dihydro-1H-purine-2,6-dione

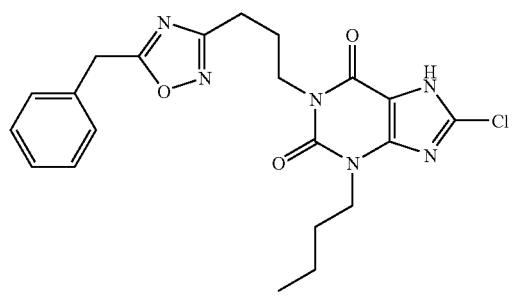

A solution of 3-[5-(phenylmethyl)-1,2,4-oxadiazol-3-yl]-1-propanol (594 mg, 2.7 mmol) in THF (25 ml) was treated with 3-butyl-8-chloro-7-(2-propen-1-yl)-3,7-dihydro-1H-purine-2,6-dione (700 mg, 2.48 mmol) and PPh$_3$ (779 mg, 2.97 mmol) under nitrogen. DBAD (684 mg, 2.97 mmol) was added in one portion and the reaction left to react for 60 h. The mixture was partitioned between 2M HCl (aq) and EtOAc. The organic layer was separated, washed with brine, dried (MgSO$_4$) and concentrated. MeOH was added to the residue and then passed down an aminopropyl column with the product eluting with 2-4% AcOH/MeOH. Product fractions were combined and concentrated. The off-white residue was recrystallised from EtOAc:cyclohexane (1:1), giving the title compound as a white solid (696 mg, 63%).
LC/MS: m/z 443 [MH]$^+$, RT 3.4 min.
$^1$H NMR (DMSO-d$_6$) δ: 0.89 (t, 3H, J=7 Hz), 1.29 (m, 2H), 1.61 (m, 2H), 1.93 (m, 2H), 2.70 (t, 2H, J=7.5 Hz), 3.90 (t, 2H, J=7 Hz), 3.96 (t, 2H, J=7 Hz), 4.28 (2H, s), 7.31 (m, 5H), 14.4 (br s, 1H).

Example 124

3-Butyl-8-chloro-1-(3-{5-[(3-chloro-4-hydroxyphenyl)methyl]-1,2,4-oxadiazol-3-yl}propyl)-3,7-dihydro-1H-purine-2,6-dione

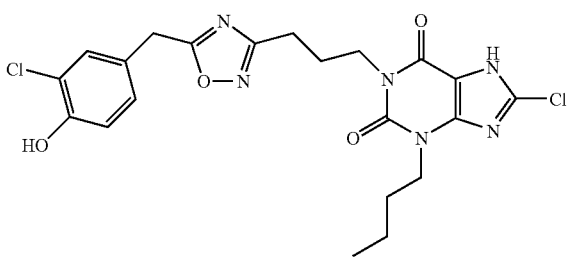

A solution of 3-chloro-4-hydroxyphenylacetic acid (24 mg, 0.13 mmol) in DMSO (1 ml) was treated with CDI (21 mg, 0.13 mmol) and left to react for 30 min. (1Z)-4-(3-Butyl-8-chloro-2,6-dioxo-2,3,6,7-tetrahydro-1H-purin-1-yl)-N-hydroxybutanimidamide (50 mg, 0.15 mmol) was added and the mixture heated in the microwave at 120° C. for 15 min. The solution was directly purified by MDAP to obtain the title compound as a white solid (12 mg, 17%).
LC/MS: m/z 493 [MH]$^+$, RT 3.2 min.

Example 125

3-Butyl-8-chloro-1-[3-(5-{[3-chloro-2-(methyloxy)phenyl]methyl}-1,2,4-oxadiazol-3-yl)propyl]-3,7-dihydro-1H-purine-2,6-dione

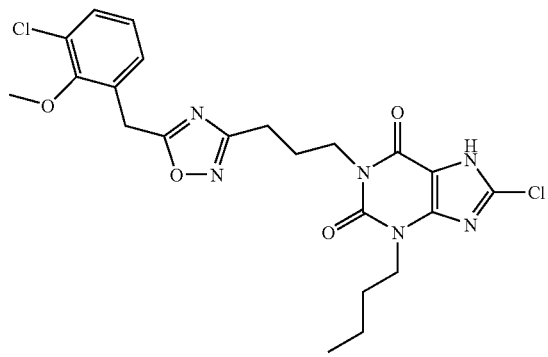

A mixture of [3-chloro-2-(methyloxy)phenyl]acetic acid (32 mg, 0.16 mmol) in DMF (1.5 ml) was treated with CDI (26 mg, 0.16 mmol) and left to react for 45 min. (1Z)-4-(3-Butyl-8-chloro-2,6-dioxo-2,3,6,7-tetrahydro-1H-purin-1-yl)-N-hydroxybutanimidamide (60 mg, 0.18 mmol) was added and the mixture heated in the microwave at 140° C. for 15 min. After cooling, the reaction was partitioned between 2M HCl (aq) and EtOAc. The organic layer was separated then concentrated and purified by the MDAP. The title compound was obtained as a white solid (25 mg, 28%).

LC/MS: m/z 507 [MH]$^+$, RT 3.5 min.

Example 126

3-Butyl-8-chloro-1-(3-{5-[(3-fluoro-4-hydroxyphenyl)methyl]-1,2,4-oxadiazol-3-yl}propyl)-3,7-dihydro-1H-purine-2,6-dione

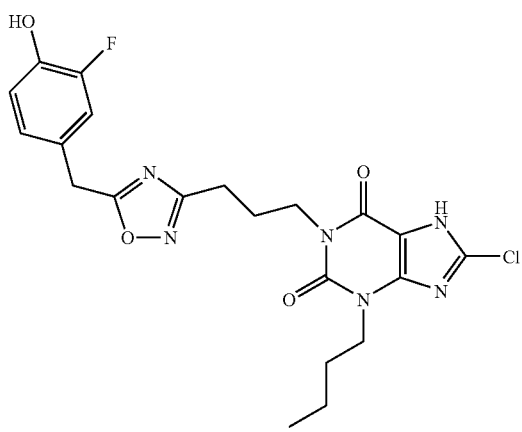

A mixture of (3-fluoro-4-hydroxyphenyl)acetic acid (27 mg, 0.16 mmol) in DMF (1.5 ml) was treated with CDI (26 mg, 0.16 mmol) and left to react for 45 min. (1Z)-4-(3-Butyl-8-chloro-2,6-dioxo-2,3,6,7-tetrahydro-1H-purin-1-yl)-N-hydroxybutanimidamide (60 mg, 0.18 mmol) was added and the mixture heated in the microwave at 140° C. for 15 min. After cooling, the reaction was partitioned between 2M HCl (aq) and EtOAc. The organic layer was separated then concentrated and purified by MDAP. The title compound was obtained as a white solid (10 mg, 12%).

LC/MS: m/z 477 [MH]$^+$, RT 3.2 min.

Example 127

8-chloro-3-pentyl-1-[4-(5-phenyl-1,2,4-oxadiazol-3-yl)butyl]-3,7-dihydro-1H-purine-2,6-dione a) Preparation of 8-chloro-3-pentyl-1-[4-(5-phenyl-1,2,4-oxadiazol-3-yl)butyl]-3,7-dihydro-1H-purine-2,6-dione

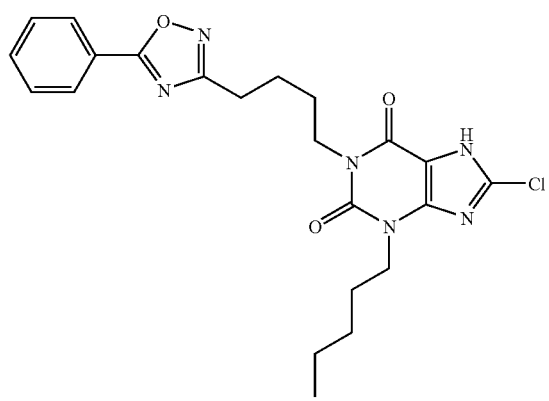

Benzoic acid (18 mg, 0.15 mmol) was treated with a solution of 1H-1,2,3-benzotriazol-1-ol hydrate (25 mg, 0.19 mmol) in DMSO (0.3 ml). To this was added a solution/suspension of N-[3-(dimethylamino)propyl]-N'-ethylcarbodiimide hydrochloride (29 mg, 0.15 mmol) in DMSO (0.3 ml) followed by a solution of 5-(8-chloro-2,6-dioxo-3-pentyl-2,3,6,7-tetrahydro-1H-purin-1-yl)-N-hydroxypentanimidamide (55 mg, 0.15 mmol) in DMSO (0.3 ml). The mixture was heated at 40° C. for 1 h, then at 80° C. for 5 h and then cooled. The mixture was subjected to purification by MDAP. Product-containing fractions were blown to dryness by a stream of nitrogen to yield the title compound as a white solid (17.2 mg, 25%).

LC/MS: m/z 457 [MH]$^+$, RT 3.67 min.

$^1$H NMR (CDCl$_3$) δ: 0.90 (t, 3H, J=6.8 Hz), 1.35 (m, 4H), 1.76 (m, 2H), 1.89 (m, 4H), 2.88 (t, 2H, J=7.2 Hz), 4.08 (t, 2H, J=7.5 Hz), 4.17 (t, 2H, J=6.7 Hz), 7.50 (m, 2H), 7.57 (m, 1H), 8.08, (d, 2H, J=7.3 Hz).

b) 5-(8-Chloro-2,6-dioxo-3-pentyl-2,3,6,7-tetrahydro-1H-purin-1-yl)-N-hydroxypentanimidamide

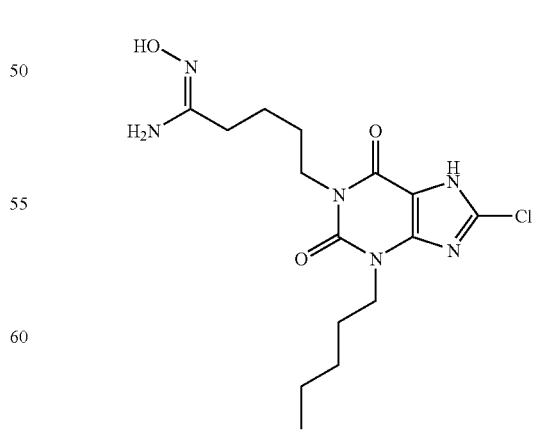

A solution of 5-(8-chloro-2,6-dioxo-3-pentyl-2,3,6,7-tetrahydro-1H-purin-1-yl)pentanenitrile (3.0 g, 8.9 mmol) in EtOH (30 ml) was treated with water (15 ml), potassium carbonate (1.48 g, 10.7 mmol) and hydroxylamine hydrochloride (0.74 g, 10.7 mmol) and then heated at 70° C. overnight. A further potassium carbonate (1.5 g, 10.9 mmol) and hydroxylamine hydrochloride (1.0 g, 14.5 mmol) were cautiously added to the mixture which was then heated to 90° C. for 24 h. The mixture was cooled and concentrated in vacuo to remove most of the EtOH. The residual mixture was treated with water (30 ml) and acidified to pH 7 by the cautious addition of 2M aqueous hydrochloric acid. The precipitated solid was filtered off, washed with water, then with diethyl ether and thoroughly dried to yield the title compound as a white solid (2.80 g, 85%).

LC/MS: m/z 371 [MH]$^+$, RT 2.27 min.

c) 5-(8-Chloro-2,6-dioxo-3-pentyl-2,3,6,7-tetrahydro-1H-purin-1-yl)pentanenitrile

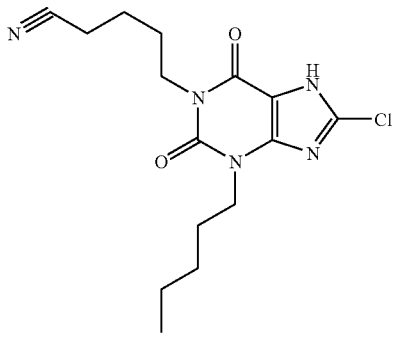

A solution of 8-chloro-3-pentyl-7-(2-propen-1-yl)-3,7-dihydro-1H-purine-2,6-dione (4.0 g, 13.5 mmol) in DMF (100 ml) was treated with caesium carbonate (4.83 g, 14.8 mmol) and 5-bromopentanenitrile (1.73 ml, 14.8 mmol). The mixture was heated at 50° C. in a nitrogen atmosphere for 19 h and then cooled. The mixture was then degassed by the repeated successive application of a vacuum and then nitrogen pressure. The mixture was then treated with tetrakis(triphenylphosphine)palladium(0) (1.1 g, 0.94 mmol) and morpholine (11.8 ml, 136 mmol). The mixture was stirred in a nitrogen atmosphere for 3 h and then partitioned between EtOAc and 2M aqueous hydrochloric acid. The organic layer was separated, washed with brine, dried (MgSO$_4$) and concentrated to reveal a yellow, oily residue. This was dissolved in MeOH, divided equally into four portions and each portion applied to a 20 g aminopropyl SPE which was then washed through with MeOH. The desired product was eluted from the cartridge with a 5% v/v solution of AcOH in MeOH. The product-containing fractions were combined and concentrated to yield the title compound as a pale yellow solid (4.03 g, 88%).

LC/MS: m/z 338 [MH]$^+$, RT 3.05 min.

The following compounds were prepared using a method analogous to that for Example 127 (8-chloro-3-pentyl-1-[4-(5-phenyl-1,2,4-oxadiazol-3-yl)butyl]-3,7-dihydro-1H-purine-2,6-dione) from the corresponding acids:

TABLE 9

| # | Structure | Name | Yield | LC/MS: |
|---|-----------|------|-------|--------|
| 128 | 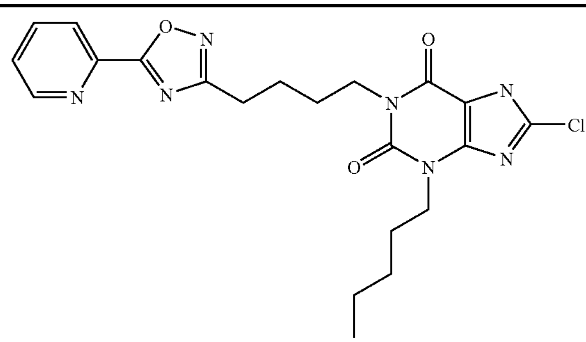 | 8-chloro-3-pentyl-1-{4-[5-(2-pyridinyl)-1,2,4-oxadiazol-3-yl]butyl}-3,7-dihydro-1H-purine-2,6-dione | 7.3 mg (11%) | m/z 458 [MH]$^+$ RT 3.21 min |
| 139 | 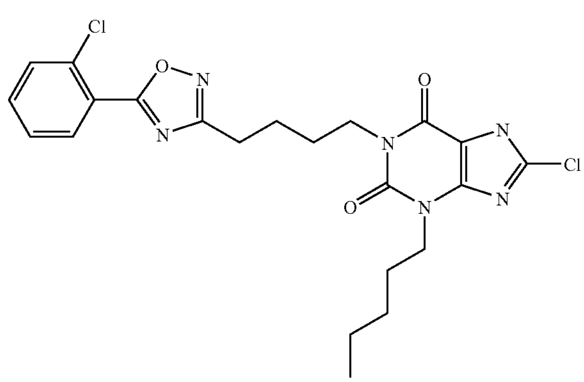 | 8-chloro-1-{4-[5-(2-chlorophenyl)-1,2,4-oxadiazol-3-yl]butyl}-3-pentyl-3,7-dihydro-1H-purine-2,6-dione | 12.8 mg (17%) | m/z 491 [MH]$^+$ RT 3.77 min |

TABLE 9-continued

| # | Structure | Name | Yield | LC/MS: |
|---|---|---|---|---|
| 130 | 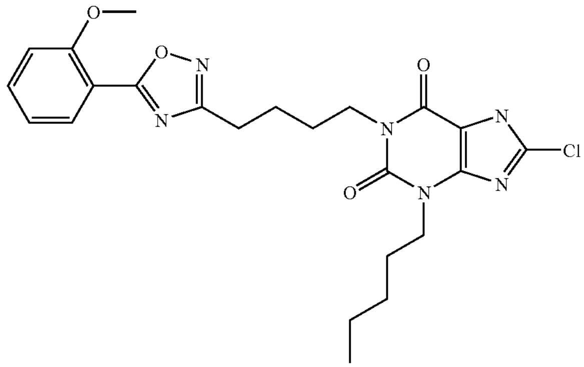 | 8-chloro-1-(4-{5-[2-(methyloxy)phenyl]-1,2,4-oxadiazol-3-yl}butyl)-3-pentyl-3,7-dihydro-1H-purine-2,6-dione | 21.7 mg (30%) | m/z 487 [MH]+ RT 3.54 min |
| 131 | 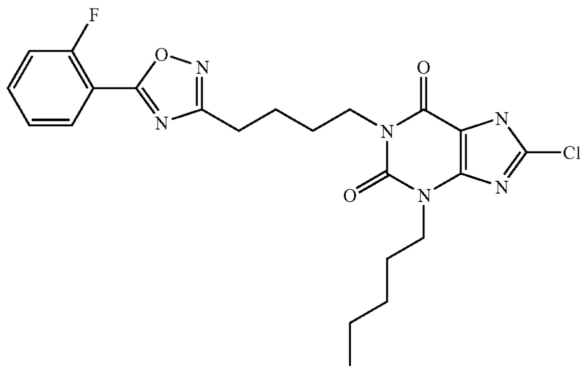 | 8-chloro-1-{4-[5-(2-fluorophenyl)-1,2,4-oxadiazol-3-yl]butyl}-3-pentyl-3,7-dihydro-1H-purine-2,6-dione | 16.6 mg (23%) | m/z 475 [MH]+ RT 3.62 min |

In addition Example 128, 8-chloro-3-pentyl-1-{4-[5-(2-pyridinyl)-1,2,4-oxadiazol-3-yl]butyl}-3,7-dihydro-1H-purine-2,6-dione has the following spectral data: $^1$H NMR (CDCl$_3$) δ: 0.89 (t, 3H, J=6.9 Hz), 1.75 (m, 4H), 1.89 (m, 6H), 2.92 (t, 21-1, J=7.1 Hz), 4.07 (t, 2H, J=7.4 Hz), 4.16 (t, 2H, J=6.9 Hz), 7.52 (m, 1H), 7.92 (m, 1H), 8.18 (m, 1H), 8.83 (m, 1H), 13.40 (br s, 1H).

Example 132

8-Chloro-1-{4-[5-(4-hydroxyphenyl)-1,2,4-oxadiazol-3-yl]butyl}-3-propyl-3,7-dihydro-1H-purine-2,6-dione

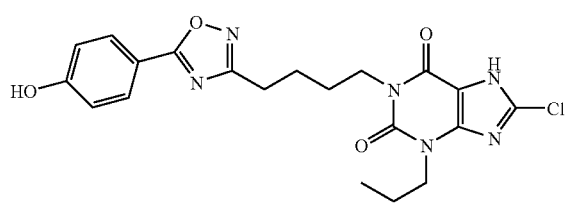

4-Hydroxybenzoic acid (18 mg, 0.13 mmol) and CDI (24 mg, 0.15 mmol) were stirred in anhydrous DMSO (0.9 ml) at rt for 1 h. (1Z)-5-(8-Chloro-2,6-dioxo-3-propyl-2,3,6,7-tetrahydro-1H-purin-1-yl)-N-hydroxypentanimidamide (50 mg, 0.15 mmol; prepared in a manner similar to (1Z)-5-(8-Chloro-2,6-dioxo-3-pentyl-2,3,6,7-tetrahydro-1H-purin-1-yl)-N-hydroxypentanimidamide as described in Example 128(b)) was added and the mixture was stirred at 90° C. for 2 h. The reaction mixture was purified by MDAP. The product fraction was combined and concentrated under high vacuum to give the title compound as a white solid (7 mg, 11%).
LC/MS: m/z 443 [MH]+, RT 3.28 min.

Example 133

3-Butyl-8-chloro-1-{4-[5-(2,6-difluorophenyl)-1,2,4-oxadiazol-3-yl]butyl}-3,7-dihydro-1H-purine-2,6-dione

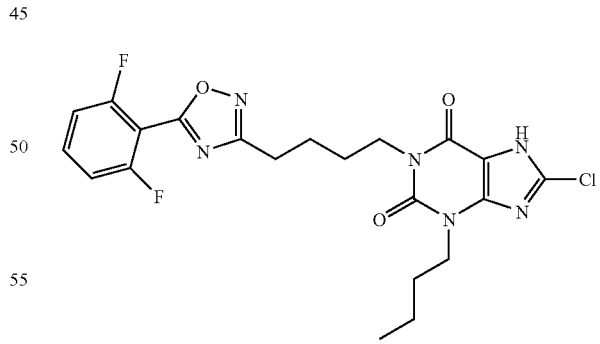

2,6-Difluorobenzoic acid (40 mg, 0.25 mmol) and CDI (45 mg, 0.28 mmol) were stirred in anhydrous DMSO (0.9 ml) at rt for 1 h. (1Z)-5-(3-Butyl-8-chloro-2,6-dioxo-2,3,6,7-tetrahydro-1H-purin-1-yl)-N-hydroxypantanimidamide (100 mg, 0.28 mmol) was added and the mixture was stirred at 90° C. for 16 h. The reaction mixture was purified by MDAP. The product fraction was combined and concentrated to give the title compound as a white solid (18 mg, 15%).
LC/MS: m/z 479 [MH]+, RT 3.40 min.

Example 134

3-Butyl-8-chloro-1-{4-[5-(2-fluorophenyl)-1,2,4-oxadiazol-3-yl]butyl}-3,7-dihydro-1H-purine-2,6-dione

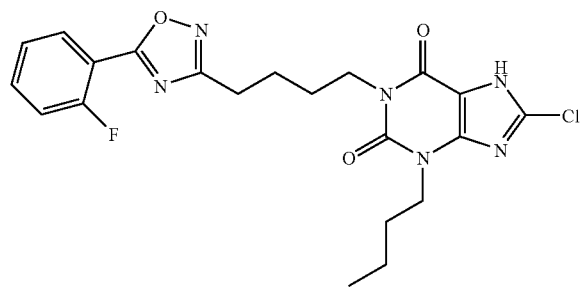

2-Fluorobenzoic acid (36 mg, 0.25 mmol) and CDI (45 mg, 0.28 mmol) were stirred in anhydrous DMSO (0.9 ml) at rt for 1 h. (1Z)-5-(3-Butyl-8-chloro-2,6-dioxo-2,3,6,7-tetrahydro-1H-purin-1-yl)-N-hydroxypentanimidamide (100 mg, 0.28 mmol) was added and the mixture was stirred at 90° C. for 16 h. The mixture was purified by MDAP. The product fraction was combined and concentrated to give the title compound as a white solid (33 mg, 29%).

LC/MS: m/z 461 [MH]+, RT 3.44 min.

Example 135

3-Butyl-8-chloro-1-{4-[5-(4-chloro-2-pyridinyl)-1,2,4-oxadiazol-3-yl]butyl}-3,7-dihydro-1H-purine-2,6-dione

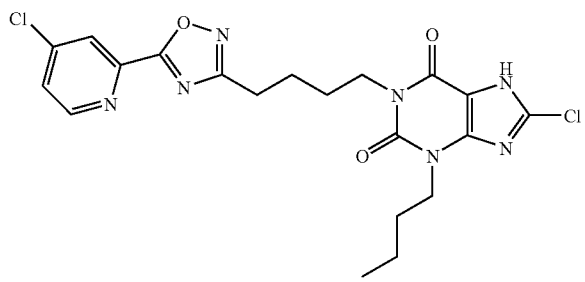

4-Chloro-2-pyridinecarboxylic acid (40 mg, 0.25 mmol) and CDI (45 mg, 0.28 mmol) were stirred in anhydrous DMSO (0.9 ml) at rt for 1 h. (1Z)-5-(3-Butyl-8-chloro-2,6-dioxo-2,3,6,7-tetrahydro-1H-purin-1-yl)-N-hydroxypentanimidamide (100 mg, 0.28 mmol) was added and the mixture was stirred at 90° C. for 16 h. The reaction mixture was purified by MDAP. The product fraction was combined and concentrated to give the title compound as a white solid (13 mg, 11%).

LC/MS: m/z 478 [MH]+, RT 3.31 min.

$^1$H NMR (DMSO-$d_6$) $\delta_H$ 14.4 (br. s, 1H), 8.79 (d, 1H, J=6 Hz), 8.24 (d, 1H, J=2 Hz), 7.88 (dd, 1H, J=6 Hz & 2 Hz), 3.91 (m, 4H), 2.85 (t, 2H, J=7.5 Hz), 1.56-1.76 (m, 6H), 1.28 (m, 2H), 0.87 (t, 3H, J=7.5 Hz) ppm.

Example 136

3-Butyl-8-chloro-1-{4-[5-(3-methyl-2-pyridinyl)-1,2,4-oxadiazol-3-yl]butyl}-3,7-dihydro-1H-purine-2,6-dione

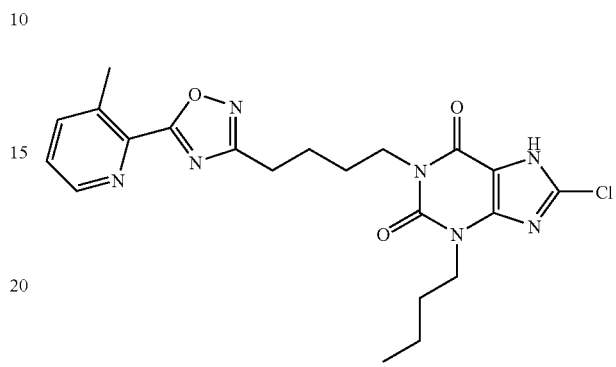

3-Methyl-2-pyridinecarboxylic acid (35 mg, 0.25 mmol) and CDI (45 mg, 0.28 mmol) were stirred in anhydrous DMSO (0.9 ml) at rt for 1 h. (1Z)-5-(3-Butyl-8-chloro-2,6-dioxo-2,3,6,7-tetrahydro-1H-purin-1-yl)-N-hydroxypentanimidamide (100 mg, 0.28 mmol) was added and the mixture was stirred at 90° C. for 16 h. The reaction mixture was purified by MDAP. The product fraction was combined and concentrated to give the title compound as a white solid 14 mg, 12%).

LC/MS: m/z 458 [MH]+, RT 3.13 min.

Example 137

3-Butyl-8-chloro-1-{4-[5-(2-pyridinyl)-1,2,4-oxadiazol-3-yl]butyl}-3,7-dihydro-1H-purine-2,6-dione Method A

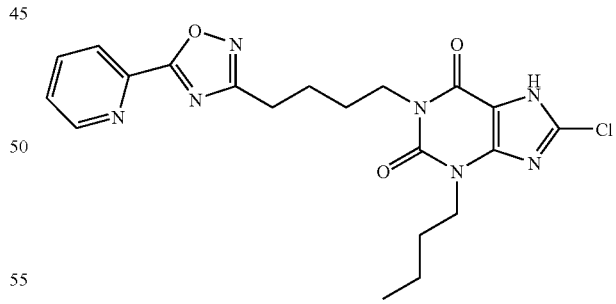

2-Pyridinecarboxylic acid (31 mg, 0.25 mmol) and CDI (45 mg, 0.28 mmol) were stirred in anhydrous DMSO (0.5 ml) at rt for 1 h. A solution of (1Z)-5-(3-Butyl-8-chloro-2,6-dioxo-2,3,6,7-tetrahydro-1H-purin-1-yl)-N-hydroxypentanimidamide (100 mg, 0.28 mmol) in DMSO (0.4 ml) was added and the mixture was stirred at 90° C. for 16 h. The reaction mixture was purified directly by MDAP. The product fractions were combined and concentrated to give the title compound as a white solid (14 mg, 12%).

LC/MS: m/z 444 [MH]+, RT 3.01 min.

$^1$H NMR (DMSO-$d_6$) δ: 0.87 (t, 3H, J=7 Hz), 1.27 (m, 2H), 1.65 (m, 6H), 2.84 (t, 2H, J=7 Hz), 3.91 (m, 4H), 7.70 (dd 1H, J=5 & 7 Hz), 8.07 (m, 1H), 8.19 (d, 1H, J=8 Hz), 8.81 (d, 1H, J=5 Hz), 14.5 (br. s, 1H).

Method B

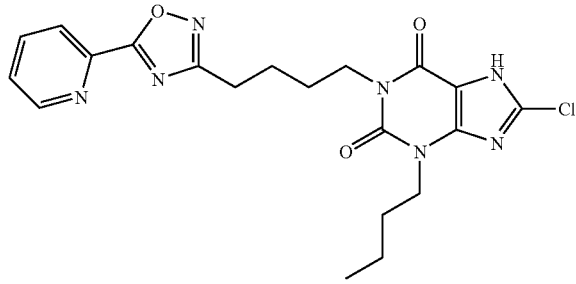

2-Pyridinecarboxylic acid (675 mg, 5.3 mmol) and CDI (909 mg, 5.6 mmol) were stirred in anhydrous DMF (30 ml) at rt under nitrogen for 90 mins. (1Z)-5-(3-Butyl-8-chloro-2,6-dioxo-2,3,6,7-tetrahydro-1H-purin-1-yl)-N-hydroxypentanimidamide (2.0 g, 5.6 mmol) and DMF (10 ml) were added and the mixture was stirred at 100° C. for 20 h. The reaction mixture was cooled to rt then partitioned between sat. NH$_4$Cl (aq) solution and EtOAc. The organic layer was separated, and the aqueous solution extracted with EtOAc. The combined extracts were washed with brine, dried MgSO$_4$ and concentrated giving an orange liquid. This was purified using the Companion™ system giving two identical white solids (649 mg; 240 mg).

LC/MS: m/z 444 [MH]$^+$, RT 3.04 min.

Method C

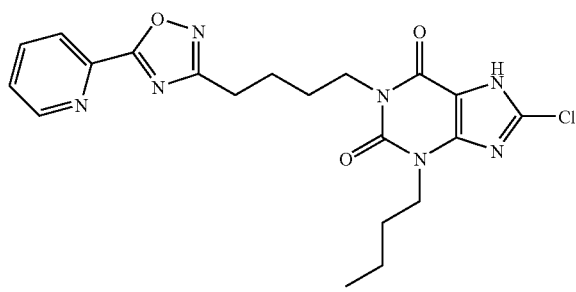

A 12-L, round-bottom flask was equipped with an overhead, mechanical stirrer, a temperature probe with a J-KEM temperature controller, a condenser and a nitrogen inlet adapter. The flask was charged with picolinic acid (0.180 kg, 1.46 mol), MIBK (4.0 L), 1,1'-carbonyldiimidazole (0.23 kg, 1.42 mol,) and more MIBK (0.66 L). The mixture was stirred and warmed to 50° C. over approximately 1 hour, and the temperature overshot to 56° C. The solids dissolved during the heat up to 50° C. and carbon dioxide was generated. After 1 hour at 50° C., (1Z)-5-(3-Butyl-8-chloro-2,6-dioxo-2,3,6,7-tetrahydro-1H-purin-1-yl)-N-hydroxypentanimidamide (0.467 kg, 1.31 mol) was added to the reaction. The mixture was then warmed to 90° C. over 1 hour. HPLC analysis of the reaction after heating at 90° C. for 5.5 hours indicated that the reaction was complete. The heat was turned off, and 1.0 N hydrochloric acid solution (2.33 L) was added. The temperature dropped to 61° C. After stirring overnight, the product precipitated and was filtered. The filtercake was washed with water (1×2.23 L, 1×2.43 L) and heptanes (1.40 L). The wet cake was dried in a vacuum oven at 50° C. for 22 hours to give 396 g of product (68%) HPLC analysis 97.7% (AUC) $t_R$=18.6 min.

Methods A, B and C of Example 137 produce substantially crystalline 3-Butyl-8-chloro-1-{4-[5-(2-pyridinyl)-1,2,4-oxadiazol-3-yl]butyl}-3,7-dihydro-1H-purine-2,6-dione Form 2.

Method D

Formation of 3-Butyl-8-chloro-1-{4-[5-(2-pyridinyl)-1,2,4-oxadiazol-3-yl]butyl}-3,7-dihydro-1H-purine-2,6-dione Form 1

The reaction vessel was charged with 3-Butyl-8-chloro-1-{4-[5-(2-pyridinyl)-1,2,4-oxadiazol-3-yl]butyl}-3,7-dihydro-1H-purine-2,6-dione (1 wt), acetone (20 vol) and water (0.6 vol). The mixture was stirred and warmed to 50-60° C. and agitated for a minimum of 1 hour. A solution was formed which is clarified at this temperature by filtration through a 1 micron filter into a 2$^{nd}$ reaction vessel. The solution was cooled over approximately 3 hours to 33-38° C. and seeded at this temperature with 3-Butyl-8-chloro-1-{4-[5-(2-pyridinyl)-1,2,4-oxadiazol-3-yl]butyl}-3,7-dihydro-1H-purine-2,6-dione (Form 1, 0.01 wt). The thin suspension was agitated at this temperature for a minimum of 1 hour then cooled to 20-25° C. and held at this temperature for a minimum of 12 hours. The suspension thus formed was cooled to 13-17° C. and held at this temperature for a minimum of 1 hour. The suspension was then sampled*, and the solid collected by filtration in the laboratory. The solid was dried and analysed by xrpd/DSC to check form. If the form is as required (Form 1) the batch is filtered, washed (2×3 vol acetone) and dried in a vacuum oven at 50° C. The batch is offloaded once analysis shows solvent levels (acetone, water) to be at acceptable.

Expected yield (75-80% w/w).

If the form of the sample taken at * is shown to be other than pure Form 1, then the batch is reheated to 35-45° C. and agitated at this temperature for a minimum of 1 hour. The thin suspension is then cooled to 20-25° C. and held at this temperature for a minimum of 12 hours. The suspension thus formed is then cooled to 13-17° C. and held at this temperature for a minimum of 1 hour. The suspension is then sampled, and the solid collected by filtration in the laboratory. The solid is dried and analysed by xrpd/DSC to check form. If the form is as required (Form 1) the batch is filtered, washed and dried as described previously. If the form is not pure Form 1, then the cycle from  is repeated until a satisfactory result is obtained.

X-Ray Powder Diffraction (XRPD)

Figure 2:
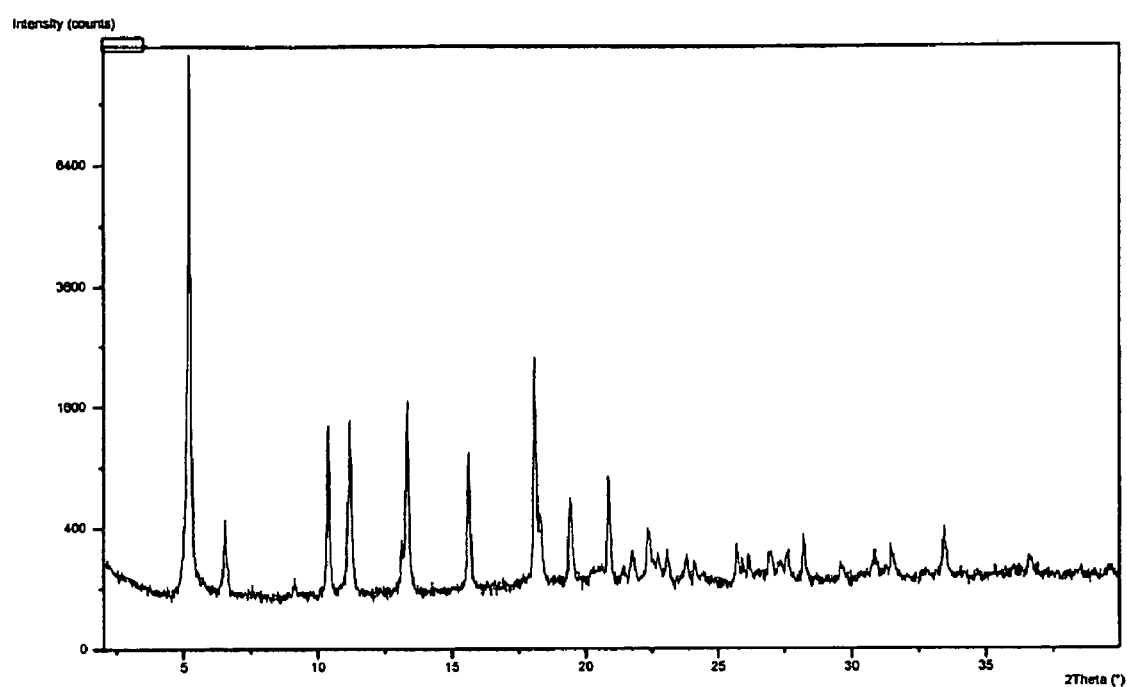
FIG. 2: XRPD data of substantially crystalline 3-Butyl-8-chloro-1-{4-[5-(2-pyridinyl)-1,2,4-oxadiazol-3-yl]butyl}-3,7-dihydro-1H-purine-2,6-dione form 2.
Figure 3:
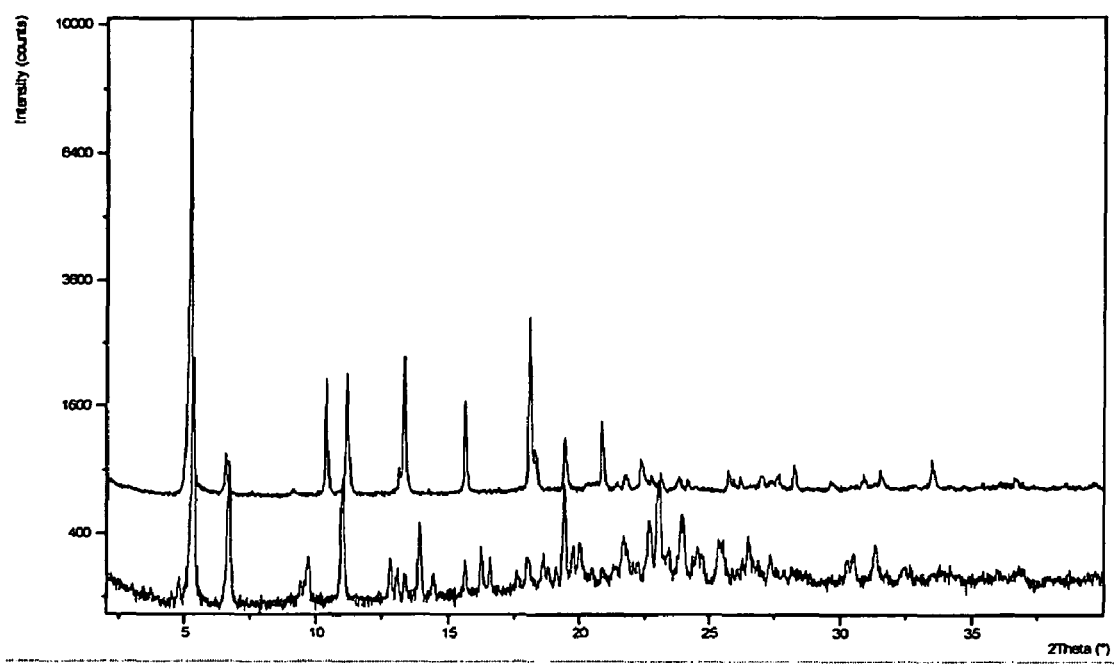
FIG. 3: Overlay of XRPD data for substantially crystalline 3-Butyl-8-chloro-1-{4-[5-(2-pyridinyl)-1,2,4-oxadiazol-3-yl]butyl}-3,7-dihydro-1H-purine-2,6-dione Form 1 and Form 2.

X-ray powder diffraction (XRPD) data are shown in FIGS. 1-3. The data were acquired on a PANalytical X'Pert Pro powder diffractometer, model PW3040/60, serial number DY1850 using an X'Celerator detector. The acquisition conditions were: radiation: Cu Kα, generator tension: 40 kV, generator current: 45 mA, start angle: 2.0° 2θ, end angle: 40.0° 2θ, step size: 0.0167° 2θ, time per step: 31.75 seconds.

Example 138

3-Butyl-8-chloro-1-{4-[5-(4-hydroxyphenyl)-1,2,4-oxadiazol-3-yl]butyl}-3,7-dihydro-1H-purine-2,6-dione

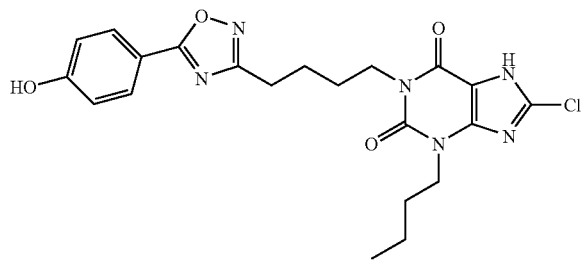

4-Hydroxybenzoic acid (35 mg, 0.25 mmol) and CDI (45 mg, 0.28 mmol) were stirred in anhydrous DMSO (0.9 ml) at rt for 1 h. (1Z)-5-(3-Butyl-8-chloro-2,6-dioxo-2,3,6,7-tetrahydro-1H-purin-1-yl)-N-hydroxypentanimidamide (100 mg, 0.28 mmol) was added and the mixture was stirred at 90° C. for 16 h. The mixture was purified by MDAP to give the title compound as a white solid (5 mg, 4%).

LC/MS: m/z 459 [MH]$^+$, RT 3.24 min.

Example 139

8-Chloro-1-[4-(5-phenyl-1,2,4-oxadiazol-3-yl)butyl]-3-propyl-3,7-dihydro-1H-purine-2,6-dione

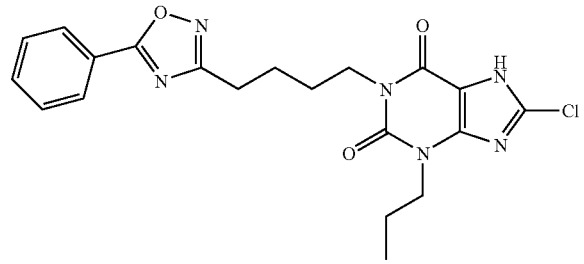

Benzoic acid (9 mg, 0.074 mmol) and CDI (13 mg, 0.081 mmol) were stirred in anhydrous DMSO (0.9 ml) at rt for 1 h. (1Z)-5-(8-Chloro-2,6-dioxo-3-propyl-2,3,6,7-tetrahydro-1H-purin-1-yl)-N-hydroxypentanimidamide (28 mg, 0.081 mmol) was added and the mixture was stirred at 80° C. for 4 h. The mixture was purified by MDAP to give the title compound as a white solid (0.6 mg, 2%).

LC/MS: m/z 429 [MH]$^+$, RT 3.21 min.

$^1$H NMR (MeOH-d$_4$) δ: 0.93 (t, 3H, J=7.5 Hz), 1.74 (m, 4H), 1.84 (m, 2H), 2.84 (t, 2H, J=7 Hz), 3.97 (t, 2H, J=7.5 Hz), 4.08 (t, 2H, J=7 Hz), 7.57 (dd, 2H, J=7 & 7.5 Hz), 7.65 (dd, 1H, J=7 & 7.5 Hz), 8.08 (d, 2H, J=7.5 Hz).

Example 140

3-Butyl-8-chloro-1-{4-[5-(2-chloro-6-fluorophenyl)-1,2,4-oxadiazol-3-yl]butyl}-3,7-dihydro-1H-purine-2,6-dione

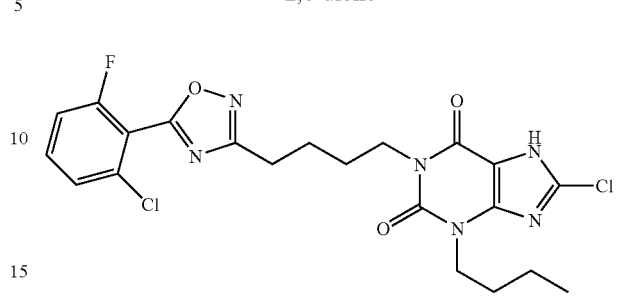

2-Chloro-6-fluorobenzoic acid (44 mg, 0.25 mmol) and CDI (45 mg, 0.28 mmol) were stirred in anhydrous DMSO (0.9 ml) at rt for 1 h. (1Z)-5-(3-Butyl-8-chloro-2,6-dioxo-2,3,6,7-tetrahydro-1H-purin-1-yl)-N-hydroxypentanimidamide (100 mg, 0.28 mmol) was added and the mixture was stirred at 90° C. for 16 h. The mixture was purified by MDAP. The product fraction was combined and concentrated to give the title compound as a white solid (6.4 mg, 5%).

LC/MS: m/z 495 [MH]$^+$, RT 3.58 min.

Example 141

3-Butyl-8-chloro-1-{4-[5-(5-hydroxy-2-pyridinyl)-1,2,4-oxadiazol-3-yl]butyl}-3,7-dihydro-1H-purine-2,6-dione

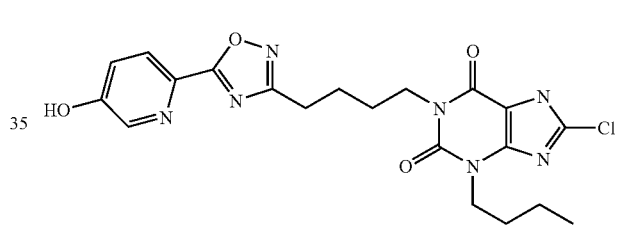

5-Hydroxy-2-pyridinecarboxylic acid (24 mg, 0.17 mmol) and CDI (31 mg, 0.19 mmol) were stirred in anhydrous DMSO (0.9 ml) at rt for 1 h. (1Z)-5-(3-Butyl-8-chloro-2,6-dioxo-2,3,6,7-tetrahydro-1H-purin-1-yl)-N-hydroxypentanimidamide (68 mg, 0.19 mmol) was added and the mixture was stirred at 90° C. for 16 h. The mixture was purified by MDAP and the product fractions concentrated to give the title compound as a white solid (19 mg, 24%).

LC/MS: m/z 459 [MH]$^+$, RT 3.03 min.

Example 142

8-Chloro-3-pentyl-1-{4-[5-(3-thienyl)-1,2,4-oxadiazol-3-yl]butyl}-3,7-dihydro-1H-purine-2,6-dione

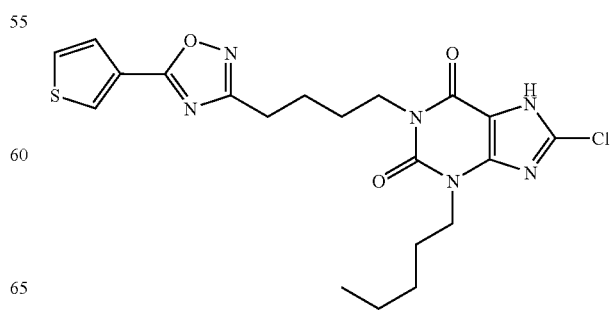

A solution of (1Z)-5-(8-chloro-2,6-dioxo-3-pentyl-2,3,6,7-tetrahydro-1H-purin-1-yl)-N-hydroxypentanimidamide (50 mg, 0.13 mmol) in EtOH (1 ml) was treated with a 21% solution of NaOEt in EtOH (55 µl, 0.21 mmol) and ethyl 3-thiophenecarboxylate (18 µl, 0.13 mmol). The mixture was heated in the microwave at 150° C. for 10 min. After cooling, the reaction was partitioned between 2M HCl (aq) and EtOAc. The organic layer was separated and the aqueous extracted again with EtOAc. The combined extracts were concentrated and purified by the MDAP. The title compound was obtained as an off-white solid (20 mg, 32%).

LC/MS: m/z 463 [MH]+, RT 3.6 min.

Example 143

8-Chloro-3-pentyl-1-{4-[5-(2-thienyl)-1,2,4-oxadiazol-3-yl]butyl}-3,7-dihydro-1H-purine-2,6-dione

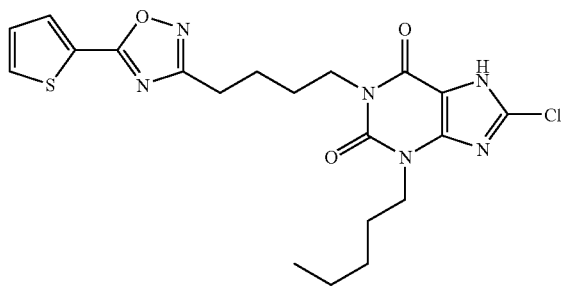

2-Thiophenecarboxylic acid (14 mg, 0.11 mmol) was dissolved in NMP (0.9 ml) and treated with CDI (18 mg, 0.11 mmol). After 1 h, (1Z)-5-(8-chloro-2,6-dioxo-3-pentyl-2,3,6,7-tetrahydro-1H-purin-1-yl)-N-hydroxypentanimidamide (50 mg, 0.13 mmol) was added and the mixture heated in the microwave at 150° C. for 15 min. The solution was directly purified by MDAP to obtain the title compound which was then freeze dried from 1,4-dioxane to give the title compound as a white solid (19 mg, 31%).

LC/MS: m/z 463 [MH]+, RT 3.5 min.

Example 144

8-Chloro-3-pentyl-1-{4-[5-(1,3-thiazol-2-yl)-1,2,4-oxadiazol-3-yl]butyl}-3,7-dihydro-1H-purine-2,6-dione

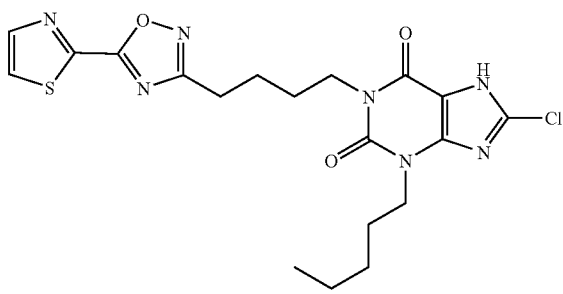

A solution of (1Z)-5-(8-chloro-2,6-dioxo-3-pentyl-2,3,6,7-tetrahydro-1H-purin-1-yl)-N-hydroxypentanimidamide (50 mg, 0.13 mmol) in EtOH (1.5 ml) was treated with a 21% solution of NaOEt in EtOH (50 µl, 0.13 mmol) and ethyl 1,3-thiazole-2-carboxylate (18 mg, 0.11 mmol). The mixture was heated in the microwave at 170° C. for 10 min. After cooling, the reaction was partitioned between 2M HCl (aq) and EtOAc. The organic layer was separated then concentrated and purified by the MDAP. The title compound was obtained as a white solid (13 mg, 21%).

LC/MS: m/z 464 [MH]+, RT 3.3 min.
$^1$H NMR (DMSO-$d_6$) δ: 0.83 (t, 3H, J=7 Hz), 1.21-1.32 (m, 4H), 1.60-1.77 (m, 6H), 2.84 (t, 2H, J=7 Hz), 3.91 (m, 4H), 8.23 (d, 1H, J=3 Hz), 8.27 (d, 1H, J=3 Hz), 14.4 (br s, 1H).

Example 145

3-butyl-8-chloro-1-{4-[3-(2-pyridinyl)-1,2,4-oxadiazol-5-yl]butyl}-3,7-dihydro-1H-purine-2,6-dione a) Preparation of 3-butyl-8-chloro-1-{4-[3-(2-pyridinyl)-1,2,4-oxadiazol-5-yl]butyl}-3,7-dihydro-1H-purine-2,6-dione

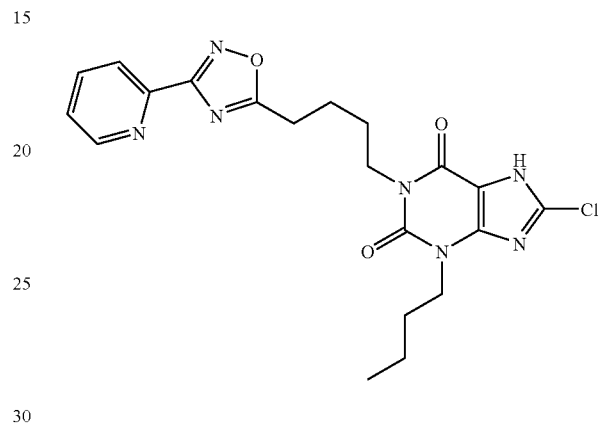

To a mixture of ethyl 5-(3-butyl-8-chloro-2,6-dioxo-2,3,6,7-tetrahydro-1H-purin-1-yl)pentanoate (120 mg, 0.32 mmol) and of N-hydroxy-2-pyridinecarboximidamide (50 mg, 0.36 mmol) in EtOH (2 ml) was added a 21% (w/v) solution of sodium ethoxide in EtOH (0.225 ml, 0.62 mmol) and then heated in a sealed vial in a microwave oven at 140° C. for 10 min. The cooled mixture was evaporated to dryness and the residue partitioned between chloroform (5 ml) and saturated aqueous ammonium chloride (5 ml). The organic phase was evaporated to dryness and the crude product subjected to purification by MDAP. Product containing fractions were combined and evaporated to dryness. The product was triturated to a solid in a small amount of diethyl ether then dried to reveal the title compound as a white solid (44 mg, 31%).

LC/MS: m/z 444 [MH]+, RT 3.03 min.
$^1$H NMR (CDCl$_3$) δ: 0.96 (t, 3H, J=7.3 Hz), 1.40 (m, 2H), 1.74 (m, 2H), 1.88 (m, 2H), 1.99 (m, 2H), 3.07 (t, 2H, J=7.5 Hz), 4.09 (t, 2H, J=7.5 Hz), 4.17 (t, 2H, J=7.0 Hz), 7.43 (m, 1H), 7.64 (m, 1H), 8.10 (m, 1H), 8.79 (m, 1H).

b) Preparation of N-hydroxy-2-pyridinecarboximidamide

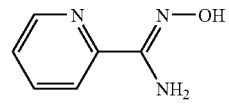

To a mixture of 2-pyridinecarbonitrile (3 g, 29 mmol) and potassium carbonate (4.1 g, 30 mmol) in EtOH (30 ml) was added water (15 ml) and, cautiously, hydroxylamine hydrochloride (2.9 g, 42 mmol) and then heated at reflux for 6 h, cooled and evaporated to dryness. The residue was treated with water (100 ml) and the suspended solid product filtered off, washed with water and dried to yield the title compound as a white solid (2.28 g, 57%).
$^1$H NMR (DMSO-$d_6$) δ: 5.85 (br s, 2H), 7.40 (m, 1H), 7.79 (m, 1H), 7.86 (m, 1H), 8.55 (m, 1H), 9.92 (s, 1H)

Example 146

3-Butyl-8-chloro-1-[4-(3-phenyl-1,2,4-oxadiazol-5-yl)butyl]-3,7-dihydro-1H-purine-2,6-dione

Method A a) 3-Butyl-8-chloro-1-[4-(3-phenyl-1,2,4-oxadiazol-5-yl)butyl]-3,7-dihydro-1H-purine-2,6-dione

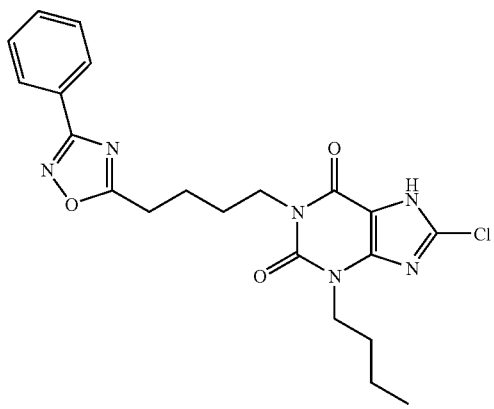

Ethyl 5-(3-butyl-8-chloro-2,6-dioxo-2,3,6,7-tetrahydro-1H-purin-1-yl)pentanoate (74 mg, 0.2 mmol) and benzamidoxime (30 mg, 0.22 mmol) were suspended in dry EtOH (1 ml) and ethanolic sodium ethoxide (21% by wt., 0.111 ml, 0.3 mmol) was added. The mixture was gently warmed until solids were dissolved and then heated in the microwave reactor at 140° C. for 10 min. The mixture was then partitioned between EtOAc and 2M HCl and the organic phase dried ($Na_2SO_4$) and evaporated. MDAP afforded the pure title compound (40.7 mg).

LC/MS: m/z 443 [MH]$^+$, RT 3.67 min.

$^1$H NMR (DMSO-d$_6$) δ: 0.89 (t, 3H, J=7 Hz), 1.22-1.34 (m, 2H), 1.57-1.75 (m, 4H), 1.75-1.86 (m, 2H), 3.05 (t, 2H, J=7 Hz), 3.88-3.98 (m, 4H), 7.52-7.63 (m, 3H), 7.95-8.0 (m, 2H).

b) Ethyl 5-(3-butyl-8-chloro-2,6-dioxo-2,3,6,7-tetrahydro-1H-purin-1-yl)pentanoate

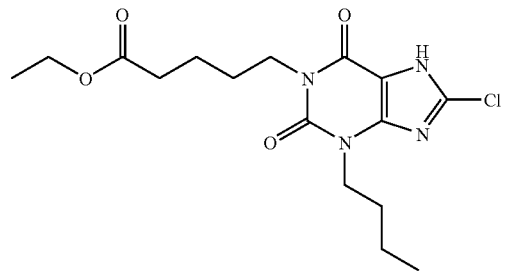

To 3-butyl-8-chloro-7-(2-propen-1-yl)-3,7-dihydro-1H-purine-2,6-dione (1.5 g, 5.31 mmol) in dry DMF (25 ml) was added $Cs_2CO_3$ (1.905 g, 5.84 mmol), followed by ethyl 5-bromovalerate (1.46 g, 6.99 mmol). The mixture was heated at 55° C. for 18 h then allowed to cool. It was degassed by repeatedly evacuating and readmitting nitrogen, then morpholine (3.70 ml, 42.5 mmol) and tetrakis(triphenylphosphine)palladium(0) (1.0 g, 0.865 mmol) were added and the mixture stirred for 5 h. EtOAc (75 ml), 2M HCl (40 ml) and water (20 ml) were added and the organic phase was separated, washed with brine (3×25 ml), filtered to remove some insoluble yellow solid, dried ($Na_2SO_4$) and evaporated. The residue (2.5 g) was purified by aminopropyl SPE (20 g), loading in THF-MeOH (1:1), washing with MeOH and eluting the product with DCM-MeOH (1:1) containing 5% added AcOH to afford the title compound (1.53 g).

LC/MS: m/z 371 MH$^+$, RT 3.18 min

Method B a) 3-Butyl-8-chloro-1-[4-(3-phenyl-1,2,4-oxadiazol-5-yl)butyl]-3,7-dihydro-1H-purine-2,6-dione

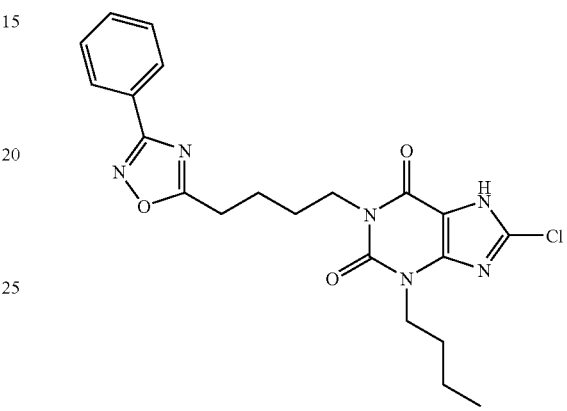

CDI (0.98 g, 6.1 mmol) was added to a solution of 5-(3-butyl-8-chloro-2,6-dioxo-2,3,6,7-tetrahydro-1H-purin-1-yl)pentanoic acid (1.89 g, 5.5 mmol) in DMF (15 ml) and stirred under nitrogen for 1.5 h. Benzamidoxime (0.91 g, 6.1 mmol) was added and the mixture stirred at 110° C. overnight. The reaction mixture was partitioned between EtOAc and 2M HCl. The organic layer was separated, washed with brine, dried (MgSO$_4$) and evaporated. The crude product was crystallised from methanol and then further purified using the Companion™ system and a gradient elution from cyclohexane to EtOAc. Product containing fractions were combined and evaporated to give the title compound as a white solid (850 mg).

LC/MS: m/z 443 [MH]$^+$, RT 3.52 min.

$^1$H NMR (MeOH-d$_4$) δ: 0.94 (t, 3H, J=7.5 Hz), 1.31-1.41 (m, 2H), 1.65-1.73 (m, 2H), 1.75-1.83 (m, 2H), 1.87-1.96 (m, 2H), 3.04 (t, 2H, J=7.5 Hz), 4.01 (t, 2H, J=7.5 Hz), 4.06 (t, 2H, J=7 Hz), 7.46-7.55 (m, 3H), 7.98-8.02 (m, 2H).

b) 5-(3-Butyl-8-chloro-2,6-dioxo-2,3,6,7-tetrahydro-1H-purin-1-yl)pentanoic acid

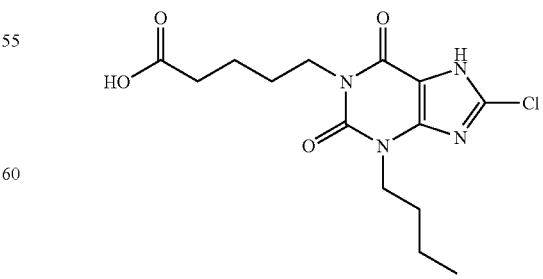

A mixture of ethyl 5-(3-butyl-8-chloro-2,6-dioxo-2,3,6,7-tetrahydro-1H-purin-1-yl)pentanoate (2.8 g, 7.55 mmol), LiOH (542 mg, 22.7 mmol), water (2.5 ml) and methanol (50 ml) was stirred at rt for 60 h. The mixture was portioned between water and EtOAc and the pH of the aqueous phase adjusted to pH 4-5. The organic layer was separated, washed with brine, dried (MgSO$_4$) and evaporated to give the title compound as a white solid (2.18 g).

LC/MS: m/z 343 [MH]$^+$, RT 2.69 min.

Example 147

8-Chloro-3-pentyl-1-[4-(3-phenyl-1,2,4-oxadiazol-5-yl)butyl]-3,7-dihydro-1H-purine-2,6-dione

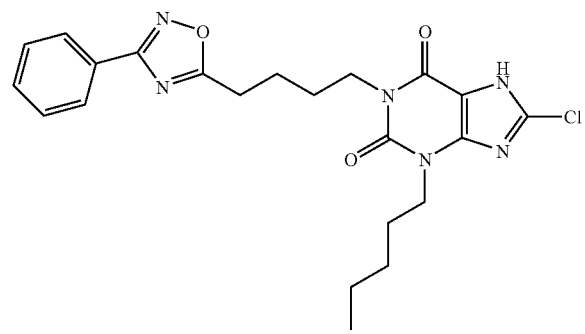

A mixture of methyl 5-(8-chloro-2,6-dioxo-3-pentyl-2,3,6,7-tetrahydro-1H-purin-1-yl)pentanoate (50 mg, 0.13 mmol), benzamidine oxime (20 mg, 0.15 mmol) and a 21% solution of NaOEt in EtOH (76 µl, 0.20 mmol) in EtOH (1.5 ml) was heated in the microwave at 140° C. for 10 min. After cooling the reaction was partitioned between 2M HCl (aq) and EtOAc. The organic layer was separated, dried (MgSO$_4$) and concentrated. Purification by the MDAP gave the title compound as a white solid (25 mg, 41%).

LC/MS: m/z 457 [MH]$^+$, RT 3.7 min.
$^1$H NMR (DMSO-d$_6$) δ: 0.82 (t, 3H, J=7 Hz), 1.25 (m, 4H), 1.66 (m, 4H), 1.79 (m, 2H), 3.04 (t, 2H, J=7 Hz), 3.92 (4H, m), 7.57 (m, 3H), 7.97 (m, 2H), 14.5 (br s, 1H).

Example 148

3-Butyl-8-chloro-1-{4-[3-(3-hydroxyphenyl)-1,2,4-oxadiazol-5-yl]butyl}-3,7-dihydro-1H-purine-2,6-dione

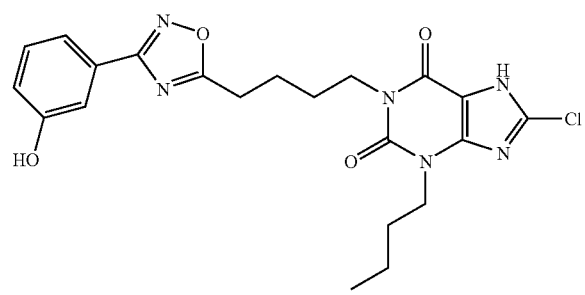

A mixture of ethyl 5-(3-butyl-8-chloro-2,6-dioxo-2,3,6,7-tetrahydro-1H-purin-1-yl)pentanoate (50 mg, 0.13 mmol), N,3-dihydroxybenzenecarboximidamide (25 mg, 0.16 mmol), 21% solution of NaOEt in EtOH (55 µl, 0.15 mmol) and EtOH (1.5 ml) was heated in the microwave at 180° C. for 10 min. Another aliquot of 21% solution of NaOEt in EtOH (55 µl, 0.21 mmol) was added and the mixture heated in the microwave at 175° C. for 30 min. After cooling the reaction was partitioned between 2M HCl (aq) and EtOAc. The organic layer was separated, concentrated and purified by the MDAP. The title compound was obtained as an off-white solid (20 mg, 32%).

LC/MS: m/z 459 [MH]$^+$, RT 3.3 min.

Example 149

8-Chloro-1-{4-[3-(4-hydroxyphenyl)-1,2,4-oxadiazol-5-yl]butyl}-3-pentyl-3,7-dihydro-1H-purine-2,6-dione

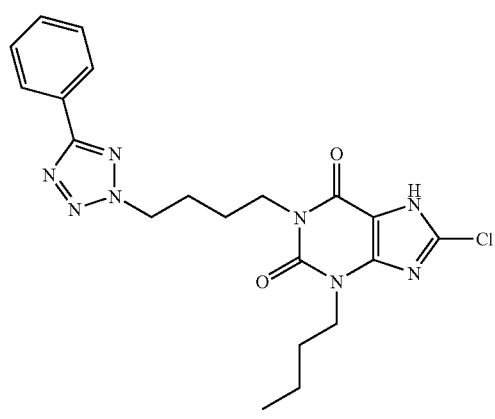

A solution of 5-(8-chloro-2,6-dioxo-3-pentyl-2,3,6,7-tetrahydro-1H-purin-1-yl)pentanoic acid (50 mg, 0.14 mmol) in DMF (2 ml) was treated with CDI (23 mg, 0.14 mmol) and stirred at rt for 30 min. N,4-dihydroxybenzenecarboximidamide (26 mg, 0.17 mmol) was added and the mixture heated in the microwave at 120° C. for 15 min. After cooling the reaction was partitioned between 2M HCl (aq) and EtOAc. The organic layer was separated, concentrated and purified by the MDAP. The title compound was obtained as an off-white solid (17 mg, 26%).

LC/MS: m/z 473 [MH]$^+$, RT 3.5 min.

Example 150

3-Butyl-8-chloro-1-[4-(5-phenyl-2H-tetrazol-2-yl)butyl]-3,7-dihydro-1H-purine-2,6-dione A mixture of 4-[3-butyl-8-chloro-2,6-dioxo-7-(2-propen-1-yl)-2,3,6,7-tetrahydro-1H-purin-1-yl]butyl methanesulfonate (50 mg, 0.12 mmol), Cs$_2$CO$_3$ (45 mg, 0.14 mmol) and DMF (3 ml) was treated with 5-phenyl-1H-tetrazole (20 mg, 0.14 mmol) and stirred for 60 h at 50° C. After cooling, the mixture was degassed by applying a vacuum and then nitrogen was introduced. Pd(PPh$_3$)$_4$ (20 mg, 0.017 mmol) was added and the mixture degassed once more. Morpholine (150 µl, 1.7 mmol) was added and the mixture was stirred under nitrogen for 18 h, then partitioned between 2M HCl (aq) and EtOAc. The organic layer was separated and the aqueous layer extracted again with EtOAc. The combined extracts were concentrated, giving a yellow residue. MeOH was added and then passed down an NH$_2$-propyl column with the product eluting with 2% AcOH/MeOH. Further purification by MDAP gave the title compound as an off-white solid (15 mg, 29%).

LC/MS: m/z 443 [MH]$^+$, RT 3.4 min.

$^1$H NMR (DMSO-d$_6$) δ: 0.86 (t, 3H, J=7 Hz), 1.26 (m, 2H), 1.59 (m, 4H), 1.97 (m, 2H), 3.90 (m, 4H), 4.76 (t, 2H, J=7 Hz), 7.54 (m, 3H), 8.02 (m, 2H), 14.4 (br s, 1H).

Example 151

3-Butyl-8-chloro-1-[4-(5-oxo-4-phenyl-4,5-dihydro-1H-tetrazol-1-yl)butyl]-3,7-dihydro-1H-purine-2,6-dione

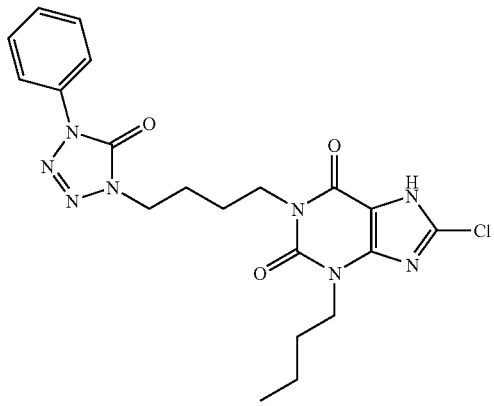

A mixture of 4-[3-butyl-8-chloro-2,6-dioxo-7-(2-propen-1-yl)-2,3,6,7-tetrahydro-1H-purin-1-yl]butyl methanesulfonate (50 mg, 0.12 mmol), Cs$_2$CO$_3$ (45 mg, 0.14 mmol) and DMF (3 ml) was treated with 1-phenyl-1,2-dihydro-5H-tetrazol-5-one (23 mg, 0.14 mmol) and stirred for 60 h at 50° C. After cooling, the mixture was degassed by applying a vacuum and then nitrogen was introduced. Pd(PPh$_3$)$_4$ (20 mg, 0.017 mmol) was added and the mixture degassed once more. Morpholine (150 μl, 1.7 mmol) was added and the mixture was stirred under nitrogen for 18 h, then partitioned between 2M HCl (aq) and EtOAc. The organic layer was separated and the aqueous layer extracted again with EtOAc. The combined extracts were concentrated, giving a yellow residue. MeOH was added and then passed down an aminopropyl column with the product eluting with 2% AcOH/MeOH. Further purification by MDAP gave the title compound as an off-white solid (27 mg, 51%). NB. ca. 10% O-alkylated material present.

LC/MS: m/z 459 [MH]$^+$, RT 3.1 min.

$^1$H NMR (DMSO-d$_6$) δ: 0.88 (t, 3H, J=7 Hz), 1.28 (m, 2H), 1.62 (m, 4H), 1.79 (m, 2H), 3.91 (m, 4H), 4.03 (m, 2H), 7.44 (m, 1H), 7.57 (m, 2H), 7.85 (m, 2H), 14.5 (br s, 1H).

Example 152

3-butyl-8-chloro-1-{4-[3-(4-hydroxyphenyl)-1,2,4-oxadiazol-5-yl]butyl}-3,7-dihydro-1H-purine-2,6-dione

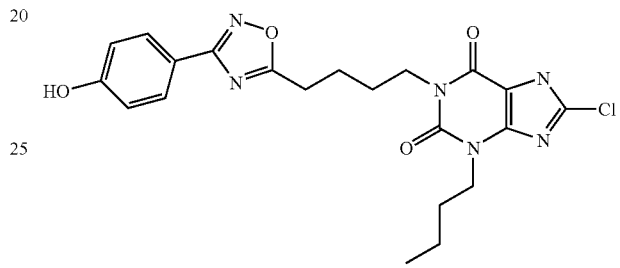

A stirred solution of 5-(3-butyl-8-chloro-2,6-dioxo-2,3,6,7-tetrahydro-1H-purin-1-yl)pentanoic acid (100 mg, 0.29 mmol) in DMF (4 ml) was treated with CDI (52 mg, 0.32 mmol). After 1 h, N,4-dihydroxybenzenecarboximidamide was added and the mixture heated at 100° C. for 6 h. On cooling, the reaction mixture was partitioned between 2M HCl (aq) and EtOAc. The organic layer was separated, washed with brine, dried (MgSO4) and concentrated. Purification by MDAP afforded the title compound as a pale grey solid (72 mg).

LC/MS: m/z 459 [MH]$^+$, RT 3.27 min.

The following compounds (Table 10) were prepared using a method analogous to that for Example 146, using the appropriate amidoxime.

TABLE 10

| Example | Structure | Yield (mg) | LC/MS |
|---|---|---|---|
| 153 | 3-butyl-8-chloro-1-{4-[3-(phenylmethyl)-1,2,4-oxadiazol-5-yl]butyl}-3,7-dihydro-1H-purine-2,6-dione | 48.4 | m/z 457 [MH]$^+$ RT 3.56 min |

TABLE 10-continued

| Example | Structure | Yield (mg) | LC/MS |
|---|---|---|---|
| 154 | 3-butyl-8-chloro-1-{4-[3-(4-fluorophenyl)-1,2,4-oxadiazol-5-yl]butyl}-3,7-dihydro-1H-purine-2,6-dione | 35.8 | m/z 461 [MH]+ RT 3.74 min |
| 155 | 3-butyl-8-chloro-1-(4-{3-[(2-chloro-4-fluorophenyl)methyl]-1,2,4-oxadiazol-5-yl}butyl)-3,7-dihydro-1H-purine-2,6-dione | 48.2 | m/z 509 [MH]+ RT 3.74 min |

Comparative Example A

3-Butyl-8-chloro-1-{3-[3-(1-phenylcyclopentyl)-1,2,4-oxadiazol-5-yl]propyl}-3,7-dihydro-1H-purine-2,6-dione Ethyl 4-(3-butyl-8-chloro-2,6-dioxo-2,3,6,7-tetrahydro-1H-purin-1-yl)butanoate (53 mg, 0.15 mmol), N-hydroxy-1-phenylcyclopentanecarboximidamide (34 mg, 0.165 mmol) and sodium methoxide (20 mg, 0.37 mmol) in dry MeOH (0.75 ml) were heated at 140° C. in the microwave reactor for 10 min. The mixture was then partitioned between ethyl acetate and 2M HCl, the organic phase evaporated and the product purified by MDAP to give the title compound as a solid (29.1 mg).

LC/MS: m/z 497 [MH]+, RT 3.76 min.

Example 156

1-[3-(3-bicyclo[4.2.0]octa-1,3,5-trien-7-yl-1,2,4-oxadiazol-5-yl)propyl]-3-butyl-8-chloro-3,7-dihydro-1H-purine-2,6-dione

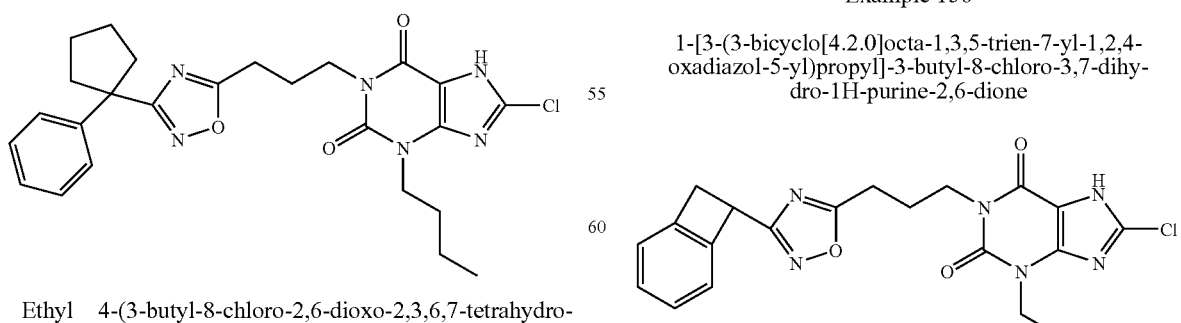

This compound was prepared using a method analogous to that for comparative example A, using the appropriate amidoxime.

Yield (mg): 28.8
LC/MS: m/z 455 [MH]+, RT 3.43 min.

Example 157

3-Butyl-8-chloro-1-[3-(3-{[4-(methyloxy)phenyl]methyl}-1,2,4-oxadiazol-5-yl)propyl]-3,7-dihydro-1H-purine-2,6-dione

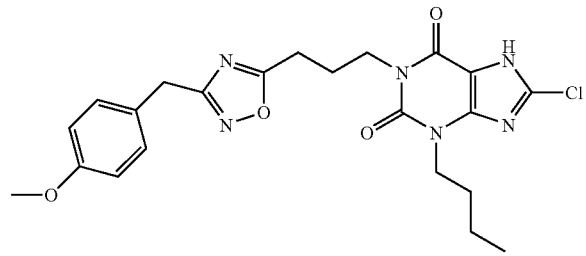

Prepared using a method analogous to that used for Example 93, except an additional final purification step using HPLC was employed. Yield 6.0 mg.

LC/MS: m/z 473 [MH]+, RT 3.27 min.

The following compounds (Table 11) were prepared using a method analogous to that for Example 75, using the appropriate amidoxime [with the exception that for Example 162 the crude product was stirred in EtOH (0.75 ml) with 2M NaOH (0.5 ml) overnight prior to the usual EtOAc/HCl workup and MDAP; Example 164 was isolated as an impurity from the preparation of Example 165 and was separated from it by HPLC; for Examples 166, and 167 the pH during aqueous workup was adjusted to approximately 5 prior to extraction; additionally Example 167 was further purified by silica SPE (2 g, DCM-MeOH 40:1 then 20:1) after MDAP].

TABLE 11

| Example | Structure | Yield (mg) | LC/MS |
|---|---|---|---|
| 158 | 3-butyl-8-chloro-1-[3-(3-{[5-chloro-2-(methyloxy)phenyl]methyl}-1,2,4-oxadiazol-5-yl)propyl]-3,7-dihydro-1H-purine-2,6-dione | 39.5 | m/z 507 [MH]+ RT 3.58 min |
| 169 | 1-(3-{3-[4,5-bis(methyloxy)-2,3-dihydro-1H-inden-1-yl]-1,2,4-oxadiazol-5-yl}propyl)-3-butyl-8-chloro-3,7-dihydro-1H-purine-2,6-dione | 35.8 | m/z 529 [MH]+ RT 3.41 min |

TABLE 11-continued

| Example | Structure | Yield (mg) | LC/MS |
|---|---|---|---|
| 160 | 3-butyl-8-chloro-1-(3-{3-[(2,5-dichlorophenyl)methyl]-1,2,4-oxadiazol-5-yl}propyl)-3,7-dihydro-1H-purine-2,6-dione | 9.7 | m/z 511 [MH]+ RT 3.63 min |
| 161 | 3-butyl-8-chloro-1-(3-{3-[(1-methyl-1H-pyrrol-2-yl)methyl]-1,2,4-oxadiazol-5-yl}propyl)-3,7-dihydro-1H-purine-2,6-dione | 18.0 | m/z 446 [MH]+ RT 3.15 min |
| 162 | 3-butyl-8-chloro-1-(3-{3-[(4-methyl-1,3-thiazol-2-yl)methyl]-1,2,4-oxadiazol-5-yl}propyl)-3,7-dihydro-1H-purine-2,6-dione | 15.5 | m/z 464 [MH]+ RT 2.94 min |
| 163 | 3-butyl-8-chloro-1-(3-{3-[(2,4-difluorophenyl)methyl]-1,2,4-oxadiazol-5-yl}propyl)-3,7-dihydro-1H-purine-2,6-dione | 33.5 | m/z 479 [MH]+ RT 3.35 min |

TABLE 11-continued

| Example | Structure | Yield (mg) | LC/MS |
|---|---|---|---|
| 164 | 3-butyl-8-chloro-1-(3-{3-[(2,3,6-trichlorophenyl)methyl]-1,2,4-oxadiazol-5-yl}propyl)-3,7-dihydro-1H-purine-2,6-dione | 4.6 | m/z 545 [MH]+ RT 3.71 min |
| 165 | 3-butyl-8-chloro-1-(3-{3-[(2,4,5-trichlorophenyl)methyl]-1,2,4-oxadiazol-5-yl}propyl)-3,7-dihdydro-1H-purine-2,6-dione | 17.7 | m/z 545 [MH]+ RT 3.79 min |
| 166 | 3-butyl-8-chloro-1-(3-{3-[(4-chloro-1H-pyrazol-1-yl)methyl]-1,2,4-oxadiazol-5-yl}propyl)-3,7-dihydro-1H-purine-2,6-dione | 39.2 | m/z 467 [MH]+ RT 3.24 min |
| 167 | 3-butyl-8-chloro-1-{3-[3-(2-pyridinylmethyl)-1,2,4-oxadiazol-5-yl]propyl}-3,7-dihydro-1H-purine-2,6-dione | 23.6 | m/z 444 [MH]+ RT 2.92 min |

TABLE 11-continued

| Example | Structure | Yield (mg) | LC/MS |
|---|---|---|---|
| 168 | 3-butyl-8-chloro-1-(3-{3-[(2-chloro-6-fluorophenyl)methyl]-1,2,4-oxadiazol-5-yl}propyl)-3,7-dihydro-1H-purine-2,6-dione | 38.8 | m/z 495 [MH]+ RT 3.43 min |
| 169 | 3-butyl-8-chloro-1-[3-(3-{[3-fluoro-4-(methyloxy)phenyl]methyl}-1,2,4-oxadiazol-5-yl)propyl]-3,7-dihydro-1H-purine-2,6-dione | 27 | m/z 491 [MH]+ RT 3.31 min |

The following compounds (Table 12) were prepared using a method analogous to that for Example 90, using the appropriate amidoxime [with the exception that Example 170 was conducted on half the scale of Example 90 and during workup the aqueous phase was neutralised prior to extraction; Example 171 was conducted on half the scale of Example 90 and the crude product stirred with 2M NaOH (0.5 ml) in EtOH (1 ml) for 5 h prior to workup and MDAP; for Example 175 0.185 ml (0.5 mmol) of 21% NaOEt was used].

TABLE 12

| Example | Structure | Yield (mg) | LC/MS |
|---|---|---|---|
| 170 | 3-butyl-8-chloro-1-{3-[3-(3-pyridinylmethyl)-1,2,4-oxadiazol-5-yl]propyl}-3,7-dihydro-1H-purine-2,6-dione | 20 | m/z 444 [MH]+ RT 2.74 min |

TABLE 12-continued

| Example | Structure | Yield (mg) | LC/MS |
|---|---|---|---|
| 171 | 3-butyl-8-chloro-1-(3-{3-[(5-methyl-3-isoxazolyl)methyl]-1,2,4-oxadiazol-5-yl}propyl)-3,7-dihydro-1H-purine-2,6-dione | 7.2 | m/z 448 [MH]⁺ RT 3.13 min |
| 172 | 3-butyl-8-chloro-1-[3-(3-phenyl-1,2,4-oxadiazol-5-yl)propyl]-3,7-dihydro-1H-purine-2,6-dione | 36.7 | m/z 429 [MH]⁺ RT 3.36 min |
| 173 | 3-butyl-8-chloro-1-{3-[3-(4-fluorophenyl)-1,2,4-oxadiazol-5-yl]propyl}-3,7-dihydro-1H-purine-2,6-dione | 41.1 | m/z 447 [MH]⁺ RT 3.42 min |
| 174 | 3-butyl-8-chloro-1-{3-(5-chloro-2-thienyl)-1,2,4-oxadiazol-5-yl]propyl}-3,7-dihydro-1H-purine-2,6-dione | 36.7 | m/z 469 [MH]⁺ RT 3.60 min |

TABLE 12-continued

| Example | Structure | Yield (mg) | LC/MS |
|---|---|---|---|
| 175 | 1-[3-(3-{(3,4-bis(methyloxy)phenyl]methyl}-1,2,4-oxadiazol-5-yl)propyl]-3-butyl-8-chloro-3,7-dihydro-1H-purine-2,6-dione | 47.0 | m/z 503 [MH]+ RT 3.14 min |
| 176 | 3-butyl-8-chloro-1-(3-{3-[(pentafluorophenyl)methyl]-1,2,4-oxadiazol-5-yl}propyl)-3,7-dihydro-1H-purine-2,6-dione | 29.2 | m/z 533 [MH]+ RT 3.62 min |
| 177 | N-[4-({5-[3-(3-butyl-8-chloro-2,6-dioxo-2,3,6,7-tetrahydro-1H-purin-1-yl)propyl]-1,2,4-oxadiazol-3-yl}methyl)phenyl]acetamide | 29.8 | m/z 500 [MH]+ RT 3.01 min |
| 178 | 3-butyl-8-chloro-1-[3-(3-{[4-(trifluoromethyl)phenyl]methyl}-1,2,4-oxadiazol-5-yl)propyl]-3,7-dihydro-1H-purine-2,6-dione | 37.7 | m/z 511 [MH]+ RT 3.65 min |

TABLE 12-continued

| Example | Structure | Yield (mg) | LC/MS |
|---|---|---|---|
| 179 | 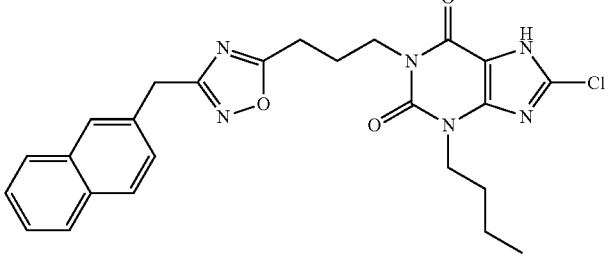 3-butyl-8-chloro-1-{3-[3-(2-naphthalenylmethyl)-1,2,4-oxadiazol-5-yl]propyl}-3,7-dihydro-1H-purine-2,6-dione | 47.5 | m/z 493 [MH]+ RT 3.69 min |

Example 180

3-Butyl-8-chloro-1-(3-{3-[(2-oxo-2,3-dihydro-1H-benzimidazol-5-yl)methyl]-1,2,4-oxadiazol-5-yl}propyl)-3,7-dihydro-1H-purine-2,6-dione

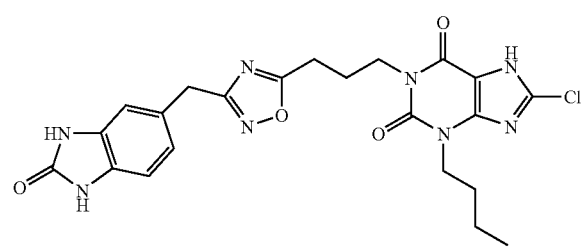

Synthesised by a method analogous to that for Example 99 with the exception that a further 2 equivalents of 21% sodium ethoxide (0.11 ml) was used, the extra heating time was 20 min. and the product was isolated by filtration followed by trituration with hot MeOH. Yield 14.5 mg.

LC/MS: m/z 499 [MH]+, RT 2.78 min.

The following compounds (Table 13) were prepared by a method analogous to that for Example 1 [with the exception that Examples 181-186 were all synthesised on a scale starting from 50 mg of 8-chloro-3-pentyl-7-(2-propen-1-yl)-1-[3-(1H-pyrazol-4-yl)propyl]-3,7-dihydro-1H-purine-2,6-dione; Examples 184, 186, 188, 189 and 190 were additionally purified by MDAP following aminopropyl SPE; Example 185 was additionally purified by recrystallisation from MeOH following aminopropyl SPE; for Example 191, 128 mg (1.2 mmol) of sodium carbonate was used; during workup the aqueous phase was adjusted to pH6 prior to extraction; and the product was purified by MDAP then by further HPLC; for Example 184 solids which precipitated during workup were combined with the EtOAc extracts prior to SPE].

TABLE 13

| Example | Structure | Yield (mg) | LC/MS |
|---|---|---|---|
| 181 | 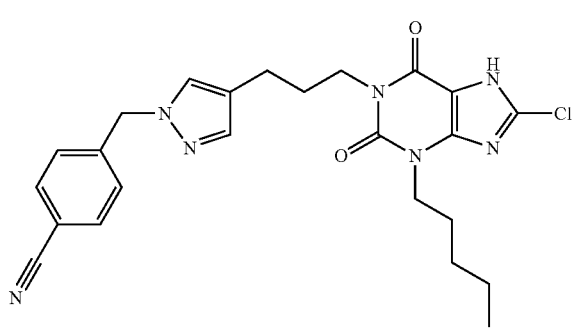 4-({4-[3-(8-chloro-2,6-dioxo-3-pentyl-2,3,6,7-tetrahydro-1H-purin-1-yl)propyl]-1H-pyrazol-1-yl}methyl)benzonitrile | 36.0 | m/z 480 [MH]+ RT 3.24 min |

| Example | Structure | Yield (mg) | LC/MS |
|---|---|---|---|
| 182 | 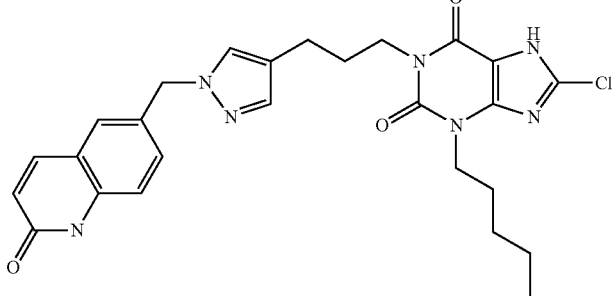<br>8-chloro-1-(3-{1-[(1-methyl-2-oxo-1,2-dihydro-6-quinolinyl)methyl]-1H-pyrazol-4-yl}propyl)-3-pentyl-3,7-dihydro-1H-purine-2,6-dione | 7.6 | m/z 536 [MH]+<br>RT 3.03 min |
| 183 | 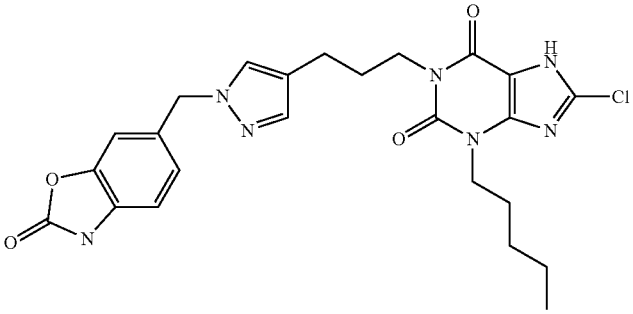<br>8-chloro-1-(3-{1-[(3-methyl-2-oxo-2,3-dihydro-1,3-benzoxazol-6-yl)methyl]-1H-pyrazol-4-yl}propyl)-3-pentyl-3,7-dihydro-1H-purine-2,6-dione | 34.0 | m/z 526 [MH]+<br>RT 3.11 min |
| 184 | 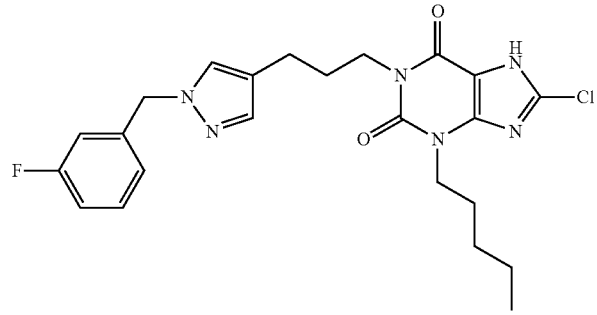<br>8-chloro-1-(3-{1-[(3-fluorophenyl)methyl]-1H-pyrazol-4-yl}propyl)-3-pentyl-3,7-dihydro-1H-purine-2,6-dione | 26.2 | m/z 473 [MH]+<br>RT 3.38 min |

| Example | Structure | Yield (mg) | LC/MS |
|---|---|---|---|
| 185 | methyl 3-({4-[3-(8-chloro-2,6-dioxo-3-pentyl-2,3,6,7-tetrahydro-1H-purin-1-yl)propyl]-1H-pyrazol-1-yl}methyl)-4-isothiazolecarboxylate | 16.2 | m/z 520 [MH]+<br>RT 3.12 min |
| 186 | 1-{3-[1-(1,3-benzothiazol-2-ylmethyl)-1H-pyrazol-4-yl]propyl}-8-chloro-3-pentyl-3,7-dihydro-1H-purine-2,6-dione | 21.0 | m/z 512 [MH]+<br>RT 3.36 min |
| 187 | 8-chloro-1-(3-{1-[(2,6-dichlorophenyl)methyl]-1H-pyrazol-4-yl}propyl)-3-pentyl-3,7-dihydro-1H-purine-2,6-dione | 65.0 | m/z 523, 525 [Cl isotypes MH+]<br>RT 3.77 min |

| Example | Structure | Yield (mg) | LC/MS |
|---|---|---|---|
| 188 | 8-chloro-1-(3-{1-[(3,4-difluorophenyl)methyl]-1H-pyrazol-4-yl}propyl)-3-pentyl-3,7-dihydro-1H-purine-2,6-dione | 35.0 | m/z 491 [MH]+ RT 3.61 min |
| 189 | 8-chloro-1-[3-(1-{[(4-fluoro-3-(trifluoromethyl)phenyl]methyl}-1H-pyrazol-4-yl)propyl]-3-pentyl-3,7-dihydro-1H-purine-2,6-dione | 17.0 | m/z 541 [MH]+ RT 3.76 min |
| 190 | 8-chloro-1-(3-{1-[(3-chloro-4-fluorophenyl)methyl]-1H-pyrazol-4-yl}propyl)-3-pentyl-3,7-dihydro-1H-purine-2,6-dione | 27.0 | m/z 507 [MH]+ RT 3.73 min |

TABLE 13-continued

| Example | Structure | Yield (mg) | LC/MS |
|---|---|---|---|
| 191 | 8-chloro-3-pentyl-1-{3-[1-(2-pyridinylmethyl)-1H-pyrazol-4-yl]propyl}-3,7-dihydro-1H-purine-2,6-dione | 11.4 | m/z 456 [MH]+ RT 3.13 min |

Example 192

8-Chloro-1-(3-{1-[(4-chlorophenyl)methyl]-1H-pyrazol-4-yl}propyl)-3-pentyl-3,7-dihydro-1H-purine-2,6-dione

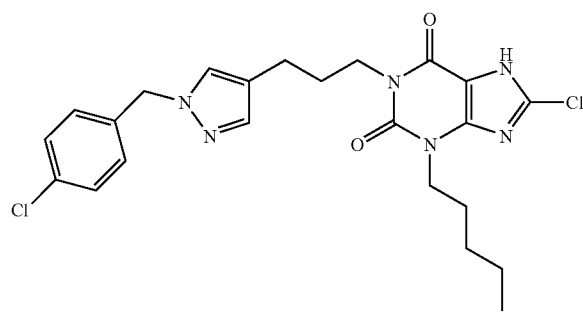

8-Chloro-3-pentyl-7-(2-propen-1-yl)-1-[3-(1H-pyrazol-4-yl)propyl]-3,7-dihydro-1H-purine-2,6-dione (50 mg, 0.123 mmol) in dry DMF (1.5 ml) was stirred with sodium carbonate (75 mg, 0.708 mmol) and 4-chlorobenzyl bromide (150 mg, 0.73 mmol) at 40° C. for 18 h. The mixture was partitioned between EtOAc and water, the organic phase washed with brine, dried and evaporated. The product was purified by normal phase chromatography on silica (Companion System, EtOAc—cyclohexane gradient) giving an oil (44 mg). This was stirred in degassed, dry DMF (1 ml) with tetrakis(triphenylphosphine)palladium(0) (19 mg) and morpholine (0.072 ml) under nitrogen for 6 h. The mixture was partitioned between EtOAc and 2M HCl and the organic phase evaporated and purified by the usual aminopropyl SPE procedure. Yield 21.0 mg.

LC/MS: m/z 489 [MH+], RT 3.59 min.

The following compounds (Table 14) were prepared by a method analogous to that for Example 6 [with the exception that for Example 193 a second portion of Pd(PPh3)4 was added after 5 h, stirring was continued overnight, and final purification was achieved by HPLC; for Example 195 required additional purification by MDAP; Example 200 required additional purification by recrystallisation from MeOH; Example 201 required additional purification by trituration with MeOH].

TABLE 14

| Example | Structure | Yield (mg) | LC/MS |
|---|---|---|---|
| 193 | 8-chloro-1-{3-[1-(1,2,4-oxadiazol-3-ylmethyl)-1H-pyrazol-4-yl]propyl}-3-pentyl-3,7-dihydro-1H-purine-2,6-dione | 7.3 | m/z 447 [MH]+ RT 3.06 min |

TABLE 14-continued

| Example | Structure | Yield (mg) | LC/MS |
|---|---|---|---|
| 194 | 8-chloro-1-(3-{1-[(4-methylphenyl)methyl]-1H-pyrazol-4-yl}propyl)-3-pentyl-3,7-dihydro-1H-purine-2,6-dione | 23.7 | m/z 469 [MH]$^+$<br>RT 3.49 min |
| 195 | 8-chloro-1-(3-{1-[(5-methyl-3-isoxazolyl)methyl]-1H-pyrazol-4-yl}propyl)-3-pentyl-3,7-dihydro-1H-purine-2,6-dione | 29.0 | m/z 460 [MH]$^+$<br>RT 3.10 min |
| 196 | 8-chloro-1-[3-(1-{[3-(methyloxy)phenyl]methyl}-1H-pyrazol-4-yl)propyl]-3-pentyl-3,7-dihydro-1H-purine-2,6-dione | 56.0 | m/z 485 [MH]$^+$<br>RT 3.41 min |

TABLE 14-continued

| Example | Structure | Yield (mg) | LC/MS |
|---|---|---|---|
| 197 | 8-chloro-3-pentyl-1-[3-(1-{[3-(trifluoromethyl)phenyl]methyl}-1H-pyrazol-4-yl)propyl]-3,7-dihydro-1H-purine-2,6-dione | 47.0 | m/z 523 [MH]+ RT 3.61 min |
| 198 | 8-chloro-1-(3-{1-[(2-methylphenyl)methyl]-1H-pyrazol-4-yl}propyl)-3-pentyl-3,7-dihydro-1H-purine-2,6-dione | 44.0 | m/z 469 [MH]+ RT 3.54 min |
| 199 | 3-({4-[3-(8-chloro-2,6-dioxo-3-pentyl-2,3,6,7-tetrahydro-1H-purin-1-yl)propyl]-1H-pyrazol-1-yl}methyl)benzonitrile | 51.0 | m/z 480 [MH]+ RT 3.32 min |

TABLE 14-continued

| Example | Structure | Yield (mg) | LC/MS |
|---|---|---|---|
| 200 | 8-chloro-1-(3-{1-[(3,5-dimethylphenyl)methyl]-1H-pyrazol-4-yl}propyl)-3-pentyl-3,7-dihydro-1H-purine-2,6-dione | 36.7 | m/z 483 [MH]+ RT 3.66 min |
| 201 | 8-chloro-3-pentyl-1-[3-(1-{[4-(1H-1,2,4-triazol-1-yl)phenyl]methyl}-1H-pyrazol-4-yl)propyl]-3,7-dihydro-1H-purine-2,6-dione | 21.2 | m/z 522 [MH]+ RT 3.09 min |

Example 202

8-Chloro-1-(3-{1-[(5-chloro-2-thienyl)methyl]-1H-pyrazol-4-yl}propyl)-3-pentyl-3,7-dihydro-1H-purine-2,6-dione

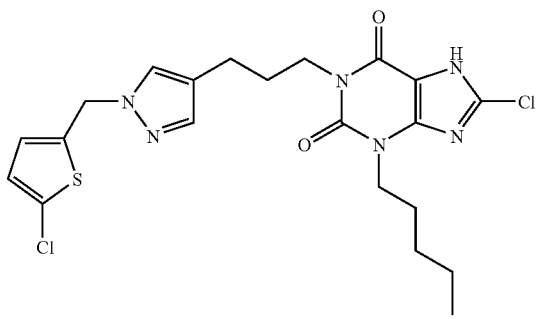

To 8-chloro-3-pentyl-7-(2-propen-1-yl)-1-[3-(1H-pyrazol-4-yl)propyl]-3,7-dihydro-1H-purine-2,6-dione (61 mg, 0.15 mmol) in dry THF (1 ml) at −78° C., under nitrogen, was added potassium t-butoxide (1M in THF, 0.15 ml), followed by 2-chloro-5-(chloromethyl)thiophene (25 mg, 0.15 mmol). Stirring was continued at −78° C. for 15 min, then at room temperature for 1 h and finally at 60° C. for 18 h. The solution was degassed and morpholine (0.13 ml) and tetrakis(triphenylphosphine)palladium(0) (35 mg) added and stirring continued for 6 h. Further quantities (0.2 ml morpholine, 50 mg Pd(PPh$_3$)$_4$) were added and stirring continued overnight. Worked up by partition between EtOAc and 2M HCl, the organic phase evaporated and purified by the standard aminopropyl SPE procedure followed by MDAP yielding title compound as a white solid (5.1 mg).

LC/MS: m/z 495 [MH]+, RT 3.68 min.

Example 203

3-Butyl-8-chloro-1-{3-[5-(phenylmethyl)-1,3,4-oxadiazol-2-yl]propyl}-3,7-dihydro-1H-purine-2,6-dione

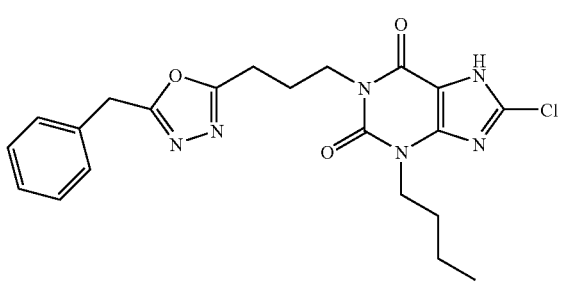

To 3-butyl-8-chloro-7-(2-propen-1-yl)-3,7-dihydro-1H-purine-2,6-dione (99 mg, 0.35 mmol) in dry DMF (2 ml) was added cesium carbonate (137 mg, 0.42 mmol) followed by a solution in dry DMF (1 ml) of 2-(3-chloropropyl)-5-(phenylmethyl)-1,3,4-oxadiazole (99 mg, 0.42 mmol). The mixture was stirred under nitrogen and heated at 55° C. for 2.5 h then stirred at room temperature overnight. The mixture was degassed by repeatedly evacuating and admitting nitrogen and then tetrakis(triphenylphosphine)palladium(0) (81 mg, 0.07 mmol) and morpholine (0.305 ml, 3.5 mmol) were added and stirring was continued for 5 h EtOAc and 2M HCl were added and the mixture stirred for 20 min then filtered. The organic phase was separated and evaporated, and the product was purified by aminopropyl SPE (5 g) washing with THF-MeOH (1:1) then with MeOH and eluting the acidic product with DCM-MeOH (1:1) containing 5% added AcOH. The product thus obtained was purified further by MDAP to yield the title compound (92 mg).

LC/MS: m/z 443 [MH]$^+$, RT 3.18 min.

The following compounds (Table 15) were prepared by a method analogous to that for Example 203, with the exception that Example 211 was further purified by HPLC.

TABLE 18

| Example | Product structure | Xanthine precursor | Alkylating agent | Yield (mg) | LC/MS |
|---|---|---|---|---|---|
| 204 | 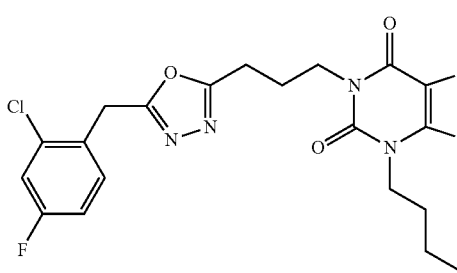 3-butyl-8-chloro-1-(3-{5-[(2-chloro-4-fluorophenyl)methyl]-1,3,4-oxadiazol-2-yl}propyl)-3,7-dihydro-1H-purine-2,6-dione | 3-butyl-8-chloro-7-(2-propen-1-yl)-3,7-dihydro-1H-purine-2,6-dione (99 mg) | 2-[(2-chloro-4-fluorophenyl)methyl]-5-(3-chloropropyl)-1,3,4-oxadiazole (121 mg) | 90 | m/z 495 [MH]$^+$ RT 3.34 min |
| 205 | 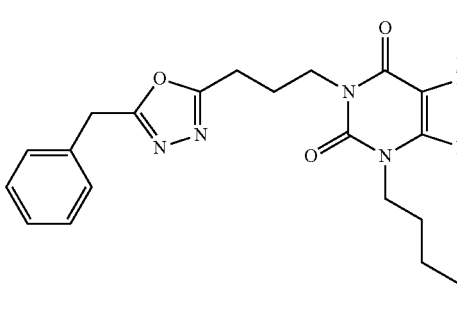 8-chloro-3-pentyl-1-{3-[5-(phenylmethyl)-1,3,4-oxadiazol-2-yl]propyl}-3,7-dihydro-1H-purine-2,6-dione | 8-chloro-3-pentyl-7-(2-propen-1-yl)-3,7-dihydro-1H-purine-2,6-dione (104 mg) | 2-(3-chloropropyl)-5-(phenylmethyl)-1,3,4-oxadiazole (99 mg) | 98 | m/z 457 [MH]$^+$ RT 3.35 min |
| 206 | 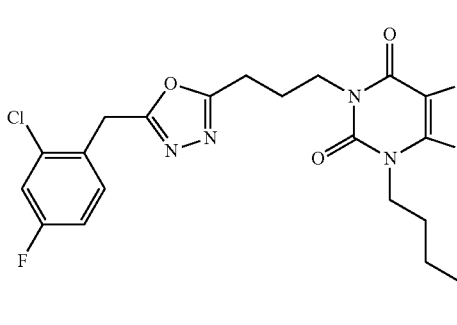 8-chloro-1-(3-{5-[(2-chloro-4-fluorophenyl)methyl]-1,3,4-oxadiazol-2-yl}propyl)-3-pentyl-3,7-dihydro-1H-purine-2,6-dione | 8-chloro-3-pentyl-7-(2-propen-1-yl)-3,7-dihydro-1H-purine-2,6-dione (104 mg) | 2-[(2-chloro-4-fluorophenyl)methyl]-5-(3-chloropropyl)-1,3,4-oxadiazole (121 mg) | 98 | m/z 509 [MH]$^+$ RT 3.52 min |

TABLE 18-continued

| Example | Product structure | Xanthine precursor | Alkylating agent | Yield (mg) | LC/MS |
|---|---|---|---|---|---|
| 207 | 8-chloro-1-(3-{5-[(2,4-difluorophenyl)methyl]-1,3,4-oxadiazol-2-yl}propyl)-3-pentyl-3,7-dihydro-1H-purine-2,6-dione | 8-chloro-3-pentyl-7-(2-propen-1-yl)-3,7-dihydro-1H-purine-2,6-dione (104 mg) | 2-(3-chloropropyl)-5-[(2,4-difluorophenyl)methyl]-1,3,4-oxadiazole (111 mg) | 43 | m/z 493 [MH]$^+$ RT 3.40 min |
| 208 | 8-chloro-3-(3-cyclopropylpropyl)-1-{3-[5-(phenylmethyl)-1,3,4-oxadiazol-2-yl]propyl}-3,7-dihydro-1H-purine-2,6-dione | 8-chloro-3-(3-cyclopropylpropyl)-7-(2-propen-1-yl)-3,7-dihydro-1H-purine-2,6-dione (108 mg) | 2-(3-chloropropyl)-5-(phenylmethyl)-1,3,4-oxadiazole (99 mg) | 95 | m/z 469 [MH]$^+$ RT 3.34 min |
| 209 | 8-chloro-1-(3-{5-[(2-chloro-4-fluorophenyl)methyl]-1,3,4-oxadiazol-2-yl}propyl)-3-(3-cyclopropylpropyl)-3,7-dihydro-1H-purine-2,6-dione | 8-chloro-3-(3-cyclopropylpropyl)-7-(2-propen-1-yl)-3,7-dihydro-1H-purine-2,6-dione (108 mg) | 2-[(2-chloro-4-fluorophenyl)methyl]-5-(3-chloropropyl)-1,3,4-oxadiazole (121 mg) | 99 | m/z 521 [MH]$^+$ RT 3.51 min |

TABLE 18-continued

| Example | Product structure | Xanthine precursor | Alkylating agent | Yield (mg) | LC/MS |
|---|---|---|---|---|---|
| 210 | 8-chloro-3-(3-cyclopropylpropyl)-1-(3-{5-[(2,4-difluorophenyl)methyl]-1,3,4-oxadiazol-2-yl}propyl)-3,7-dihydro-1H-purine-2,6-dione | 8-chloro-3-(3-cyclopropyl-propyl)-7-(2-propen-1-yl)-3,7-dihydro-1H-purine-2,6-dione (108 mg) | 2-(3-chloropropyl)-5-[(2,4-difluorophenyl)methyl]-1,3,4-oxadiazole (111 mg) | 49 | m/z 505 [MH]+ RT 3.40 min |
| 211 | 3-butyl-8-chloro-1-(3-{5-[(2,4-difluorophenyl)methyl]-1,3,4-oxadiazol-2-yl}propyl)-3,7-dihydro-1H-purine-2,6-dione | 3-butyl-8-chloro-7-(2-propen-1-yl)-3,7-dihydro-1H-purine-2,6-dione (99 mg) | 2-(3-chloropropyl)-5-[(2,4-difluorophenyl)methyl]-1,3,4-oxadiazole (111 mg) | 38.9 | m/z 479 [MH]+ RT 3.31 min |

Synthesis of chloropropyl 1,3,4-oxadiazole Intermediates from Table 15

2-[(2-chloro-4-fluorophenyl)methyl]-5-(3-chloropropyl)-1,3,4-oxadiazole
2-(3-chloropropyl)-5-[(2,4-difluorophenyl)methyl]-1,3,4-oxadiazole
2-(3-chloropropyl)-5-(phenylmethyl)-1,3,4-oxadiazole Diacyl hydrazines (500 mg, synthesis below) were stirred in dry toluene (4 ml) and phosphorus oxychloride (4 ml) was added. The mixtures were heated at 90° C. for 2 h then allowed to cool and the solvents evaporated. The residues were dissolved in dry toluene, evaporated and then partitioned between EtOAc and aqueous NaHCO$_3$. The organic phases were washed with brine, dried over Na$_2$SO$_4$ and evaporated to give the required oxadiazoles as colourless oils. These were not purified further but reacted directly with the xanthines as above.

| Diacyl hydrazine | Oxadiazole product | Yield (mg) | LC/MS |
|---|---|---|---|
| 4-chloro-N′-(phenylacetyl)butanohydrazide | 2-(3-chloropropyl)-5-(phenylmethyl)-1,3,4-oxadiazole | 446 | m/z 237 [MH]+ RT 2.94 min |

-continued

| Diacyl hydrazine | Oxadiazole product | Yield (mg) | LC/MS |
|---|---|---|---|
| 4-chloro-N'-[(2-chloro-4-fluorophenyl)acetyl]butanohydrazide | 2-[(2-chloro-4-fluorophenyl)methyl]-5-(3-chloropropyl)-1,3,4-oxadiazole | 405 | m/z 289 [MH]+ RT 3.17 min |
| 4-chloro-N'-[(2,4-difluorophenyl)acetyl]butanohydrazide | 2-(3-chloropropyl)-4-[(2,4-difluorophenyl)methyl]-1,3,4-oxadiazole | 333 | m/z 273 [MH]+ RT 3.03 min |

Preparation of 4-chloro-N'-(phenylacetyl)butanohydrazide

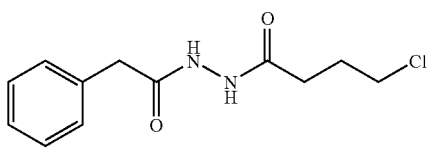

To 4-chlorobutyryl chloride (1.12 ml, 10 mmol) in dry DCM (10 ml) was added, dropwise, over 40 min, a mixture of phenylacetic hydrazide (1.5 g, 10 mmol) and DIPEA (1.77 ml, 10.2 mmol) in dry DCM (40 ml) at room temperature. A dense white precipitate formed. After a further 20 min. 2M HCl (30 ml) was added and the title compound (white solid) was filtered off, washed with water and dried (2.24 g).

LC/MS: m/z 255 [MH]+, RT 2.20 min.

Preparation of 4-chloro-N'-[(2-chloro-4-fluorophenyl)acetyl]butanohydrazide

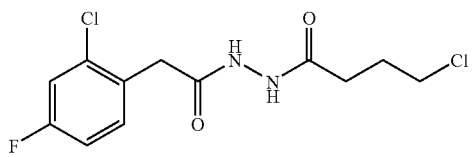

(i) A solution of 2-chloro-4-fluorophenylacetyl chloride (10 mmol) in dry DCM (15 ml) was added over 20 min to a mixture of t-butyl carbazate (1.32 g, 10 mmol) and DIPEA (1.77 ml, 10.2 mmol) in dry DCM (20 ml). After stirring for a further 2 h, the mixture was washed with 1M HCl then with aqueous NaHCO₃. A white solid precipitated at this point, which was filtered off, washed with water and DCM then dried to yield 1,1-dimethylethyl 2-[(2-chloro-4-fluorophenyl)acetyl]hydrazinecarboxylate (1.94 g).

(ii) This compound (1.92 g, 6.34 mmol) was suspended in dioxan (2 ml) and 4M HCl in dioxan (5 ml) was added. A dense white precipitate formed. After 1 h the mixture was partitioned between EtOAc and saturated aqueous NaHCO₃ and the organic phase washed with brine, dried (Na₂SO₄) and evaporated giving 2-(2-chloro-4-fluorophenyl)acetohydrazide as a white solid (1.07 g).

(iii) A mixture of 2-(2-chloro-4-fluorophenyl)acetohydrazide (909 mg, 4.5 mmol) and DIPEA (0.817 ml, 4.7 mmol) in dry DCM (65 ml) was added over 20 min to 4-chlorobutyryl chloride (0.505 ml, 4.5 mmol) in dry DCM (5 ml). After 1.5 h, 2M HCl was added and the precipitated 4-chloro-N-[(2-chloro-4-fluorophenyl)acetyl]butanohydrazide was filtered off, washed with water and dried (1.24 g).

LC/MS: m/z 307 [MH]+, RT 2.61 min.

Preparation of 2-(3-chloropropyl)-5-[(2,4-difluorophenyl)methyl]-1,3,4-oxadiazole

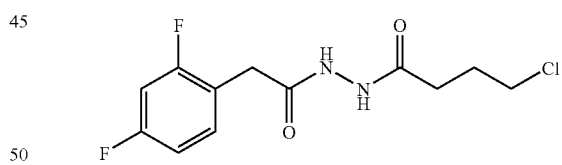

(i) A solution of 2,4-difluorophenylacetyl chloride (10 mmol) in dry DCM (15 ml) was added over 10 min. to a mixture of t-butyl carbazate (1.32 g, 10 mmol) and DIPEA (1.77 ml, 10.2 mmol) in dry DCM (20 ml). After stirring for 1.5 h the mixture was washed with 1M HCl then with aqueous NaHCO₃. The organic phase was evaporated to afford 1,1-dimethylethyl 2-[(2,4-difluorophenyl)acetyl]hydrazinecarboxylate as a white solid.

(ii) 1,1-dimethylethyl 2-[(2,4-difluorophenyl)acetyl]hydrazinecarboxylate (10 mmol) in dioxan (5 ml) was stirred with 4M HCl in dioxan (8 ml) for 1.5 h. The mixture was partitioned between EtOAc and saturated aqueous NaHCO₃ and the organic phase washed with brine, dried (Na₂SO₄) and evaporated. Reaction was incomplete so the residue was stirred again with 4M HCl in dioxan (10 ml) for 2.5 h. Workup as previously gave 2-(2,4-difluorophenyl)acetohydrazide as a solid (570 mg).

(iii) A mixture of 2-(2,4-difluorophenyl)acetohydrazide (570 mg, 3.06 mmol) and DIPEA (0.553 ml, 3.2 mmol) in dry DCM (30 ml) was added to 4-chlorobutyryl chloride (0.343 ml, 3.06 mmol) in dry DCM (5 ml) over 15 min. An immediate white precipitate formed. After stirring for 1 h, 2M HCl (20 ml) was added and the solid 2-(3-chloropropyl)-5-[(2,4-difluorophenyl)methyl]-1,3,4-oxadiazole was filtered off, washed with water and dried (726 mg).

LC/MS: m/z 291 [MH]⁺, RT 2.45 min.

Example 212

3-Butyl-8-chloro-1-[4-(3-phenyl-5-isoxazolyl)butyl]-3,7-dihydro-1H-purine-2,6-dione a) 3-Butyl-8-chloro-1-[4-(3-phenyl-5-isoxazolyl)butyl]-3,7-dihydro-1H-purine-2,6-dione

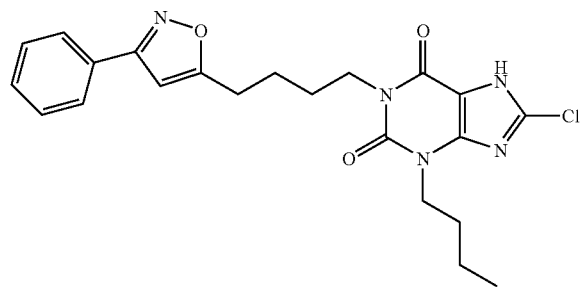

3-Butyl-8-chloro-7-(2-propen-1-yl)-3,7-dihydro-1H-purine-2,6-dione (100 mg, 0.354 mmol) and 4-(3-phenyl-5-isoxazolyl)-1-butanol (77 mg, 0.355 mmol) were dissolved in dry THF (4 ml) under nitrogen. A solution of dibenzyl azodicarboxylate (94%, 224 mg, 0.708 mmol) in dry THF (2 ml) was added. The mixture was cooled to 0° C. and a solution of triphenylphosphine (185 mg, 0.708 mmol) in dry THF (1 ml) was added. The mixture was stirred for 20 min at 0° C. then at room temperature overnight. The mixture was degassed then stirred with morpholine (0.308 ml) and tetrakis(triphenylphosphine)palladium(0) (82 mg) for 4.5 h. A further 60 mg of tetrakis(triphenylphosphine)palladium(0) was added and stirring continued overnight. The reaction was worked up by partition between EtOAc and 2M HCl, the organic phase evaporated and purified by aminopropyl SPE (5 g) washing with THF-MeOH (1:1), MeOH and eluting with DCM-MeOH (1:1) containing 5% AcOH. Further purification by MDAP afforded the title compound (56 mg).

LC/MS: m/z 442 [MH]⁺, RT 3.59 min.

b) 4-(3-Phenyl-5-isoxazolyl)-1-butanol

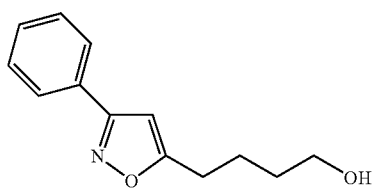

To N-hydroxybenzenecarboximidoyl chloride (622 mg, 4 mmol) in dry DCM (6 ml) was added 5-hexyn-1-ol (431 mg, 4.4 mmol). The mixture was cooled to 0° C. under nitrogen as triethylamine (0.612 ml, 4.4 mmol) was added dropwise over 10 min. Stirred for a further 20 min at 0° C. then at room temperature overnight. The mixture was washed with water and the organic phase evaporated. The product was purified by silica SPE (20 g) eluting with EtOAc-cyclohexane (1:2, then 3:1) to give a white waxy solid (443 mg).

LC/MS: m/z 218 [MH]⁺, RT 2.74 min.

Example 213

3-Butyl-8-chloro-1-{3-[3-(phenylmethyl)-5-isoxazolyl]propyl}-3,7-dihydro-1H-purine-2,6-dione a) 3-Butyl-8-chloro-1-{3-[3-(phenylmethyl)-5-isoxazolyl]propyl}-3,7-dihydro-1H-purine-2,6-dione

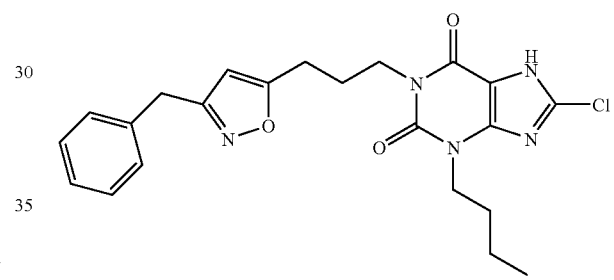

Prepared analogously to 3-butyl-8-chloro-1-[4-(3-phenyl-5-isoxazolyl)butyl]-3,7-dihydro-1H-purine-2,6-dione (Example 213) using half the molar quantities, starting from 3-butyl-8-chloro-7-(2-propen-1-yl)-3,7-dihydro-1H-purine-2,6-dione (50 mg, 0.177 mmol) and 3-[3-(phenylmethyl)-5-isoxazolyl]-1-propanol (38.4 mg, 0.177 mmol). Yield 24.2 mg, LC/MS: m/z 442 [MH]⁺, RT 3.43 min.

b) 3-[3-(Phenylmethyl)-5-isoxazolyl]-1-propanol

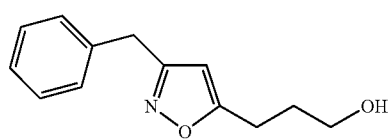

Synthesised as with 4-(3-phenyl-5-isoxazolyl)-1-butanol, using N-hydroxy-2-phenylethanimidoyl chloride (253 mg, 1.5 mmol) and 4-pentyn-1-ol (139 mg, 1.65 mmol). Yield 61 mg of pale yellow oil.

LC/MS: m/z 218 [MH]⁺, RT 2.62 min.

Comparative Example B

8-Chloro-1-[3-(2-furanyl)propyl]-3-pentyl-3,7-dihydro-1H-purine-2,6-dione, sodium salt

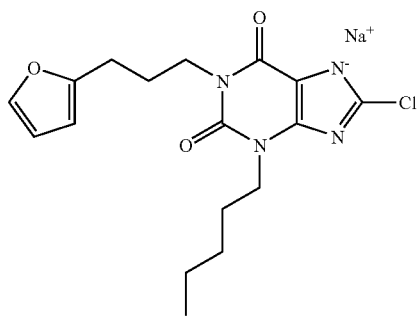

A GreenHouse™ tube equipped with a stirrer was charged with a 0.25 ml aliquot of a 0.54M solution of 8-chloro-3-pentyl-7-(2-propen-1-yl)-3,7-dihydro-1H-purine-2,6-dione (0.13 mmol) in THF. To the mixture was added 3-(2-furanyl)-1-propanol (21 mg, 0.16 mmol, 1.2 eq) in THF (0.25 ml), followed by a 0.25 ml aliquot of a 0.71M solution of bis(1,1-dimethylethyl) (E)-1,2-diazenedicarboxylate (0.18 mmol) in THF and then a 0.25 ml aliquot of a 0.71M solution of triphenylphosphine (0.18 mmol) in THF. The solution was stirred in a GreenHouse™ under nitrogen for 16 h. To the mixture was added a further 0.25 ml aliquot of a 1.4M solution of bis(1,1-dimethylethyl) (E)-1,2-diazenedicarboxylate (0.36 mmol) in THF and then a further 0.25 ml aliquot of a 1.4M solution of triphenylphosphine (0.36 mmol) in THF. The mixture was stirred for 16 h under a stream of nitrogen.

Tetrakis(triphenylphosphine)palladium(0) (16 mg, 0.014 mmol) and morpholine (0.12 ml, 1.35 mmol) were added to the mixture which was stirred for 16 h under a stream of nitrogen. The reaction mixture was concentrated under nitrogen and the crude material dissolved in aqueous NaOH solution (0.5 ml, 2M). The resulting solution was purified using aminopropyl SPE (eluting with AcOH in DCM and MeOH). Further purification using C18 SPE (eluting with a water, ammonia and MeCN mixture) afforded the title compound as a clear gum (22 mg, 45%).

LC/MS: m/z 365 [MH]$^+$, RT 3.48 min.

$^1$H NMR (DMSO-d$_6$) δ: 0.85 (t, 3H, J=7 Hz), 1.35-1.19 (m, 4H), 1.62 (m, 2H), 1.79 (m, 2H), 2.59 (t, 2H, J=8 Hz), 3.93-3.80 (m, 4H), 6.14 (d, 1H, J=3 Hz), 6.32 (dd, 1H, J=3 and 2 Hz), 7.48 (d, 1H, J=2 Hz).

The following compounds (Table 16) were prepared by a method analogous to that for Comparative Example B.

TABLE 16

| Example | Structure | Yield (mg) | LC/MS |
|---|---|---|---|
| 214 | 8-chloro-1-{3-[2,5-dioxo-4-(phenylmethyl)-1-imidazolidinyl]propyl}-3-pentyl-3,7-dihydro-1H-purine-2,6-dione, sodium salt | 9 | m/z 487 [MH]$^+$ RT 3.15 min |
| 215 | 1-[3-(4-biphenylyl)propyl]-8-chloro-3-pentyl-3,7-dihydro-1H-purine-2,6-dione, sodium salt | 19 | m/z 451 [MH]$^+$ RT 4.06 min |

The following compounds (Table 17) were prepared using a method analogous to that for Example 113, from the corresponding acids and (1Z)-4-(3-butyl-8-chloro-2,6-dioxo-2,3,6,7-tetrahydro-1H-purin-1-yl)-N-hydroxybutanimidamide.

TABLE 17

| Example | Name | Compound: R1= | LC/MS |
|---|---|---|---|
| 216 | 3-butyl-8-chloro-1-{3-[5-(3-methylphenyl)-1,2,4-oxadiazol-3-yl]propyl}-3,7-dihydro-1H-purine-2,6-dione | | m/z 443 [MH]+ RT 3.47 min |
| 217 | 3-butyl-8-chloro-1-{3-[5-(4-methylphenyl)-1,2,4-oxadiazol-3-yl]propyl}-3,7-dihydro-1H-purine-2,6-dione | | m/z 443 [MH]+ RT 3.34 min |
| 218 | 3-butyl-8-chloro-1-[3-(5-{[4-(dimethylamino)phenyl]methyl}-1,2,4-oxadiazol-3-yl)propyl]-3,7-dihydro-1H-purine-2,6-dione | | m/z 486 [MH]+ RT 3.24 min |
| 219 | 3-butyl-8-chloro-1-{3-[5-(3-thienylmethyl)-1,2,4-oxadiazol-3-yl]propyl}-3,7-dihydro-1H-purine-2,6-dione | | m/z 449 [MH]+ RT 3.24 min |

TABLE 17-continued

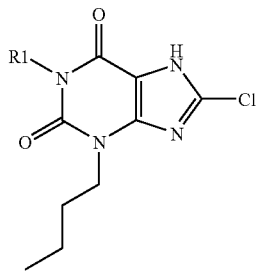

| Example | Name | Compound: R1= | LC/MS |
|---|---|---|---|
| 220 | 3-butyl-8-chloro-1-{3-[5-(1H-indol-3-ylmethyl)-1,2,4-oxadiazol-3-yl]propyl}-3,7-dihydro-1H-purine-2,6-dione | | m/z 482 [MH]+ RT 3.29 min |

Example 221

8-Chloro-3-propyl-1-{4-[3-(2-pyridinyl)-1,2,4-oxadiazol-5-yl]butyl}-3,7-dihydro-1H-purine-2,6-dione a) 8-Chloro-3-propyl-1-{4-[3-(2-pyridinyl)-1,2,4-oxadiazol-5-yl]butyl}-3,7-dihydro-1H-purine-2,6-dione

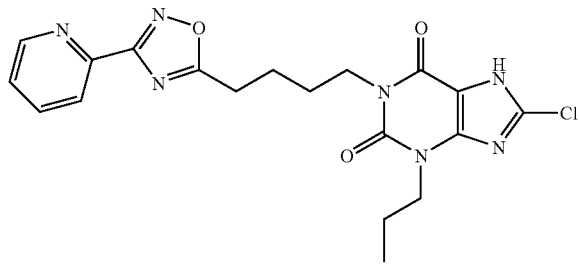

A solution of 8-chloro-7-(2-propen-1-yl)-1-{4-[3-(2-pyridinyl)-1,2,4-oxadiazol-5-yl]butyl}-3,7-dihydro-1H-purine-2,6-dione (40 mg, 0.09 mmol) in DMF (3 ml) was treated with potassium carbonate (15 mg, 0.11 mmol) and 1-iodopropane (19 mg, 0.11 mmol). The mixture was heated at 40° C. for 3 h then at 70° C. for a further 3 h. The mixture was cooled and degassed by the successive application of vacuum and nitrogen gas. The mixture was then treated with a solution of tetrakis(triphenylphosphine)palladium(0) (10 mg, 0.009 mmol) and morpholine (0.1 ml, 1.2 mmol) and then stirred overnight. The mixture was evaporated and partitioned between chloroform (2 ml) and water (2 ml). The aqueous phase was extracted with further chloroform (2 ml) and the combined organics evaporated and the residue dissolved in methanol (2 ml). The solution was applied to a 1 g aminopropyl SPE and eluted with methanol and then with 5% acetic acid in methanol. Product-containing fractions were pooled and evaporated and the product further purified by MDAP to reveal 8-chloro-3-propyl-1-{4-[3-(2-pyridinyl)-1,2,4-oxadiazol-5-yl]butyl}-3,7-dihydro-1H-purine-2,6-dione (1.4 mg) as a white solid.

LC/MS: m/z 430 [MH]+, RT 2.84 min.

b) 8-Chloro-7-(2-propen-1-yl)-1-{4-[3-(2-pyridinyl)-1,2,4-oxadiazol-5-yl]butyl}-3,7-dihydro-1H-purine-2,6-dione

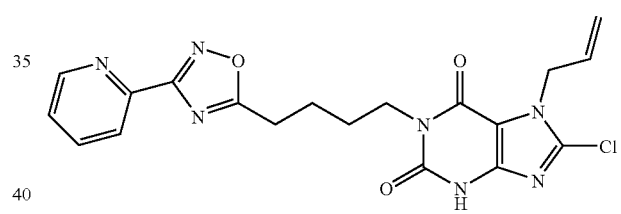

A suspension of N-hydroxy-2-pyridinecarboximidamide (1.15 g, 8.4 mmol) in anhydrous THF (20 ml) was treated with sodium methoxide (0.38 g, 7.0 mmol) and the mixture stirred for 5 min. The mixture was treated with ethyl 5-[8-chloro-2,6-dioxo-7-(2-propen-1-yl)-2,3,6,7-tetrahydro-1H-purin-1-yl]pentanoate (2 g, 5.6 mmol) and the stirred for about 5 min until all the material had dissolved. The mixture was then sealed and heated in a microwave at 120° C. for 15 min then cooled and partitioned between ethyl acetate (100 ml) and saturated aqueous sodium bicarbonate (50 ml). The aqueous phase was extracted with further ethyl acetate (50 ml) and the combined organics dried (MgSO$_4$), filtered and evaporated. The product was purified by flash chromatography using a gradient elution from 1:9 ethyl acetate/cyclohexane to ethyl acetate to reveal 8-chloro-7-(2-propen-1-yl)-1-{4-[3-(2-pyridinyl)-1,2,4-oxadiazol-5-yl]butyl}-3,7-dihydro-1H-purine-2,6-dione (1.49 g) as a white solid.

LC/MS: m/z 428 [MH]+, RT 2.70 min.

Similarly prepared was 8-chloro-1-(3-{3-[(2,4-difluorophenyl)methyl]-1,2,4-oxadiazol-5-yl}propyl)-7-(2-propen-1-yl)-3,7-dihydro-1H-purine-2,6-dione using ethyl 4-[8-chloro-2,6-dioxo-7-(2-propen-1-yl)-2,3,6,7-tetrahydro-1H-purin-1-yl]butanoate.

LC/MS: m/z 463 [MH]+, RT 3.09 min.

c) Ethyl 5-[8-chloro-2,6-dioxo-7-(2-propen-1-yl)-2,3,6,7-tetrahydro-1H-purin-1-yl]pentanoate

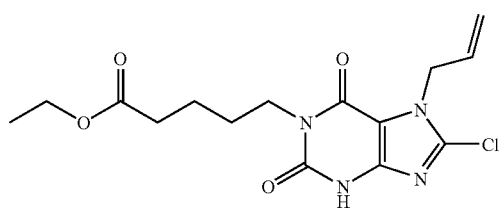

A solution of 8-chloro-7-(2-propen-1-yl)-3-({[2-(trimethylsilyl)ethyl]oxy}methyl)-3,7-dihydro-1H-purine-2,6-dione (10 g, 28 mmol) in DMF (10 ml) was treated with potassium carbonate (4.8 g, 35 mmol) and ethyl 5-bromopentanoate (6.5 g, 31 mmol) and then heated to 70° C. for 3 h, cooled and evaporated. The residue was partitioned between ethyl acetate (100 ml) and water (50 ml). The organic phase was dried (MgSO$_4$), filtered and evaporated and the crude intermediate dissolved in dichloromethane (90 ml), treated with trifluoroacetic acid (17 ml) and the mixture stirred at ambient temperature overnight. Toluene (50 ml) was added and the mixture evaporated to dryness. The product was purified by flash chromatography using a gradient elution from cyclohexane to ethyl acetate to reveal 8.65 g of ethyl 5-[8-chloro-2,6-dioxo-7-(2-propen-1-yl)-2,3,6,7-tetrahydro-1H-purin-1-yl]pentanoate as a white solid.

LC/MS: m/z 355 [MH]$^+$, RT 2.75 min.

Similarly prepared was ethyl 4-[8-chloro-2,6-dioxo-7-(2-propen-1-yl)-2,3,6,7-tetrahydro-1H-purin-1-yl]butanoate.

LC/MS: m/z 341 [MH]$^+$, RT 2.61 min.

d) 8-Chloro-7-(2-propen-1-yl)-3-({[2-(trimethylsilyl)ethyl]oxy}methyl)-3,7-dihydro-1H-purine-2,6-dione

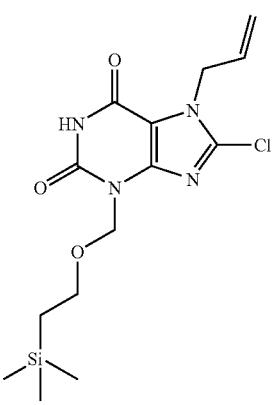

To a solution of 8-chloro-7-(2-propen-1-yl)-3,7-dihydro-1H-purine-2,6-dione (5 g, 22.1 mmol) in DMF (80 ml) was added 2-2-(trimethylsilyl)ethoxymethyl chloride (4.3 ml, 24.2 mmol) and sodium carbonate (2.6 g, 24.2 mmol). After stirring at room temperature overnight further 2-2-(trimethylsilyl)ethoxymethyl chloride (4.3 ml, 24.2 mmol) and sodium carbonate (1.3 g, 12.1 mmol) were added and stirring continued for 2 h. The reaction mixture was then partitioned between 5% LiCl aq and ethyl acetate. The organic extract was separated, washed with brine, dried (MgSO$_4$) and concentrated. Purification by Biotage™ chromatratphy using a silica cartridge eluting 1:4-1:2 ethyl acetate/cyclohexane afforded the title compound (3.14 g, 40%).

m/z 374 [MNH$_4$]$^+$

The following compounds (Table 18) were prepared by a method analogous to that for Example 221, from 8-chloro-7-(2-propen-1-yl)-1-{4-[3-(2-pyridinyl)-1,2,4-oxadiazol-5-yl]butyl}-3,7-dihydro-1H-purine-2,6-dione and the appropriate alkylating agent.

TABLE 18

| Example | R$^2$= | Name | Yield (mg) | m/z | RT (min) |
|---|---|---|---|---|---|
| 222 | *—CH$_3$ | 8-chloro-3-methyl-1-{4-[3-(2-pyridinyl)-1,2,4-oxodiazol-5-yl]butyl}-3,7-dihydro-1H-purine-2,6-dione | 1.7 | 402 | 2.53 |
| 223 | *—ethyl | 8-chloro-3-ethyl-1-{4-[3-(2-pyridinyl)-1,2,4-oxodiazol-5-yl]butyl}-3,7-dihydro-1H-purine-2,6-dione | 1.4 | 416 | 2.66 |
| 224 | *—isobutyl | 8-chloro-3-(2-methylpropyl)-1-{4-[3-(2-pyridinyl)-1,2,4-oxadiazol-5-yl]butyl}-3,7-dihydro-1H-purine-2,6-dione | 2.0 | 444 | 2.99 |
| 225 | *—isopentyl | 8-chloro-3-(2-methylbutyl)-1-{4-[3-(2-pyridinyl)-1,2,4-oxadiazol-5-yl]butyl}-3,7-dihydro-1H-purine-2,6-dione | 1.6 | 458 | 3.21 |
| 226 | *—(CH$_2$)$_3$CF$_3$ | 8-chloro-1-{4-[3-(2-pyridinyl)-1,2,4-oxadiazol-5-yl]butyl}-3-(4,4,4-trifluorobutyl)-3,7-dihydro-1H-purine-2,6-dione | 2.1 | 498 | 3.07 |
| 227 | *—CH$_2$CH$_2$OPh | 8-chloro-3-[2-(phenyloxy)ethyl]-1-{4-[3-(2-pyridinyl)-1,2,4-oxadiazol-5-yl]butyl}-3,7-dihydro-1H-purine-2,6-dione | 1.7 | 508 | 3.11 |
| 228 | *—(CH$_2$)$_3$OMe | 8-chloro-3-[3-(methyloxy)propyl]-1-{4-[3-(2-pyridinyl)-1,2,4-oxadiazol-5-yl]butyl}-3,7-dihydro-1H-purine-2,6-dione | 1.0 | 460 | 2.65 |

The following compounds (Table 19) were prepared by a method analogous to that for Example 221, from 8-chloro-1-(3-{3-[(2,4-difluorophenyl)methyl]-1,2,4-oxadiazol-5-yl}propyl)-7-(2-propen-1-yl)-3,7-dihydro-1H-purine-2,6-dione and the appropriate alkylating agent.

TABLE 19

| Example | R= | Name | Yield (mg) | m/z | RT (min) |
|---|---|---|---|---|---|
| 229 | *—CH₃ | 8-chloro-1-(3-{3-[(2,4-difluorophenyl)methyl]-1,2,4-oxadiazol-5-yl}propyl)-3-methyl-3,7-dihydro-1H-purine-2,6-dione | 1.7 | 437 | 2.92 |
| 230 | *—ethyl | 8-chloro-1-(3-{3-[(2,4-difluorophenyl)methyl]-1,2,4-oxadiazol-5-yl}propyl)-3-ethyl-3,7-dihydro-1H-purine-2,6-dione | 1.4 | 451 | 3.06 |
| 231 | *—propyl | 8-chloro-1-(3-{3-[(2,4-difluorophenyl)methyl]-1,2,4-oxadiazol-5-yl}propyl)-3-propyl-3,7-dihydro-1H-purine-2,6-dione | 2.2 | 465 | 3.22 |
| 232 | *—pentyl | 8-chloro-1-(3-{3-[(2,4-difluorophenyl)methyl]-1,2,4-oxadiazol-5-yl}propyl)-3-pentyl-3,7-dihydro-1H-purine-2,6-dione | 2.6 | 493 | 3.54 |
| 233 | *—CH₂CH₂OH | 8-chloro-1-(3-{3-[(2,4-difluorophenyl)methyl]-1,2,4-oxadiazol-5-yl}propyl)-3-(2-hydroxyethyl)-3,7-dihydro-1H-purine-2,6-dione | 2.7 | 467 | 2.72 |
| 234 | *—(CH₂)₃OH | 8-chloro-1-(3-{3-[(2,4-difluorophenyl)methyl]-1,2,4-oxadiazol-5-yl}propyl)-3-(3-hydroxypropyl)-3,7-dihydro-1H-purine-2,6-dione | 2.0 | 481 | 2.77 |
| 235 | *—(CH₂)₄OH | 8-chloro-1-(3-{3-[(2,4-difluorophenyl)methyl]-1,2,4-oxadiazol-5-yl}propyl)-3-(4-hydroxybutyl)-3,7-dihydro-1H-purine-2,6-dione | 1.4 | 495 | 2.80 |
| 236 | *—CH₂-cyclopropyl | 8-chloro-3-(cyclopropylmethyl)-1-(3-{3-[(2,4-difluorophenyl)methyl]-1,2,4-oxadiazol-5-yl}propyl)-3,7-dihydro-1H-purine-2,6-dione | 1.8 | 477 | 3.30 |

TABLE 19-continued

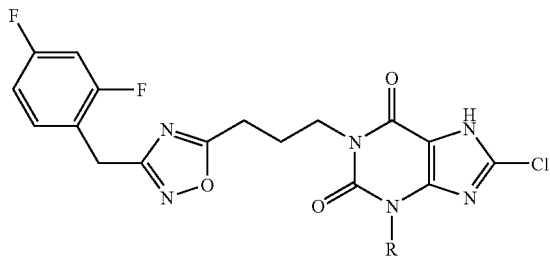

| Example | R= | Name | Yield (mg) | m/z | RT (min) |
|---|---|---|---|---|---|
| 237 | * isobutyl | 8-chloro-1-(3-{3-[(2,4-difluorophenyl)methyl]-1,2,4-oxadiazol-5-yl}propyl)-3-(2-methylpropyl)-3,7-dihydro-1H-purine-2,6-dione | 3.5 | 479 | 3.36 |
| 238 | * isopentyl | 8-chloro-1-(3-{3-[(2,4-difluorophenyl)methyl]-1,2,4-oxadiazol-5-yl}propyl)-3-(3-methylbutyl)-3,7-dihydro-1H-purine-2,6-dione | 3.1 | 493 | 3.53 |
| 239 | * cyclobutylmethyl | 8-chloro-3-(cyclobutylmethyl)-1-(3-{3-[(2,4-difluorophenyl)methyl]-1,2,4-oxadiazol-5-yl}propyl)-3,7-dihydro-1H-purine-2,6-dione | 2.2 | 491 | 3.45 |
| 240 | * 4,4,4-trifluorobutyl | 8-chloro-1-(3-{3-[(2,4-difluorophenyl)methyl]-1,2,4-oxadiazol-5-yl}propyl)-3-(4,4,4-trifluorobutyl)-3,7-dihydro-1H-purine-2,6-dione | 3.0 | 533 | 3.39 |
| 241 | * 3,3,3-trifluoropropyl | 8-chloro-1-(3-{3-[(2,4-difluorophenyl)methyl]-1,2,4-oxadiazol-5-yl}propyl)-3-(3,3,3-trifluoropropyl)-3,7-dihydro-1H-purine-2,6-dione | 2.7 | 519 | 3.34 |
| 242 | * 2-phenyloxyethyl | 8-chloro-1-(3-{3-[(2,4-difluorophenyl)methyl]-1,2,4-oxadiazol-5-yl}propyl)-3-[2-(phenyloxy)ethyl]-3,7-dihydro-1H-purine-2,6-dione | 1.6 | 543 | 3.44 |
| 243 | * 2-(ethyloxy)ethyl | 8-chloro-1-(3-{3-[(2,4-difluorophenyl)methyl]-1,2,4-oxadiazol-5-yl}propyl)-3-[2-(ethyloxy)ethyl]-3,7-dihydro-1H-purine-2,6-dione | 2.8 | 495 | 3.11 |

TABLE 19-continued

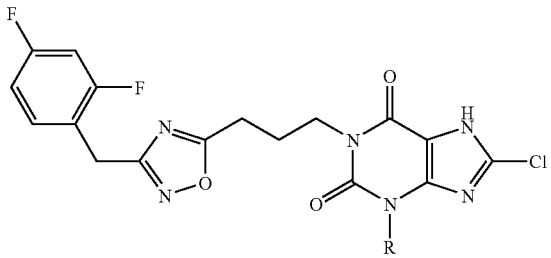

| Example | R= | Name | Yield (mg) | m/z | RT (min) |
|---|---|---|---|---|---|
| 244 | * ~~O~~ | 8-chloro-1-(3-{3-[(2,4-difluorophenyl)methyl]-1,2,4-oxadiazol-5-yl}propyl)-3-[2-(methyloxy)ethyl]-3,7-dihydro-1H-purine-2,6-dione | 2.6 | 481 | 2.98 |
| 245 | * ~~O~~ | 8-chloro-1-(3-{3-[(2,4-difluorophenyl)methyl]-1,2,4-oxadiazol-5-yl}propyl)-3-[3-(methyloxy)propyl]-3,7-dihydro-1H-purine-2,6-dione | 2.1 | 495 | 3.04 |

Example 246

8-Chloro-1-{4-[2-oxo-3-(phenylmethyl)-1-pyrrolidinyl]butyl}-3-pentyl-3,7-dihydro-1H-purine-2,6-dione a) 8-Chloro-1-{4-[2-oxo-3-(phenylmethyl)-1-pyrrolidinyl]butyl}-3-pentyl-3,7-dihydro-1H-purine-2,6-dione

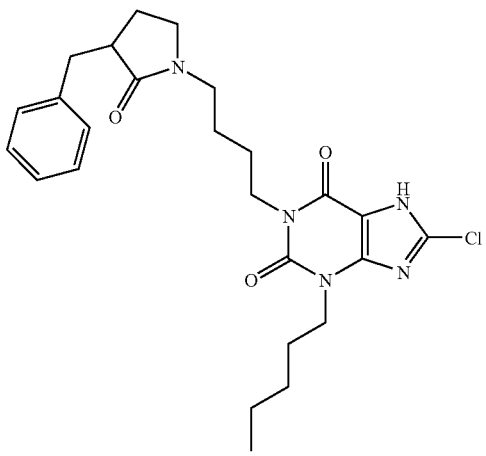

A solution of 8-chloro-1-{4-[2-oxo-3-(phenylmethyl)-1-pyrrolidinyl]butyl}-3-pentyl-7-(2-propen-1-yl)-3,7-dihydro-1H-purine-2,6-dione (0.35 g, 0.67 mmol), Pd(PPh$_3$)$_4$ (0.082 g, 0.07 mmol) and morpholine (0.6 ml, 6.7 mmol) in THF (10 ml) was degassed (sequential evacuation followed by addition of nitrogen×3) then stirred for 4 h. The solution was then loaded onto an aminopropyl SPE (5 g) and eluted first with MeOH then 5% AcOH/MeOH to provide the title compound containing a small impurity. Further purification over silica (10 g SPE, gradient elution ether/ethyl acetate 1:0 to 0:1) provided the title compound as a clear oil (0.10 g, 31%).

LC/MS: m/z 486 [MH]$^+$ b) 8-Chloro-1-{4-[2-oxo-3-(phenylmethyl)-1-pyrrolidinyl]butyl}-3-pentyl-7-(2-propen-1-yl)-3,7-dihydro-1H-purine-2,6-dione Prepared as with 8-chloro-1-(2-hydroxy-6-phenylhexyl)-3-pentyl-7-(2-propen-1-yl)-3,7-dihydro-1H-purine-2,6-dione using 1-(4-bromobutyl)-3-(phenylmethyl)-2-pyrrolidinone as the alkylating agent, potassium carbonate as base and heating at 50° C. for 18 h. Yield 86%.

LC/MS: m/z 526 [MH]$^+$ c) 1-(4-bromobutyl)-3-(phenylmethyl)-2-pyrrolidinone

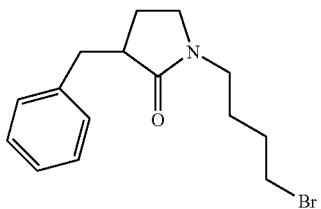

To a solution of 3-(phenylmethyl)-2-pyrrolidinone (0.23 g, 1.3 mmol) and 1,4-dibromobutane (0.57 g, 4.2 mmol) in DMF (5 ml) was added sodium t-butoxide (0.151 g, 1.6 mmol) and the solution stirred for 18 h. The solution was concentrated and the residues chromatographed over silica (20 g SPE, eluting first with cyclohexane then with DCM) to provide the title compound as a colourless oil containing a trace of DMF (0.25 g, 61%).
LC/MS: m/z 311 [MH]$^+$

Example 247

8-Chloro-1-{4-[2-oxo-1-(phenylmethyl)-3-Pyrrolidinyl]butyl}-3-pentyl-3,7-dihydro-1H-purine-2,6-dione a) 8-Chloro-1-{4-[2-oxo-1-(phenylmethyl)-3-pyrrolidinyl]butyl}-3-pentyl-3,7-dihydro-1H-purine-2,6-dione

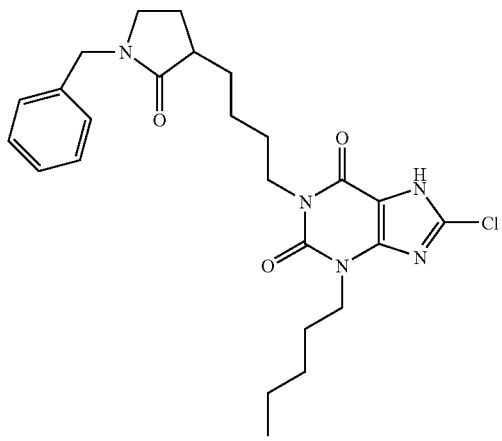

To a solution of 8-chloro-3-pentyl-7-(2-propen-1-yl)-3,7-dihydro-1H-purine-2,6-dione (0.086 g, 0.29 mmol) and 3-(4-bromobutyl)-1-(phenylmethyl)-2-pyrrolidinone (0.17 g, 0.55 mmol, 1:1 mixture with 2-(phenylmethyl)-2-azaspiro[4.4]nonan-1-one) in THF (5 ml) was added potassium carbonate (0.08 g, 0.58 mmol) and the mixture heated and stirred at 50° C. for 18 h. The solution was allowed to cool then degassed (sequential evacuation followed by addition of nitrogen×3) and Pd(PPh$_3$)$_4$ (0.09 g, 0.077 mmol) followed by morpholine (0.2 ml, 2.2 mmol) added and the solution stirred at ambient temperature for 18 h. The solution was separated between ethyl acetate and dil HCl and the organics washed with brine, dried and concentrated. Purification of the residues using an aminopropyl SPE (5 g) eluting first with MeOH then 5% AcOH/MeOH yielded the title compound as a yellow oil which crystallised on standing under ether (0.031 g, 22%).
LC/MS: m/z 486 [MH]$^+$ b) 3-(4-Bromobutyl)-1-(phenylmethyl)-2-pyrrolidinone

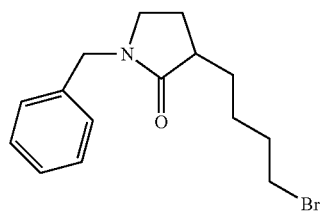

To a solution of 1-(phenylmethyl)-2-pyrrolidinone (0.47 g, 2.7 mmol) in THF (10 ml) at −78° C. was added lithium hexamethyldisilylazine (2.8 ml, 2.7 mmol, 1M solution) over 5 min. After 15 min 1,4-dibromobutane (0.32 ml, 2.7 mmol) was added and the solution allowed to attain ambient temperature over 2 h then stirred for a further 18 h. The solution was separated between ethyl acetate and water and the organics isolated, dried and concentrated. Chromatography over silica (20 g SPE) eluting with cyclohexane then DCM and finally ether provided a clear oil which was a 1:1 mixture of the title compound and 2-(phenylmethyl)-2-azaspiro[4.4]nonan-1-one (0.17 g). This was used in the next step without further purification.
LC/MS: m/z 310, 312 [MH]$^+$

Comparative Example C

8-Chloro-1-(5-{5-[(3,4-dichlorophenyl)methyl]-2H-tetrazol-2-yl}pentyl)-3-pentyl-3,7-dihydro-1H-purine-2,6-dione

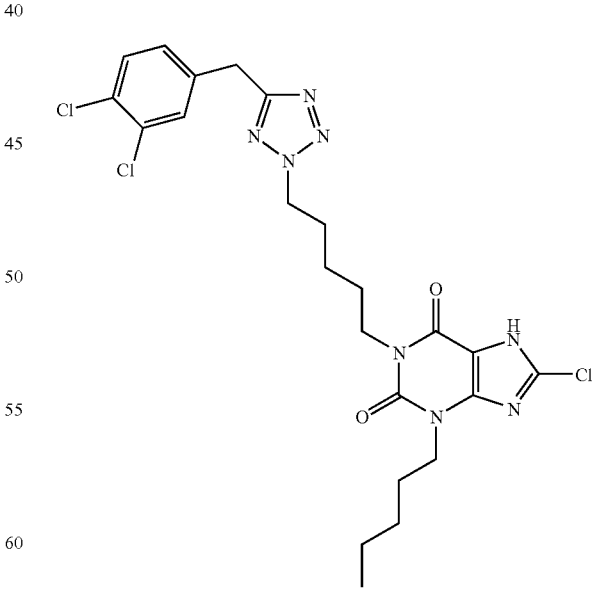

To a solution of 8-chloro-3-pentyl-7-(2-propen-1-yl)-3,7-dihydro-1H-purine-2,6-dione (0.18 g, 0.61 mmol) in THF (5 ml) was added 5-{5-[(3,4-dichlorophenyl)methyl]-2H-tetrazol-2-yl}-1-pentanol (0.191 g, 0.61 mmol; prepared in similar fashion to Example 35), triphenylphosphine (0.36 g, 1.3 mmol) and finally dibenzylazodicarboxylate (0.40 g, 1.3 mmol). The solution was stirred for 18 h after which Pd(PPh₃)₄ (0.16 g, 0.137 mmol) followed by morpholine (0.75 ml, 8.3 mmol) was added and the solution stirred at ambient temperature for 6 h. The solution was loaded onto an aminopropyl SPE (5 g) and eluted with MeOH then 5% AcOH/MeOH to yield the title compound containing minor impurities. Further chromatography (silica SPE, 20 g) eluting with ether yielded the title compound as a white solid (0.061 g, 18%).

LC/MS: m/z 553 [MH]$^+$

Example 248

8-Chloro-1-{3-[5-(4-chlorophenyl)-1H-pyrazol-3-yl] propyl}-3-pentyl-3,7-dihydro-1H-purine-2,6-dione

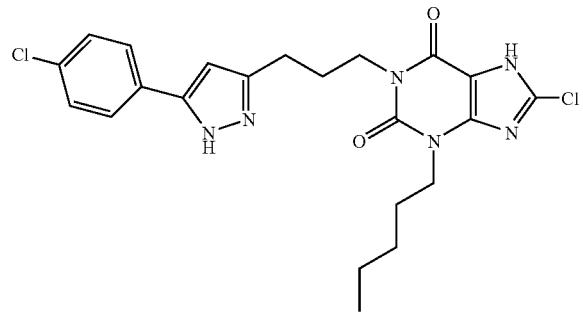

Prepared as with 8-chloro-1-(5-{5-[(3,4-dichlorophenyl) methyl]-2H-tetrazol-2-yl}pentyl)-3-pentyl-3,7-dihydro-1H-purine-2,6-dione (Comparative Example C) using 3-[5-(4-chlorophenyl)-1H-pyrazol-3-yl]-1-propanol. The final product material was washed with ether to yield the title compound as a cream solid (30%).

LC/MS: m/z 475 [MH]$^+$

Example 249

3-Butyl-8-chloro-1-{4-[5-(1-methyl-1H-1,2,3-triazol-4-yl)-1,2,4-oxadiazol-3-yl]butyl}-3,7-dihydro-1H-purine-2,6-dione A solution of the 1-methyl-1H-1,2,3-triazole-4-carboxylic acid (18 mg, 0.14 mmol) in DMF (0.5 ml) was treated with CDI (23 mg, 0.14 mmol) at rt for 1 h. A solution of (1Z)-5-(3-butyl-8-chloro-2,6-dioxo-2,3,6,7-tetrahydro-1H-purin-1-yl)-N-hydroxypentanimidamide (50 mg, 0.14 mmol) in DMSO (0.4 ml) was added to the mixture then heated to 100° C. for 18 h. The reaction mixture was purified by MDAP to give the title compound as a white solid (18 mg).

LC/MS: m/z 448 [MH]$^+$, RT 2.86 min.

The following compounds (Table 20) were prepared using a method analogous to that for Example 249, using the appropriate carboxylic acid.

TABLE 20

| Example | Structure | Name | Yield (mg) | LC/MS |
|---|---|---|---|---|
| 250 | 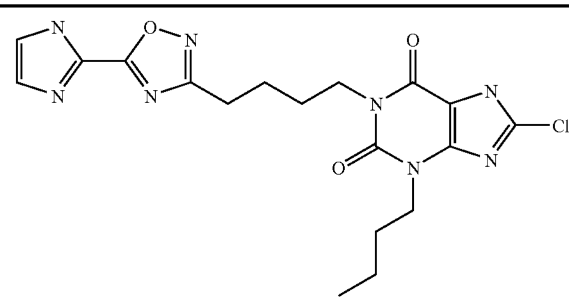 | 3-butyl-8-chloro-1-{4-[5-(1H-imidazol-2-yl)-1,2,4-oxadiazol-3-yl]butyl}-3,7-dihydro-1H-purine-2,6-dione | 16 | m/z 433 [MH]$^+$ RT 2.79 min |
| 251 | 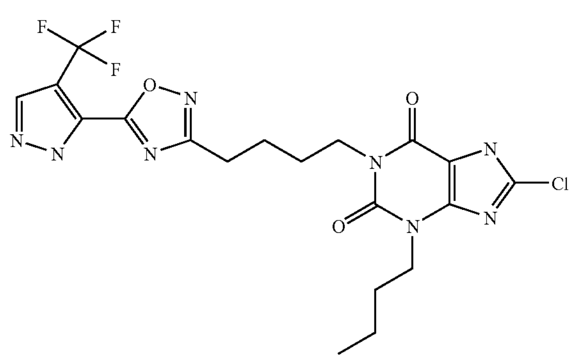 | 3-butyl-8-chloro-1-(4-{5-[4-(trifluoromethyl)-1H-pyrazol-5-yl]-1,2,4-oxadiazol-3-yl}butyl)-3,7-dihydro-1H-purine-2,6-dione | 19 | m/z 501 [MH]$^+$ RT 3.28 min |

TABLE 20-continued

| Example | Structure | Name | Yield (mg) | LC/MS |
|---|---|---|---|---|
| 252 | 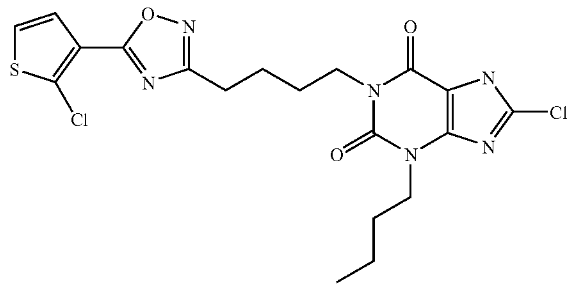 | 3-butyl-8-chloro-1-{4-[5-(2-chloro-3-thienyl)-1,2,4-oxadiazol-3-yl]butyl}-3,7-dihydro-1H-purine-2,6-dione | 26 | m/z 483 [MH]+ RT 3.59 min |
| 253 | 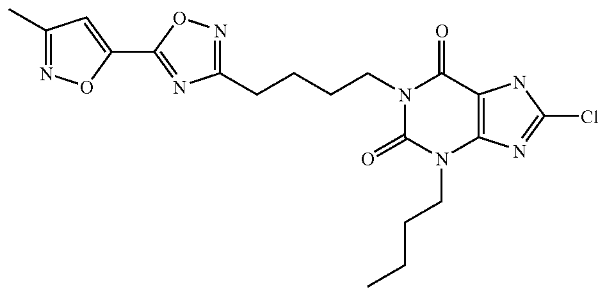 | 3-butyl-8-chloro-1-{4-[5-(3-methyl-5-isoxazolyl)-1,2,4-oxadiazol-3-yl]butyl}-3,7-dihydro-1H-purine-2,6-dione | 25 | m/z 448 [MH]+ RT 3.21 min |
| 254 | 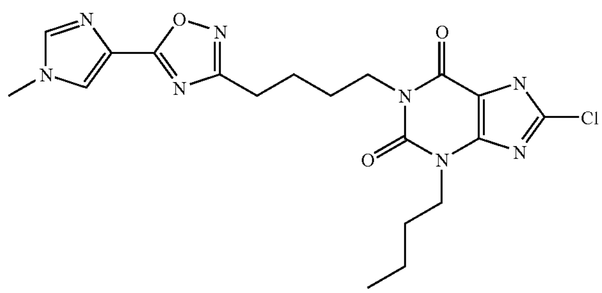 | 3-butyl-8-chloro-1-{4-[5-(1-methyl-1H-imidazol-4-yl)-1,2,4-oxadiazol-3-yl]butyl}-3,7-dihydro-1H-purine-2,6-dione | 16 | m/z 447 [MH]+ RT 2.74 min |
| 255 | 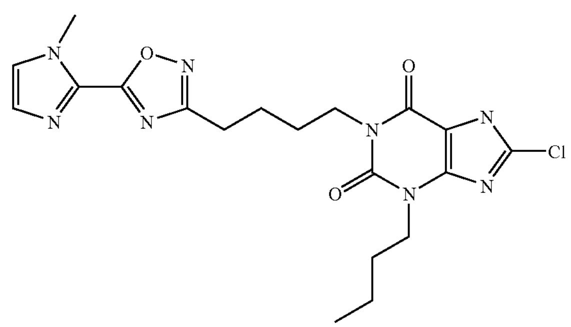 | 3-butyl-8-chloro-1-{4-[5-(1-methyl-1H-imidazol-2-yl)-1,2,4-oxadiazol-3-yl]butyl}-3,7-dihydro-1H-purine-2,6-dione | 9 | m/z 447 [MH]+ RT 2.91 min |
| 256 | 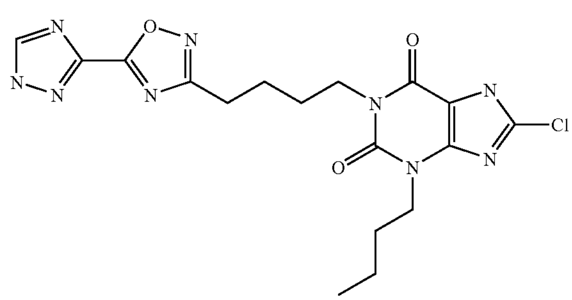 | 3-butyl-8-chloro-1-{4-[5-(1H-1,2,4-triazol-3-yl)-1,2,4-oxadiazol-3-yl]butyl}-3,7-dihydro-1H-purine-2,6-dione | 10 | m/z 434 [MH]+ RT 2.73 min |

TABLE 20-continued

| Example | Structure | Name | Yield (mg) | LC/MS |
|---|---|---|---|---|
| 257 | 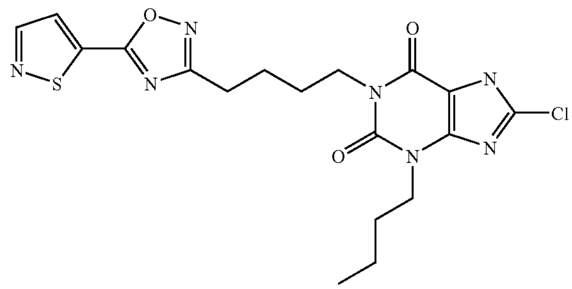 | 3-butyl-8-chloro-1-{4-[5-(5-isothiazolyl)-1,2,4-oxadiazol-3-yl]butyl}-3,7-dihydro-1H-purine-2,6-dione | 17 | m/z 450 [MH]$^+$ RT 3.34 min |
| 258 | 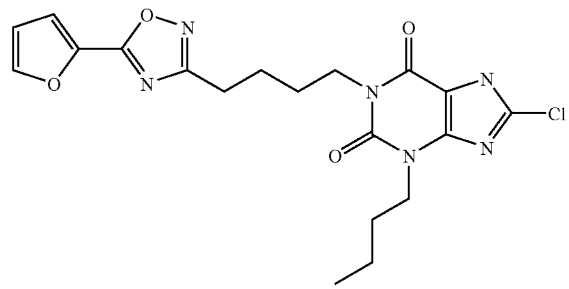 | 3-butyl-8-chloro-1-{4-[5-(2-furanyl)-1,2,4-oxadiazol-3-yl]butyl}-3,7-dihydro-1H-purine-2,6-dione | 26 | m/z 433 [MH]$^+$ RT 3.27 min |
| 259 | 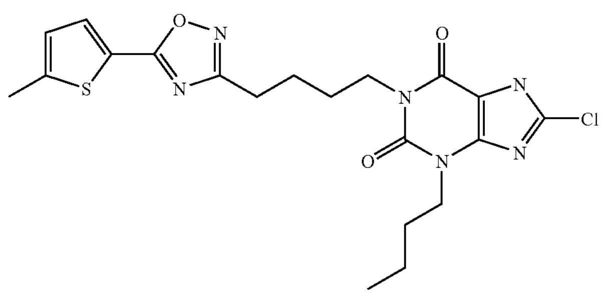 | 3-butyl-8-chloro-1-{4-[5-(5-methyl-2-thienyl)-1,2,4-oxadiazol-3-yl]butyl}-3,7-dihydro-1H-purine-2,6-dione | 29 | m/z 463 [MH]$^+$ RT 3.61 min |
| 260 | 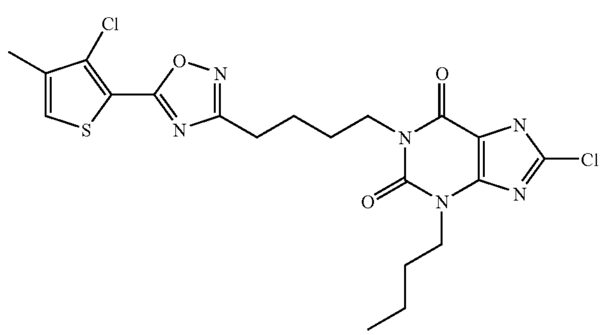 | 3-butyl-8-chloro-1-{4-[5-(3-chloro-4-methyl-2-thienyl)-1,2,4-oxadiazol-3-yl]butyl}-3,7-dihydro-1H-purine-2,6-dione | 30 | m/z 497 [MH]$^+$ RT 3.76 min |
| 261 | 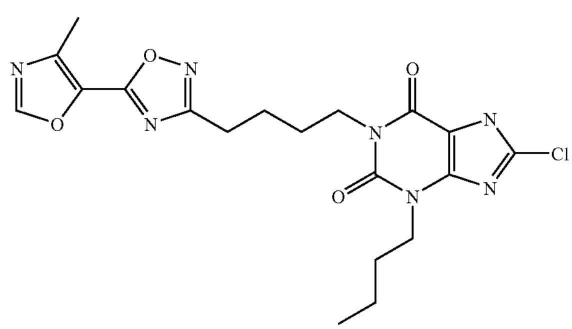 | 3-butyl-8-chloro-1-{4-[5-(4-methyl-1,3-oxazol-5-yl)-1,2,4-oxadiazol-3-yl]butyl}-3,7-dihydro-1H-purine-2,6-dione | 25 | m/z 448 [MH]$^+$ RT 3.13 min |

TABLE 20-continued

| Example | Structure | Name | Yield (mg) | LC/MS |
|---|---|---|---|---|
| 262 | 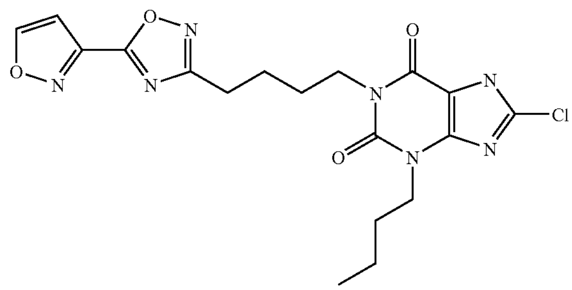 | 3-butyl-8-chloro-1-{4-[5-(3-isoxazolyl)-1,2,4-oxadiazol-3-yl]butyl}-3,7-dihydro-1H-purine-2,6-dione | 23 | m/z 434 [MH]+ RT 3.20 min |
| 263 | 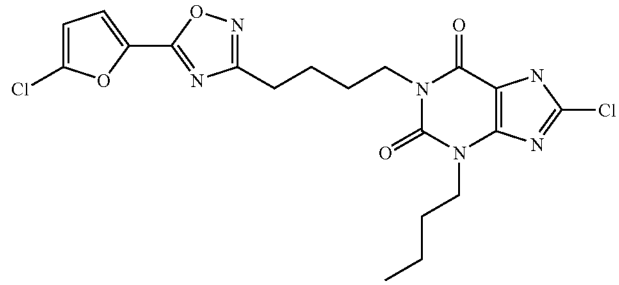 | 3-butyl-8-chloro-1-{4-[5-(5-chloro-2-furanyl)-1,2,4-oxadiazol-3-yl]butyl}-3,7-dihydro-1H-purine-2,6-dione | 27 | m/z 467 [MH]+ RT 3.51 min |
| 264 | 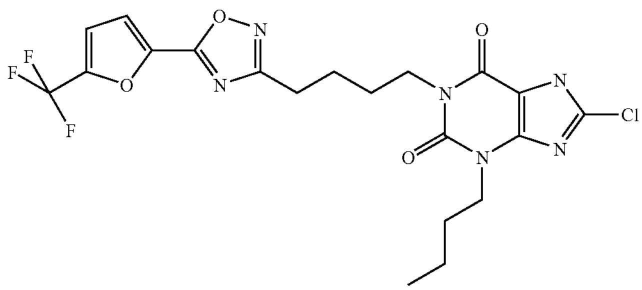 | 3-butyl-8-chloro-1-(4-{5-[5-(trifluoromethyl)-2-furanyl]-1,2,4-oxadiazol-3-yl}butyl)-3,7-dihydro-1H-purine-2,6-dione | 27 | m/z 501 [MH]+ RT 3.61 min |
| 265 | 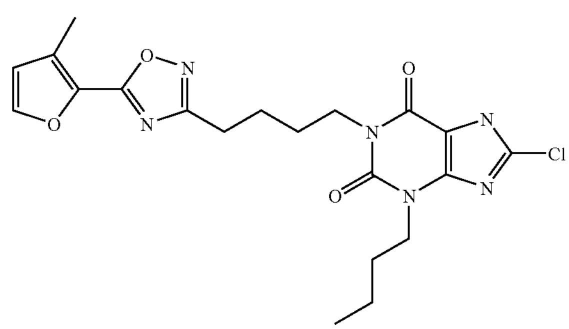 | 3-butyl-8-chloro-1-{4-[5-(3-methyl-2-furanyl)-1,2,4-oxadiazol-3-yl]butyl}-3,7-dihydro-1H-purine-2,6-dione | 27 | m/z 447 [MH]+ RT 3.43 min |
| 266 | 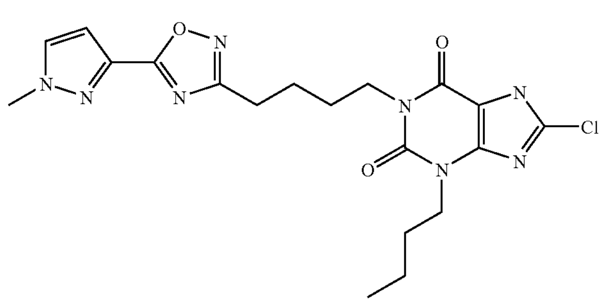 | 3-butyl-8-chloro-1-{4-[5-(1-methyl-1H-pyrazol-3-yl)-1,2,4-oxadiazol-3-yl]butyl}-3,7-dihydro-1H-purine-2,6-dione | 25 | m/z 447 [MH]+ RT 3.02 min |

TABLE 20-continued

| Example | Structure | Name | Yield (mg) | LC/MS |
|---|---|---|---|---|
| 267 | 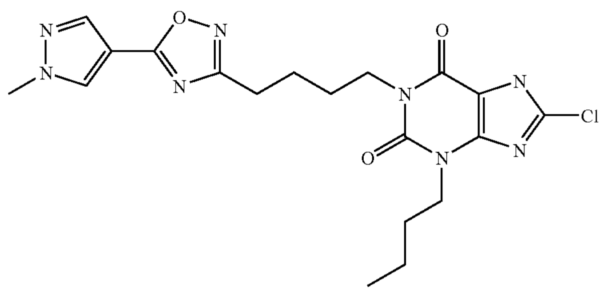 | 3-butyl-8-chloro-1-{4-[5-(1-methyl-1H-pyrazol-4-yl)-1,2,4-oxadiazol-3-yl]butyl}-3,7-dihydro-1H-purine-2,6-dione | 8 | m/z 447 [MH]+ RT 2.99 min |
| 268 | 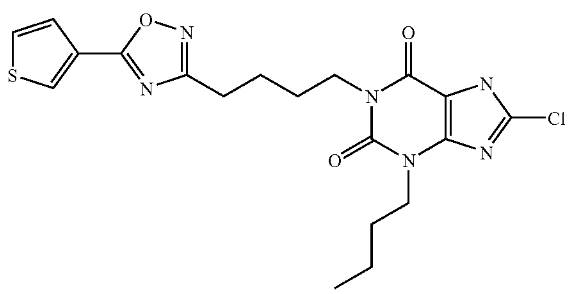 | 3-butyl-8-chloro-1-{4-[5-(3-thienyl)-1,2,4-oxadiazol-3-yl]butyl}-3,7-dihydro-1H-purine-2,6-dione | 19 | m/z 4449 [MH]+ RT 3.43 min |
| 269 | 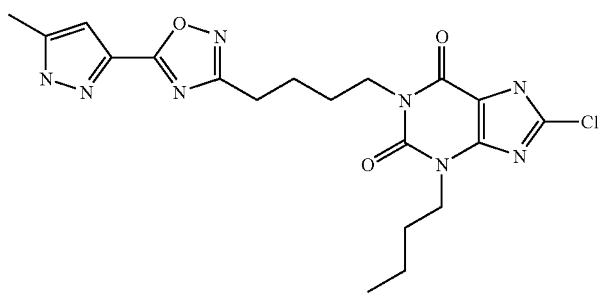 | 3-butyl-8-chloro-1-{4-[5-(5-methyl-1H-pyrazol-3-yl)-1,2,4-oxadiazol-3-yl]butyl}-3,7-dihydro-1H-purine-2,6-dione | 26 | m/z 447 [MH]+ RT 3.03 min |
| 270 | 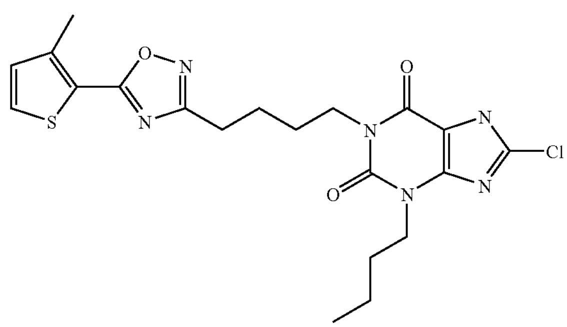 | 3-butyl-8-chloro-1-{4-[5-(3-methyl-2-thienyl)-1,2,4-oxadiazol-3-yl]butyl}-3,7-dihydro-1H-purine-2,6-dione | 27 | m/z 463 [MH]+ RT 3.62 min |
| 271 | 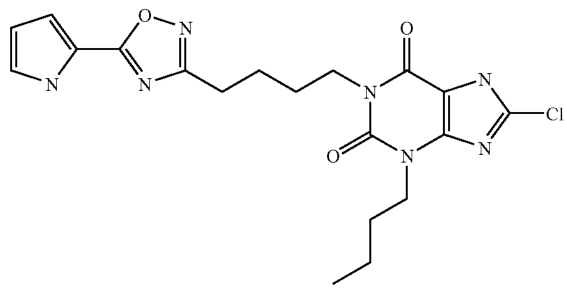 | 3-butyl-8-chloro-1-{4-[5-(1H-pyrrol-2-yl)-1,2,4-oxadiazol-3-yl]butyl}-3,7-dihydro-1H-purine-2,6-dione | 13 | m/z 432 [MH]+ RT 3.26 min |

TABLE 20-continued

| Example | Structure | Name | Yield (mg) | LC/MS |
|---|---|---|---|---|
| 272 | 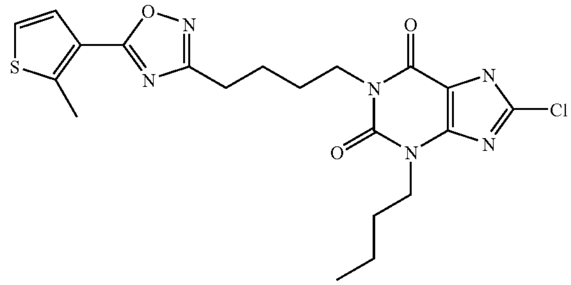 | 3-butyl-8-chloro-1-{4-[5-(2-methyl-3-thienyl)-1,2,4-oxadiazol-3-yl]butyl}-3,7-dihydro-1H-purine-2,6-dione | 18 | m/z 463 [MH]+ RT 3.64 min |
| 273 | 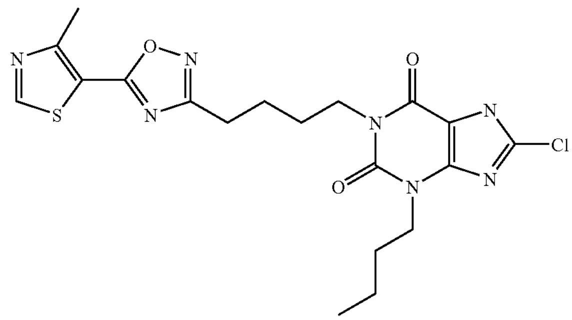 | 3-butyl-8-chloro-1-{4-[5-(4-methyl-1,3-thiazol-5-yl)-1,2,4-oxadiazol-3-yl]butyl}-3,7-dihydro-1H-purine-2,6-dione | 24 | m/z 464 [MH]+ RT 3.26 min |
| 274 | 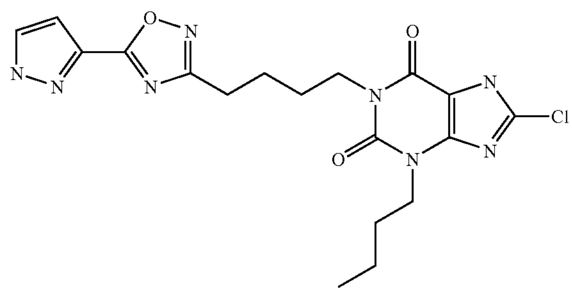 | 3-butyl-8-chloro-1-{4-[5-(1H-pyrazol-3-yl)-1,2,4-oxadiazol-3-yl]butyl}-3,7-dihydro-1H-purine-2,6-dione | 20 | m/z 433 [MH]+ RT 3.00 min |
| 275 | 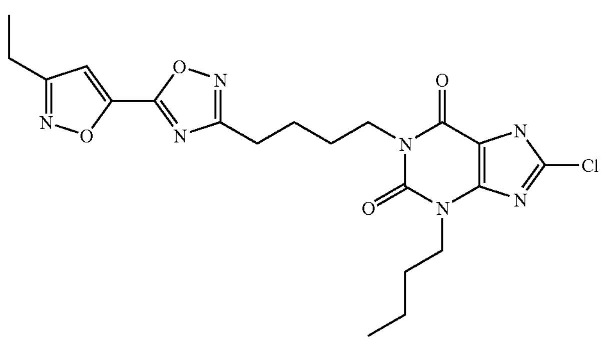 | 3-butyl-8-chloro-1-{4-[5-(3-ethyl-5-isoxazolyl)-1,2,4-oxadiazol-3-yl]butyl}-3,7-dihydro-1H-purine-2,6-dione | 20 | m/z 462 [MH]+ RT 3.43 min |
| 276 | 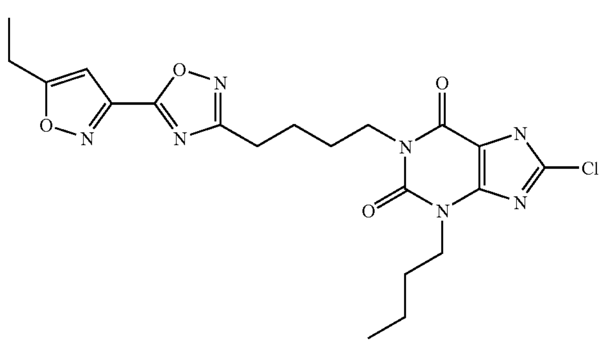 | 3-butyl-8-chloro-1-{4-[5-(5-ethyl-3-isoxazolyl)-1,2,4-oxadiazol-3-yl]butyl}-3,7-dihydro-1H-purine-2,6-dione | 23 | m/z 462 [MH]+ RT 3.46 min |

TABLE 20-continued

| Example | Structure | Name | Yield (mg) | LC/MS |
|---|---|---|---|---|
| 277 | 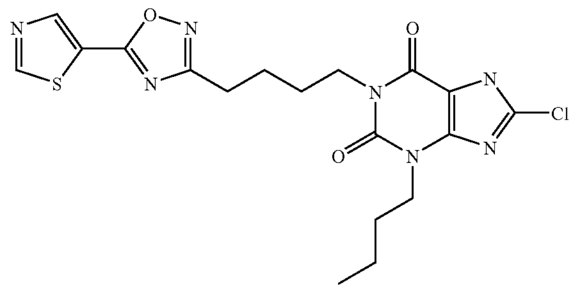 | 3-butyl-8-chloro-1-{4-[5-(1,3-thiazol-5-yl)-1,2,4-oxadiazol-3-yl]butyl}-3,7-dihydro-1H-purine-2,6-dione | 20 | m/z 450 [MH]+ RT 3.13 min |
| 278 | 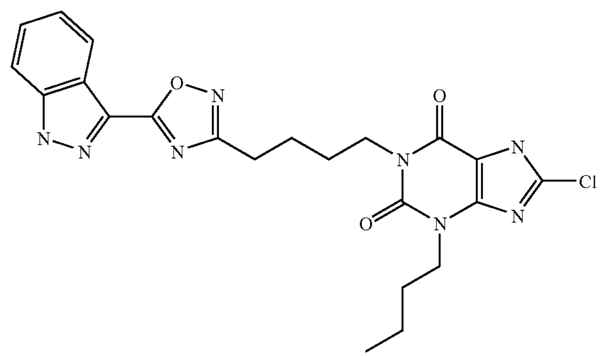 | 3-butyl-8-chloro-1-{4-[5-(1H-indazol-3-yl)-1,2,4-oxadiazol-3-yl]butyl}-3,7-dihydro-1H-purine-2,6-dione | 24 | m/z 483 [MH]+ RT 3.50 min |
| 279 | 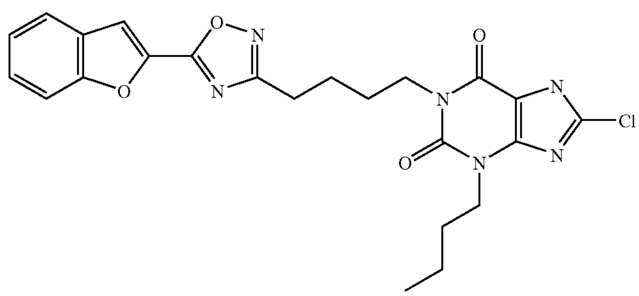 | 1-{4-[5-(1-benzofuran-2-yl)-1,2,4-oxadiazol-3-yl]butyl}-3-butyl-8-chloro-3,7-dihydro-1H-purine-2,6-dione | 6 | m/z 483 [MH]+ RT 3.72 min |
| 280 | 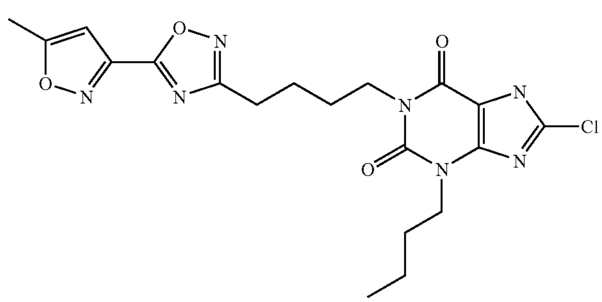 | 3-butyl-8-chloro-1-{4-[5-(5-methyl-3-isoxazolyl)-1,2,4-oxadiazol-3-yl]butyl}-3,7-dihydro-1H-purine-2,6-dione | 13 | m/z 448 [MH]+ RT 3.30 min |
| 2810 | 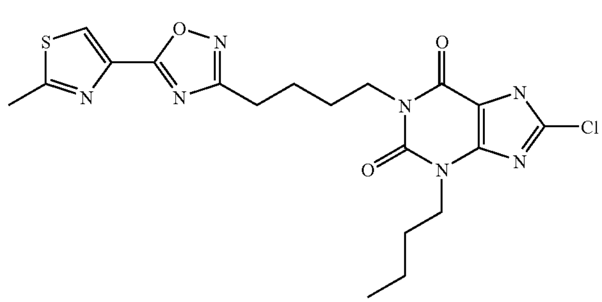 | 3-butyl-8-chloro-1-{4-[5-(2-methyl-1,3-thiazol-4-yl)-1,2,4-oxadiazol-3-yl]butyl}-3,7-dihydro-1H-purine-2,6-dione | 20 | m/z 464 [MH]+ RT 3.14 min |

TABLE 20-continued

| Example | Structure | Name | Yield (mg) | LC/MS |
|---|---|---|---|---|
| 282 | 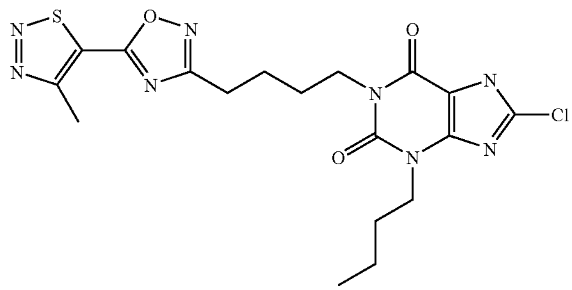 | 3-butyl-8-chloro-1-{4-[5-(4-methyl-1,2,3-thiadiazol-5-yl)-1,2,4-oxadiazol-3-yl]butyl}-3,7-dihydro-1H-purine-2,6-dione | 14 | m/z 465 [MH]+ RT 3.40 min |
| 283 | 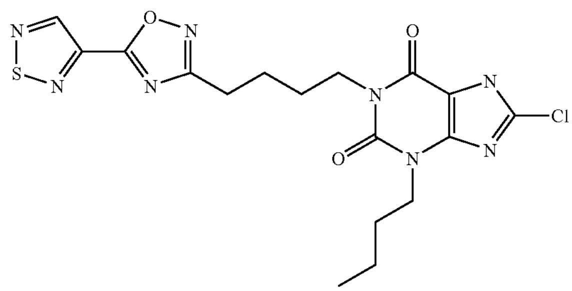 | 3-butyl-8-chloro-1-{4-[5-(1,2,5-thiadiazol-3-yl)-1,2,4-oxadiazol-3-yl]butyl}-3,7-dihydro-1H-purine-2,6-dione | 24 | m/z 451 [MH]+ RT 3.27 min |
| 284 | 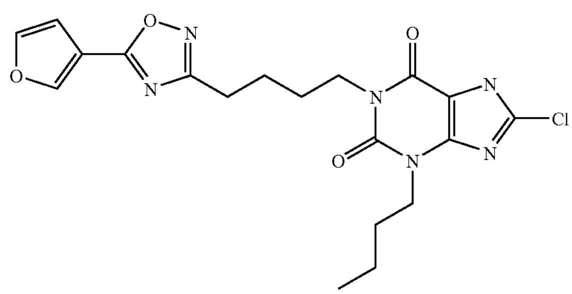 | 3-butyl-8-chloro-1-{4-[5-(3-furanyl)-1,2,4-oxadiazol-3-yl]butyl}-3,7-dihydro-1H-purine-2,6-dione | 21 | m/z 433 [MH]+ RT 3.29 min |
| 285 | 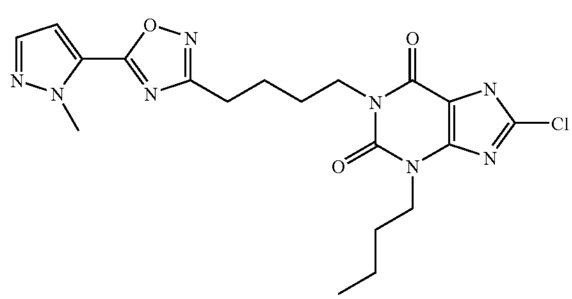 | 3-butyl-8-chloro-1-{4-[5-(1-methyl-1H-pyrazol-5-yl)-1,2,4-oxadiazol-3-yl]butyl}-3,7-dihydro-1H-purine-2,6-dione | 23 | m/z 447 [MH]+ RT 3.22 min |

TABLE 20-continued

| Example | Structure | Name | Yield (mg) | LC/MS |
|---|---|---|---|---|
| 286 | 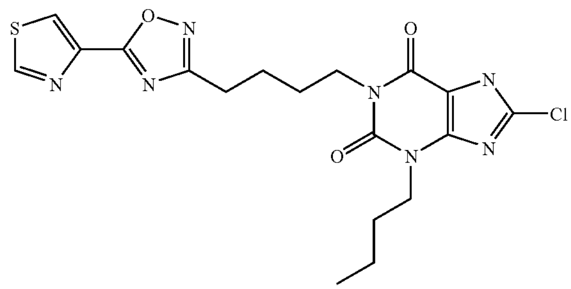 | 3-butyl-8-chloro-1-{4-[5-(1,3-thiazol-4-yl)-1,2,4-oxadiazol-3-yl]butyl}-3,7-dihydro-1H-purine-2,6-dione | 20 | m/z 450 [MH]+ RT 3.06 min |
| 287 | 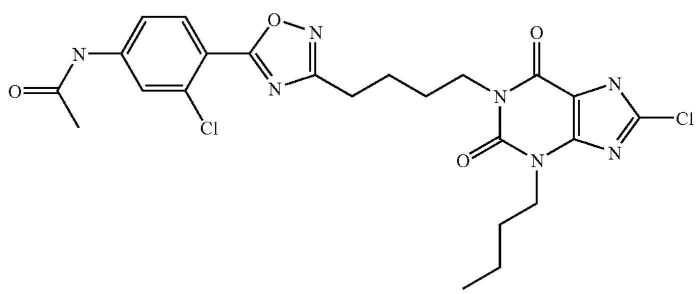 | N-(4-{3-[4-(3-butyl-8-chloro-2,6-dioxo-2,3,6,7-tetrahydro-1H-purin-1-yl)butyl]-1,2,4-oxadiazol-5-yl}-3-chlorophenyl) acetamide | 23 | m/z 534 [MH]+ RT 3.44 min |
| 288 | 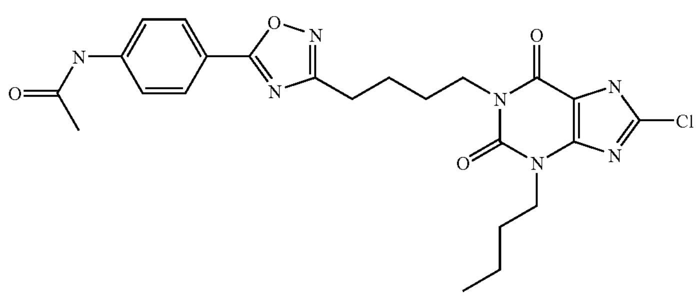 | N-(4-{3-[4-(3-butyl-8-chloro-2,6-dioxo-2,3,6,7-tetrahydro-1H-purin-1-yl)butyl]-1,2,4-oxadiazol-5-yl}phenyl)acetamide | 16 | m/z 500 [MH]+ RT 3.23 min |
| 289 | 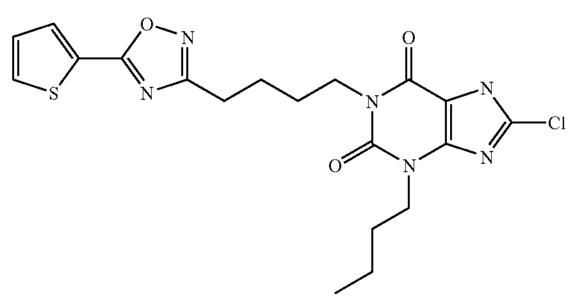 | 3-butyl-8-chloro-1-{4-[5-(2-thienyl)-1,2,4-oxadiazol-3-yl]butyl}-3,7-dihydro-1H-purine-2,6-dione | 27 | m/z 449 [MH]+ RT 3.45 min |
| 290 | 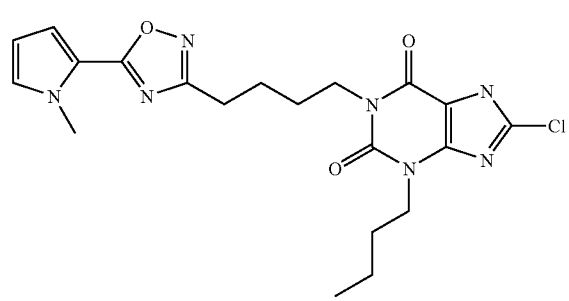 | 3-butyl-8-chloro-1-{4-[5-(1-methyl-1H-pyrrol-2-yl)-1,2,4-oxadiazol-3-yl]butyl}-3,7-dihydro-1H-purine-2,6-dione | 15 | m/z 446 [MH]+ RT 3.45 min |

Example 291

8-Chloro-1-{4-[3-(2,4-difluorophenyl)-1,2,4-oxadiazol-5-yl]butyl}-3-ethyl-3,7-dihydro-1H-purine-2,6-dione a) 8-Chloro-1-{4-[3-(2,4-difluorophenyl)-1,2,4-oxadiazol-5-yl]butyl}-3-ethyl-3,7-dihydro-1H-purine-2,6-dione

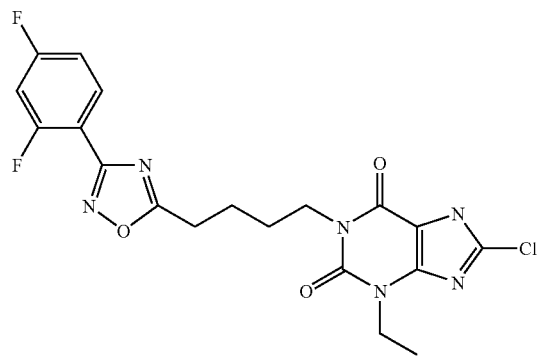

A solution of 5-(8-chloro-3-ethyl-2,6-dioxo-2,3,6,7-tetrahydro-1H-purin-1-yl)pentanoic acid (0.05 g, 0.16 mmol) in DMSO (1 ml) was treated with CDI (0.029 g, 0.18 mmol) and the mixture stirred at room temperature for 1 h. Subsequently, the mixture was treated with 2,4-difluorobenzamidoxime (0.03 g, 0.18 mmol) and then heated to 120° C. for 30 min. The product was purified from the crude mixture using MDAP. Product-containing fractions were evaporated using a stream of nitrogen and the resulting colourless gum triturated in ether and dried to reveal the title compound as a white solid (50 mg, 70%).

LC/MS: m/z 451 [MH]$^+$, RT 2.23 min.

b) 5-(8-chloro-3-ethyl-2,6-dioxo-2,3,6,7-tetrahydro-1H-purin-1-yl)pentanoic acid

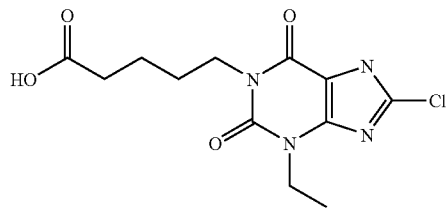

A solution of ethyl 5-(8-chloro-3-ethyl-2,6-dioxo-2,3,6,7-tetrahydro-1H-purin-1-yl)pentanoate (2.3 g, 6.7 mmol) in methanol (75 ml) was treated with water (3 ml) and lithium hydroxide (0.481 g, 20.1 mmol) and the mixture stirred at 40° C. for 17 h. The mixture was evaporated to dryness and the residue treated with 50 ml of ethyl acetate and 50 ml of water. The 2 phases were separated and the aqueous phase adjusted to pH5 using 2M aqueous hydrochloric acid. The precipitated product was filtered off and dried to yield 5-(8-chloro-3-ethyl-2,6-dioxo-2,3,6,7-tetrahydro-1H-purin-1-yl)pentanoic acid as a white solid (1.99 g, 95%).

LC/MS: m/z 315 [MH]$^+$, RT 2.34 min.

c) Ethyl 5-(8-chloro-3-ethyl-2,6-dioxo-2,3,6,7-tetrahydro-1H-purin-1-yl)pentanoate

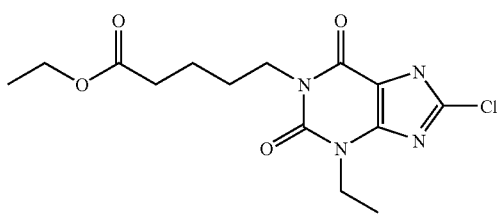

A solution of 8-chloro-7-(2-propen-1-yl)-3-ethyl-3,7-dihydro-1H-purine-2,6-dione (3 g, 11.8 mmol) in DMF (40 ml) was treated with potassium carbonate (1.9 g, 14.1 mmol) and ethyl 5-bromopentanoate (2.24 ml, 14.1 mmol) and the mixture heated in a nitrogen atmosphere at 70° C. for 5 h and then cooled. The mixture was degassed by the repeated application of vacuum followed by backfilling with nitrogen gas and then treated with tetrakis(triphenylphosphine)palladium(0) (1.36 g, 1.1 mmol) and morpholine (10.3 ml, 118 mmol). The mixture was stirred in a nitrogen atmosphere for 4 h and then evaporated to dryness. The residue was partitioned between 100 ml of ethyl acetate and 100 ml of water. The aqueous phase was re-extracted with 100 ml of ethyl acetate and the combined organics dried over magnesium sulfate, filtered and evaporated. The residue was triturated in diethyl ether, filtered and dried to reveal ethyl 5-(8-chloro-3-ethyl-2,6-dioxo-2,3,6,7-tetrahydro-1H-purin-1-yl)pentanoate compound as a white solid (2.3 g, 57%).

LC/MS: m/z 343 [MH]$^+$, RT 2.73 min.

The following compounds (Table 21) were prepared by a method analogous to that for Example 291.

TABLE 21

| Example | Structure | Precursor | Yield (mg) | LC/MS |
|---|---|---|---|---|
| 292 | 8-chloro-1-{4-[3-(2-chlorophenyl)-1,2,4-oxidiazol-5-yl]butyl}-3-ethyl-3,7-dihydro-1H-purine-2,6-dione | 5-(8-chloro-3-ethyl-2,6-dioxo-2,3,6,7-tetrahydro-1H-purin-1-yl)pentanoic acid | 33 | m/z 449 [MH]$^+$ RT 3.27 min |

TABLE 21-continued

| Example | Structure | Precursor | Yield (mg) | LC/MS |
|---|---|---|---|---|
| 293 | 8-chloro-1-[4-(3-phenyl1,2,4-oxidiazol-5-yl)butyl]-3-ethyl-3,7-dihydro-1H-purine-2,6-dione | 5-(8-chloro-3-ethyl-2,6-dioxo-2,3,6,7-tetrahydro-1H-purin-1-yl)pentanoic acid | 32 | m/z 415 [MH]$^+$ RT 3.22 min |
| 294 | 8-chloro-3-ethyl-1-{4-[3-(4-fluorophenyl)-1,2,4-oxidiazol-5-yl]butyl}-3,7-dihydro-1H-purine-2,6-dione | 5-(8-chloro-3-ethyl-2,6-dioxo-2,3,6,7-tetrahydro-1H-purin-1-yl)pentanoic acid | 31 | m/z 433 [MH]$^+$ RT 3.26 min |
| 295 | 8-chloro-3-ethyl-1-{4-[3-(2-pyrazinyl)-1,2,4-oxidiazol-5-yl]butyl}-3,7-dihydro-1H-purine-2,6-dione | 5-(8-chloro-3-ethyl-2,6-dioxo-2,3,6,7-tetrahydro-1H-purin-1-yl)pentanoic acid | 2 | m/z 417 [MH]$^+$ RT 2.54 min |
| 296 | 8-chloro-3-ethyl-1-{4-[3-(2-fluorophenyl)-1,2,4-oxidiazol-5-yl]butyl}-3,7-dihydro-1H-purine-2,6-dione | 5-(8-chloro-3-ethyl-2,6-dioxo-2,3,6,7-tetrahydro-1H-purin-1-yl)pentanoic acid | 38 | m/z 433 [MH]$^+$ RT 3.12 min |

TABLE 21-continued

| Example | Structure | Precursor | Yield (mg) | LC/MS |
|---|---|---|---|---|
| 297 | 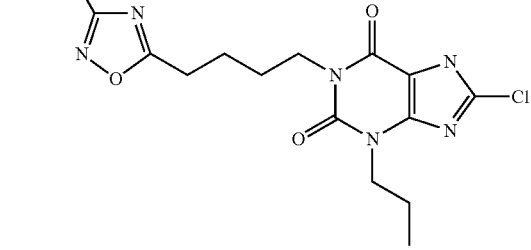<br>8-chloro-1-{4-[3-(2-fluorophenyl)-1,2,4-oxidiazol-5-yl]butyl}-3-propyl-3,7-dihydro-1H-purine-2,6-dione | 5-(8-chloro-3-propyl-2,6-dioxo-2,3,6,7-tetrahydro-1H-purin-1-yl)pentanoic acid | 29 | m/z 447 [MH]+ RT 3.28 min |
| 298 | 8-chloro-1-[4-(3-phenyl-1,2,4-oxidiazol-5-yl)butyl]-3-propyl-3,7-dihydro-1H-purine-2,6-dione | 5-(8-chloro-3-propyl-2,6-dioxo-2,3,6,7-tetrahydro-1H-purin-1-yl)pentanoic acid | 11 | m/z 429 [MH]+ RT 3.35 min |
| 299 | 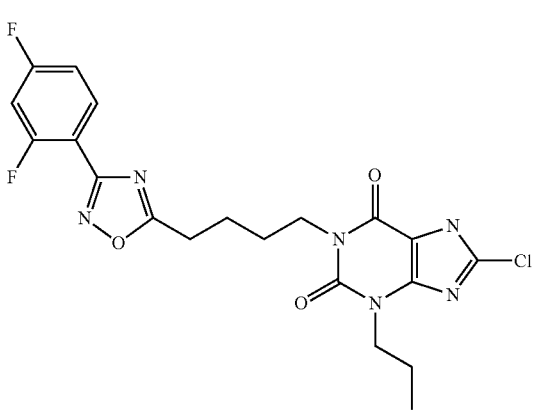<br>8-chloro-1-{4-[3-(2,4-difluorophenyl)-1,2,4-oxidiazol-5-yl]butyl}-3-propyl-3,7-dihydro-1H-purine-2,6-dione | 5-(8-chloro-3-propyl-2,6-dioxo-2,3,6,7-tetrahydro-1H-purin-1-yl)pentanoic acid | 32 | m/z 465 [MH]+ RT 3.40 min |

TABLE 21-continued

| Example | Structure | Precursor | Yield (mg) | LC/MS |
|---------|-----------|-----------|------------|-------|
| 300 | 8-chloro-1-{4-[3-(2-chlorophenyl)-1,2,4-oxidiazol-5-yl]butyl}-3-propyl-3,7-dihydro-1H-purine-2,6-dione | 5-(8-chloro-3-propyl-2,6-dioxo-2,3,6,7-tetrahydro-1H-purin-1-yl)pentanoic acid | 25 | m/z 463 [MH]$^+$ RT 3.40 min |
| 301 | 8-chloro-1-{4-[3-(4-fluorophenyl)-1,2,4-oxidiazol-5-yl]butyl}-3-propyl-3,7-dihydro-1H-purine-2,6-dione | 5-(8-chloro-3-propyl-2,6-dioxo-2,3,6,7-tetrahydro-1H-purin-1-yl)pentanoic acid | 26 | m/z 447 [MH]$^+$ RT 3.44 min |
| 302 | 8-chloro-3-propyl-1-{4-[3-(2-pyrazinyl)-1,2,4-oxidiazol-5-yl]butyl}-3,7-dihydro-1H-purine-2,6-dione | 5-(8-chloro-3-propyl-2,6-dioxo-2,3,6,7-tetrahydro-1H-purin-1-yl)pentanoic acid | 25 | m/z 431 [MH]$^+$ RT 3.09 min |

The following compounds (Table 22) were prepared using a method analogous to that for Example 127, using the appropriate acid.

TABLE 22

| Example | Structure | Name | Yield (mg) | LC/MS |
|---|---|---|---|---|
| 303 | 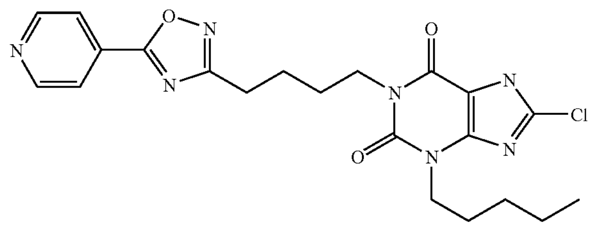 | 8-chloro-3-pentyl-1-{4-[5-(4-pyridinyl)-1,2,4-oxadiazol-3-yl]butyl}-3,7-dihydro-1H-purine-2,6-dione | 8.0 | m/z 458 [MH]$^+$ RT 3.25 min |
| 304 | 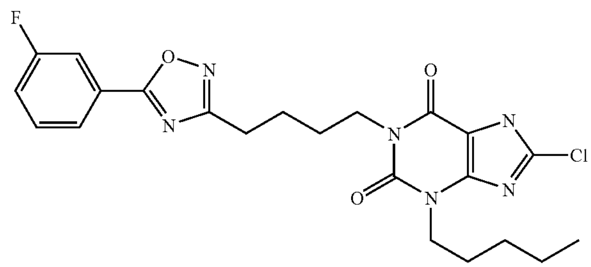 | 8-chloro-1-{4-[5-(3-fluorophenyl)-1,2,4-oxadiazol-3-yl]butyl}-3-pentyl-3,7-dihydro-1H-purine-2,6-dione | 9.1 | m/z 475 [MH]$^+$ RT 3.73 min |
| 305 | 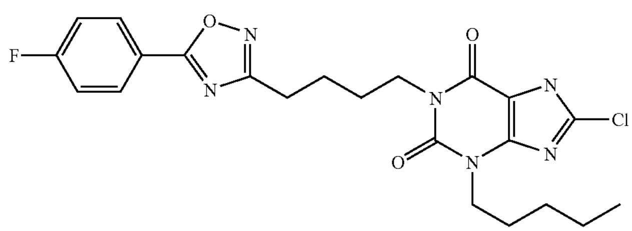 | 8-chloro-1-{4-[5-(4-fluorophenyl)-1,2,4-oxadiazol-3-yl]butyl}-3-pentyl-3,7-dihydro-1H-purine-2,6-dione | 16.1 | m/z 475 [MH]$^+$ RT 3.69 min |
| 306 | 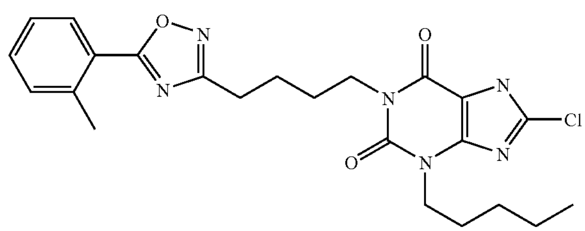 | 8-chloro-1-{4-[5-(2-methylphenyl)-1,2,4-oxadiazol-3-yl]butyl}-3-pentyl-3,7-dihydro-1H-purine-2,6-dione | 22.9 | m/z 471 [MH]$^+$ RT 3.82 min |
| 307 | 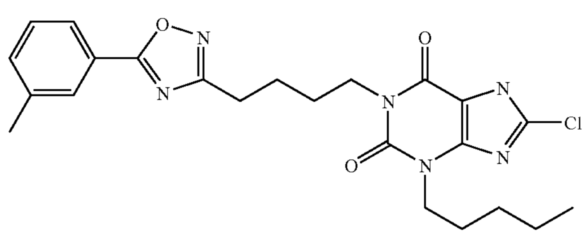 | 8-chloro-1-{4-[5-(3-methylphenyl)-1,2,4-oxadiazol-3-yl]butyl}-3-pentyl-3,7-dihydro-1H-purine-2,6-dione | 18.0 | m/z 471 [MH]$^+$ RT 3.81 min |
| 308 | 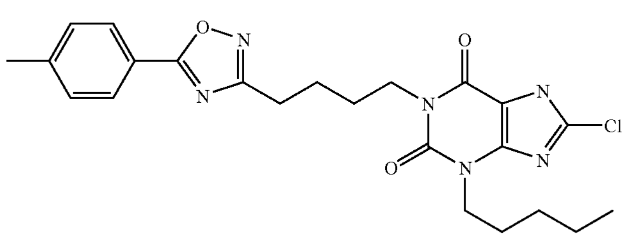 | 8-chloro-1-{4-[5-(4-methylphenyl)-1,2,4-oxadiazol-3-yl]butyl}-3-pentyl-3,7-dihydro-1H-purine-2,6-dione | 25.0 | m/z 471 [MH]$^+$ RT 3.80 min |

TABLE 22-continued

| Example | Structure | Name | Yield (mg) | LC/MS |
|---|---|---|---|---|
| 309 | 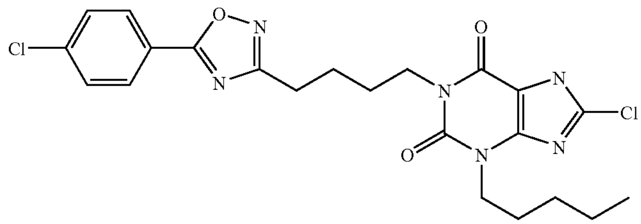 | 8-chloro-1-{4-[5-(4-chlorophenyl)-1,2,4-oxadiazol-3-yl]butyl}-3-pentyl-3,7-dihydro-1H-purine-2,6-dione | 16.6 | m/z 491 [MH]+ RT 3.89 min |
| 310 | 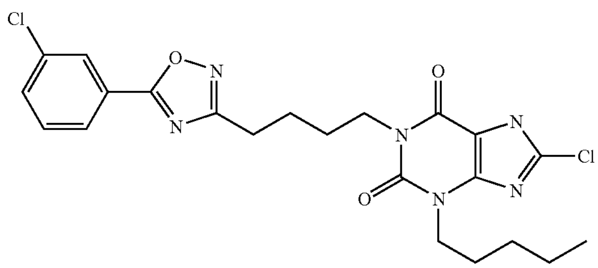 | 8-chloro-1-{4-[5-(3-chlorophenyl)-1,2,4-oxadiazol-3-yl]butyl}-3-pentyl-3,7-dihydro-1H-purine-2,6-dione | 12.8 | m/z 491 [MH]+ RT 3.91 min |
| 311 | 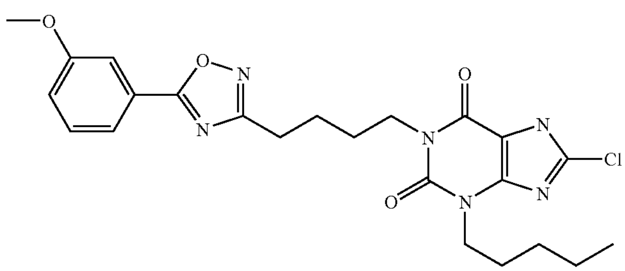 | 8-chloro-1-(4-{5-[3-(methyloxy)phenyl]-1,2,4-oxadiazol-3-yl}butyl)-3-pentyl-3,7-dihydro-1H-purine-2,6-dione | 23.0 | m/z 487 [MH]+ RT 3.71 min |
| 312 | 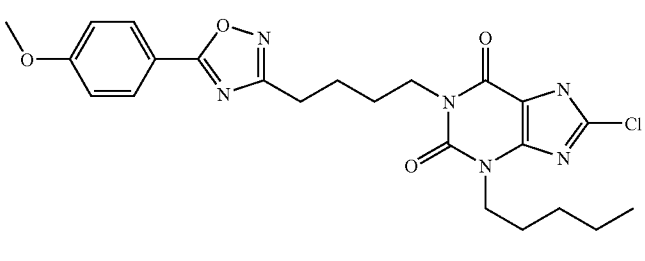 | 8-chloro-1-(4-{5-[4-(methyloxy)phenyl]-1,2,4-oxadiazol-3-yl}butyl)-3-pentyl-3,7-dihydro-1H-purine-2,6-dione | 15.8 | m/z 487 [MH]+ RT 3.67 min |
| 313 | 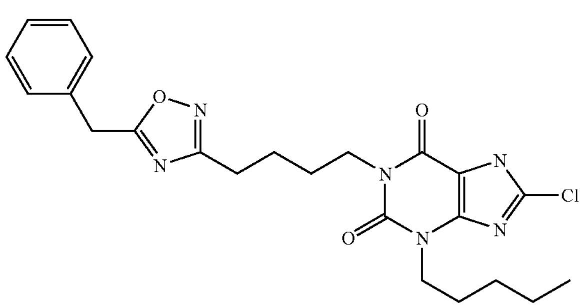 | 8-chloro-3-pentyl-1-{4-[5-(phenylmethyl)-1,2,4-oxadiazol-3-yl]butyl}-3,7-dihydro-1H-purine-2,6-dione | 21.0 | m/z 471 [MH]+ RT 3.55 min |

TABLE 22-continued

| Example | Structure | Name | Yield (mg) | LC/MS |
|---|---|---|---|---|
| 314 | 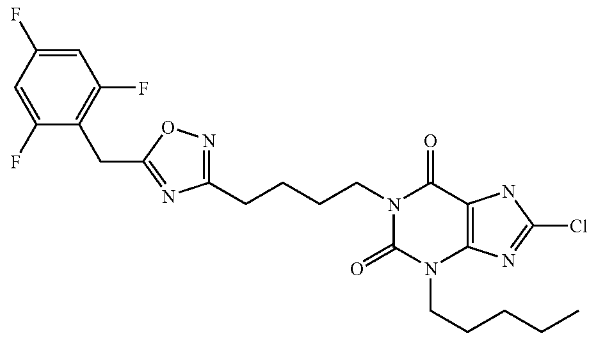 | 8-chloro-3-pentyl-1-(4-{5-[(2,4,6-trifluorophenyl)methyl]-1,2,4-oxadiazol-3-yl}butyl)-3,7-dihydro-1H-purine-2,6-dione | 29.3 | m/z 525 [MH]+ RT 3.62 min |
| 315 | 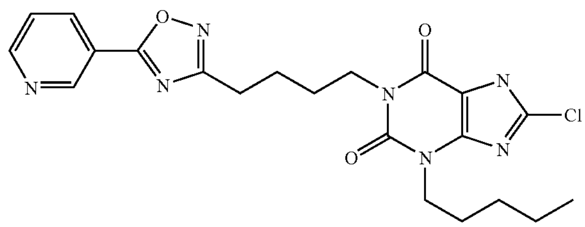 | 8-chloro-3-pentyl-1-{4-[5-(3-pyridinyl)-1,2,4-oxadiazol-3-yl]butyl}-3,7-dihydro-1H-purine-2,6-dione | 8.2 | m/z 458 [MH]+ RT 3.23 min |

The following compounds (Table 23) were prepared using a method analogous to that for Example 19, using the appropriate tetrazole and 3-[3-alkyl-8-chloro-2,6-dioxo-7-(2-propen-1-yl)-2,3,6,7-tetrahydro-1H-purin-1-yl]propyl methanesulfonate. MDAP was employed to further purify those compounds insufficiently pure following normal phase chromatography.

TABLE 23

| Example | Structure | Name | Yield (mg) | LC/MS |
|---|---|---|---|---|
| 316 | 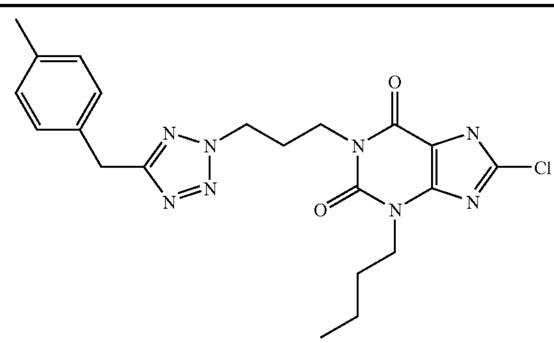 | 3-butyl-8-chloro-1-(3-{5-[(4-methylphenyl)methyl]-2H-tetrazol-2-yl}propyl)-3,7-dihydro-1H-purine-2,6-dione | 35.1 | m/z 457 [MH]+ RT 3.40 min |
| 317 | 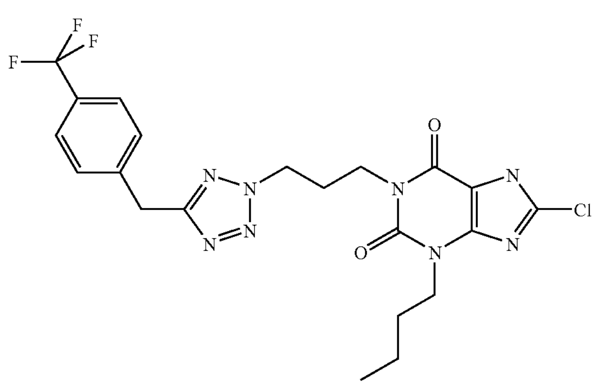 | 3-butyl-8-chloro-1-[3-(5-{[4-(trifluoromethyl)phenyl]methyl}-2H-tetrazol-2-yl)propyl]-3,7-dihydro-1H-purine-2,6-dione | 43.6 | m/z 511 [MH]+ RT 3.52 min |

TABLE 23-continued

| Example | Structure | Name | Yield (mg) | LC/MS |
|---|---|---|---|---|
| 318 | 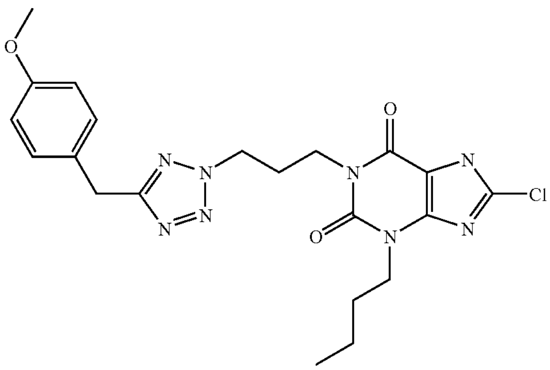 | 3-butyl-8-chloro-1-[3-(5-{[4-(methyloxy)phenyl]methyl}-2H-tetrazol-2-yl)propyl]-3,7-dihydro-1H-purine-2,6-dione | 38.2 | m/z 473 [MH]+ RT 3.24 min |
| 319 | 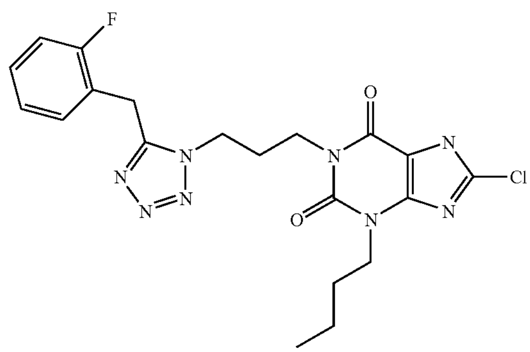 | 3-butyl-8-chloro-1-(3-{5-[(2-fluorophenyl)methyl]-1H-tetrazol-1-yl}propyl)-3,7-dihydro-1H-purine-2,6-dione | 13.7 | m/z 461 [MH]+ RT 3.07 min |
| 320 | 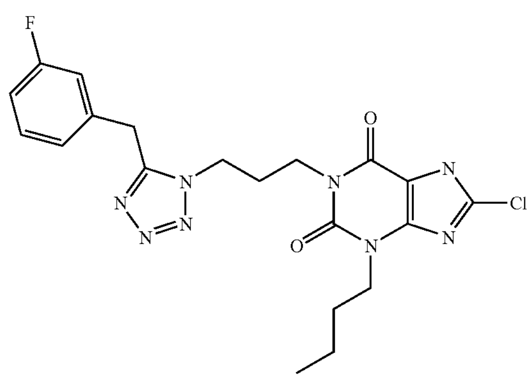 | 3-butyl-8-chloro-1-(3-{5-[(3-fluorophenyl)methyl]-1H-tetrazol-1-yl}propyl)-3,7-dihydro-1H-purine-2,6-dione | 15.0 | m/z 461 [MH]+ RT 3.10 min |
| 321 | 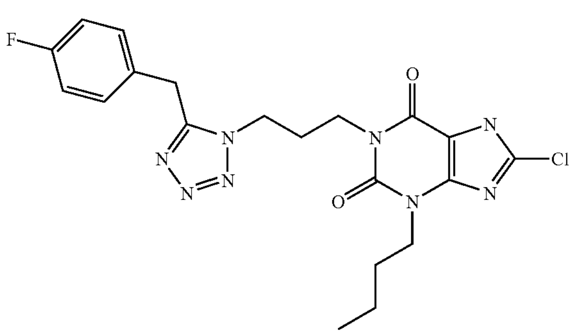 | 3-butyl-8-chloro-1-(3-{5-[(4-fluorophenyl)methyl]-1H-tetrazol-1-yl}propyl)-3,7-dihydro-1H-purine-2,6-dione | 17.7 | m/z 461 [MH]+ RT 3.10 min |

TABLE 23-continued

| Example | Structure | Name | Yield (mg) | LC/MS |
|---|---|---|---|---|
| 322 | 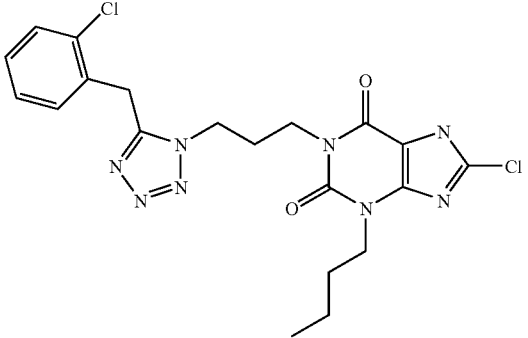 | 3-butyl-8-chloro-1-(3-{5-[(2-chlorophenyl)methyl]-1H-tetrazol-1-yl}propyl)-3,7-dihydro-1H-purine-2,6-dione | 8.4 | m/z 477 [MH]+ RT 3.17 min |
| 323 | 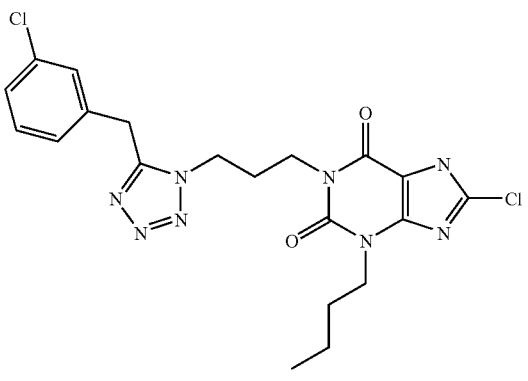 | 3-butyl-8-chloro-1-(3-{5-[(3-chlorophenyl)methyl]-1H-tetrazol-1-yl}propyl)-3,7-dihydro-1H-purine-2,6-dione | 16.4 | m/z 477 [MH]+ RT 3.23 min |
| 324 | 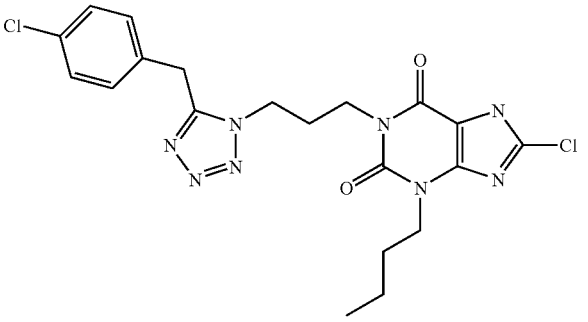 | 3-butyl-8-chloro-1-(3-{5-[(4-chlorophenyl)methyl]-1H-tetrazol-1-yl}propyl)-3,7-dihydro-1H-purine-2,6-dione | 17.0 | m/z 477 [MH]+ RT 3.24 min |
| 325 | 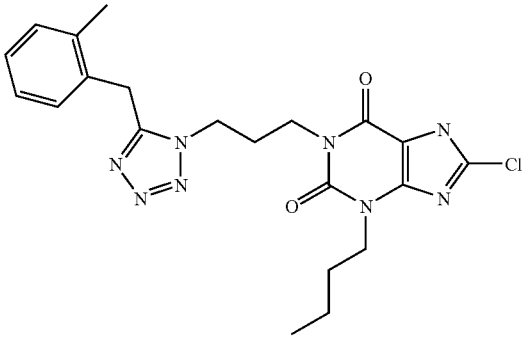 | 3-butyl-8-chloro-1-(3-{5-[(2-methylphenyl)methyl]-1H-tetrazol-1-yl}propyl)-3,7-dihydro-1H-purine-2,6-dione | 15.1 | m/z 457 [MH]+ RT 3.15 min |

TABLE 23-continued

| Example | Structure | Name | Yield (mg) | LC/MS |
|---|---|---|---|---|
| 326 | 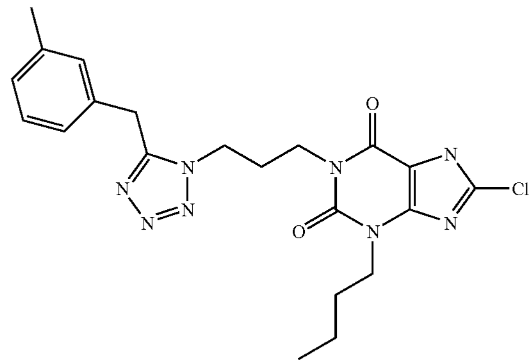 | 3-butyl-8-chloro-1-(3-{5-[(3-methylphenyl)methyl]-1H-tetrazol-1-yl}propyl)-3,7-dihydro-1H-purine-2,6-dione | 18.6 | m/z 457 [MH]+ RT 3.18 min |
| 327 | 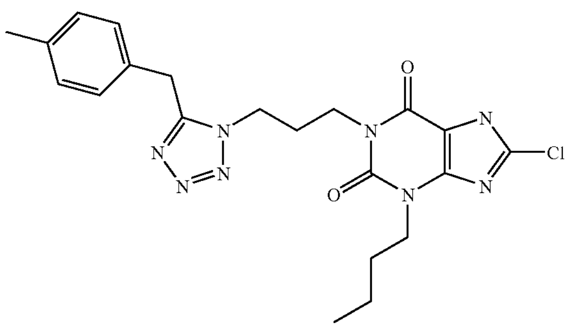 | 3-butyl-8-chloro-1-(3-{5-[(4-methylphenyl)methyl]-1H-tetrazol-1-yl}propyl)-3,7-dihydro-1H-purine-2,6-dione | 16.3 | m/z 457 [MH]+ RT 3.19 min |
| 328 | 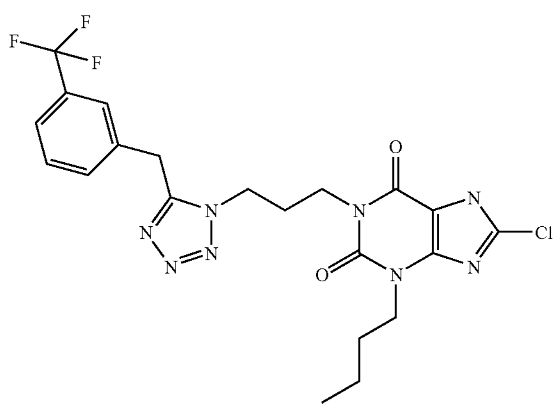 | 3-butyl-8-chloro-1-[3-(5-{[3-(trifluoromethyl)phenyl]methyl}-1H-tetrazol-1-yl)propyl]-3,7-dihydro-1H-purine-2,6-dione | 17.7 | m/z 511 [MH]+ RT 3.31 min |
| 329 | 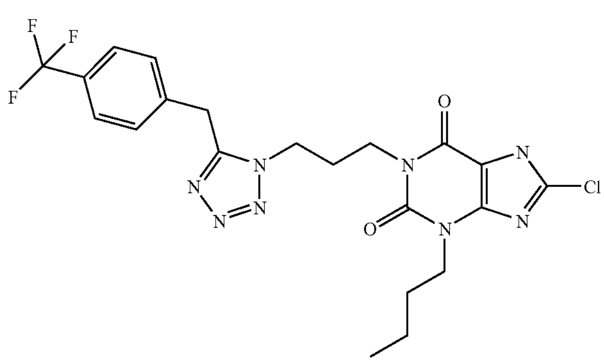 | 3-butyl-8-chloro-1-[3-(5-{[4-(trifluoromethyl)phenyl]methyl}-1H-tetrazol-1-yl)propyl]-3,7-dihydro-1H-purine-2,6-dione | 21.6 | m/z 511 [MH]+ RT 3.33 min |

TABLE 23-continued

| Example | Structure | Name | Yield (mg) | LC/MS |
|---|---|---|---|---|
| 330 | 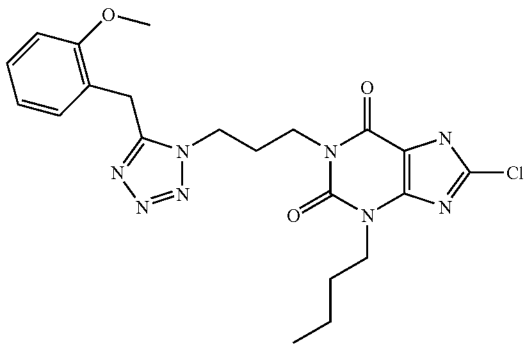 | 3-butyl-8-chloro-1-[3-(5-{[2-(methyloxy)phenyl]methyl}-1H-tetrazol-1-yl)propyl]-3,7-dihydro-1H-purine-2,6-dione | 16.3 | m/z 473 [MH]+ RT 3.10 min |
| 331 | 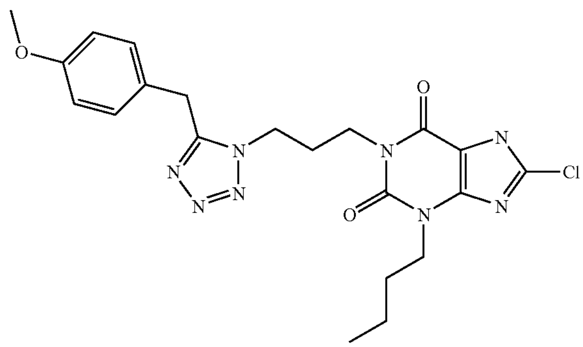 | 3-butyl-8-chloro-1-[3-(5-{[4-(methyloxy)phenyl]methyl}-1H-tetrazol-1-yl)propyl]-3,7-dihydro-1H-purine-2,6-dione | 20.8 | m/z 473 [MH]+ RT 3.05 min |
| 332 | 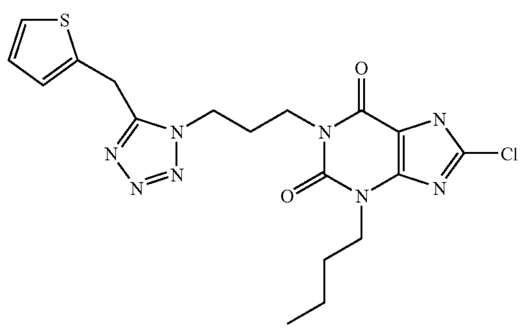 | 3-butyl-8-chloro-1-{3-[5-(2-thienylmethyl)-1H-tetrazol-1-yl]propyl}-3,7-dihydro-1H-purine-2,6-dione | 11.8 | m/z 448 [MH]+ RT 3.02 min |
| 333 | 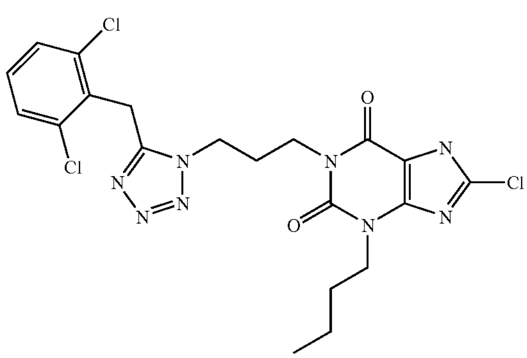 | 3-butyl-8-chloro-1-(3-{5-[(2,6-dichlorophenyl)methyl]-1H-tetrazol-1-yl}propyl)-3,7-dihydro-1H-purine-2,6-dione | 12.4 | m/z 512 [MH]+ RT 3.27 min |

TABLE 23-continued

| Example | Structure | Name | Yield (mg) | LC/MS |
|---|---|---|---|---|
| 334 | 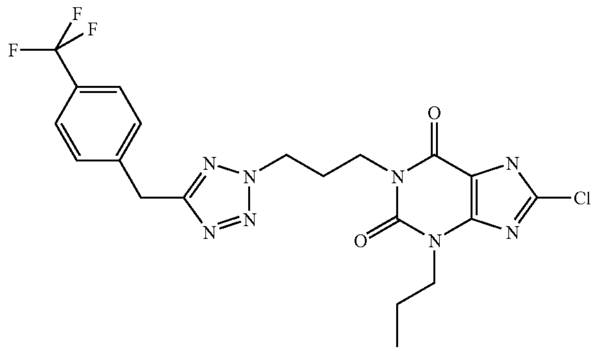 | 8-chloro-3-propyl-1-[3-(5-{[4-(trifluoromethyl)phenyl]methyl}-2H-tetrazol-2-yl)propyl]-3,7-dihydro-1H-purine-2,6-dione | 15.5 | m/z 497 [MH]+ RT 3.38 min |
| 335 | 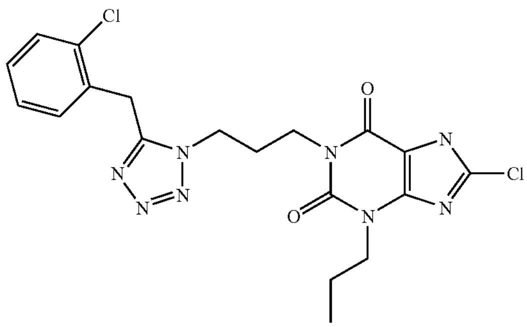 | 8-chloro-1-(3-{5-[(2-chlorophenyl)methyl]-1H-tetrazol-1-yl}propyl)-3-propyl-3,7-dihydro-1H-purine-2,6-dione | 1.6 | m/z 463 [MH]+ RT 3.00 min |
| 336 | 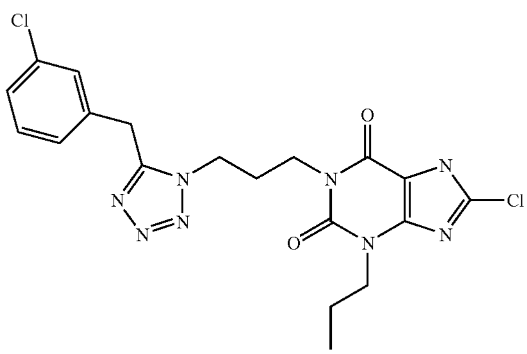 | 8-chloro-1-(3-{5-[(3-chlorophenyl)methyl]-1H-tetrazol-1-yl}propyl)-3-propyl-3,7-dihydro-1H-purine-2,6-dione | 7.1 | m/z 463 [MH]+ RT 3.06 min |
| 337 | 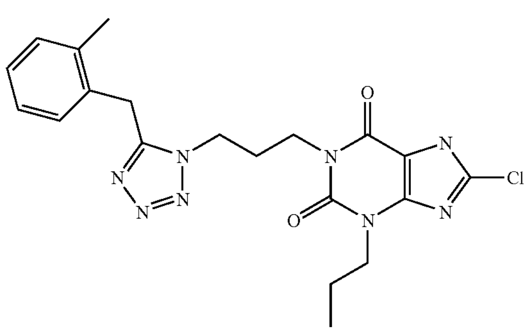 | 8-chloro-1-(3-{5-[(2-methylphenyl)methyl]-1H-tetrazol-1-yl}propyl)-3-propyl-3,7-dihydro-1H-purine-2,6-dione | 7.2 | m/z 443 [MH]+ RT 2.97 min |

TABLE 23-continued

| Example | Structure | Name | Yield (mg) | LC/MS |
|---|---|---|---|---|
| 338 | 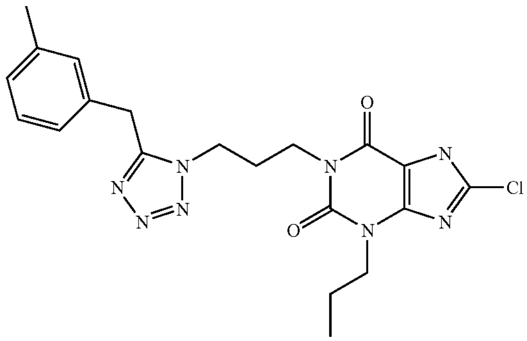 | 8-chloro-1-(3-{5-[(3-methylphenyl)methyl]-1H-tetrazol-1-yl}propyl)-3-propyl-3,7-dihydro-1H-purine-2,6-dione | 5.7 | m/z 443 [MH]+ RT 3.01 min |
| 339 | 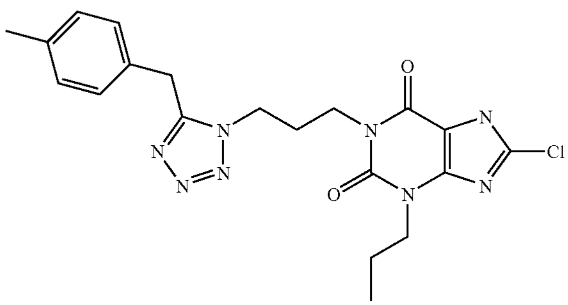 | 8-chloro-1-(3-{5-[(4-methylphenyl)methyl]-1H-tetrazol-1-yl}propyl)-3-propyl-3,7-dihydro-1H-purine-2,6-dione | 5.5 | m/z 443 [MH]+ RT 3.01 min |
| 340 | 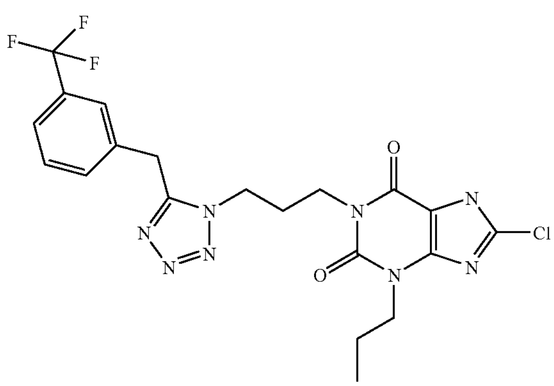 | 8-chloro-3-propyl-1-[3-(5-{[3-(trifluoromethyl)phenyl]methyl}-1H-tetrazol-1-yl)propyl]-3,7-dihydro-1H-purine-2,6-dione | 3.3 | m/z 497 [MH]+ RT 3.16 min |
| 341 | 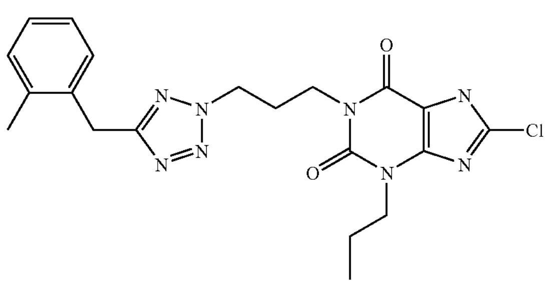 | 8-chloro-1-(3-{5-[(2-methylphenyl)methyl]-2H-tetrazol-2-yl}propyl)-3-propyl-3,7-dihydro-1H-purine-2,6-dione | 24.1 | m/z 443 [MH]+ RT 3.20 min |

TABLE 23-continued

| Example | Name | Yield (mg) | LC/MS |
|---|---|---|---|
| 342 | 8-chloro-1-(3-{5-[(2-fluorophenyl)methyl]-1H-tetrazol-1-yl}propyl)-3-propyl-3,7-dihydro-1H-purine-2,6-dione | 1.3 | m/z 447 [MH]+ RT 2.89 min |
| 343 | 8-chloro-3-propyl-1-{3-[5-(2-thienylmethyl)-1H-tetrazol-1-yl]propyl}-3,7-dihydro-1H-purine-2,6-dione | 5.2 | m/z 435 [MH]+ RT 2.83 min |
| 344 | 8-chloro-1-[3-(5-{[4-(methyloxy)phenyl]methyl}-1H-tetrazol-1-yl)propyl]-3-propyl-3,7-dihydro-1H-purine-2,6-dione | 1.2 | m/z 459 [MH]+ RT 2.87 min |
| 345 | 8-chloro-1-[3-(5-{[4-(methyloxy)phenyl]methyl}-2H-tetrazol-2-yl)propyl]-3-propyl-3,7-dihydro-1H-purine-2,6-dione | 19.7 | m/z 459 [MH]+ RT 3.07 min |

TABLE 23-continued

| Example | Structure | Name | Yield (mg) | LC/MS |
|---|---|---|---|---|
| 346 | 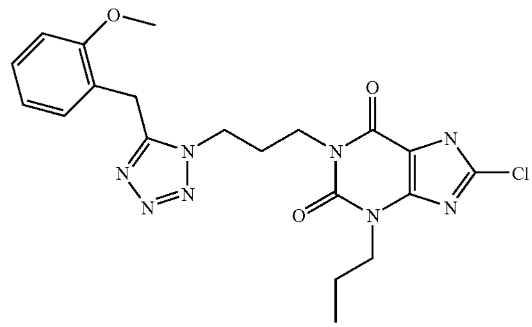 | 8-chloro-1-[3-(5-{[2-(methyloxy)phenyl]methyl}-1H-tetrazol-1-yl)propyl]-3-propyl-3,7-dihydro-1H-purine-2,6-dione | 1.9 | m/z 459 [MH]+ RT 2.92 min |
| 347 | 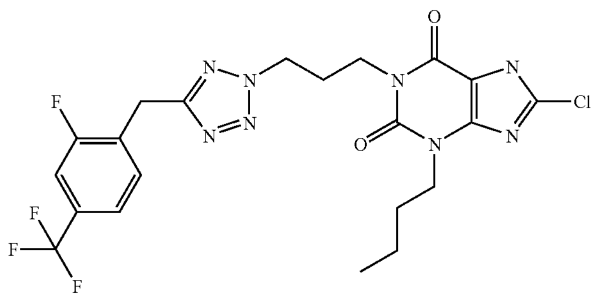 | 3-butyl-8-chloro-1-[3-(5-{[2-fluoro-4-(trifluoromethyl)phenyl]methyl}-2H-tetrazol-2-yl)propyl]-3,7-dihydro-1H-purine-2,6-dione | 24.5 | m/z 529 [MH]+ RT 3.22 min |
| 348 | 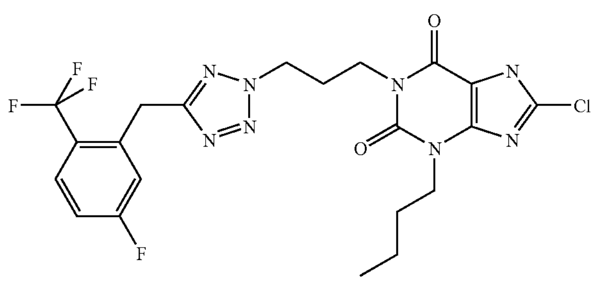 | 3-butyl-8-chloro-1-[3-(5-{[5-fluoro-2-(trifluoromethyl)phenyl]methyl}-2H-tetrazol-2-yl)propyl]-3,7-dihydro-1H-purine-2,6-dione | 25.3 | m/z 529 [MH]+ RT 3.51 min |
| 349 | 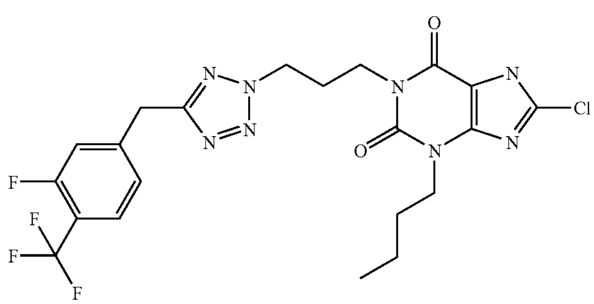 | 3-butyl-8-chloro-1-[3-(5-{[3-fluoro-4-(trifluoromethyl)phenyl]methyl}-2H-tetrazol-2-yl)propyl]-3,7-dihydro-1H-purine-2,6-dione | 11.5 | m/z 529 [MH]+ RT 3.56 min |
| 350 | 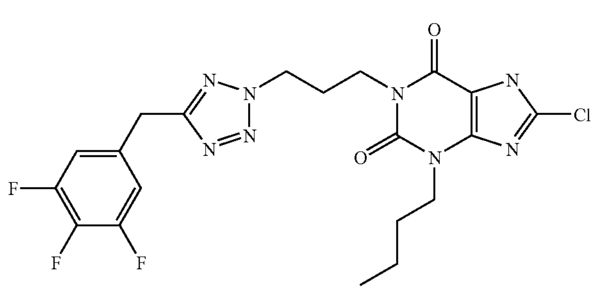 | 3-butyl-8-chloro-1-(3-{5-[(3,4,5-trifluorophenyl)methyl]-2H-tetrazol-2-yl}propyl)-3,7-dihydro-1H-purine-2,6-dione | 19.4 | m/z 497 [MH]+ RT 3.45 min |

TABLE 23-continued

| Example | Structure | Name | Yield (mg) | LC/MS |
|---|---|---|---|---|
| 351 | 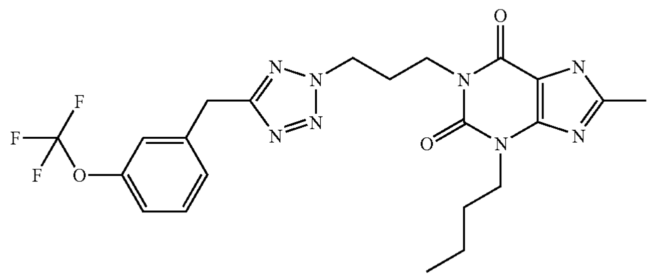 | 3-butyl-8-chloro-1-{3-[5-({3-[(trifluoromethyl)oxy]phenyl}methyl)-2H-tetrazol-2-yl]propyl}-3,7-dihydro-1H-purine-2,6-dione | 27.2 | m/z 527 [MH]+ RT 3.55 min |
| 352 | 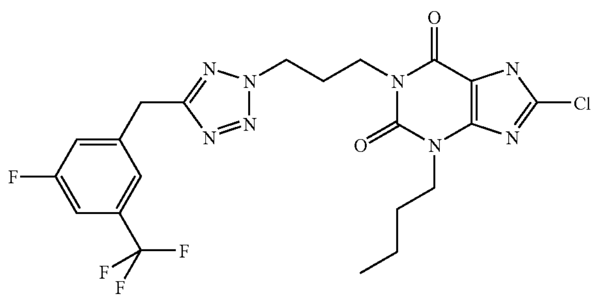 | 3-butyl-8-chloro-1-[3-(5-{[3-fluoro-5-(trifluoromethyl)phenyl]methyl}-2H-tetrazol-2-yl)propyl]-3,7-dihydro-1H-purine-2,6-dione | 19.8 | m/z 529 [MH]+ RT 3.56 min |
| 353 | 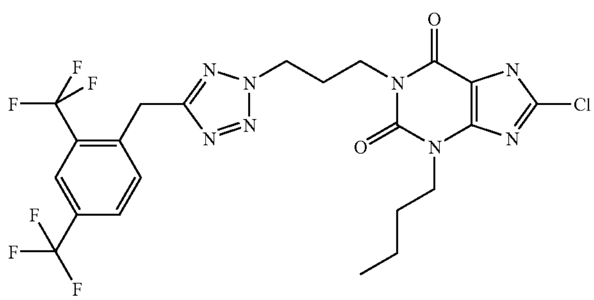 | 1-[3-(5-{[2,4-bis(trifluoromethyl)phenyl]methyl}-2H-tetrazol-2-yl)propyl]-3-butyl-8-chloro-3,7-dihydro-1H-purine-2,6-dione | 36.6 | m/z 579 [MH]+ RT 3.72 min |
| 354 | 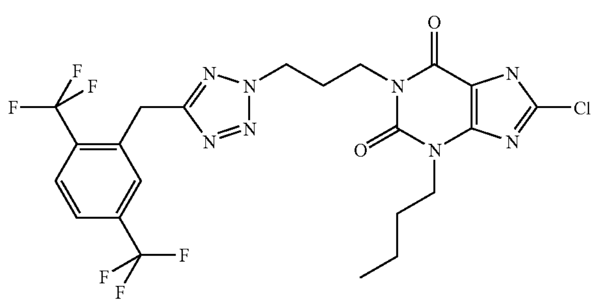 | 1-[3-(5-{[2,5-bis(trifluoromethyl)phenyl]methyl}-2H-tetrazol-2-yl)propyl]-3-butyl-8-chloro-3,7-dihydro-1H-purine-2,6-dione | 50.3 | m/z 579 [MH]+ RT 3.65 min |
| 355 | 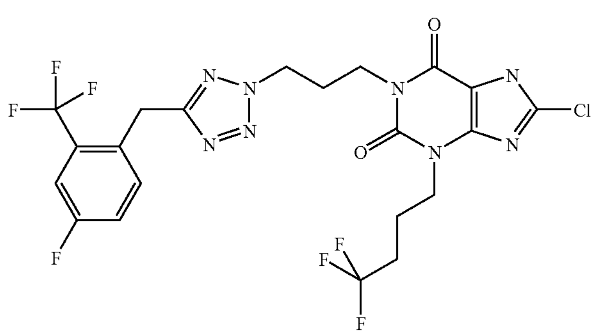 | 8-chloro-1-[3-(5-{[4-fluoro-2-(trifluoromethyl)phenyl]methyl}-2H-tetrazol-2-yl)propyl]-3-(4,4,4-trifluorobutyl)-3,7-dihydro-1H-purine-2,6-dione | 25.0 | m/z 583 [MH]+ RT 3.50 min |

TABLE 23-continued

| Example | Structure | Name | Yield (mg) | LC/MS |
|---|---|---|---|---|
| 356 | 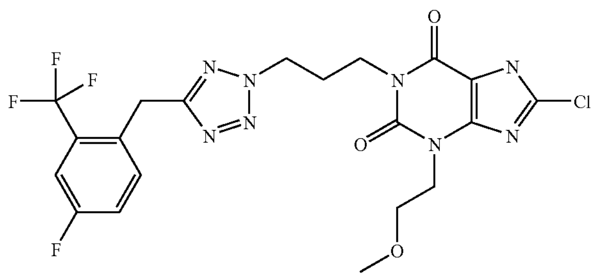 | 8-chloro-1-[3-(5-{[4-fluoro-2-(trifluoromethyl)phenyl]methyl}-2H-tetrazol-2-yl)propyl]-3-[2-(methyloxy)ethyl]-3,7-dihydro-1H-purine-2,6-dione | 23.0 | m/z 531 [MH]+ RT 3.16 min |
| 357 | 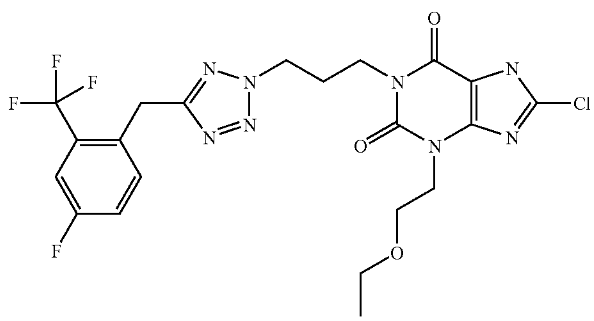 | 8-chloro-3-[2-(ethyloxy)ethyl]-1-[3-(5-{[4-fluoro-2-(trifluoromethyl)phenyl]methyl}-2H-tetrazol-2-yl)propyl]-3,7-dihydro-1H-purine-2,6-dione | 13.1 | m/z 545 [MH]+ RT 3.30 min |
| 358 | 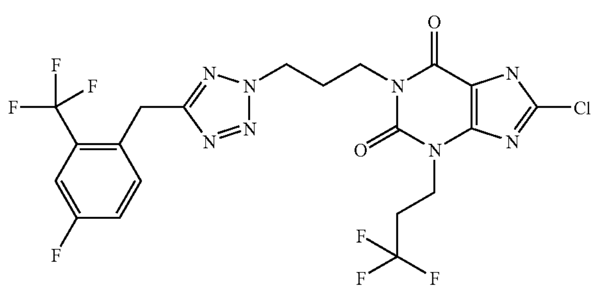 | 8-chloro-1-[3-(5-{[4-fluoro-2-(trifluoromethyl)phenyl]methyl}-2H-tetrazol-2-yl)propyl]-3-(3,3,3-trifluoropropyl)-3,7-dihydro-1H-purine-2,6-dione | 36.3 | m/z 569 [MH]+ RT 3.46 min |
| 359 | 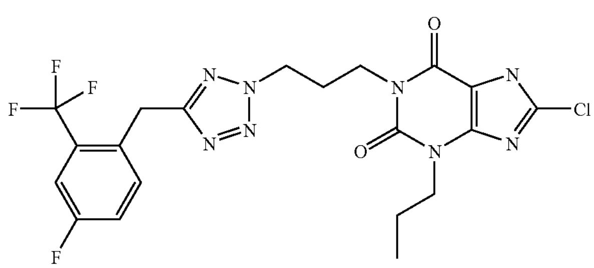 | 8-chloro-1-[3-(5-{[4-fluoro-2-(trifluoromethyl)phenyl]methyl}-2H-tetrazol-2-yl)propyl]-3-propyl-3,7-dihydro-1H-purine-2,6-dione | 32.0 | m/z 515 [MH]+ RT 3.37 min |
| 360 | 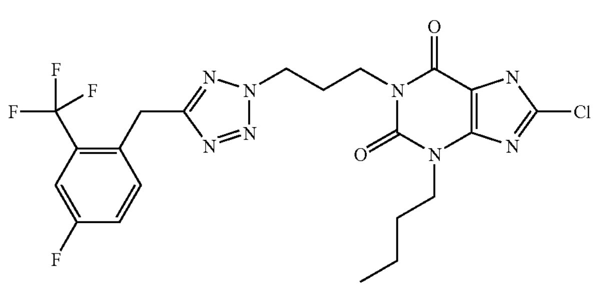 | 3-butyl-8-chloro-1-[3-(5-{[4-fluoro-2-(trifluoromethyl)phenyl]methyl}-2H-tetrazol-2-yl)propyl]-3,7-dihydro-1H-purine-2,6-dione | 30.3 | m/z 529 [MH]+ RT 3.53 min |

TABLE 23-continued

| Example | Structure | Name | Yield (mg) | LC/MS |
|---|---|---|---|---|
| 361 | 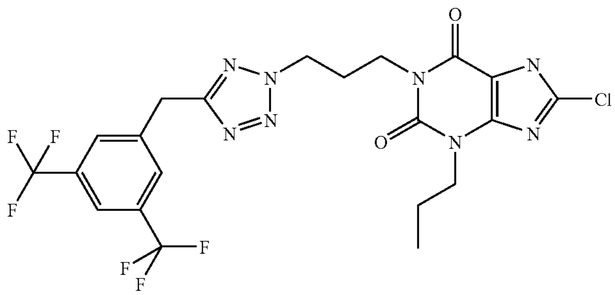 | 1-[3-(5-{[3,5-bis(trifluoromethyl)phenyl]methyl}-2H-tetrazol-2-yl)propyl]-8-chloro-3-propyl-3,7-dihydro-1H-purine-2,6-dione | 22.9 | m/z 565 [MH]+ RT 3.54 min |
| 362 | 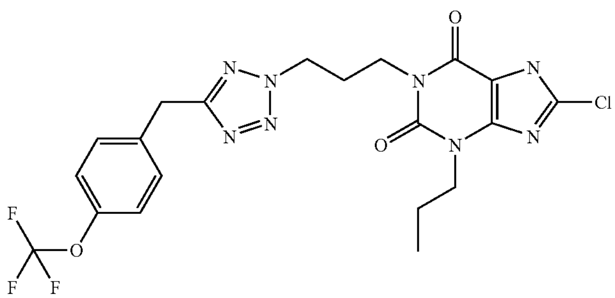 | 8-chloro-3-propyl-1-{3-[5-({4-[(trifluoromethyl)oxy]phenyl}methyl)-2H-tetrazol-2-yl]propyl}-3,7-dihydro-1H-purine-2,6-dione | 21.6 | m/z 513 [MH]+ RT 3.42 min |
| 363 | 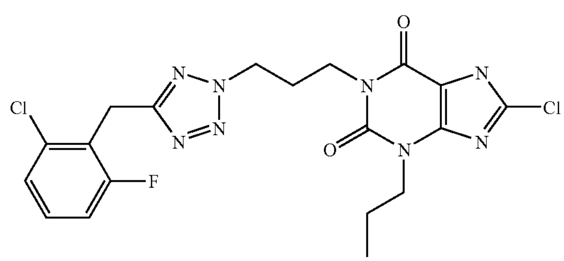 | 8-chloro-1-(3-{5-[(2-chloro-6-fluorophenyl)methyl]-2H-tetrazol-2-yl}propyl)-3-propyl-3,7-dihydro-1H-purine-2,6-dione | 12.4 | m/z 481 [MH]+ RT 3.20 min |
| 364 | 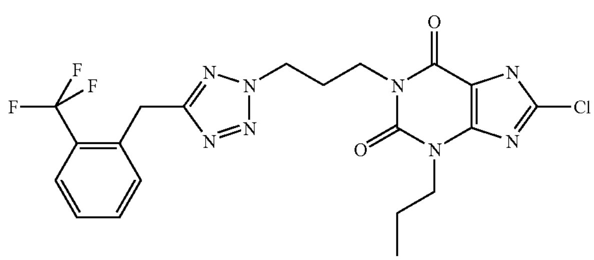 | 8-chloro-3-propyl-1-[3-(5-{[2-(trifluoromethyl)phenyl]methyl}-2H-tetrazol-2-yl)propyl]-3,7-dihydro-1H-purine-2,6-dione | 17.7 | m/z 497 [MH]+ RT 3.26 min |
| 365 | 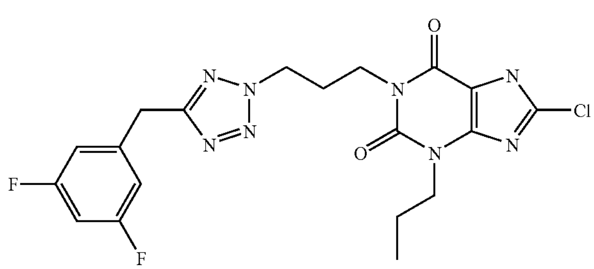 | 8-chloro-1-(3-{5-[(3,5-difluorophenyl)methyl]-2H-tetrazol-2-yl}propyl)-3-propyl-3,7-dihydro-1H-purine-2,6-dione | 21.6 | m/z 465 [MH]+ RT 3.16 min |

TABLE 23-continued

| Example | Structure | Name | Yield (mg) | LC/MS |
|---|---|---|---|---|
| 366 | 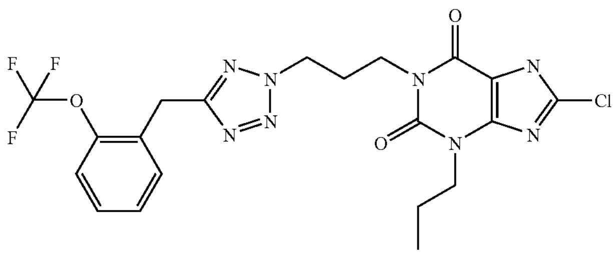 | 8-chloro-3-propyl-1-{3-[5-({2-[(trifluoromethyl)oxy]phenyl}methyl)-2H-tetrazol-2-yl]propyl}-3,7-dihydro-1H-purine-2,6-dione | 22.3 | m/z 513 [MH]+ RT 3.27 min |
| 367 | 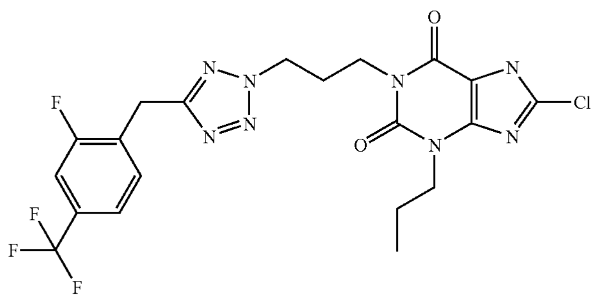 | 8-chloro-1-[3-(5-{[2-fluoro-4-(trifluoromethyl)phenyl]methyl}-2H-tetrazol-2-yl)propyl]-3-propyl-3,7-dihydro-1H-purine-2,6-dione | 9.7 | m/z 515 [MH]+ RT 3.40 min |
| 368 | 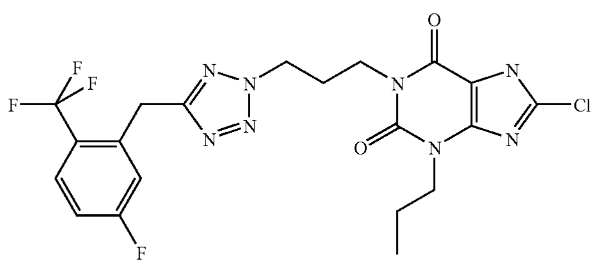 | 8-chloro-1-[3-(5-{[5-fluoro-2-(trifluoromethyl)phenyl]methyl}-2H-tetrazol-2-yl)propyl]-3-propyl-3,7-dihydro-1H-purine-2,6-dione | 26.8 | m/z 515 [MH]+ RT 3.26 min |
| 369 | 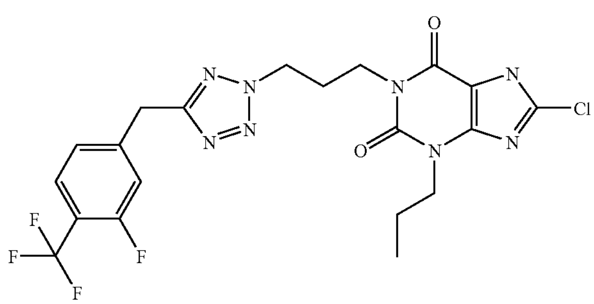 | 8-chloro-1-[3-(5-{[3-fluoro-4-(trifluoromethyl)phenyl]methyl}-2H-tetrazol-2-yl)propyl]-3-propyl-3,7-dihydro-1H-purine-2,6-dione | 20.7 | m/z 515 [MH]+ RT 3.31 min |
| 370 | 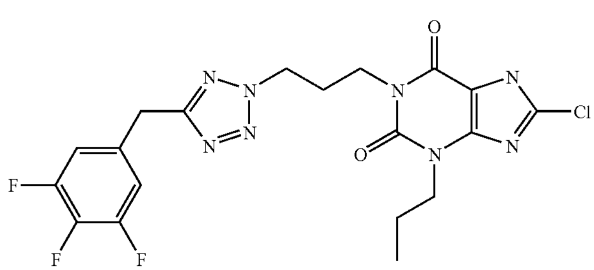 | 8-chloro-3-propyl-1-(3-{5-[(3,4,5-trifluorophenyl)methyl]-2H-tetrazol-2-yl}propyl)-3,7-dihydro-1H-purine-2,6-dione | 10.2 | m/z 483 [MH]+ RT 3.23 min |

TABLE 23-continued

| Example | Structure | Name | Yield (mg) | LC/MS |
|---|---|---|---|---|
| 371 | 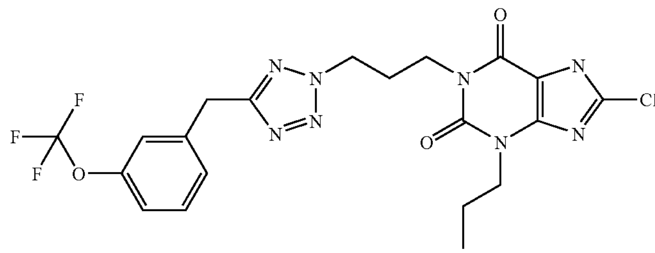 | 8-chloro-3-propyl-1-{3-[5-({3-[(trifluoromethyl)oxy]phenyl}methyl)-2H-tetrazol-2-yl]propyl}-3,7-dihydro-1H-purine-2,6-dione | 9.8 | m/z 513 [MH]+ RT 3.35 min |
| 372 | 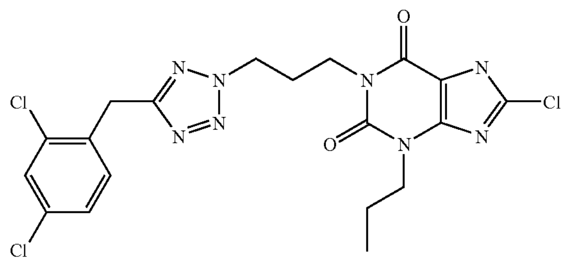 | 8-chloro-1-(3-{5-[(2,4-dichlorophenyl)methyl]-2H-tetrazol-2-yl}propyl)-3-propyl-3,7-dihydro-1H-purine-2,6-dione | 27.6 | m/z 497 [MH]+ RT 3.40 min |
| 373 | 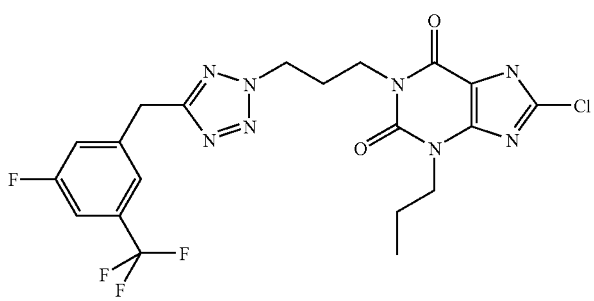 | 8-chloro-1-[3-(5-{[3-fluoro-5-(trifluoromethyl)phenyl]methyl}-2H-tetrazol-2-yl)propyl]-3-propyl-3,7-dihydro-1H-purine-2,6-dione | 17.6 | m/z 515 [MH]+ RT 3.23 min |
| 374 | 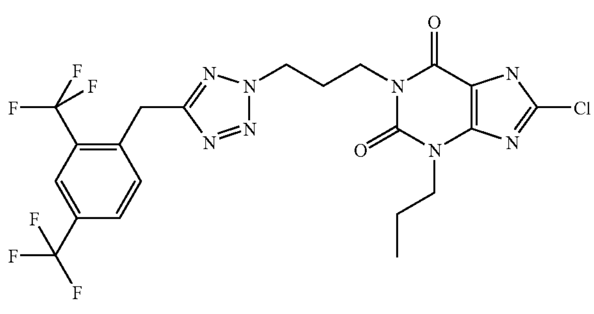 | 1-[3-(5-{[2,4-bis(trifluoromethyl)phenyl]methyl}-2H-tetrazol-2-yl)propyl]-8-chloro-3-propyl-3,7-dihydro-1H-purine-2,6-dione | 21.0 | m/z 565 [MH]+ RT 3.40 min |
| 375 | 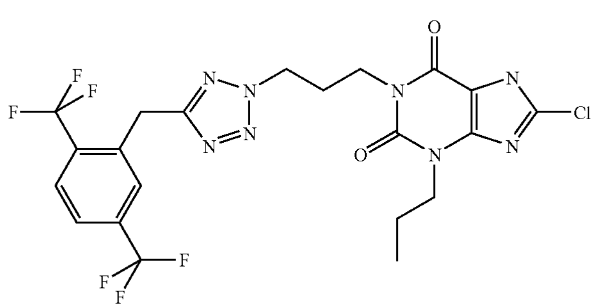 | 1-[3-(5-{[2,5-bis(trifluoromethyl)phenyl]methyl}-2H-tetrazol-2-yl)propyl]-8-chloro-3-propyl-3,7-dihydro-1H-purine-2,6-dione | 9.7 | m/z 565 [MH]+ RT 3.50 min |

TABLE 23-continued

| Example | Structure | Name | Yield (mg) | LC/MS |
|---|---|---|---|---|
| 376 | 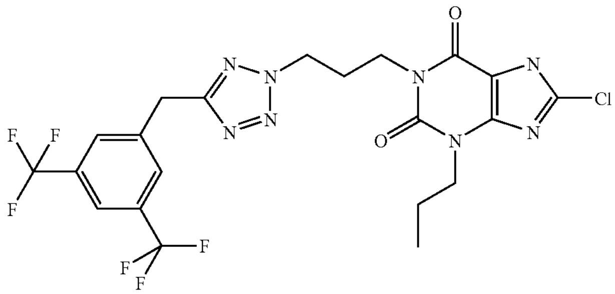 | 1-[3-(5-{[3,5-bis(trifluoromethyl)phenyl]methyl}-2H-tetrazol-2-yl)propyl]-3-butyl-8-chloro-3,7-dihydro-1H-purine-2,6-dione | 28.1 | m/z 579 [MH]+ RT 3.68 min |
| 377 | 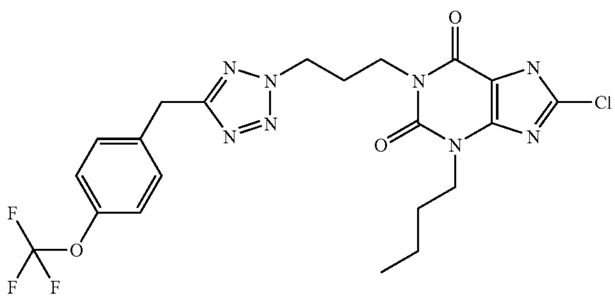 | 3-butyl-8-chloro-1-{3-[5-({4-[(trifluoromethyl)oxy]phenyl}methyl)-2H-tetrazol-2-yl]propyl}-3,7-dihydro-1H-purine-2,6-dione | 32.1 | m/z 527 [MH]+ RT 3.57 min |
| 378 | 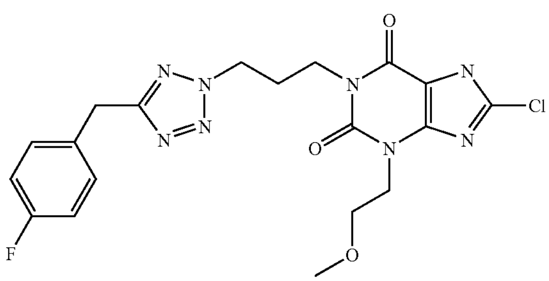 | 8-chloro-1-(3-{5-[(4-fluorophenyl)methyl]-2H-tetrazol-2-yl}propyl)-3-[2-(methyloxy)ethyl]-3,7-dihydro-1H-purine-2,6-dione | 15.0 | m/z 463 [MH]+ RT 2.89 min |
| 379 | 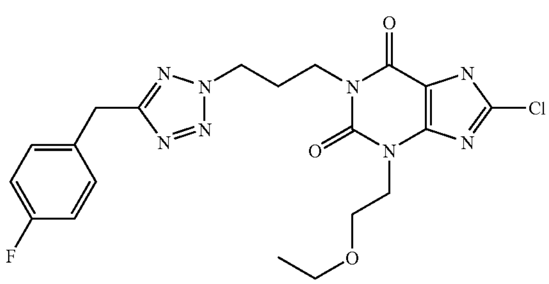 | 8-chloro-3-[2-(ethyloxy)ethyl]-1-(3-{5-[(4-fluorophenyl)methyl]-2H-tetrazol-2-yl}propyl)-3,7-dihydro-1H-purine-2,6-dione | 12.6 | m/z 477 [MH]+ RT 3.03 min |
| 380 | 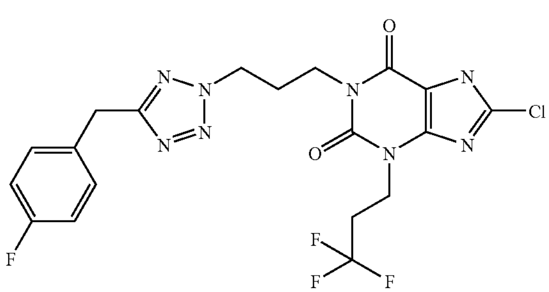 | 8-chloro-1-(3-{5-[(4-fluorophenyl)methyl]-2H-tetrazol-2-yl}propyl)-3-(3,3,3-trifluoropropyl)-3,7-dihydro-1H-purine-2,6-dione | 17.6 | m/z 501 [MH]+ RT 3.21 min |

TABLE 23-continued

| Example | Structure | Name | Yield (mg) | LC/MS |
|---|---|---|---|---|
| 381 | 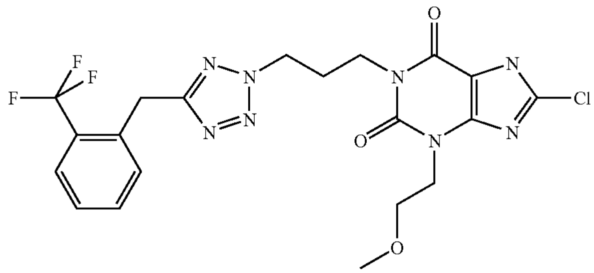 | 8-chloro-3-[2-(methyloxy)ethyl]-1-[3-(5-{[2-(trifluoromethyl)phenyl]methyl}-2H-tetrazol-2-yl)propyl]-3,7-dihydro-1H-purine-2,6-dione | 14.2 | m/z 513 [MH]+ RT 3.10 min |
| 382 | 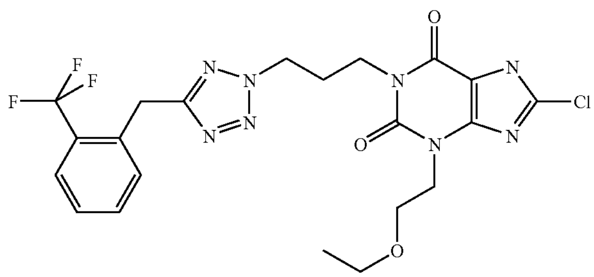 | 8-chloro-3-[2-(ethyloxy)ethyl]-1-[3-(5-{[2-(trifluoromethyl)phenyl]methyl}-2H-tetrazol-2-yl)propyl]-3,7-dihydro-1H-purine-2,6-dione | 20.8 | m/z 527 [MH]+ RT 3.18 min |
| 383 | 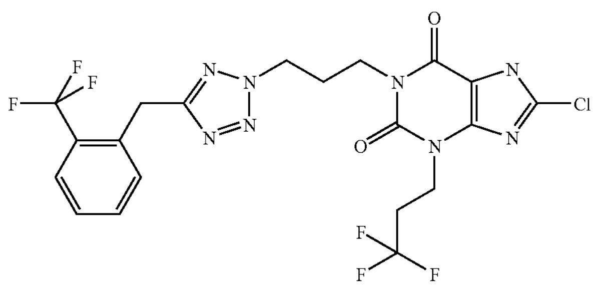 | 8-chloro-1-[3-(5-{[2-(trifluoromethyl)phenyl]methyl}-2H-tetrazol-2-yl)propyl]-3-(3,3,3-trifluoropropyl)-3,7-dihydro-1H-purine-2,6-dione | 35.8 | m/z 551 [MH]+ RT 3.35 min |
| 384 | 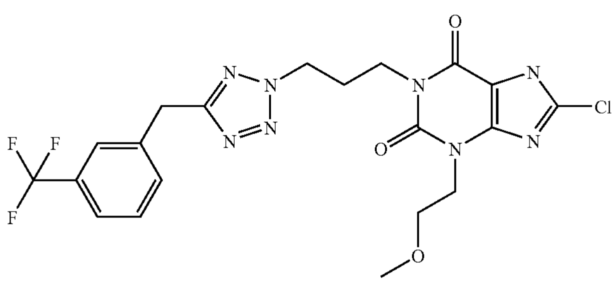 | 8-chloro-3-[2-(methyloxy)ethyl]-1-[3-(5-{[3-(trifluoromethyl)phenyl]methyl}-2H-tetrazol-2-yl)propyl]-3,7-dihydro-1H-purine-2,6-dione | 15.3 | m/z 513 [MH]+ RT 3.14 min |
| 385 | 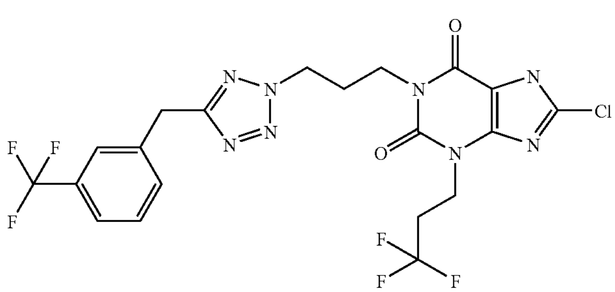 | 8-chloro-1-[3-(5-{[3-(trifluoromethyl)phenyl]methyl}-2H-tetrazol-2-yl)propyl]-3-(3,3,3-trifluoropropyl)-3,7-dihydro-1H-purine-2,6-dione | 29.4 | m/z 551 [MH]+ RT 3.42 min |

TABLE 23-continued

| Example | Structure | Name | Yield (mg) | LC/MS |
|---|---|---|---|---|
| 386 | 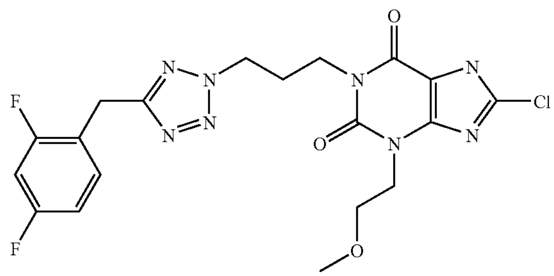 | 8-chloro-1-(3-{5-[(2,4-difluorophenyl)methyl]-2H-tetrazol-2-yl}propyl)-3-[2-(methyloxy)ethyl]-3,7-dihydro-1H-purine-2,6-dione | 17.8 | m/z 481 [MH]+ RT 2.96 min |
| 387 | 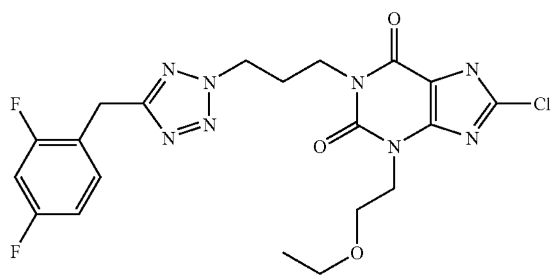 | 8-chloro-1-(3-{5-[(2,4-difluorophenyl)methyl]-2H-tetrazol-2-yl}propyl)-3-[2-(ethyloxy)ethyl]-3,7-dihydro-1H-purine-2,6-dione | 14.4 | m/z 495 [MH]+ RT 2.86 min |
| 388 | 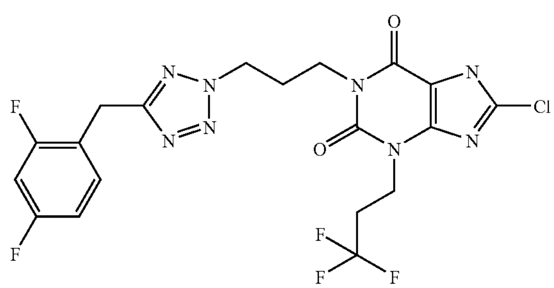 | 8-chloro-1-(3-{5-[(2,4-difluorophenyl)methyl]-2H-tetrazol-2-yl}propyl)-3-(3,3,3-trifluoropropyl)-3,7-dihydro-1H-purine-2,6-dione | 29.9 | m/z 519 [MH]+ RT 3.19 min |
| 389 | 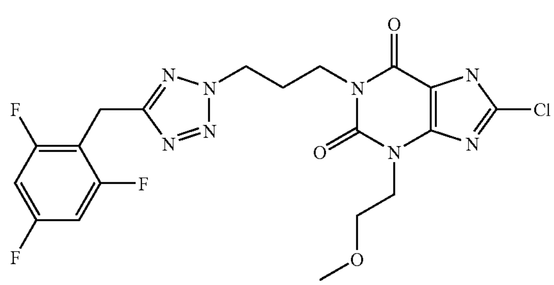 | 8-chloro-3-[2-(methyloxy)ethyl]-1-(3-{5-[(2,4,6-trifluorophenyl)methyl]-2H-tetrazol-2-yl}propyl)-3,7-dihydro-1H-purine-2,6-dione | 21.3 | m/z 499 [MH]+ RT 2.93 min |
| 390 | 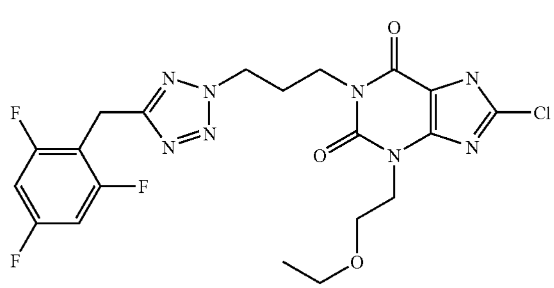 | 8-chloro-3-[2-(ethyloxy)ethyl]-1-(3-{5-[(2,4,6-trifluorophenyl)methyl]-2H-tetrazol-2-yl}propyl)-3,7-dihydro-1H-purine-2,6-dione | 15.5 | m/z 513 [MH]+ RT 2.93 min |

TABLE 23-continued

| Example | Structure | Name | Yield (mg) | LC/MS |
|---|---|---|---|---|
| 391 | 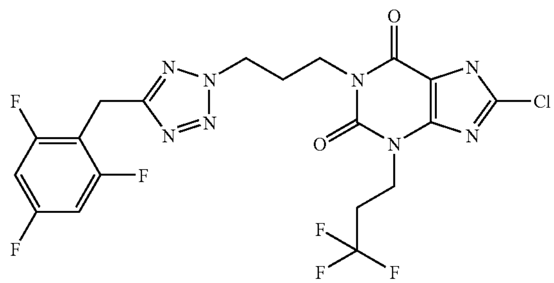 | 8-chloro-1-(3-{5-[(2,4,6-trifluorophenyl)methyl]-2H-tetrazol-2-yl}propyl)-3-(3,3,3-trifluoropropyl)-3,7-dihydro-1H-purine-2,6-dione | 32.3 | m/z 537 [MH]+ RT 3.29 min |
| 392 | 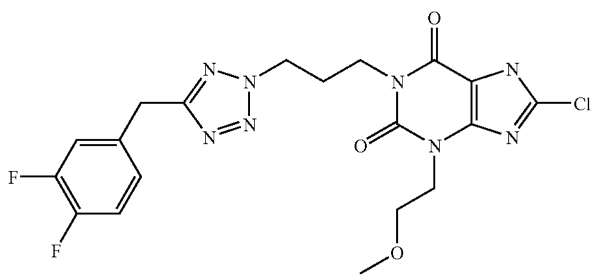 | 8-chloro-1-(3-{5-[(3,4-difluorophenyl)methyl]-2H-tetrazol-2-yl}propyl)-3-[2-(methyloxy)ethyl]-3,7-dihydro-1H-purine-2,6-dione | 14.5 | m/z 481 [MH]+ RT 2.97 min |
| 393 | 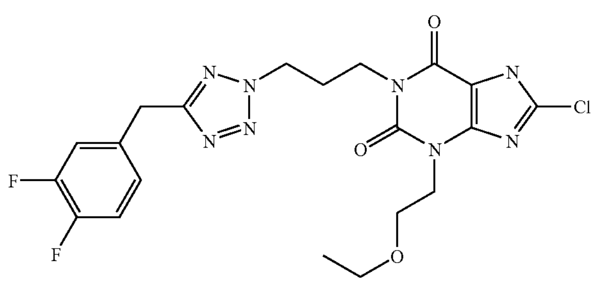 | 8-chloro-1-(3-{5-[(3,4-difluorophenyl)methyl]-2H-tetrazol-2-yl}propyl)-3-[2-(ethyloxy)ethyl]-3,7-dihydro-1H-purine-2,6-dione | 7.2 | m/z 495 [MH]+ RT 3.06 min |
| 394 | 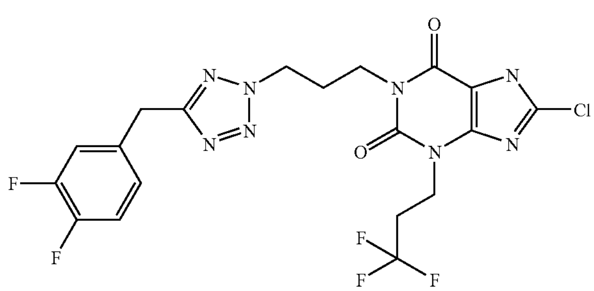 | 8-chloro-1-(3-{5-[(3,4-difluorophenyl)methyl]-2H-tetrazol-2-yl}propyl)-3-(3,3,3-trifluoropropyl)-3,7-dihydro-1H-purine-2,6-dione | 27.8 | m/z 519 [MH]+ RT 3.27 min |
| 395 | 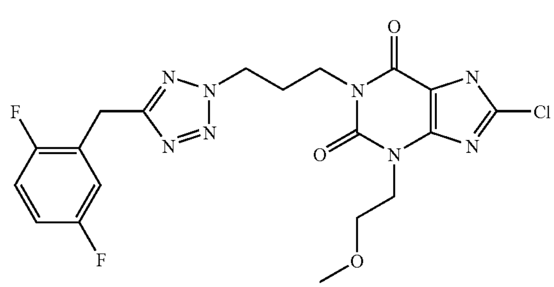 | 8-chloro-1-(3-{5-[(2,5-difluorophenyl)methyl]-2H-tetrazol-2-yl}propyl)-3-[2-(methyloxy)ethyl]-3,7-dihydro-1H-purine-2,6-dione | 17.1 | m/z 481 [MH]+ RT 2.89 min |

TABLE 23-continued

| Example | Structure | Name | Yield (mg) | LC/MS |
|---|---|---|---|---|
| 396 | 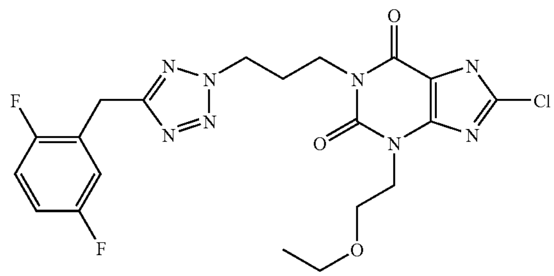 | 8-chloro-1-(3-{5-[(2,5-difluorophenyl)methyl]-2H-tetrazol-2-yl}propyl)-3-[2-(ethyloxy)ethyl]-3,7-dihydro-1H-purine-2,6-dione | 13.5 | m/z 495 [MH]+ RT 3.05 min |
| 397 | 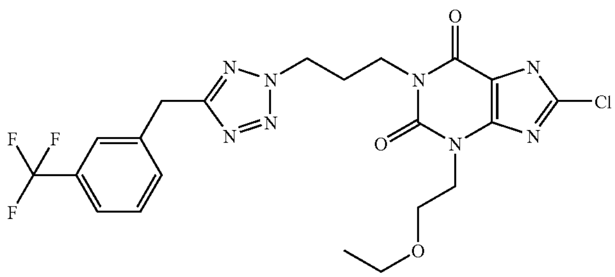 | 8-chloro-3-[2-(ethyloxy)ethyl]-1-[3-(5-{[3-(trifluoromethyl)phenyl]methyl}-2H-tetrazol-2-yl)propyl]-3,7-dihydro-1H-purine-2,6-dione | 14.6 | m/z 527 [MH]+ RT 3.26 min |
| 398 | 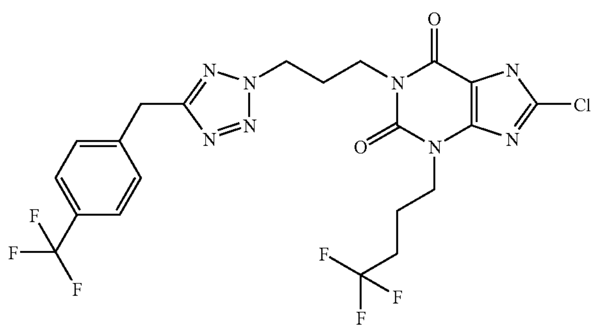 | 8-chloro-3-(4,4,4-trifluorobutyl)-1-[3-(5-{[4-(trifluoromethyl)phenyl]methyl}-2H-tetrazol-2-yl)propyl]-3,7-dihydro-1H-purine-2,6-dione | 12.1 | m/z 565 [MH]+ RT 3.51 min |
| 399 | 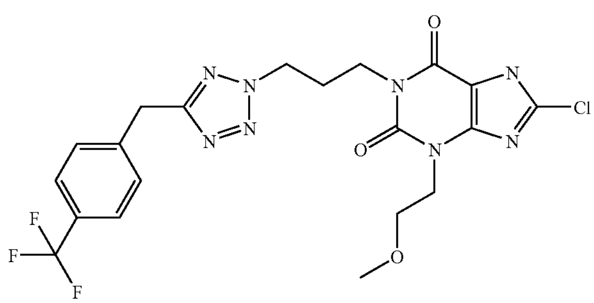 | 8-chloro-3-[2-(methyloxy)ethyl]-1-[3-(5-{[4-(trifluoromethyl)phenyl]methyl}-2H-tetrazol-2-yl)propyl]-3,7-dihydro-1H-purine-2,6-dione | 17.3 | m/z 513 [MH]+ RT 3.17 min |
| 400 | 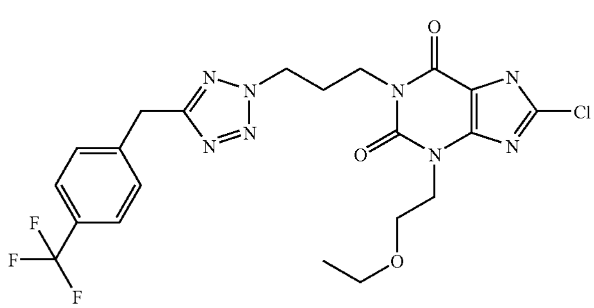 | 8-chloro-3-[2-(ethyloxy)ethyl]-1-[3-(5-{[4-(trifluoromethyl)phenyl]methyl}-2H-tetrazol-2-yl)propyl]-3,7-dihydro-1H-purine-2,6-dione | 15.2 | m/z 527 [MH]+ RT 3.30 min |

TABLE 23-continued

| Example | Structure | Name | Yield (mg) | LC/MS |
|---|---|---|---|---|
| 401 | 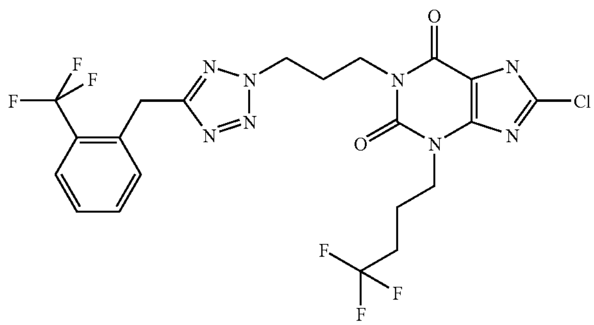 | 8-chloro-3-(4,4,4-trifluorobutyl)-1-[3-(5-{[2-(trifluoromethyl)phenyl]methyl}-2H-tetrazol-2-yl)propyl]-3,7-dihydro-1H-purine-2,6-dione | 5.8 | m/z 565 [MH]$^+$ RT 3.46 min |
| 402 | 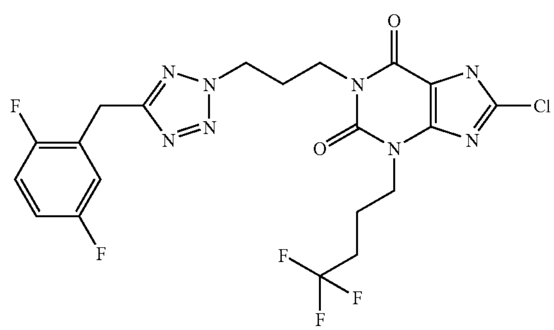 | 8-chloro-1-(3-{5-[(2,5-difluorophenyl)methyl]-2H-tetrazol-2-yl}propyl)-3-(4,4,4-trifluorobutyl)-3,7-dihydro-1H-purine-2,6-dione | 14.7 | m/z 533 [MH]$^+$ RT 3.34 min |
| 403 | 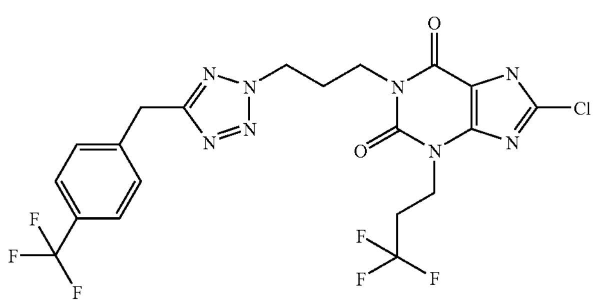 | 8-chloro-1-[3-(5-{[4-(trifluoromethyl)phenyl]methyl}-2H-tetrazol-2-yl)propyl]-3-(3,3,3-trifluoropropyl)-3,7-dihydro-1H-purine-2,6-dione | 26.1 | m/z 551 [MH]$^+$ RT 3.46 min |
| 404 | 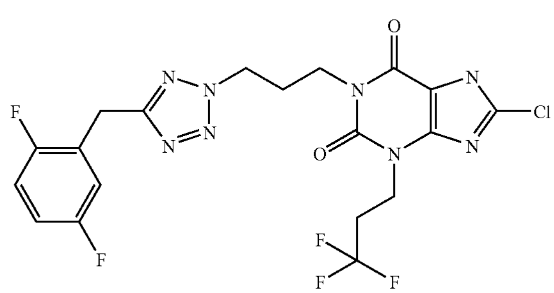 | 8-chloro-1-(3-{5-[(2,5-difluorophenyl)methyl]-2H-tetrazol-2-yl}propyl)-3-(3,3,3-trifluoropropyl)-3,7-dihydro-1H-purine-2,6-dione | 18.0 | m/z 519 [MH]$^+$ RT 3.29 min |

TABLE 23-continued

| Example | Structure | Name | Yield (mg) | LC/MS |
|---|---|---|---|---|
| 405 | 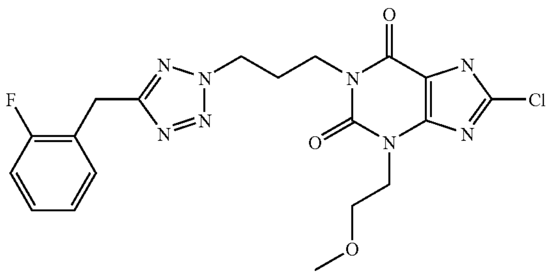 | 8-chloro-1-(3-{5-[(2-fluorophenyl)methyl]-2H-tetrazol-2-yl}propyl)-3-[2-(methyloxy)ethyl]-3,7-dihydro-1H-purine-2,6-dione | 3.4 | m/z 463 [MH]$^+$ RT 2.84 min |
| 406 | 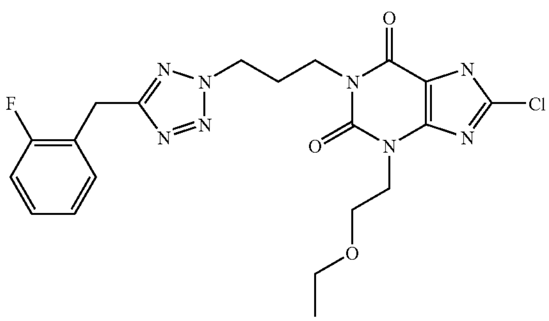 | 8-chloro-3-[2-(ethyloxy)ethyl]-1-(3-{5-[(2-fluorophenyl)methyl]-2H-tetrazol-2-yl}propyl)-3,7-dihydro-1H-purine-2,6-dione | 8.2 | m/z 477 [MH]$^+$ RT 2.85 min |
| 407 | 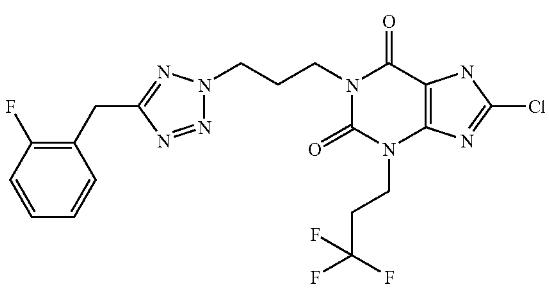 | 8-chloro-1-(3-{5-[(2-fluorophenyl)methyl]-2H-tetrazol-2-yl}propyl)-3-(3,3,3-trifluoropropyl)-3,7-dihydro-1H-purine-2,6-dione | 32.7 | m/z 501 [MH]$^+$ RT 3.25 min |

Example 408

3-Butyl-8-chloro-1-{3-[4-(phenylmethyl)-1-piperazinyl]propyl}-3,7-dihydro-1H-purine-2,6-dione

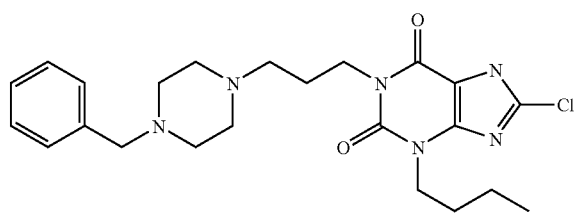

A solution of 3-[3-butyl-8-chloro-2,6-dioxo-7-(2-propen-1-yl)-2,3,6,7-tetrahydro-1H-purin-1-yl]propyl methanesulfonate (0.08 g, 0.19 mmol) in DMF (5 ml) was treated with potassium carbonate (0.08 g, 0.6 mmol) and 1-benzylpiperazine (0.04 g, 0.23 mmol) and then heated at 70° C. for 2 h. The mixture was cooled, evaporated to dryness and partitioned between 10 ml of DCM and 10 ml of water. The organic phase was evaporated to dryness and the residue dissolved in anhydrous THF (5 ml). The solution was cautiously degassed by the repeated application of vacuum to the reaction mixture and subsequent backfilling with nitrogen gas and then treated with tetrakis(triphenylphosphine)palladium(0) (0.010 g, 0.009 mmol) and morpholine (0.200 ml, 2.3 mmol) and the mixture stirred for 2 h in a nitrogen atmosphere. The mixture was evaporated and the residue taken up in 5 ml of methanol and added to a 2 g aminopropyl SPE cartridge which was then washed with methanol and the product eluted using a 3% solution of acetic acid in methanol. Product-containing fractions were pooled and evaporated to dryness. The product was then purified by flash chromatography using a gradient elution from DCM/2% Acetic acid to DCM/20% MeOH/2% Acetic acid and the final product freeze-dried from 1,4-dioxan to give the title compound as a white solid (0.021 g, 24%).

LC/MS: m/z 459 [MH]$^+$, RT 2.37 min.

The following compounds (Table 24) were prepared by the appropriate general methodology described above.

| Example | Structure | Name | LC/MS |
|---|---|---|---|
| 409 | 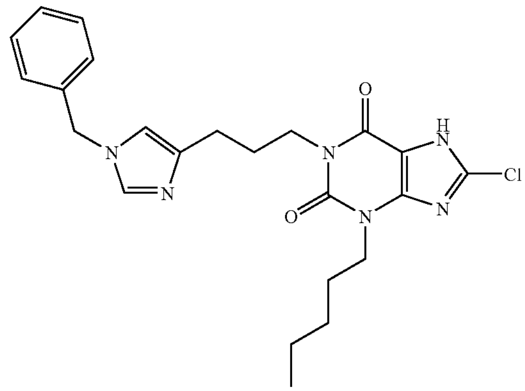 | 8-chloro-3-pentyl-1-{3-[1-(phenylmethyl)-1H-imidazol-4-yl]propyl}-3,7-dihydro-1H-purine-2,6-dione | m/z 455 [MH]+ RT 2.61 min |
| 410 | 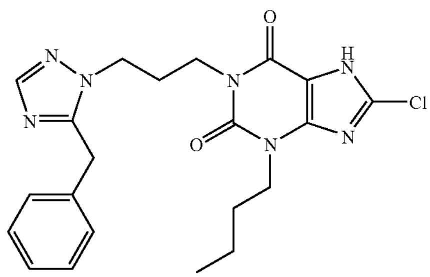 | 3-butyl-8-chloro-1-{3-[5-(phenylmethyl)-1H-1,2,4-triazol-1-yl]propyl}-3,7-dihydro-1H-purine-2,6-dione | m/z 442 [MH]+ 2.94 min |
| 411 | 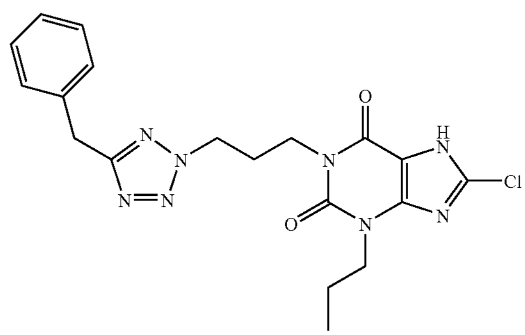 | 8-chloro-1-{3-[5-(phenylmethyl)-2H-tetrazol-2-yl]propyl}-3-propyl-3,7-dihydro-1H-purine-2,6-dione | m/z 429 [MH]+ RT 3.14 min |
| 412 | 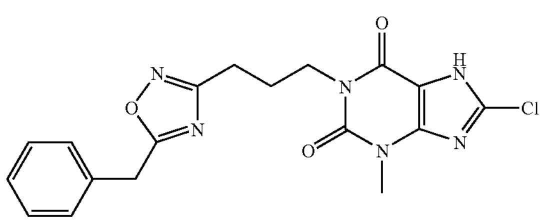 | 8-chloro-3-methyl-1-{3-[5-(phenylmethyl)-1,2,4-oxadiazol-3-yl]propyl}-3,7-dihydro-1H-purine-2,6-dione | m/z 401 [MH]+ RT 2.88 min |
| 413 | 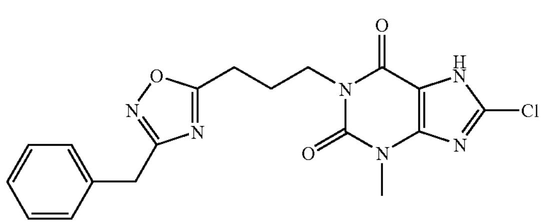 | 8-chloro-3-methyl-1-{3-[3-(phenylmethyl)-1,2,4-oxadiazol-5-yl]propyl}-3,7-dihydro-1H-purine-2,6-dione | m/z 401 [MH]+ RT 2.89 min |

TABLE 24-continued

| Example | Structure | Name | LC/MS |
|---|---|---|---|
| 414 | 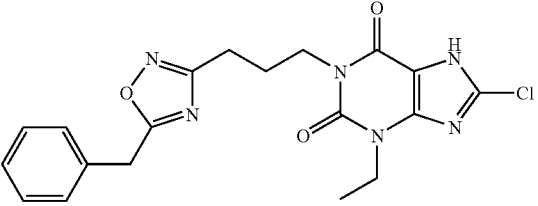 | 8-chloro-3-ethyl-1-{3-[5-(phenylmethyl)-1,2,4-oxadiazol-3-yl]propyl}-3,7-dihydro-1H-purine-2,6-dione | m/z 415 [MH]+ RT 2.97 min |
| 415 | 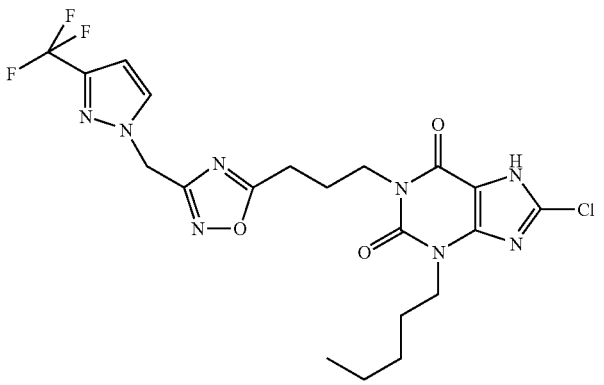 | 8-chloro-3-pentyl-1-[3-(3-{[3-(trifluoromethyl)-1H-pyrazol-1-yl]methyl}-1,2,4-oxadiazol-5-yl)propyl]-3,7-dihydro-1H-purine-2,6-dione | m/z 515 [MH]+ RT 3.43 min |
| 416 | 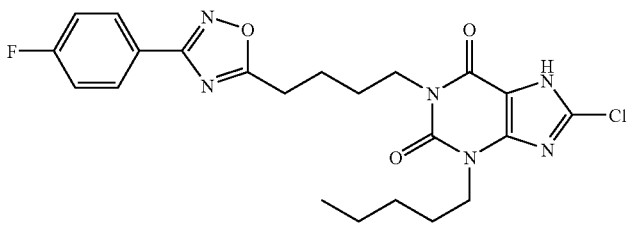 | 8-chloro-1-{4-[3-(4-fluorophenyl)-1,2,4-oxadiazol-5-yl]butyl}-3-pentyl-3,7-dihydro-1H-purine-2,6-dione | m/z 475 [MH]+ RT 3.71 min |
| 417 | 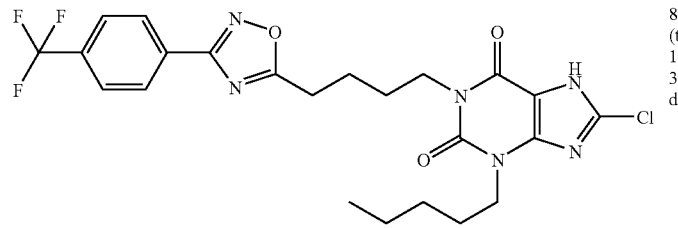 | 8-chloro-3-pentyl-1-(4-{3-[4-(trifluoromethyl)phenyl]-1,2,4-oxadiazol-5-yl}butyl)-3,7-dihydro-1H-purine-2,6-dione | m/z 525 [MH]+ RT 3.92 min |
| 418 | 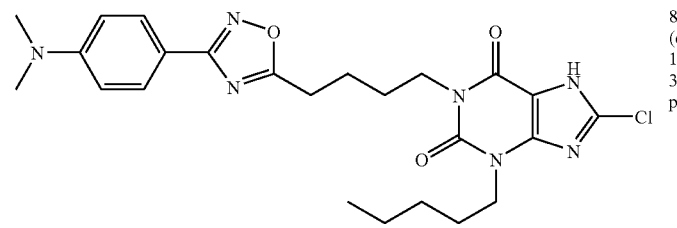 | 8-chloro-1-(4-{3-[4-(dimethylamino)phenyl]-1,2,4-oxadiazol-5-yl}butyl)-3-pentyl-3,7-dihydro-1H-purine-2,6-dione | m/z 500 [MH]+ RT 3.73 min |
| 419 | 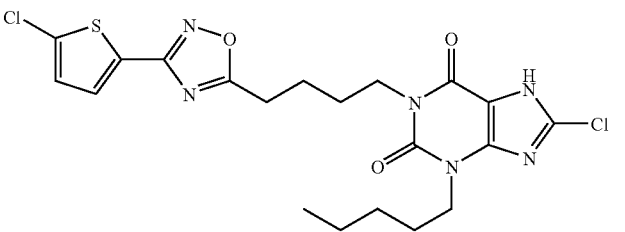 | 8-chloro-1-{4-[3-(5-chloro-2-thienyl)-1,2,4-oxadiazol-5-yl]butyl}-3-pentyl-3,7-dihydro-1H-purine-2,6-dione | m/z 497 [MH]+ RT 3.88 min |

TABLE 24-continued

| Example | Structure | Name | LC/MS |
|---|---|---|---|
| 420 | 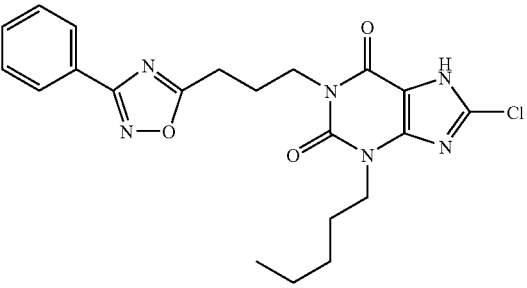 | 8-chloro-3-pentyl-1-[3-(3-phenyl-1,2,4-oxadiazol-5-yl)propyl]-3,7-dihydro-1H-purine-2,6-dione | m/z 443 [MH]+ RT 3.51 min |
| 421 | 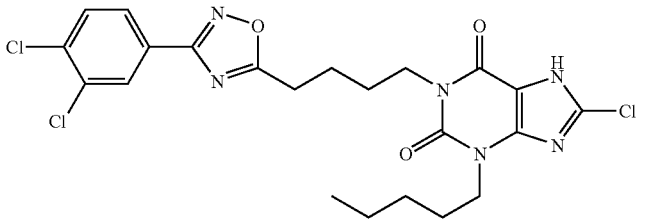 | 8-chloro-1-{4-[3-(3,4-dichlorophenyl)-1,2,4-oxadiazol-5-yl]butyl}-3-pentyl-3,7-dihydro-1H-purine-2,6-dione | m/z 525 [MH]+ RT 4.12 min |
| 422 | 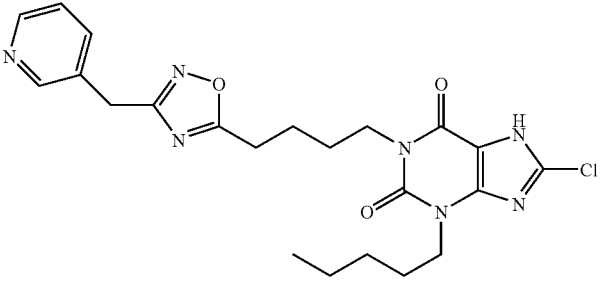 | 8-chloro-3-pentyl-1-{4-[3-(pyridin-3-ylmethyl)-1,2,4-oxadiazol-5-yl]butyl}-3,7-dihydro-1H-purine-2,6-dione | m/z 472 [MH]+ RT 2.90 min |
| 423 | 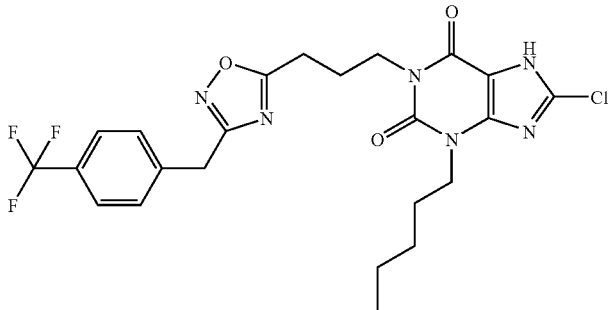 | 8-chloro-3-pentyl-1-[3-(3-{[4-(trifluoromethyl)phenyl]methyl}-1,2,4-oxadiazol-5-yl)propyl]-3,7-dihydro-1H-purine-2,6-dione | m/z 525 [MH]+ RT 3.69 min |
| 424 | 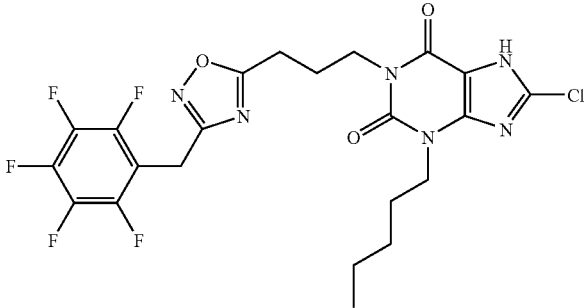 | 8-chloro-1-(3-{3-[(pentafluorophenyl)methyl]-1,2,4-oxadiazol-5-yl}propyl)-3-pentyl-3,7-dihydro-1H-purine-2,6-dione | m/z 547 [MH]+ RT 3.66 min |

TABLE 24-continued

| Example | Structure | Name | LC/MS |
|---|---|---|---|
| 425 | 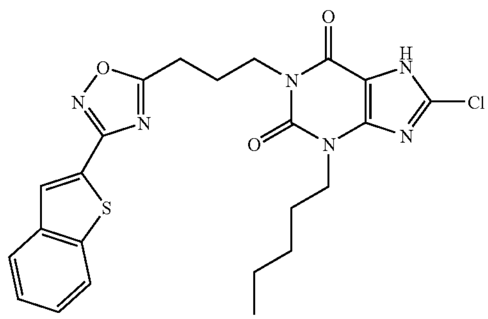 | 1-{3-[3-(1-benzothien-2-yl)-1,2,4-oxadiazol-5-yl]propyl}-8-chloro-3-pentyl-3,7-dihydro-1H-purine-2,6-dione | m/z 499 [MH]+ RT 3.77 min |
| 426 | 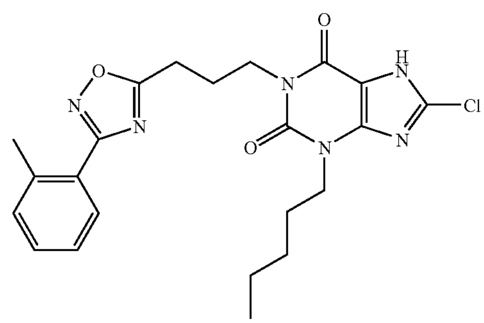 | 8-chloro-1-{3-[3-(2-methylphenyl)-1,2,4-oxadiazol-5-yl]propyl}-3-pentyl-3,7-dihydro-1H-purine-2,6-dione | m/z 457 [MH]+ RT 3.62 min |
| 427 | 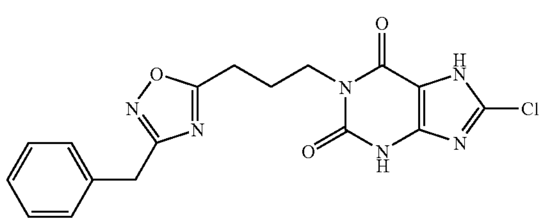 | 8-chloro-1-{3-[3-(phenylmethyl)-1,2,4-oxadiazol-5-yl]propy}-3,7-dihydro-1H-purine-2,6-dione | m/z 387 [MH]+ RT 2.63 min |
| 428 | 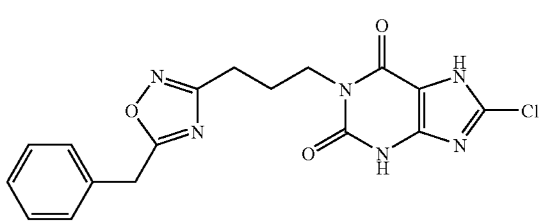 | 8-chloro-1-{3-[5-(phenylmethyl)-1,2,4-oxadiazol-3-yl]propyl}-3,7-dihydro-1H-purine-2,6-dione | m/z 387 [MH]+ RT 2.65 min |
| 429 | 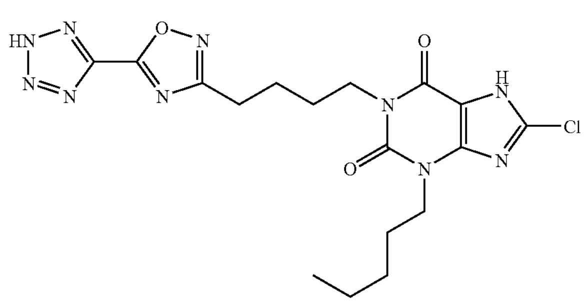 | 8-chloro-3-pentyl-1-{4-[5-(1H-tetrazol-5-yl)-1,2,4-oxadiazol-3-yl]butyl}-3,7-dihydro-1H-purine-2,6-dione | m/z 449 [MH]+ RT 4.03 min |

TABLE 24-continued

| Example | Structure | Name | LC/MS |
|---|---|---|---|
| 430 | 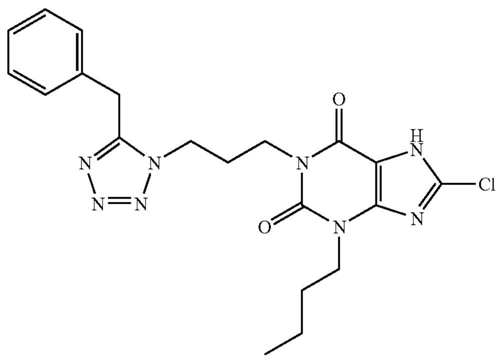 | 3-butyl-8-chloro-1-{3-[5-(phenylmethyl)-1H-tetrazol-1-yl]propyl}-3,7-dihydro-1H-purine-2,6-dione | m/z 443 [MH]+ RT 3.11 min |
| 431 | 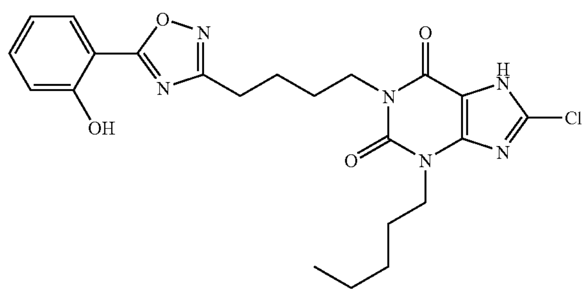 | 8-chloro-1-{4-[5-(2-hydroxyphenyl)-1,2,4-oxadiazol-3-yl]butyl}-3-pentyl-3,7-dihydro-1H-purine-2,6-dione | m/z 473 [MH]+ RT 3.84 min |
| 432 | 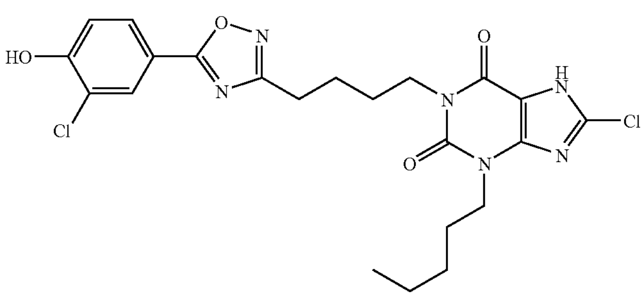 | 8-chloro-1-{4-[5-(3-chloro-4-hydroxyphenyl)-1,2,4-oxadiazol-3-yl]butyl}-3-pentyl-3,7-dihydro-1H-purine-2,6-dione | m/z 507 [MH]+ RT 3.74 min |
| 433 | 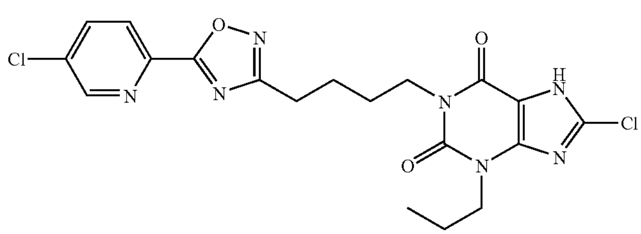 | 8-chloro-1-{4-[5-(5-chloropyridin-2-yl)-1,2,4-oxadiazol-3-yl]butyl}-3-propyl-3,7-dihydro-1H-purine-2,6-dione | m/z 464 [MH]+ RT 3.30 min |
| 434 | 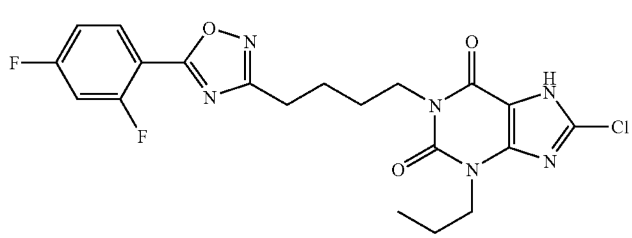 | 8-chloro-1-{4-[5-(2,4-difluorophenyl)-1,2,4-oxadiazol-3-yl]butyl}-3-propyl-3,7-dihydro-1H-purine-2,6-dione | m/z 465 [MH]+ RT 3.48 min |

TABLE 24-continued

| Example | Structure | Name | LC/MS |
|---|---|---|---|
| 435 | 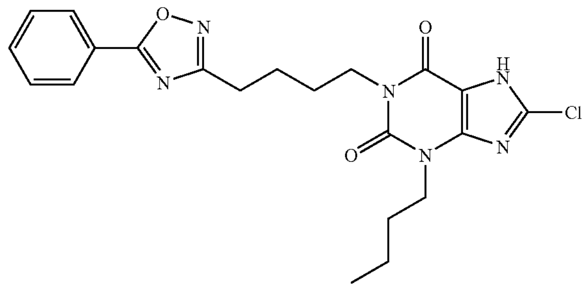 | 3-butyl-8-chloro-1-[4-(5-phenyl-1,2,4-oxadiazol-3-yl)butyl]-3,7-dihydro-1H-purine-2,6-dione | m/z 443 [MH]+ RT 3.49 min |
| 436 | 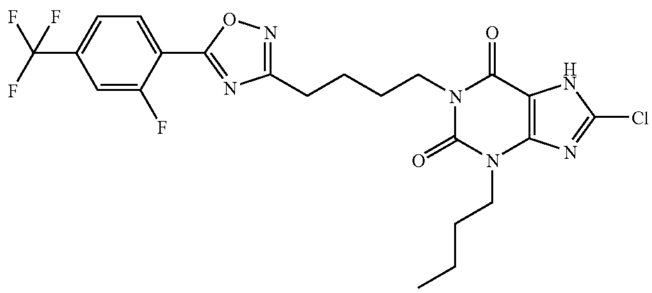 | 3-butyl-8-chloro-1-(4-{5-[2-fluoro-4-(trifluoromethyl)phenyl]-1,2,4-oxadiazol-3-yl}butyl)-3,7-dihydro-1H-purine-2,6-dione | m/z 529 [MH]+ RT 3.71 min |
| 437 | 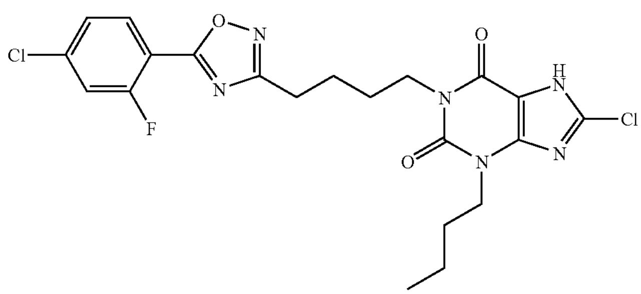 | 3-butyl-8-chloro-1-{4-[5-(4-chloro-2-fluorophenyl)-1,2,4-oxadiazol-3-yl]butyl}-3,7-dihydro-1H-purine-2,6-dione | m/z 495 [MH]+ RT 3.64 min |
| 438 | 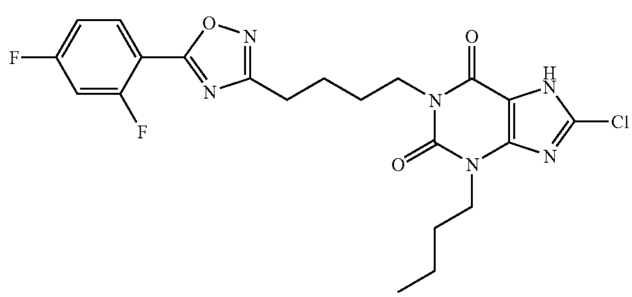 | 3-butyl-8-chloro-1-{4-[5-(2,4-difluorophenyl)-1,2,4-oxadiazol-3-yl]butyl}-3,7-dihydro-1H-purine-2,6-dione | m/z 479 [MH]+ RT 3.49 min |
| 439 | 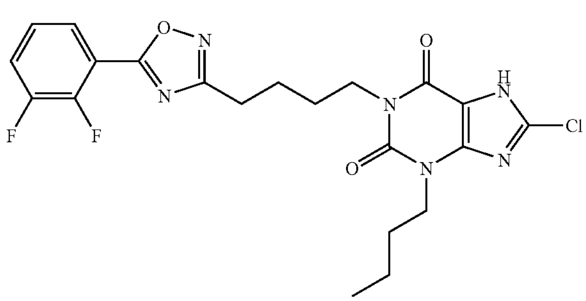 | 3-butyl-8-chloro-1-{4-[5-(2,3-difluorophenyl)-1,2,4-oxadiazol-3-yl]butyl}-3,7-dihydro-1H-purine-2,6-dione | m/z 479 [MH]+ RT 3.53 min |

TABLE 24-continued

| Example | Structure | Name | LC/MS |
|---|---|---|---|
| 440 | 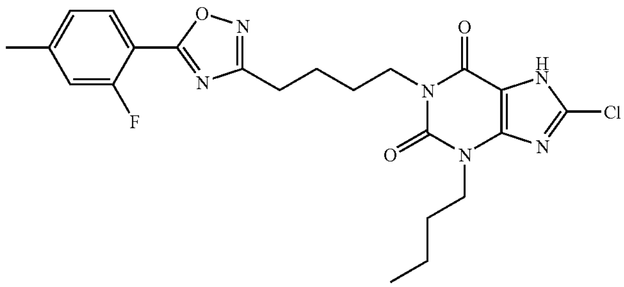 | 3-butyl-8-chloro-1-{4-[5-(2-fluoro-4-methylphenyl)-1,2,4-oxadiazol-3-yl]butyl}-3,7-dihydro-1H-purine-2,6-dione | m/z 475 [MH]+ RT 3.51 min |
| 441 | 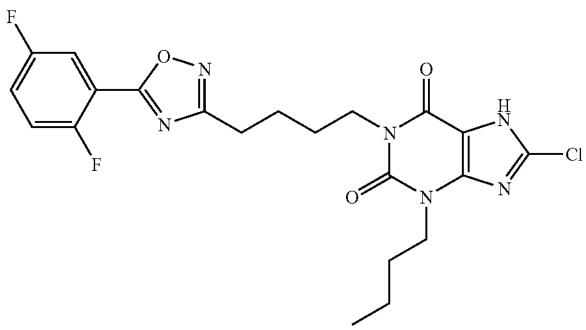 | 3-butyl-8-chloro-1-{4-[5-(2,5-difluorophenyl)-1,2,4-oxadiazol-3-yl]butyl}-3,7-dihydro-1H-purine-2,6-dione | m/z 479 [MH]+ RT 3.50 min |
| 442 | 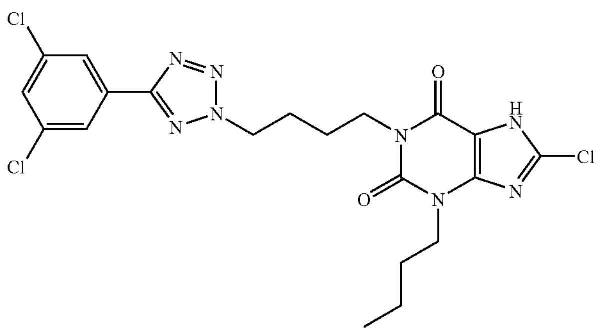 | 3-butyl-8-chloro-1-{4-[5-(3,5-dichlorophenyl)-2H-tetrazol-2-yl]butyl}-3,7-dihydro-1H-purine-2,6-dione | m/z 511 [MH]+ RT 3.92 min |
| 443 | 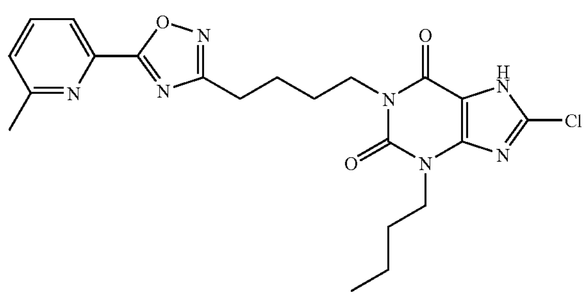 | 3-butyl-8-chloro-1-{4-[5-(6-methylpyridin-2-yl)-1,2,4-oxadiazol-3-yl]butyl}-3,7-dihydro-1H-purine-2,6-dione | m/z 458 [MH]+ RT 3.12 min |
| 444 | 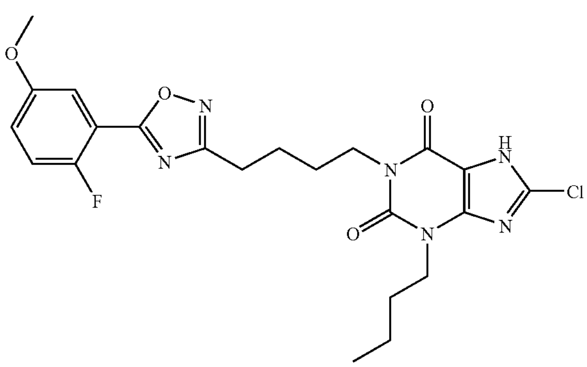 | 3-butyl-8-chloro-1-(4-{5-[2-fluoro-5-(methyloxy)phenyl]-1,2,4-oxadiazol-3-yl}butyl)-3,7-dihydro-1H-purine-2,6-dione | m/z 491 [MH]+ RT 3.51 min |

TABLE 24-continued

| Example | Structure | Name | LC/MS |
|---|---|---|---|
| 445 | 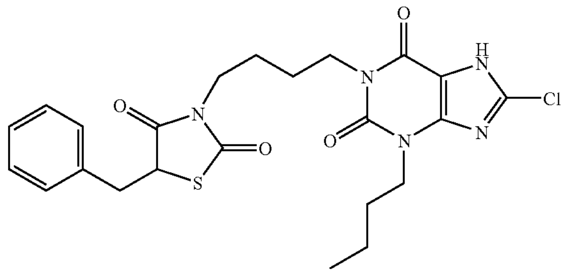 | 3-butyl-8-chloro-1-{4-[2,4-dioxo-5-(phenylmethyl)-1,3-thiazolidin-3-yl]butyl}-3,7-dihydro-1H-purine-2,6-dione | m/z 504 [MH]$^+$ RT 3.36 min |
| 446 | 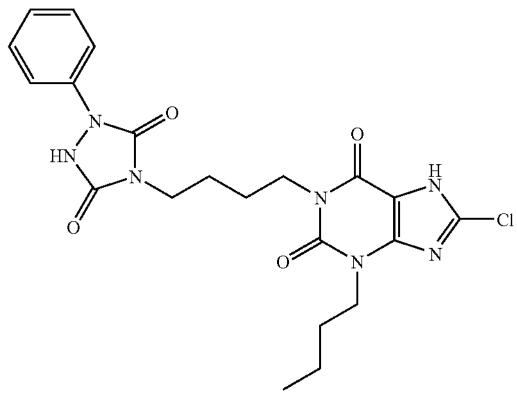 | 3-butyl-8-chloro-1-[4-(3,5-dioxo-1-phenyl-1,2,4-triazolidin-4-yl)butyl]-3,7-dihydro-1H-purine-2,6-dione | m/z 474 [MH]$^+$ RT 2.91 min |
| 447 | 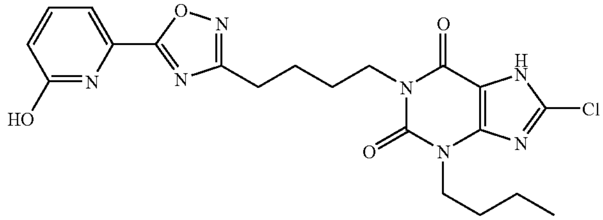 | 3-butyl-8-chloro-1-{4-[5-(6-oxo-1,6-dihydropyridin-2-yl)-1,2,4-oxadiazol-3-yl]butyl}-3,7-dihydro-1H-purine-2,6-dione | m/z 460 [MH]$^+$ RT 2.86 min |
| 448 | 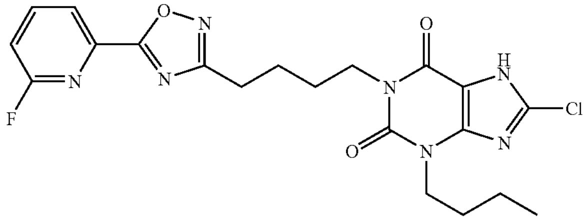 | 3-butyl-8-chloro-1-{4-[5-(6-fluoropyridin-2-yl)-1,2,4-oxadiazol-3-yl]butyl}-3,7-dihydro-1H-purine-2,6-dione | m/z 462 [MH]$^+$ RT 3.23 min |
| 449 | 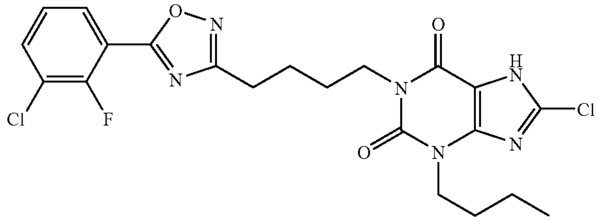 | 3-butyl-8-chloro-1-{4-[5-(3-chloro-2-fluorophenyl)-1,2,4-oxadiazol-3-yl]butyl}-3,7-dihydro-1H-purine-2,6-dione | m/z 495 [MH]$^+$ RT 3.69 min |
| 450 | 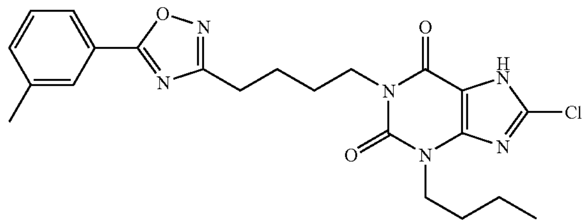 | 3-butyl-8-chloro-1-{4-[5-(3-methylphenyl)-1,2,4-oxadiazol-3-yl]butyl}-3,7-dihydro-1H-purine-2,6-dione | m/z 457 [MH]$^+$ RT 3.67 min |

TABLE 24-continued

| Example | Structure | Name | LC/MS |
|---|---|---|---|
| 451 | 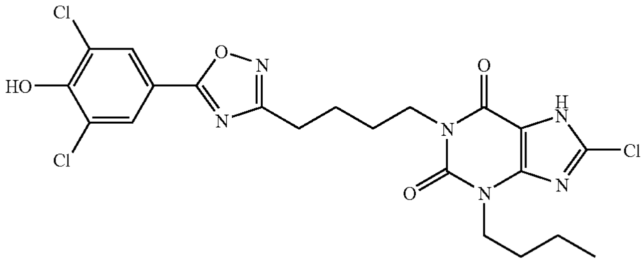 | 3-butyl-8-chloro-1-{4-[5-(3,5-dichloro-4-hydroxyphenyl)-1,2,4-oxadiazol-3-yl]butyl}-3,7-dihydro-1H-purine-2,6-dione | m/z 527 [MH]$^+$ RT 3.92 min |
| 452 | 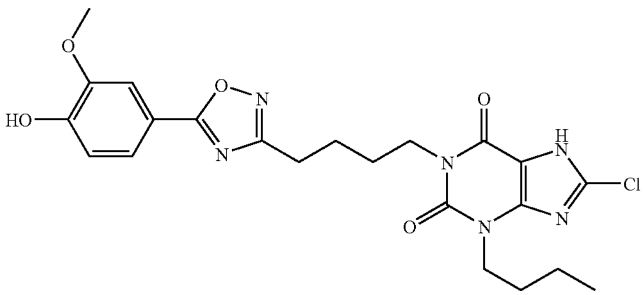 | 3-butyl-8-chloro-1-(4-{5-[4-hydroxy-3-(methyloxy)phenyl]-1,2,4-oxadiazol-3-yl}butyl)-3,7-dihydro-1H-purine-2,6-dione | m/z 489 [MH]$^+$ RT 3.27 min |
| 453 | 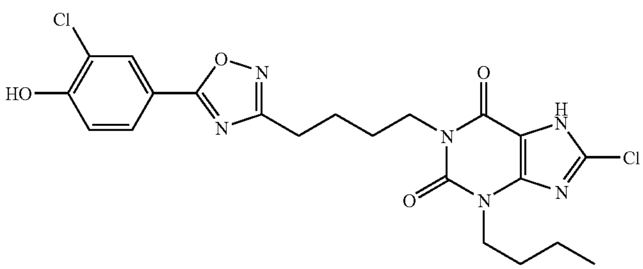 | 3-butyl-8-chloro-1-{4-[5-(3-chloro-4-hydroxyphenyl)-1,2,4-oxadiazol-3-yl]butyl}-3,7-dihydro-1H-purine-2,6-dione | m/z 493 [MH]$^+$ RT 3.61 min |
| 454 | 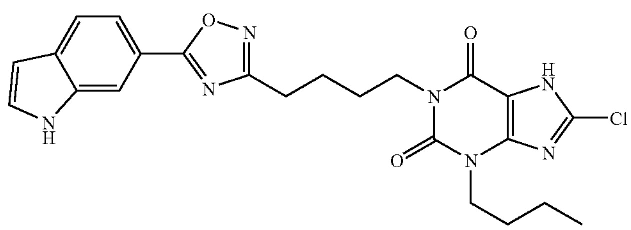 | 3-butyl-8-chloro-1-{4-[5-(1H-indol-6-yl)-1,2,4-oxadiazol-3-yl]butyl}-3,7-dihydro-1H-purine-2,6-dione | m/z 482 [MH]$^+$ RT 3.55 min |
| 455 | 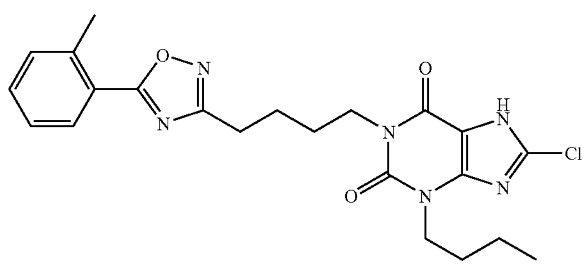 | 3-butyl-8-chloro-1-{4-[5-(2-methylphenyl)-1,2,4-oxadiazol-3-yl]butyl}-3,7-dihydro-1H-purine-2,6-dione | m/z 457 [MH]$^+$ RT 3.67 min |
| 456 | 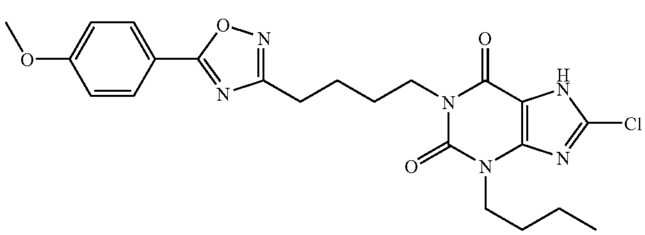 | 3-butyl-8-chloro-1-(4-{5-[4-(methyloxy)phenyl]-1,2,4-oxadiazol-3-yl}butyl)-3,7-dihydro-1H-purine-2,6-dione | m/z 473 [MH]$^+$ RT 3.51 min |

TABLE 24-continued

| Example | Structure | Name | LC/MS |
|---|---|---|---|
| 457 | 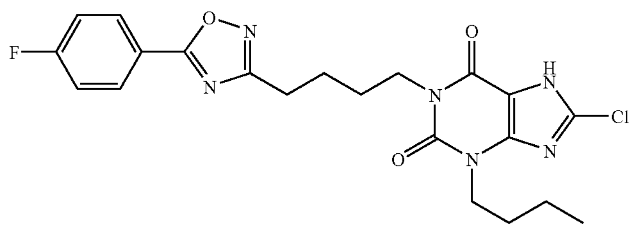 | 3-butyl-8-chloro-1-{4-[5-(4-fluorophenyl)-1,2,4-oxadiazol-3-yl]butyl}-3,7-dihydro-1H-purine-2,6-dione | m/z 461 [MH]+ RT 3.54 min |
| 458 | 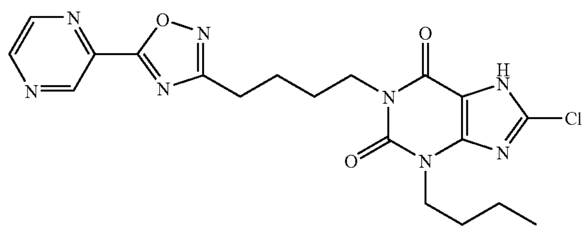 | 3-butyl-8-chloro-1-[4-(5-pyrazin-2-yl-1,2,4-oxadiazol-3-yl)butyl]-3,7-dihydro-1H-purine-2,6-dione | m/z 455 [MH]+ RT 2.96 min |
| 459 | 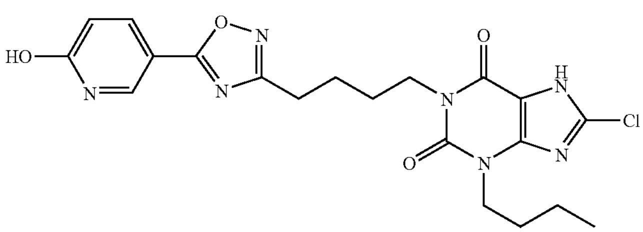 | 3-butyl-8-chloro-1-{4-[5-(6-oxo-1,6-dihydropyridin-3-yl)-1,2,4-oxadiazol-3-yl]butyl}-3,7-dihydro-1H-purine-2,6-dione | m/z 460 [MH]+ RT 2.78 min |
| 460 | 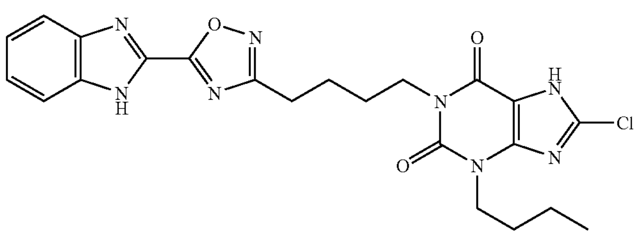 | 1-{4-[5-(1H-benzimidazol-2-yl)-1,2,4-oxadiazol-3-yl]butyl}-3-butyl-8-chloro-3,7-dihydro-1H-purine-2,6-dione | m/z 483 [MH]+ RT 3.22 min |
| 461 | 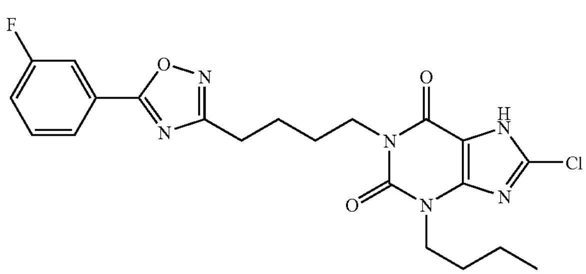 | 3-butyl-8-chloro-1-{4-[5-(3-fluorophenyl)-1,2,4-oxadiazol-3-yl]butyl}-3,7-dihydro-1H-purine-2,6-dione | m/z 461 [MH]+ RT 3.58 min |
| 462 | 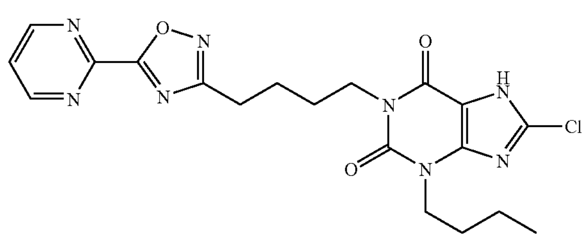 | 3-butyl-8-chloro-1-[4-(5-pyrimidin-2-yl-1,2,4-oxadiazol-3-yl)butyl]-3,7-dihydro-1H-purine-2,6-dione | m/z 445 [MH]+ RT 2.84 min |

Example 463

3-Butyl-8-chloro-1-{4-[5-(2-fluoro-4-hydroxyphenyl)-1,2,4-oxadiazol-3-yl]butyl}-3,7-dihydro-1H-purine-2,6-dione a) 3-Butyl-8-chloro-1-{4-[5-(2-fluoro-4-hydroxyphenyl)-1,2,4-oxadiazol-3-yl]butyl}-3,7-dihydro-1H-purine-2,6-dione

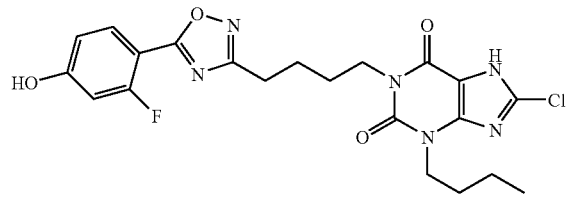

CDI (45 mg, 0.28 mmol) in anhydrous DMSO (0.5 ml) was added to 2-fluoro-4-hydroxybenzoic acid (40 mg, 0.25 mmol) and stirred at rt for 2 h. 5-(3-Butyl-8-chloro-2,6-dioxo-2,3,6,7-tetrahydro-1H-purin-1-yl)-N-hydroxypentanimidamide (100 mg, 0.28 mmol) in DMSO (0.4 ml) was added and the resulting mixture heated at 90° C. for 18 h. Purification by MDAP afforded the title compound as a solid (38 mg, 28%).

LC/MS: m/z 477 [MH]$^+$, RT 3.39 min.

$^1$H NMR (DMSO-d$_6$) δ: 0.87 (t, 3H, J=7 Hz), 1.27 (m, 2H), 1.56-1.78 (m, 6H), 2.77 (t, 2H, J=7 Hz), 3.90 (m, 4H), 6.80 (m, 2H), 7.91 (t, 1H, J=9 Hz), 11.01 (s, 1H), 14.45 (br s, 1H).

b) 5-(3-Butyl-8-chloro-2,6-dioxo-2,3,6,7-tetrahydro-1H-purin-1-yl)-N-hydroxypentanimidamide

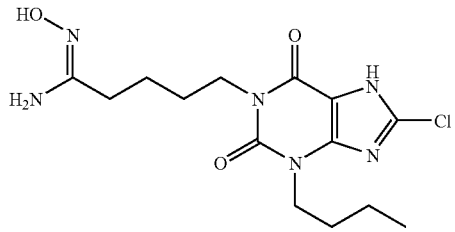

5-(3-Butyl-8-chloro-2,6-dioxo-2,3,6,7-tetrahydro-1H-purin-1-yl)pentanenitrile (8.5 g, 26 mmol) was dissolved in EtOH (100 ml). Hydroxylamine (50% in water; 2.6 ml, 39 mmol) was added and the mixture heated at 80° C. for 48 h under nitrogen. The reaction mixture was concentrated in vacuo, the resultant solid washed with methanol and dried to give the title compound as a solid (5.9 g, 47%).

LC/MS: m/z 357 [MH]$^+$, RT 2.17 min.

c) 5-(3-Butyl-8-chloro-2,6-dioxo-2,3,6,7-tetrahydro-1H-purin-1-yl)pentanenitrile

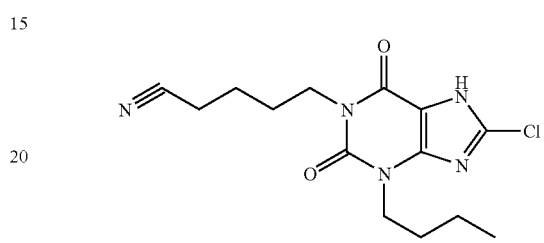

5-Bromopentanenitrile (4.54 ml, 39 mmol) and cesium carbonate (12.7 g) were added to a solution of 3-butyl-8-chloro-7-(2-propen-1-yl)-3,7-dihydro-1H-purine-2,6-dione (10 g, 35 mmol) in DMF (100 ml) and the mixture stirred under nitrogen at 40° C. overnight and allowed to cool.

The mixture was then degassed by the repeated successive application of a vacuum and then nitrogen pressure. The mixture was then treated with tetrakis(triphenylphosphine)palladium(0) (2.86 g, 2.5 mmol) and morpholine (30.8 ml, 350 mmol). The mixture was stirred in a nitrogen atmosphere for 3 h and then partitioned between EtOAc and 2M aqueous hydrochloric acid. The aqueous layer was separated and extracted with EtOAc (×2). The combined organic phases were concentrated in vacuo to give a solid that was washed with ether, filtered and dried. The filtrate was concentrated and purified on an aminopropyl column eluting with MeOH followed by 3% AcOH/MeOH. The product-containing fractions were combined and concentrated to give a solid, which was combined with the filtered product. The title compound was obtained as a solid (10.5 g, 93%).

LC/MS: m/z 324 [MH]$^+$, RT 2.75 min.

The following compounds (Table 25) were prepared using a method analogous to that for Example 463, using the appropriate carboxylic acid.

TABLE 25

| | | | |
|---|---|---|---|
| 464 | 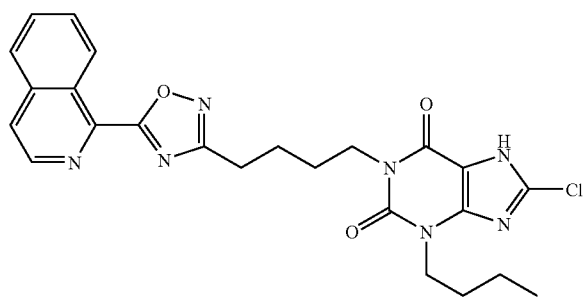 | 3-butyl-8-chloro-1-[4-(5-isoquinolin-1-yl-1,2,4-oxadiazol-3-yl)butyl]-3,7-dihydro-1H-purine-2,6-dione | m/z 494 [MH]$^+$ RT 3.49 min |

TABLE 25-continued
| | | | |
|---|---|---|---|
| 465 | 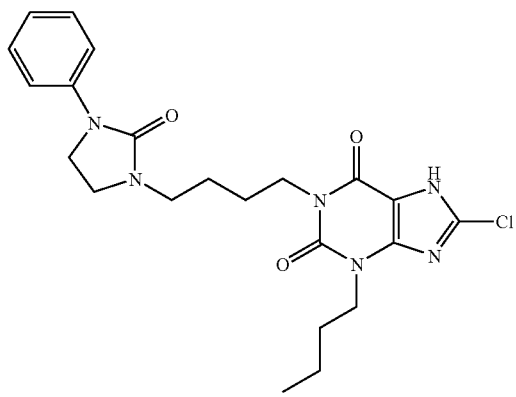 | 3-butyl-8-chloro-1-[4-(2-oxo-3-phenylimidazolidin-1-yl)butyl]-3,7-dihydro-1H-purine-2,6-dione | m/z 459 [MH]+ RT 3.23 min |
| 466 | 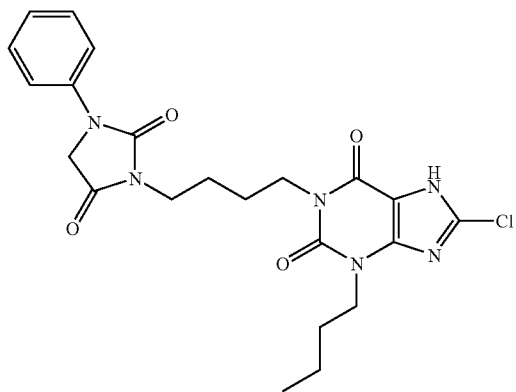 | 3-butyl-8-chloro-1-[4-(2,5-dioxo-3-phenylimidazolidin-1-yl)butyl]-3,7-dihydro-1H-purine-2,6-dione | m/z 473 [MH]+ RT 3.19 min |
| 467 | 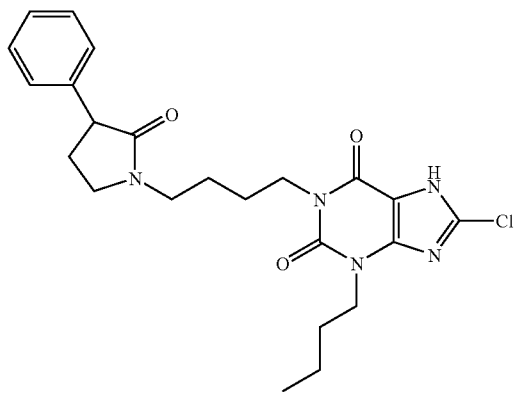 | 3-butyl-8-chloro-1-[4-(2-oxo-3-phenylpyrrolidin-1-yl)butyl]-3,7-dihydro-1H-purine-2,6-dione | m/z 458 [MH]+ RT 3.12 min |
| 468 | 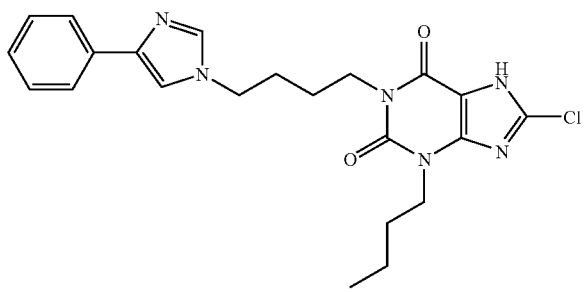 | 3-butyl-8-chloro-1-[4-(4-phenyl-1H-imidazol-1-yl)butyl]-3,7-dihydro-1H-purine-2,6-dione | m/z 441 [MH]+ RT 2.60 min |

TABLE 25-continued

| | | | |
|---|---|---|---|
| 469 | 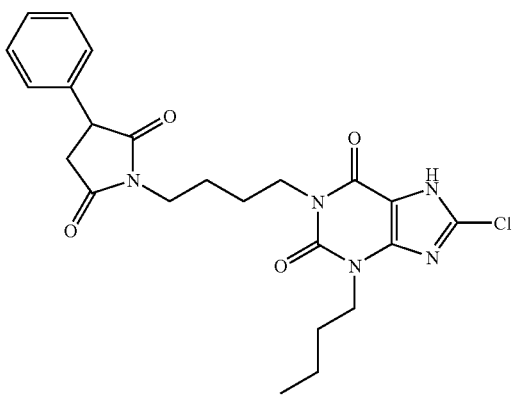 | 3-butyl-8-chloro-1-[4-(2,5-dioxo-3-phenylpyrrolidin-1-yl)butyl]-3,7-dihydro-1H-purine-2,6-dione | m/z 472 [MH]$^+$ RT 3.20 min |
| 470 | 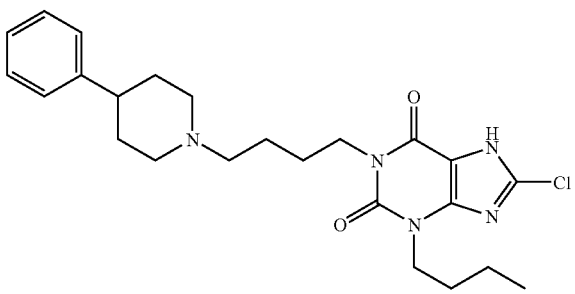 | 3-butyl-8-chloro-1-[4-(4-phenylpiperidin-1-yl)butyl]-3,7-dihydro-1H-purine-2,6-dione | m/z 458 [MH]$^+$ RT 2.56 min |
| 471 | 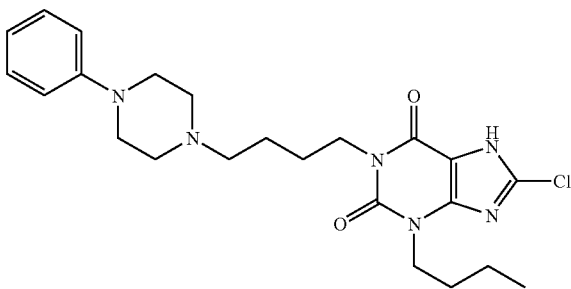 | 3-butyl-8-chloro-1-[4-(4-phenylpiperazin-1-yl)butyl]-3,7-dihydro-1H-purine-2,6-dione | m/z 459 [MH]$^+$ RT 2.49 min |
| 472 | 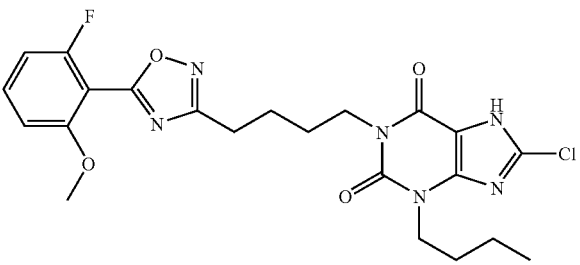 | 3-butyl-8-chloro-1-(4-{5-[2-fluoro-6-(methyloxy)phenyl]-1,2,4-oxadiazol-3-yl}butyl)-3,7-dihydro-1H-purine-2,6-dione | m/z 491 [MH]$^+$ RT 3.33 min |
| 473 | 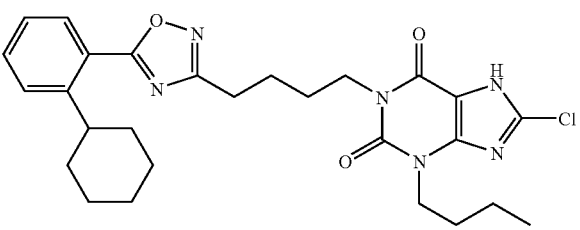 | 3-butyl-8-chloro-1-{4-[5-(2-cyclohexylphenyl)-1,2,4-oxadiazol-3-yl]butyl}-3,7-dihydro-1H-purine-2,6-dione | m/z 525 [MH]$^+$ RT 4.18 min |

TABLE 25-continued

| | | | |
|---|---|---|---|
| 474 | 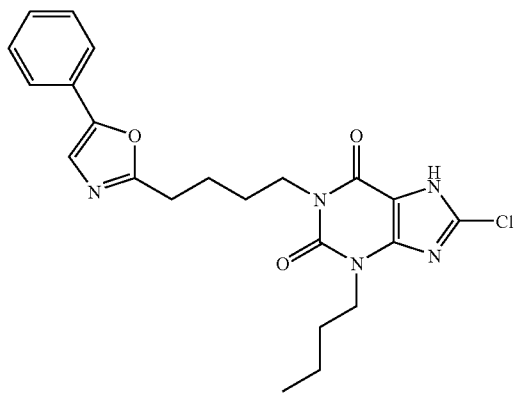 | 3-butyl-8-chloro-1-[4-(5-phenyl-1,3-oxazol-2-yl)butyl]-3,7-dihydro-1H-purine-2,6-dione | m/z 442 [MH]$^+$ RT 3.46 min |
| 475 | 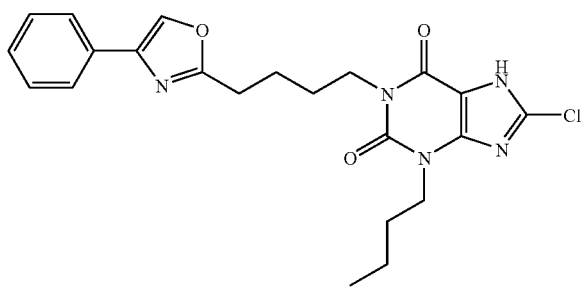 | 3-butyl-8-chloro-1-[4-(4-phenyl-1,3-oxazol-2-yl)butyl]-3,7-dihydro-1H-purine-2,6-dione | m/z 442 [MH]$^+$ RT 3.48 min |
| 476 | 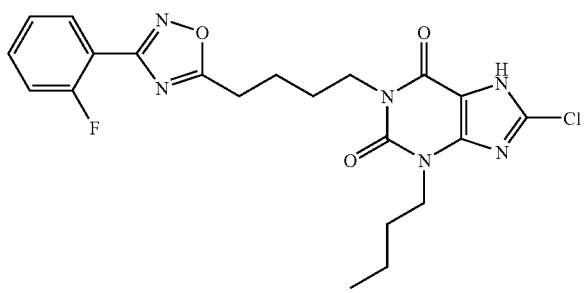 | 3-butyl-8-chloro-1-{4-[3-(2-fluorophenyl)-1,2,4-oxadiazol-5-yl]butyl}-3,7-dihydro-1H-purine-2,6-dione | m/z 461 [MH]$^+$ RT 3.45 min |
| 477 | 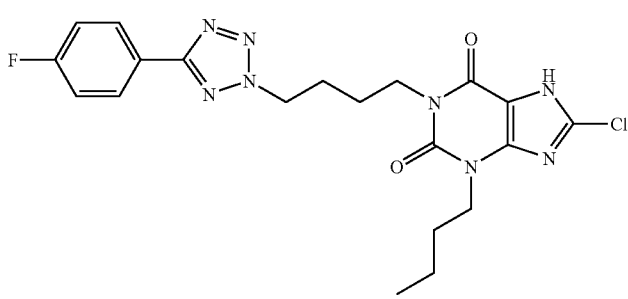 | 3-butyl-8-chloro-1-{4-[5-(4-fluorophenyl)-2H-tetrazol-2-yl]butyl}-3,7-dihydro-1H-purine-2,6-dione | m/z 461 [MH]$^+$ RT 3.47 min |
| 478 | 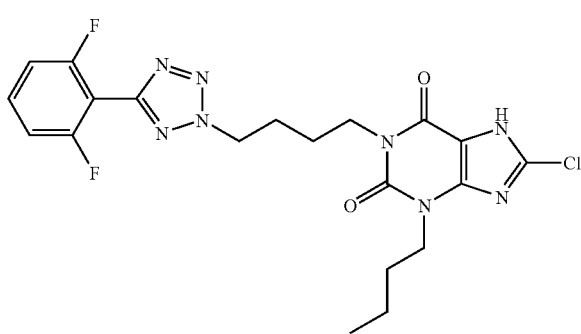 | 3-butyl-8-chloro-1-{4-[5-(2,6-difluorophenyl)-2H-tetrazol-2-yl]butyl}-3,7-dihydro-1H-purine-2,6-dione | m/z 479 [MH]$^+$ RT 3.32 min |

TABLE 25-continued

| | | | |
|---|---|---|---|
| 479 | 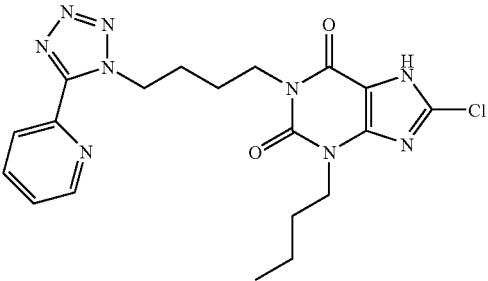 | 3-butyl-8-chloro-1-[4-(5-pyridin-2-yl-1H-tetrazol-1-yl)butyl]-3,7-dihydro-1H-purine-2,6-dione | m/z 444 [MH]+ RT 2.94 min |
| 480 | 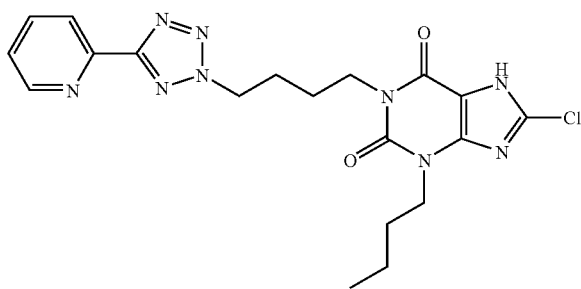 | 3-butyl-8-chloro-1-[4-(5-pyridin-2-yl-2H-tetrazol-2-yl)butyl]-3,7-dihydro-1H-purine-2,6-dione | m/z 444 [MH]+ RT 3.07 min |
| 481 | 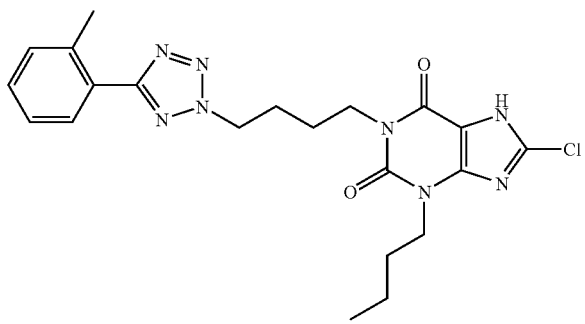 | 3-butyl-8-chloro-1-{4-[5-(2-methylphenyl)-2H-tetrazol-2-yl]butyl}-3,7-dihydro-1H-purine-2,6-dione | m/z 457 [MH]+ RT 3.54 min |
| 482 | 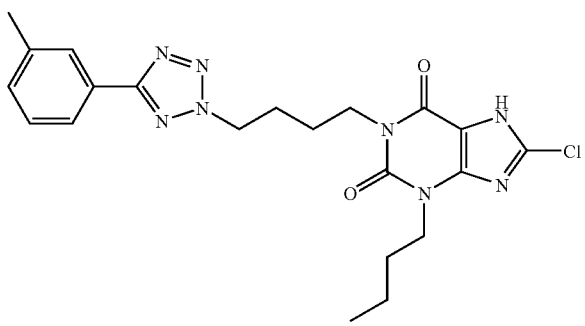 | 3-butyl-8-chloro-1-{4-[5-(3-methylphenyl)-2H-tetrazol-2-yl]butyl}-3,7-dihydro-1H-purine-2,6-dione | m/z 457 [MH]+ RT 3.56 min |
| 483 | 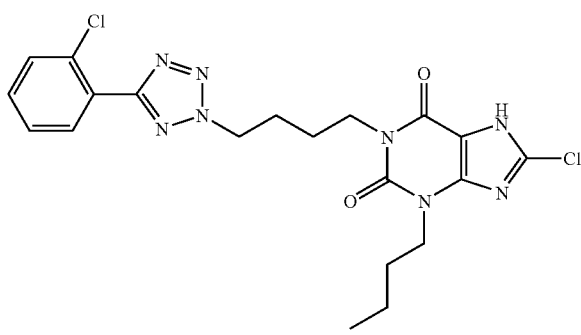 | 3-butyl-8-chloro-1-{4-[5-(2-chlorophenyl)-2H-tetrazol-2-yl]butyl}-3,7-dihydro-1H-purine-2,6-dione | m/z 477 [MH]+ RT 3.68 min |

TABLE 25-continued

| 484 | | 3-butyl-8-chloro-1-(4-{5-[4-(methyloxy)phenyl]-2H-tetrazol-2-yl}butyl)-3,7-dihydro-1H-purine-2,6-dione | m/z 473 [MH]+ RT 3.40 min |
|---|---|---|---|
| 485 | | 3-butyl-8-chloro-1-{4-[5-(4-chlorophenyl)-2H-tetrazol-2-yl]butyl}-3,7-dihydro-1H-purine-2,6-dione | m/z 477 [MH]+ RT 3.68 min |
| 486 | | 3-butyl-8-chloro-1-{4-[5-(3-fluorophenyl)-2H-tetrazol-2-yl]butyl}-3,7-dihydro-1H-purine-2,6-dione | m/z 461 [MH]+ RT 3.51 min |
| 487 | | 3-butyl-8-chloro-1-{4-[5-(2-fluorophenyl)-2H-tetrazol-2-yl]butyl}-3,7-dihydro-1H-purine-2,6-dione | m/z 461 [MH]+ RT 3.34 min |
| 488 | | 3-butyl-8-chloro-1-[4-(3-phenyl-1-pyrrolidinyl)butyl]-3,7-dihydro-1H-purine-2,6-dione | m/z 444 [MH]+ RT 2.51 min |

TABLE 25-continued

| 489 | 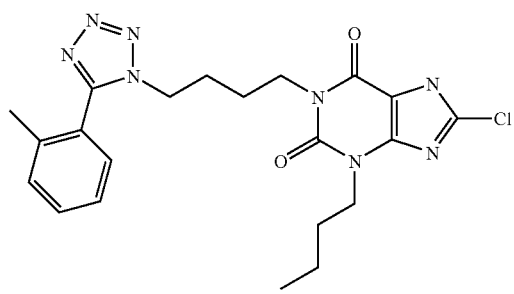 | 3-butyl-8-chloro-1-{4-[5-(2-methylphenyl)-1H-tetrazol-1-yl]butyl}-3,7-dihydro-1H-purine-2,6-dione | m/z 457 [MH]+ RT 3.16 min |
| --- | --- | --- | --- |
| 490 | 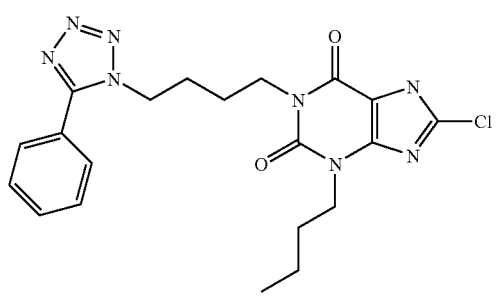 | 3-butyl-8-chloro-1-[4-(5-phenyl-1H-tetrazol-1-yl)butyl]-3,7-dihydro-1H-purine-2,6-dione | m/z 443 [MH]+ RT 3.08 min |
| 491 | 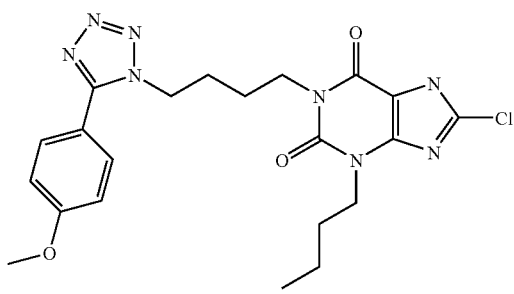 | 3-butyl-8-chloro-1-(4-{5-[4-(methyloxy)phenyl]-1H-tetrazol-1-yl}butyl)-3,7-dihydro-1H-purine-2,6-dione | m/z 473 [MH]+ RT 3.10 min |
| 492 | 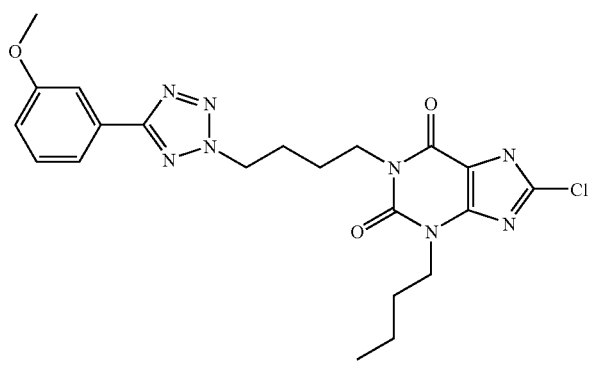 | 3-butyl-8-chloro-1-(4-{5-[3-(methyloxy)phenyl]-2H-tetrazol-2-yl}butyl)-3,7-dihydro-1H-purine-2,6-dione | m/z 473 [MH]+ RT 3.40 min |
| 493 | 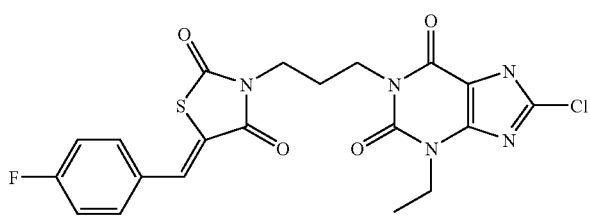 | 8-chloro-3-ethyl-1-(3-{(5Z)-5-[(4-fluorophenyl)methylidene]-2,4-dioxo-1,3-thiazolidin-3-yl}propyl)-3,7-dihydro-1H-purine-2,6-dione | m/z 478 [MH]+ RT 3.31 min |

TABLE 25-continued

| | | | |
|---|---|---|---|
| 494 | 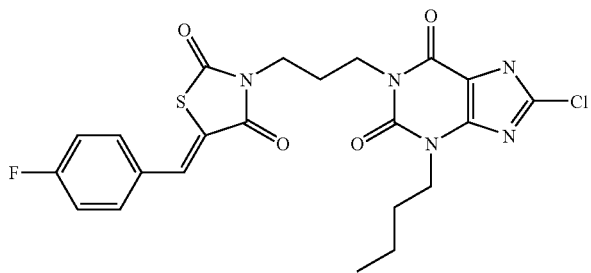 | 3-butyl-8-chloro-1-(3-{(5Z)-5-[(4-fluorophenyl)methylidene]-2,4-dioxo-1,3-thiazolidin-3-yl}propyl)-3,7-dihydro-1H-purine-2,6-dione | m/z 506 [MH]+ RT 3.63 min |
| 495 | 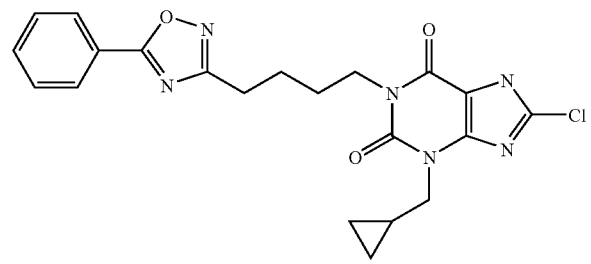 | 8-chloro-3-(cyclopropylmethyl)-1-[4-(5-phenyl-1,2,4-oxadiazol-3-yl)butyl]-3,7-dihydro-1H-purine-2,6-dione | m/z 441 [MH]+ RT 3.38 min |
| 496 | 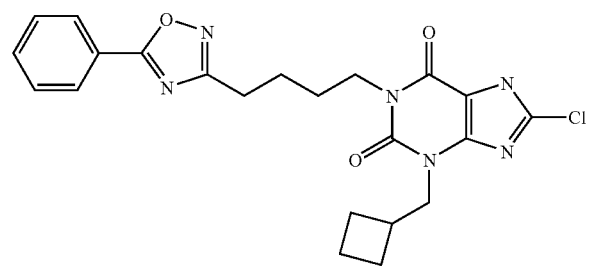 | 8-chloro-3-(cyclobutylmethyl)-1-[4-(5-phenyl-1,2,4-oxadiazol-3-yl)butyl]-3,7-dihydro-1H-purine-2,6-dione | m/z 455 [MH]+ RT 3.53 min |
| 497 | 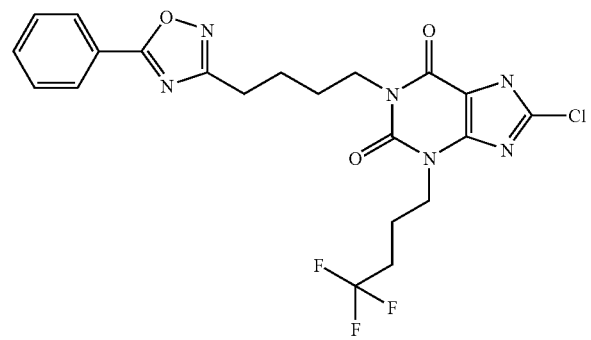 | 8-chloro-1-[4-(5-phenyl-1,2,4-oxadiazol-3-yl)butyl]-3-(4,4,4-trifluorobutyl)-3,7-dihydro-1H-purine-2,6-dione | m/z 497 [MH]+ RT 3.46 min |
| 498 | 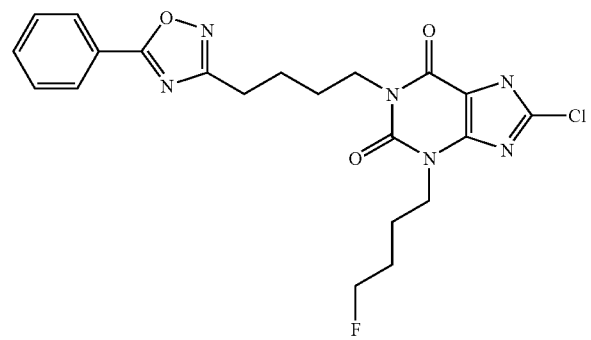 | 8-chloro-3-(4-fluorobutyl)-1-[4-(5-phenyl-1,2,4-oxadiazol-3-yl)butyl]-3,7-dihydro-1H-purine-2,6-dione | m/z 461 [MH]+ RT 3.26 min |

TABLE 25-continued

| | | | |
|---|---|---|---|
| 499 | 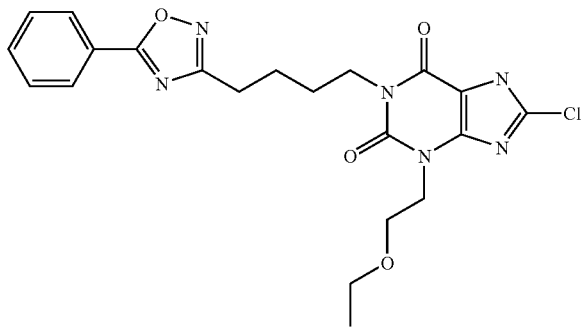 | 8-chloro-3-[2-(ethyloxy)ethyl]-1-[4-(5-phenyl-1,2,4-oxadiazol-3-yl)butyl]-3,7-dihydro-1H-purine-2,6-dione | m/z 459 [MH]+ RT 3.16 min |
| 500 | 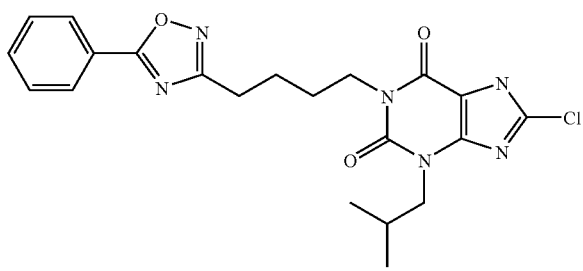 | 8-chloro-3-(2-methylpropyl)-1-[4-(5-phenyl-1,2,4-oxadiazol-3-yl)butyl]-3,7-dihydro-1H-purine-2,6-dione | m/z 443 [MH]+ RT 3.44 min |
| 501 | 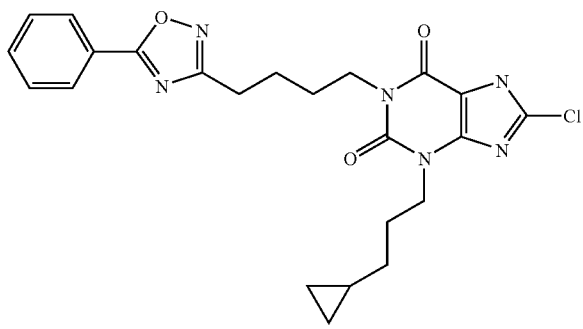 | 8-chloro-3-(3-cyclopropylpropyl)-1-[4-(5-phenyl-1,2,4-oxadiazol-3-yl)butyl]-3,7-dihydro-1H-purine-2,6-dione | m/z 469 [MH]+ RT 3.63 min |
| 502 | 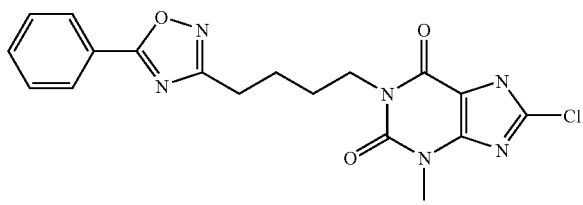 | 8-chloro-3-methyl-1-[4-(5-phenyl-1,2,4-oxadiazol-3-yl)butyl]-3,7-dihydro-1H-purine-2,6-dione | m/z 401 [MH]+ RT 2.98 min |
| 503 | 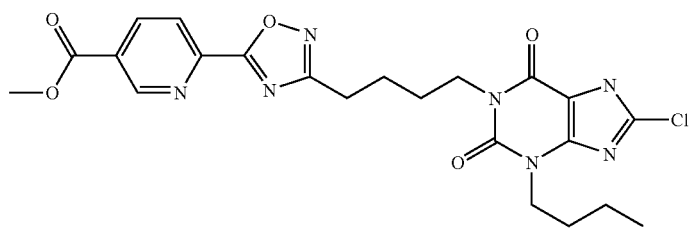 | methyl 6-{3-[4-(3-butyl-8-chloro-2,6-dioxo-2,3,6,7-tetrahydro-1H-purin-1-yl)butyl]-1,2,4-oxadiazol-5-yl}-3-pyridinecarboxylate | m/z 502 [MH]+ RT 3.22 min |

The invention claimed is:

1. A compound which is 3-butyl-8-chloro-1-(3-{5-[(4-fluorophenyl)methyl]-2H-tetrazol-2-yl}propyl)-3,7-dihydro-1H-purine-2,6-dione:

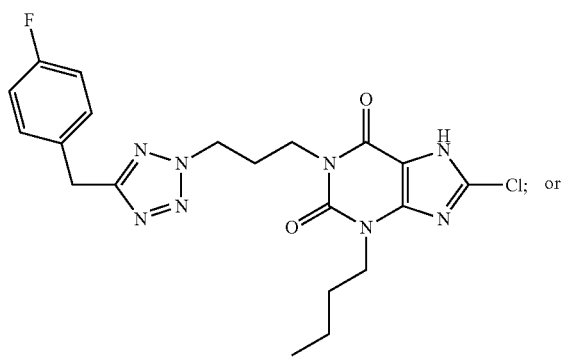

a pharmaceutically acceptable salt thereof.

2. A compound according to claim 1 which is 3-butyl-8-chloro-1-(3-{5-[(4-fluorophenyl)methyl]-2H-tetrazol-2-yl}propyl)-3,7-di hydro-1H-purine-2,6-dione:

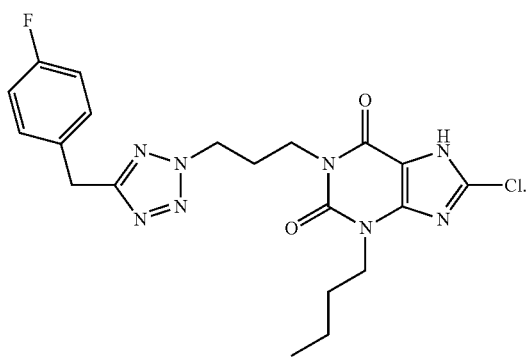

3. A method for treatment of diseases of lipid metabolism, which comprises administering an effective amount of a compound according to claim 1 to a human in need thereof.

4. The method according to claim 3, wherein the diseases of lipid metabolism are selected from diabetic dyslipidaemia, mixed dyslipidaemia, heart failure, hypercholesteraemia, cardiovascular disease, atherosclerosis, arteriosclerosis, hypertriglyceridaemia, insulin resistance, hyperlipidaemia, anorexia nervosa, obesity, coronary artery disease, thrombosis, angina, chronic renal failure, peripheral vascular disease or stroke.

5. The method according to claim 4, wherein the diseases of lipid metabolism are selected from diabetic dyslipidaemia, mixed dyslipidaemia, hypercholesteraemia, hypertriglyceridaemia or hyperlipidaemia.

6. The method according to claim 5, wherein the diseases of lipid metabolism are selected from diabetic dyslipidaemia, mixed dyslipidaemia or hyperlipoproteinaemia.

7. A method for treatment of diabetic dyslipidaemia, mixed dyslipidaemia, hypercholesteraemia, hypertriglyceridaemia or hyperlipidaemia, which comprises administering an effective amount of a compound according to claim 1 to said human in need thereof.

8. A method for treatment of diabetic dyslipidaemia, mixed dyslipidaemia, hypercholesteraemia, hypertriglyceridaemia or hyperlipidaemia, which comprises administering an effective amount of a compound according to claim 2 to a human in need thereof.

9. A method for treatment of diabetic dyslipidaemia, mixed dyslipidaemia or hyperlipoproteinaemia in a human in need thereof, which comprises administering an effective amount of a compound according to claim 1 to a human in need thereof.

10. A method for treatment of diabetic dyslipidaemia, mixed dyslipidaemia or hyperlipoproteinaemia, which comprises administering an effective amount of a compound according to claim 2 to a human in need thereof.

11. A pharmaceutical formulation comprising a compound according to claim 1 and at least one pharmaceutically acceptable diluent, excipient or carrier.

12. A pharmaceutical formulation comprising a compound according to claim 2 and at least one pharmaceutically acceptable diluent, excipient or carrier.

13. A pharmaceutical formulation comprising:
(i) a compound according to claim 1;
(ii) one or more therapeutically active agent selected from statins, bile-acid binding resins and nicotinic acid; and
(iii) one or more pharmaceutically acceptable diluent, excipient or carrier.

14. A pharmaceutical formulation comprising:
(i) a compound according to claim 2;
(ii) one or more therapeutically active agent selected from statins, bile-acid binding resins and nicotinic acid; and
(iii) one or more pharmaceutically acceptable diluent, excipient or carrier.

15. A combination for administration together or separately, sequentially or simultaneously in separate or combined pharmaceutical formulations, said combination comprising a compound according to claim 1 together with at least one therapeutically active agent selected from statins, bile-acid binding resins and nicotinic acid.

16. A combination for administration together or separately, sequentially or simultaneously in separate or combined pharmaceutical formulations, said combination comprising a compound according to claim 2 together with at least one therapeutically active agent selected from statins, bile-acid binding resins and nicotinic acid.

* * * * *